(12) United States Patent
Almirante et al.

(10) Patent No.: US 9,266,820 B2
(45) Date of Patent: Feb. 23, 2016

(54) NITRIC OXIDE DONOR COMPOUNDS

(71) Applicant: NICOX S.A., Sophia Antipois-Valbonne (FR)

(72) Inventors: Nicoletta Almirante, Milan (IT); Stefano Biondi, Pero (IT); Ennio Ongini, Segrate (IT); Laura Storoni, Cesano Maderno (IT); Alessia Nicotra, Grandate (IT)

(73) Assignee: Nicox Science Ireland, Dublin (IE)

( * ) Notice: Subject to any disclaimer, the term of this patent is extended or adjusted under 35 U.S.C. 154(b) by 0 days.

(21) Appl. No.: 14/300,049

(22) Filed: Jun. 9, 2014

(65) Prior Publication Data

US 2014/0288142 A1 Sep. 25, 2014

Related U.S. Application Data

(63) Continuation of application No. 12/525,988, filed as application No. PCT/EP2008/051092 on Jan. 30, 2008, now abandoned.

(60) Provisional application No. 60/899,422, filed on Feb. 5, 2007.

(51) Int. Cl.
| | | |
|---|---|---|
| *C07C 291/02* | (2006.01) | |
| *A61K 31/21* | (2006.01) | |
| *C07C 229/20* | (2006.01) | |
| *C07C 203/02* | (2006.01) | |
| *C07C 229/08* | (2006.01) | |
| *C07C 229/22* | (2006.01) | |
| *C07C 229/24* | (2006.01) | |
| *C07C 229/26* | (2006.01) | |
| *C07C 229/36* | (2006.01) | |
| *C07C 237/08* | (2006.01) | |
| *C07C 271/22* | (2006.01) | |
| *C07C 279/14* | (2006.01) | |
| *C07C 323/58* | (2006.01) | |
| *C07D 207/16* | (2006.01) | |
| *C07D 209/52* | (2006.01) | |
| *A61K 31/223* | (2006.01) | |
| *A61K 31/225* | (2006.01) | |
| *A61K 31/265* | (2006.01) | |
| *A61K 31/27* | (2006.01) | |
| *A61K 31/40* | (2006.01) | |
| *A61K 31/403* | (2006.01) | |
| *A61K 45/06* | (2006.01) | |

(52) U.S. Cl.
CPC ............. *C07C 229/20* (2013.01); *A61K 31/223* (2013.01); *A61K 31/225* (2013.01); *A61K 31/265* (2013.01); *A61K 31/27* (2013.01); *A61K 31/40* (2013.01); *A61K 31/403* (2013.01); *A61K 45/06* (2013.01); *C07C 203/02* (2013.01); *C07C 229/08* (2013.01); *C07C 229/22* (2013.01); *C07C 229/24* (2013.01); *C07C 229/26* (2013.01); *C07C 229/36* (2013.01); *C07C 237/08* (2013.01); *C07C 271/22* (2013.01); *C07C 279/14* (2013.01); *C07C 291/02* (2013.01); *C07C 323/58* (2013.01); *C07D 207/16* (2013.01); *C07D 209/52* (2013.01)

(58) Field of Classification Search
CPC .............................. C07C 291/02; A61K 31/21
See application file for complete search history.

(56) References Cited

U.S. PATENT DOCUMENTS

| 5,037,849 A | 8/1991 | Simon et al. |
| 5,428,061 A | 6/1995 | Sandrock et al. |
| 5,705,527 A | 1/1998 | Ishihara et al. |
| 2009/0062296 A1 | 3/2009 | Benedini et al. |

FOREIGN PATENT DOCUMENTS

| DE | 196 34 793 A1 | 3/1998 |
| EP | 0 362 575 A1 | 4/1990 |
| EP | 0 367 019 A1 | 5/1990 |
| WO | WO 91/12230 A1 | 8/1991 |
| WO | WO 03/000642 A2 | 1/2003 |
| WO | WO 03/013432 A2 | 2/2003 |
| WO | WO 2004/110432 A1 | 12/2004 |
| WO | WO 2005/030135 A2 | 4/2005 |
| WO | WO 2007/000641 A2 | 1/2007 |

OTHER PUBLICATIONS

Bonn, et al., "SP/W-5186: A Novel Sulfhydryl-Containing No Donor," Cardiovascular Drugs and Therapy, Kluwer Academic Publishers, Boston US, vol. 16, No. 3, Jan. 1, 1998, pp. 195-211.
Haj-Yehia et al. (Drug Devel. Res., 2000, 50, p. 528-536).
Souici et al. (Toxicology 165 (2001) 163-170).
Wang et al. (Chem. Rev. 2002, 102, 1091-1134).
Wermuth, "The Practice of Medicinal Chemistry," 2nd ed. 2003, Elsevier, 768 pages. Chs. 12-13 provided.

*Primary Examiner* — Robert Havlin
(74) *Attorney, Agent, or Firm* — Arent Fox LLP

(57) ABSTRACT

The invention relates to nitric oxide donor compounds and their use for treating cardiovascular diseases, inflammation, pain, fever, gastrointestinal disorders, ophthalmic diseases, hepatic disorders, renal diseases, respiratory disorders, immunological diseases, bone metabolisms dysfunctions, central and peripheral nervous system diseases, sexual dysfunctions, infectious diseases, for the inhibition of platelet aggregation and platelet adhesion, for treating pathological conditions resulting from abnormal cell proliferation, vascular diseases. The invention also relates to compositions comprising at least one nitric oxide releasing compounds of the invention and composition comprising at least one nitric oxide releasing compounds according to the invention and at least one 15 therapeutic agent.

9 Claims, No Drawings

NITRIC OXIDE DONOR COMPOUNDS

CROSS-REFERENCE TO RELATED APPLICATIONS

This application is a Continuation of U.S. patent application Ser. No. 12/525,988, filed Nov. 17, 2009, which is a National Stage entry of International Application No. PCT/EP2008/051092, filed Jan. 30, 2008, which claims benefit of U.S. Provisional Application No. 60/899,422, filed Feb. 5, 2007. The disclosures of the prior applications are hereby incorporated in their entirety by reference.

The invention relates to nitric oxide donor compounds and their pharmaceutical compositions. The invention also relates to novel compositions comprising at least one nitric oxide releasing compounds and at least one therapeutic agent.

The invention also relates to the use of the nitric oxide donor compounds and their compositions for treating cardiovascular diseases, inflammation, pain, fever, gastrointestinal disorders, ophthalmic diseases, hepatic disorders, renal diseases, respiratory disorders, immunological diseases, bone metabolism dysfunctions, central and peripheral nervous system diseases, sexual dysfunctions, infectious diseases, for the inhibition of platelet aggregation and platelet adhesion, for treating pathological conditions resulting from abnormal cell proliferation, vascular diseases.

Nitric oxide (commonly referred to as NO) has been implicated in a wide range of biological functions. As a result, NO, and materials that release NO, are candidate therapeutics for a range of diverse disease states.

Nitric oxide donor compounds have been used for many years in the treatment of various clinical conditions, particularly coronary artery disease. The nitrovasodilators such as nitroglycerin (GTN) has been used for the treatment of various types of myocardial ischemia. Because of its pathogenic nature (chronicity with acute exacerbation), prophylactic and acute treatments are necessary to prevent complications with potentially fatal outcomes (>25% death for acute MI). Particularly the phenomenon of tolerance to the anti-anginal effects or GTN and to all other existing organic nitrates is of a special clinical significance. Early development of tolerance to the drug is by far the most serious drawback of nitrate therapy.

Other known methods of NO delivery include soluble, short-term NO donors, such as S-nitroso-N-acetyl-D,L-penicillamine (SNAP) and incorporation of NO donors into polymeric matrices. In general, NO-nucleophile complexes (e.g., diazeniumdiolate ions) and NO-donating groups (e.g., S-nitrosothiols) may spontaneously decompose in aqueous environments, such as physiological or bodily fluids, to release NO. This rapid, spontaneous decomposition, however, may not be a favourable property for many therapeutic applications. Generally, a slower rate of decomposition and more steady evolution of NO are more efficacious.

Many of the existing NO donors must be administered intravenously, which results in rapid onset of decreasing blood pressure accompanied by unwanted side effects. Their effect does not extend beyond the period of infusion. Another undesirable side effect of some NO donors includes an increase in heart rate. A need exists for an NO donor compound to treat diseases that does not induce undesirable side effects.

The invention is directed to compounds that are particularly useful as nitric oxide donors having an improved pharmacological profile.

The invention provides compounds of the formula (I) and pharmaceutically acceptable salts or stereoisomers thereof

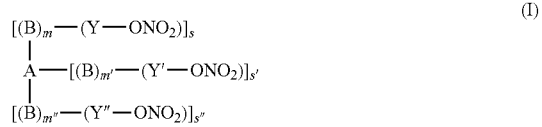

wherein:

s is 1;

s' and s" are independently selected from 0 or 1, preferably s' or s" is 1 or s' and s" are both 0;

m, m' and m" are each independently selected from 0 or 1 with the proviso that when m, m' or m" are 0, A is linked directly to the groups —(Y—ONO$_2$), —(Y'—ONO$_2$), —(Y"—ONO$_2$), preferably at least one of m, m' or m" is 1, or more preferably m, m' and m" are 0, B at each occurrence is independently selected from:

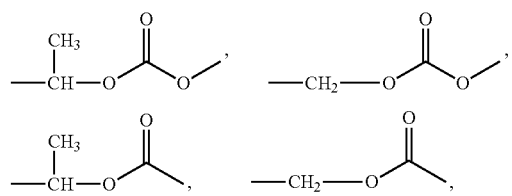

preferably B is

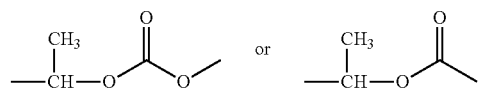

A is a radical selected from the group consisting of:

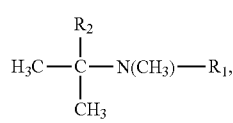

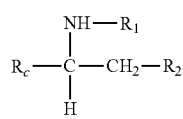

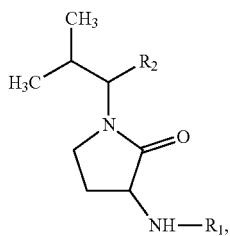
(IIe)

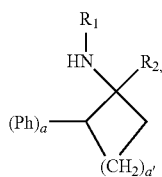
(IIf)

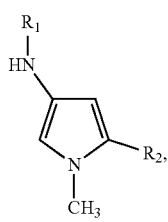
(IIg)

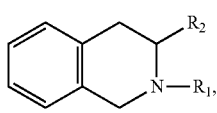
(IIh)

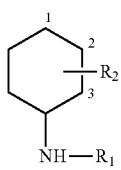
(IIi)

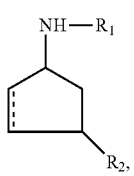
(IIj)

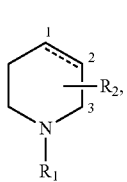
(IIk)

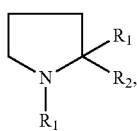
(IIl)

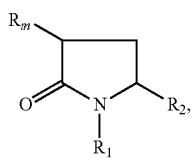
(IIm)

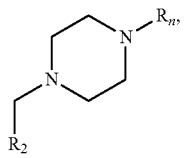
(IIn)

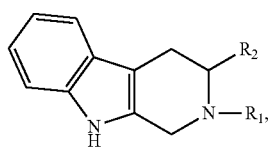
(IIo)

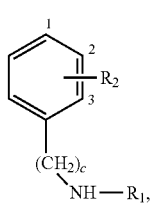
(IIp)

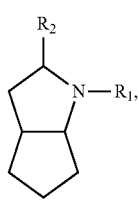
(IIq)

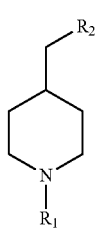
(IIr)

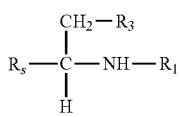
(IIs)

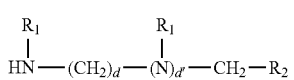
(IIt)

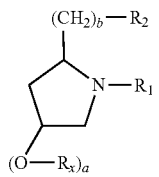
(IIu)

wherein:
in formulas (IIa)-(IIm) and (IIo)-(IIu), $R_1$ is selected from: H, —C(O)O—C(CH$_3$)$_3$, —C(O)—$R_{1x}$, —C(O)O—$R_{1x}$, wherein $R_{1x}$ is one of the groups —[(B)$_m$—(Y—ONO$_2$)]$_s$, —[(B)$_{m'}$—(Y'—ONO$_2$)]$_{s'}$, or —[(B)$_{m''}$—(Y''—ONO$_2$)]$_{s''}$ of formula (I) wherein m, m' and m'' are 0 and Y, Y' and Y'' are as below reported;
in formulas (IIa)-(IIu) $R_2$ is selected from:
—C(O)OH, —C(O)—OC(CH$_3$)$_3$, —C(O)O$R_{2x}$, —C(O)NHR$_{2xx}$, —C(O)N(CH$_3$)R$_{2xx}$ where $R_{2x}$ is one of the groups —[(B)$_m$—(Y—ONO$_2$)]$_s$, —[(B)$_{m'}$—(Y'—

$—ONO_2)]_{s'}$ or $—[(B)_{m''}—(Y''—ONO_2)]_{s''}$ of formula (I) wherein m, m' and m'' are 0 or 1, B is as above defined and Y, Y' and Y'' are as below reported, $R_{2xx}$ is one of the groups $—[(B)_m—(Y—ONO_2)]_s$, $—[(B)_{m'}—(Y'—ONO_2)]_{s'}$ or $—[(B)_{m''}—(Y''—ONO_2)]_{s''}$ of formula (I) wherein m, m' and m'' are 0 and Y, Y' and Y'' are as below reported, or $R_2$ is the group $R_4$:

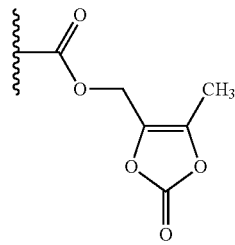

$R_4$ in formula (IIa), $R_a$ is selected from the groups consisting of:

a) $—H$, $—CH_3$, isopropyl, isobutyl, sec-butyl, tert-butyl, methylthio-$(CH_2)_2—$, phenyl, benzyl, $C_6H_5—CH_2—CH_2—$, 2-monosubstituted benzyl, or 3-monosubstituted benzyl or 4-monosubstituted benzyl with groups such as $—F$, $—Cl$, I, $—NO_2$, $—CF_3$, $—CH_3$, CN, $C_6H_5CO—$;

or $R_a$ is 2,4-dichlorobenzyl, 3,4-dichlorobenzyl, 3,4-difluorobenzyl, 3-triptophanyl-$CH_2—$, 3-benzothienyl-$CH_2—$, 4-imidazolyl-$CH_2—$, 9-anthranyl-$CH_2—$, cyclohexyl, cyclohexyl-$CH_2—$, cyclohexyl-$(CH_2)_2—$, cyclopentyl-$CH_2—$, $(C_6H_5)_2CH—$, 4-quinolyl-$CH_2—$, 3-quinolyl-$CH_2—$, 2-quinolyl-$CH_2—$, 2-quinoxalyl-$CH_2—$, 2-furyl-$CH_2—$, 1-naphtyl-$CH_2—$, 2-naphtyl-$CH_2—$, 2-pyridyl-$CH_2—$, 3-pyridyl-$CH_2—$, 4-pyridyl-$CH_2—$, 2-thienyl-$CH_2—$, 3-thienyl-$CH_2—$, $C_6H_4—CH=CH—CH_2—$, $CH_2=CH—CH_2—$, $CH\equiv CH—CH_2—$, $NH_2—CO—CH_2—$, $NH_2—CO—(CH_2)_2—$, or $—P(=O)(OCH_3)_2$;

b) $HS—CH_2—$, $R_{bx}—C(O)—S—CH_2—$, $R_{bx}—OC(O)—S—CH_2—$, $R_{bx}—NH—C(O)S—CH_2—$ wherein $R_{bx}$ is one of the groups $—[(B)_m—(Y—ONO_2)]_s$, $—[(B)_{m'}—(Y'—ONO_2)]_{s'}$ or $—[(B)_{m''}—(Y''—ONO_2)]_{s''}$ of formula (I) wherein m, m' and m'' are 0 and Y, Y' and Y'' are as below defined;

c) $R_xO—CH_2—$, $R_xO—CH(CH_3)—$, $(R_xO)$-p-$C_6H_4—CH_2—$, 4-$(R_xO)$-3,5-diiodobenzyl-, 4-$(R_xO)$-3-nitrobenzyl- wherein $R_x$ is H, $R_{xx}—C(O)—$, $R_{xx}—OC(O)—$, $R_{xx}—NHC(O)—$ wherein $R_{xx}$ is one of the groups $—[(B)_m—(Y—ONO_2)]_s$, $—[(B)_{m'}—(Y'—ONO_2)]_{s'}$ or $—[(B)_{m''}—(Y''—ONO_2)]_{s''}$ of formula (I) wherein m, m' and m'' are 0 and Y, Y' and Y'' are as below defined;

d) $R_gC(O)CH_2—NH—$, $R_gC(O)CH_2—$, $R_gC(O)(CH_2)_2—$, $R_gC(O)(CH_2)_4—$, wherein $R_g$ is OH, $(CH_3)_3CO—$, $R_{gx}—O—$, $R_{gxx}—NH—$, $R_{gxx}—N(CH_3)—$ wherein $R_{gx}$ is one of the groups $—[(B)_m—(Y—ONO_2)]_s$, $—[(B)_{m'}—(Y'—ONO_2)]_{s'}$ or $—[(B)_{m''}—Y''—ONO_2)]_{s''}$ of formula (I) wherein m, m' and m'' are 0 or 1, B is as above defined and Y, Y' and Y'' are as below reported, $R_{gxx}$ is one of the groups $—[(B)_m—(Y—ONO_2)]_s$, $—[(B)_{m'}—(Y'—ONO_2)]_{s'}$ or $—[(B)_{m''}—(Y''—ONO_2)]_{s''}$ of formula (I) wherein m, m' and m'' are 0 and Y, Y' and Y'' are as below reported, or $R_g$ is the group $R_{gg}$:

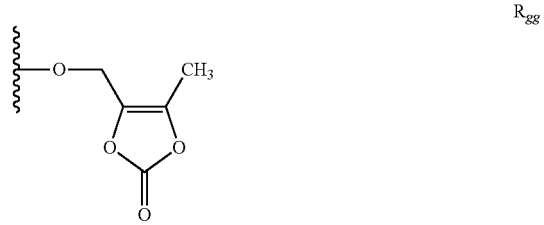 [SMILES: *OCc1oc(=O)oc1C]

$R_{gg}$ e) $R_hNH(CH_2)_p—$ or $R_iNH(=NH)NH—(CH_2)_3—$, wherein p is an integer from 0 to 4, $R_h$ is H, $(CH_3)_3C—OC(O)—$, $R_{hh}—C(O)—$ or $R_{hh}—OC(O)—$, $R_i$ is H, $R_{ii}—C(O)—$ or $R_{ii}—OC(O)—$, wherein $R_{hh}$ and $R_{ii}$ are each independently one of the groups $—[(B)_m—(Y—ONO_2)]_s$, $—[(B)_{m'}—(Y'—ONO_2)]_{s'}$ or $—[(B)_{m''}—(Y''—ONO_2)]_{s''}$ of formula (I) wherein m, m' and m'' are 0 and Y, Y' and Y'' are as below defined;

in formula (IIc) $R_c$ is selected from the following groups:

a') H, $CH_3$, isopropyl, isobutyl, sec-butyl, methylthio-$(CH_2)_2—$, phenyl, benzyl, biphenyl-$CH_2$, 3-triptophanyl-$CH_2—$, $NH_2—CO—CH_2—$, $NH_2—CO—(CH_2)_2—$;

b') $HS—CH_2—$, $R_{bx}—C(O)—S—CH_2—$, $R_{bx}—OC(O)—S—CH_2—$, $R_{bx}—NH—C(O)S—CH_2—$ wherein $R_{bx}$ is one of the groups $—[(B)_m—(Y—ONO_2)]_s$, $—[(B)_{m'}—(Y'—ONO_2)]_{s'}$ or $—[(B)_{m''}—(Y''—ONO_2)]_{s''}$ of formula (I) wherein m, m' and m'' are 0 and Y, Y' and Y'' are as below defined;

c') $R_xO—CH_2—$, $R_xO—CH(CH_3)—$, $R_xO—C_6H_4—CH_2—$ wherein $R_x$ is H, $R_{xx}—C(O)—$, $R_{xx}—OC(O)—$, $R_{xx}—NHC(O)—$ wherein $R_{xx}$ is one of the groups $—[(B)_m—(Y—ONO_2)]_s$, $—[(B')_{m'}—(Y'—ONO_2)]_{s'}$ or $—[(B'')_{m''}—(Y''—ONO_2)]_{s''}$ of formula (I) wherein m, m' and m'' are 0 and Y, Y' and Y'' are as below defined;

d') $R_gC(O)CH_2—$, $R_gC(O)(CH_2)_2—$ wherein $R_g$ is OH, $(CH_3)_3CO—$, $R_{gx}—O—$, $R_{gxx}—NH—$, $R_{gxx}—N(CH_3)—$ wherein $R_{gx}$ is one of the groups $—[(B)_m—(Y—ONO_2)]_s$, $—[(B)_{m'}—(Y'—ONO_2)]_{s'}$ or $—[(B)_{m''}—(Y''—ONO_2)]_{s''}$ of formula (I) wherein m, m' and m'' are 0 or 1, and B is as above defined and Y, Y' and Y'' are as below reported, $R_{gxx}$ is one of the groups $—[(B)_m—(Y—ONO_2)]_s$, $—[(B)_{m'}—(Y'—ONO_2)]_{s'}$ or $—[(B)_{m''}—(Y''—ONO_2)]_{s''}$ of formula (I) wherein m, m' and m'' are 0 and Y, Y' and Y'' are as below reported;

e') $R_hNH(CH_2)_p—$ or $R_iNH(=NH)NH—(CH_2)_3—$, wherein p is an integer from 0 to 4, $R_h$ is H, $(CH_3)_3C—OC(O)—$, $R_{hh}—C(O)—$ or $R_{hh}—OC(O)—$, $R_i$ is H, $R_{ii}—C(O)—$ or $R_{ii}—OC(O)—$, wherein $R_{hh}$ and $R_{ii}$ are each independently one of the groups $—[(B)_m—(Y—ONO_2)]_s$, $—[(B)_{m'}—(Y'—ONO_2)]_{s'}$ or $—[(B)_{m''}—(Y''—ONO_2)]_{s''}$ of formula (I) wherein m, m' and m'' are 0 and Y, Y' and Y'' are as below defined;

in formula (IIf) Ph is phenyl, a' is equal to 0, 1, 2, or 3, and a is equal to 0 or 1 with the proviso that a is 0 or 1 when a' is 0 and a is 0 when a' is 1, 2 or 3;

in formula (IIi) the group $R_2$ can be attached to one of the positions 1, 2 or 3 of the cyclohexyl ring;

in formulae (IIj) and (IIk) the symbol $=$ represents a single bond or a double bond;

in formula (IIk) the group $R_2$ can be attached to one of the positions 1, 2 or 3 of the piperidyl ring;

in formula (III), $R_L$ is selected from:
H, methyl, propyl, allyl, $(C_6H_5)_2CH-$, 1-naphthyl-$CH_2-$, benzyl, 2-bromobenzyl, 2-chlorobenzy, 3-chlorobenzyl, 4-fluorobenzyl, 4-bromobenzyl, 4-methylbenzyl;

in formula (IIm) $R_m$ is selected from:
benzyl, 2-bromobenzyl, 4-bromobenzyl, 4-methylbenzyl;

in formula (IIn) $R_n$ is selected from:
—H, —C(O)—$R_{nx}$, —C(O)—$R_{nx}$ or —$(CH_2)_2$—NH—$R_h$, wherein $R_h$ is —H, —C(O)O—C(CH$_3$)$_3$, —C(O)—$R_{hh}$, —C(O)O—$R_{hh}$ wherein $R_{nx}$ and $R_{hh}$ are each independently one of the groups —[(B)$_m$—(Y—ONO$_2$)]$_s$, —[(B)$_{m'}$—(Y'—ONO$_2$)]$_{s'}$ or —[(B)$_{m''}$—(Y"—ONO$_2$)]$_{s''}$ of formula (I) wherein m, m' and m" are 0 and Y, Y' and Y" are as below defined;

in formula (IIp), c is 0 or 1 and $R_2$ can be attached to the position 1, 2 or 3 of the phenyl ring;

in formula (IIs), $R_3$ is selected from:
OH, —OC(O)—$R_{3x}$, —OC(O)O—$R_{3x}$, —OC(O)—NH—$R_{3x}$ wherein $R_{3x}$ is one of the groups —[(B)$_m$—(Y—ONO$_2$)]$_s$, —[(B)$_{m'}$—(Y'—ONO$_2$)]$_{s'}$ or —[(B)$_{m''}$—(Y"—ONO$_2$)]$_{s''}$ of formula I wherein m, m' and m" are 0 and Y, Y' and Y" are as below defined;

in formula (IIs) $R_s$ is selected from the following groups:

a") —H, —CH$_3$, isopropyl, isobutyl, sec-butyl, tert-butyl, methylthio-$(CH_2)_2$—, benzyl, 2-monosubstituted benzyl, or 3-monosubstituted benzyl, 3-triptophanyl-$CH_2$—, 4-imidazolyl-$CH_2$—, $NH_2$—CO—$CH_2$—, $NH_2$—CO—$(CH_2)_2$—;

b") HS—$CH_2$—, $R_{bx}$—C(O)—S—$CH_2$—, $R_{bx}$—OC(O)—S—$CH_2$—, $R_{bx}$—NH—C(O)S—$CH_2$— wherein $R_{bx}$ is one of the groups —[(B)$_m$—(Y—ONO$_2$)]$_s$, —[(B)$_{m'}$—(Y'—ONO$_2$)]$_{s'}$ or —[(B)$_{m''}$—(Y"—ONO$_2$)]$_{s''}$ of formula (I) wherein m, m' and m" are 0 and Y, Y' and Y" are as below defined;

c") $R_xO$—$CH_2$—, $R_xO$—$CH(CH_3)$—, $(R_xO)$-p-$C_6H_4$—$CH_2$—, 4-$(R_xO)$-3,5-diiodobenzyl-, 4-$(R_xO)$-3-nitrobenzyl- wherein $R_x$ is H, $R_{xx}$—C(O)—, $R_{xx}$—OC(O)—, $R_{xx}$—NHC(O)— wherein $R_{xx}$ is one of the groups —[(B)$_m$—(Y—ONO$_2$)]$_s$, —[(B)$_{m'}$—(Y'—ONO$_2$)]$_{s'}$ or —[(B)$_{m''}$—(Y"—ONO$_2$)]$_{s''}$ of formula (I) wherein m, m' and m" are 0 and Y, Y' and Y" are as below defined;

d") $R_gC(O)CH_2$—NH—, $R_gC(O)CH_2$, $R_gC(O)(CH_2)_2$—, $R_gC(O)(CH_2)_4$—, wherein $R_g$ is OH, $(CH_3)_3CO$—, $R_{gx}$—O—, $R_{gxx}$—NH—, $R_{gxx}$—N(CH$_3$)— wherein $R_{gx}$ is one of the groups —[(B)$_m$—(Y—ONO$_2$)]$_s$—, [(B)$_{m'}$—(Y'—ONO$_2$)]$_{s'}$ or —[(B)$_{m''}$—(Y"—ONO$_2$)]$_{s''}$ of formula (I) wherein m, m' and m" are 0 or 1, B is as above defined and Y, Y' and Y" are as below reported, $R_{gxx}$ is one of the groups —[(B)$_m$—(Y—ONO$_2$)]$_s$, —[(B)$_{m'}$—(Y'—ONO$_2$)]$_{s'}$ or —[(B)$_{m''}$—(Y"—ONO$_2$)]$_{s''}$ of formula (I) wherein m, m' and m" are 0 and Y, Y' and Y" are as below reported, e") $R_hNH(CH_2)_p$— or $R_iNH(=NH)NH$—$(CH_2)_3$—, wherein p is an integer from 0 to 4, $R_h$ is H, $(CH_3)_3C$—OC(O)—, $R_{hh}$—C(O)— or $R_{hh}$—OC(O)—, $R_i$ is H, $R_{ii}$—C(O)— or $R_{ii}$—OC(O)—, wherein $R_{hh}$ and $R_{ii}$ are each independently one of the groups —[(B)$_m$—(Y—ONO$_2$)]$_s$, —[(B)$_{m'}$—(Y'—ONO$_2$)]$_{s'}$ or —[(B)$_{m''}$—(Y"—ONO$_2$)]$_{s''}$ of formula (I) wherein m, m' and m" are 0 and Y, Y' and Y" are as below defined;

in formula (IIt) d is an integer from 2 to 5, d' is 0 or 1, with the proviso that d' is 0 when d is an integer from 3 to 5, $R_t$ is H, —C(O)—$R_{tt}$ or —C(O)O—$R_{tt}$ wherein $R_{tt}$ is one of the groups —[(B)$_m$—(Y—ONO$_2$)]$_s$, —[(B')$_{m'}$—(Y'—ONO$_2$)]$_{s'}$ or —[(B")$_{m''}$—(Y"—ONO$_2$)]$_{s''}$ of formula (I) wherein m, m' and m" are 0;

in formula (IIu) a and b are each independently 0 or 1, $R_x$ is H, —C(O)—$R_{xx}$, —C(O)O—$R_{xx}$, —C(O)NH—$R_{xx}$ wherein $R_{xx}$ is one of the groups —[(B)$_m$—(Y—ONO$_2$)]$_s$, —[(B)$_{m'}$—(Y'—ONO$_2$)]$_{s'}$ or —[(B)$_{m''}$—(Y"—ONO$_2$)]$_{s''}$ of formula (I) wherein m, m' and m" are 0 and Y, Y' and Y" are as below defined;

Y, Y' and Y" of the groups (Y—ONO$_2$), —(Y'—ONO$_2$) and —(Y"—ONO$_2$) of formula (I) are bivalent radicals and they are each independently selected from:

A)
a straight or branched $C_1$-$C_{20}$ alkylene, preferably a straight or branched $C_2$-$C_{10}$ alkylene a straight or branched $C_1$-$C_{20}$ alkylene substituted with one or more —ONO$_2$ group(s), preferably a straight or branched $C_2$-$C_{10}$ alkylene substituted with a —ONO$_2$ group;

a cycloalkylene having 5 to 7 carbon atoms, the ring being optionally substituted with a straight or branched $C_1$-$C_{10}$ alkyl;

B)

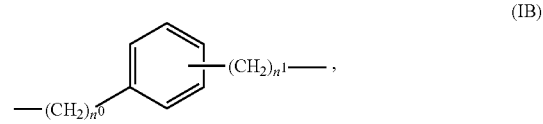

(IB)

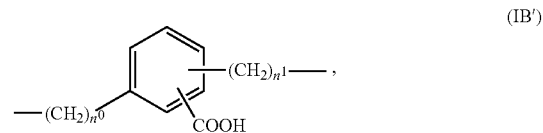

(IB')

wherein $n^0$ is an integer from 0 to 20, preferably $n^0$ is from 0 to 5, more preferably $n^0$ is 0 or 1, $n^1$ is an integer from 1 to 20, preferably $n^1$ is an integer from 1 to 10, more preferably $n^1$ is an integer from 2 to 6;

more preferably in formula (IB) and (IB') $n^0$ is 0 or 1 and $n^1$ is an integer from 1 to 10;

wherein in formulas (IB) and (IB') the —ONO$_2$ group is linked to —(CH$_2$)$_n^1$—;

C)

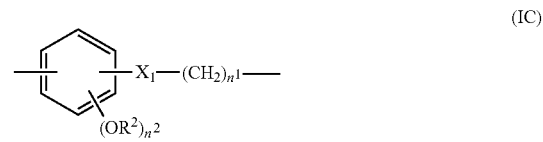

(IC)

wherein:

$n^1$ is an integer from 1 to 20, preferably $n^1$ is an integer from 1 to 10, or more preferably $n^1$ is an integer from 2 to 6, $n^2$ is an integer from 0 to 2, preferably $n^2$ is 1, $R^2$ is H or CH$_3$, preferably $R^2$ is CH$_3$, $X_1$ is —OC(O)— or —C(O)O—;

more preferably in formula (IC) $n^1$ is an integer from 1 to 10, $n^2$ is 1 and $R^2$ is CH$_3$, $X_1$ is —C(O)O—;

wherein in formula (IC) the —ONO$_2$ group is linked to —(CH$_2$)$_n^1$—;

D)

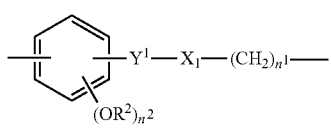
(ID)

wherein in formula (ID):
$n^1$ is an integer from 1 to 20, preferably $n^1$ is an integer from 1 to 10, or more preferably $n^1$ is an integer from 2 to 10,
$n^2$, $R^2$ and $X_1$ are as defined above;
$Y^1$ is $-CH_2-CH_2-$ or $-CH_2=CH-(CH_2)_n{}^{2a}-$ wherein $n^{2a}$ is an integer from 0 to 5, preferably $n^{2a}$ is 0,
wherein in formula (ID) the $-ONO_2$ group is linked to $-(CH_2)_n{}^1-$; preferably in formula (ID), $n^2$ is 1 and $R^2$ is $CH_3$, $Y^1$ is $-CH=CH-(CH_2)_n{}^{2a}-$ wherein $n^{2a}$ is 0, $X_1$ is $-C(O)O-$, $n^1$ is an integer from 1 to 10;

E)

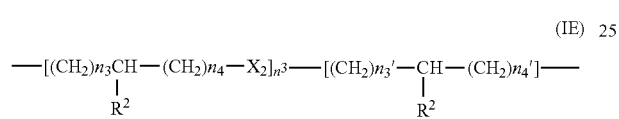
(IE)

wherein $X_2$ is $-O-$, $-S-$, $-NH-$ or $-N(CH_2CH_2OCH_3)-$, preferably $X_2$ is $-O-$ or $-NH-$,
$n^3$ is an integer from 1 to 5, preferably $n^3$ is 1,
$n_3$ is an integer from 0 to 10, preferably from 0 to 4, more preferably $n_3$ is 0,
$n_4$ an integer from 1 to 10, preferably from 1 to 4, more preferably $n_4$ is 1
preferably $n_3$ is 0 and $n_4$ is 1;
$n_{3'}$ is an integer from 0 to 10, preferably $n_{3'}$ is from 0 to 4,
$n_{4'}$ is an integer from 1 to 10, preferably from 1 to 4,
more preferably $n_{3'}$ is 0 and $n_{4'}$ is 1,
$R^2$ is H or $-CH_3$, preferably $R^2$ is H,
preferably in (IE) $n^3$ is an integer from 1 to 5, $n_3$ is 0 and $n_4$ is from 1 to 4, $n_{3'}$ is 0 and $n_{4'}$ is from 1 to 4, $R^2$ is H and $X_2$ is $-O-$ or $-NH-$,
more preferably in (IE) $n^3$ is 1, $n_3$ is 0 and $n_4$ is 1, $n_{3'}$ is 0 and $n_{4'}$ is 1, $R^2$ is H and $X_2$ is $-O-$ or $-NH-$,
wherein in formula (IE) the $-ONO_2$ group is linked to the $-(CH_2)_{n_{4'}}-$ group;

F)

(IF)

wherein:
$n^5$ is an integer from 0 to 10, preferably $n^5$ is 0 or 1;
$n^6$ is an integer from 1 to 10, preferably $n^6$ is 1;
$R^4$, $R^5$, $R^6$, $R^7$ are the same or different, and are H or straight or branched $C_1$-$C_4$ alkyl, preferably $R^4$, $R^5$, $R^6$, $R^7$ are H;

wherein in formula (IF) the $-ONO_2$ group is linked to

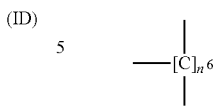

wherein $n^6$ is as defined above;
$Y^2$ is an heterocyclic saturated, unsaturated, or aromatic 5 or 6 members ring, containing one or more heteroatoms selected from nitrogen, oxygen, sulfur,
and is selected from the group consisting of:

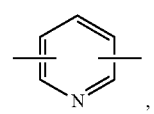
(Y1)

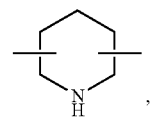
(Y2)

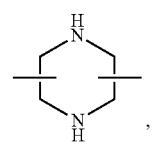
(Y3)

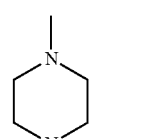
(Y4)

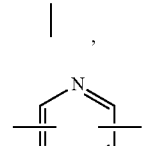
(Y5)

(Y6)

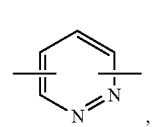
(Y7)

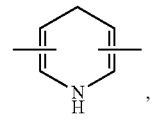
(Y8)

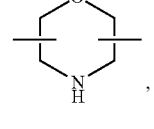
(Y9)

-continued

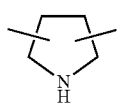 (Y10)

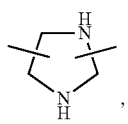 (Y11)

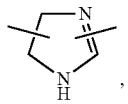 (Y12)

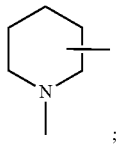 (Y13)

G)

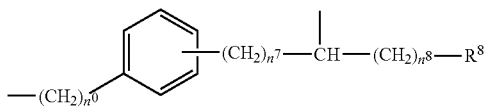 (IG)

wherein $n^0$ is an integer from 0 to 10,
$n^7$ is an integer from 1 to 10, preferably $n^7$ is an integer from 1 to 6, more preferably $n^7$ is 1;
$n^8$ is an integer from 0 to 10, preferably $n^8$ is an integer from 0 to 6, more preferably $n^8$ is 0;
$R^8$ is $CH_3$ or $CH_2ONO_2$,
more preferably in formula (IG) $n^0$ is 0, $n^7$ is 1, $n^8$ is 0 and $R^8$ is $CH_3$ or $CH_2ONO_2$,
wherein in formula (IG) the —$ONO_2$ group is linked to the group

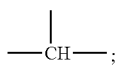;

preferably Y and Y' or Y" are equal;
preferred (Y—$ONO_2$), —(Y'—$ONO_2$) or —(Y"—$ONO_2$) groups are:

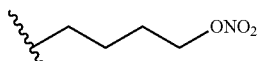

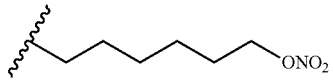

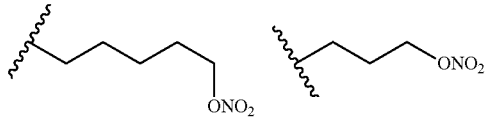

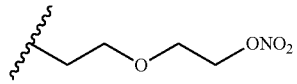

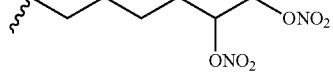

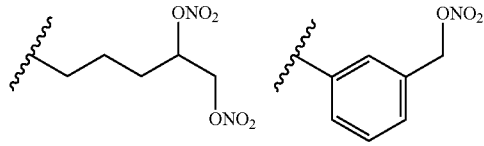

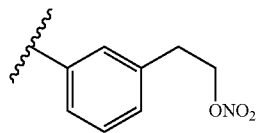

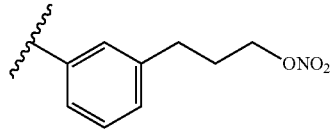

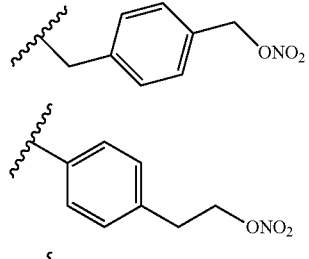

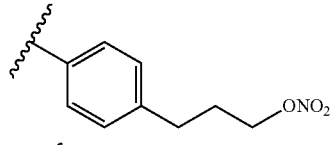

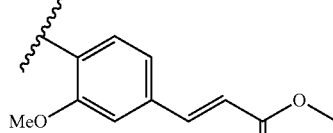

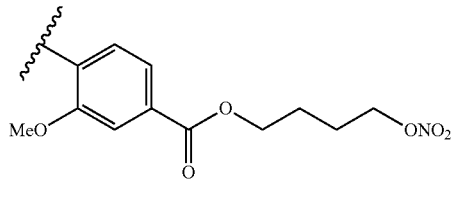

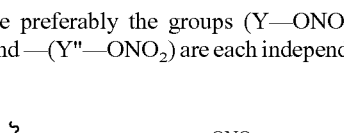

more preferably the groups (Y—$ONO_2$), —(Y"—$ONO_2$), and —(Y'"—$ONO_2$) are each independently selected from:

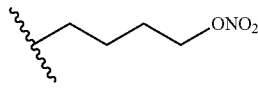

-continued

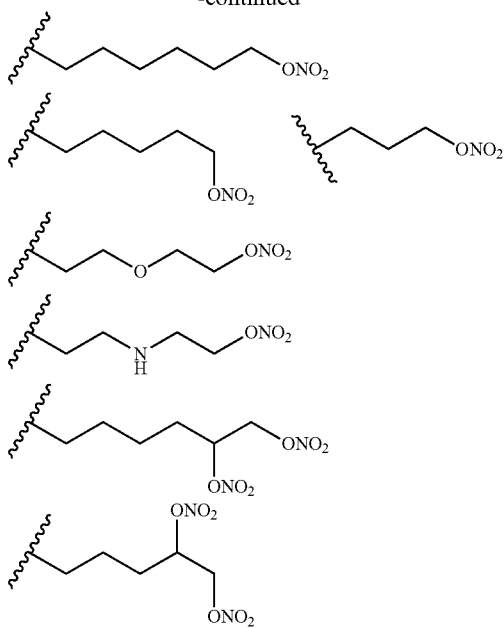

with the proviso that in formula (I) s' and s" cannot be both 1 when:
A is the radical of formulas (IIb), (IId)-(IIr), or
A is the radical of formula (IIt) wherein d is from 3 to 5 and d' is 0, or
A is the radical of formula (IIu) wherein a is 0;
with the proviso that s' and s" can be both 1 when:
A is the radical of formulas (IIa), (IIc) or (IIs) and $R_a$, $R_c$ and $R_s$ are selected from:
$R_{bx}$—C(O)—S—CH$_2$—, $R_{bx}$—OC(O)—S—CH$_2$—, $R_{bx}$—NH—C(O)S—CH$_2$— wherein $R_{bx}$ is one of the groups —[(B)$_m$—(Y—ONO$_2$)]$_s$, —[(B)$_{m'}$—(Y'—ONO$_2$)]$_{s'}$ or —[(B)$_{m''}$—(Y"—ONO$_2$)]$_{s''}$ wherein m, m' and m", B, Y, Y' and Y" are as above defined;
$R_x$O—CH$_2$—, $R_x$O—CH(CH$_3$)—, $(R_x$O)-p-C$_6$H$_4$—CH$_2$—, 4-($R_x$O)-3,5-diiodobenzyl, 4-($R_x$O)-3-nitrobenzyl- wherein $R_x$ is $R_{xx}$—C(O)—, $R_{xx}$—OC(O)— or $R_{xx}$—NHC(O)— wherein $R_{xx}$ is one of the groups —[(B)$_m$—(Y—ONO$_2$)]$_s$, —[(B)$_{m'}$—(Y'—ONO$_2$)]$_{s'}$ or —[(B)$_{m''}$—(Y"—ONO$_2$)]$_{s''}$ wherein m, m' and m", B, Y, Y' and Y" are as above defined;
$R_g$C(O)CH$_2$—NH—, $R_g$C(O)CH$_2$, $R_g$C(O)(CH$_2$)$_2$—, $R_g$C(O)(CH$_2$)$_2$—, wherein $R_g$ is OH, (CH$_3$)$_3$CO—, $R_{gx}$—O—, $R_{gxx}$—NH—, $R_{gxx}$—N(CH$_3$)— wherein $R_{gx}$ and $R_{gxx}$ are one of the groups —[(B)$_m$—(Y—ONO$_2$)]$_s$, —[(B)$_{m'}$—(Y'—ONO$_2$)]$_{s'}$ or —[(B)$_{m''}$—(Y"—ONO$_2$)]$_{s''}$ wherein m, m' and m", B, Y, Y' and Y" are as above defined;
$R_h$NH(CH$_2$)$_p$— or $R_i$NH(=NH)NH—(CH$_2$)$_3$—, wherein p is an integer from 0 to 4, $R_h$ is $R_{hh}$—C(O)— or $R_{hh}$—OC(O)—, $R_i$ is $R_{ii}$—C(O)— or $R_{ii}$—OC(O)—, wherein $R_{hh}$ and $R_{ii}$ are one of the groups —[(B)$_m$—(Y—ONO$_2$)]$_s$, —[(B)$_{m'}$—(Y'—ONO$_2$)]$_{s'}$ or —[(B)$_{m''}$—(Y"—ONO$_2$)]$_{s''}$ wherein m, m' and m", B, Y, Y' and Y" are as above defined;
A is the radical of formula (IIt) wherein d' is 1 and d is 2 and $R_t$ is —C(O)—$R_{tt}$ or —C(O)O—$R_{tt}$ wherein $R_{tt}$ is one of the groups —[(B)$_m$—(Y—ONO$_2$)]$_s$, —[(B)$_{m'}$—(Y'—ONO$_2$)]$_{s'}$ or —[(B)$_{m''}$—(Y"—ONO$_2$)]$_{s''}$ wherein m, m' and m" B, Y, Y' and Y" are as above defined;

A is the radical of formula (IIu) wherein a is 1 and $R_x$ is —C(O)—$R_{xx}$, —C(O)O—$R_{xx}$— or —C(O)NH—$R_{xx}$ wherein $R_{xx}$ is one of the groups —[(B)$_m$—(Y—ONO$_2$)]$_s$, —[(B)$_{m'}$—(Y'—ONO$_2$)]$_{s'}$ or —[(B)$_{m''}$—(Y"—ONO$_2$)]$_{s''}$ of formula (I) wherein m, m' and m", B, Y, Y' and Y" are as above defined with the proviso that the following compounds of formula (I) are excluded:
3-(nitrooxy)propyl 2-(tert-butoxycarbonylamino)-4-phenyl butanoate,
3-(nitrooxy)propyl 2-amino-4-phenylbutanoate
3-(nitrooxy)propyl 2-amino-4-phenylbutanoate hydrochloride,
4-(nitrooxy)butyl 2-(tert-butoxycarbonylamino)-4-phenylbutanoate,
4-(nitrooxy)butyl 2-amino-4-phenylbutanoate,
4-(nitrooxy)butyl 2-amino-4-phenylbutanoate hydrochloride,
(2-(nitrooxy)ethoxy)methyl 2-(tert-butoxycarbonylamino)-4-phenylbutanoate,
(2-(nitrooxy)ethoxy)methyl 2-amino-4-phenylbutanoate,
(2-(nitrooxy)ethoxy)methyl 2-amino-4-phenylbutanoate hydrochloride,
1-tert-butyl 2-(4-(nitrooxy)butyl)pyrrolidine-1,2-dicarboxylate,
4-(nitrooxy)butyl pyrrolidine-2-carboxylate hydrochloride,
4-(nitrooxy)butyl pyrrolidine-2-carboxylate hydrochloride,
1-tert-butyl 2-(3-(nitrooxy)propyl)pyrrolidine-1,2-dicarboxylate,
3-(nitrooxy)propyl pyrrolidine-2-carboxylate,
3-(nitrooxy)propyl pyrrolidine-2-carboxylate hydrochloride,
Another embodiment relates to compounds of formula (I)

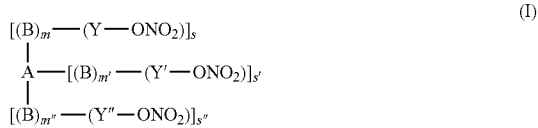

wherein s is 1 and m is 0, s' and s" are 0,
A is selected from:

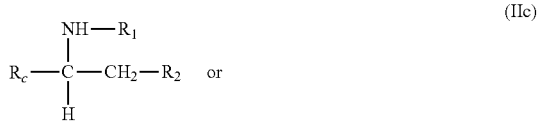

wherein
$R_1$ is H or —C(O)—OC(CH$_3$)$_3$,
$R_2$ is —C(O)OR$_{2x}$, —C(O)NHR$_{2x}$, —C(O)N(CH$_3$)R$_{2x}$ and more preferably $R_2$ is —C(O)OR$_{2x}$ or —C(O)NHR$_{2x}$, wherein $R_{2x}$ is (Y—ONO$_2$) of formula (I) wherein Y is below reported, $R_a$ of formula (IIa) is selected from:

a) H, $CH_3$, isopropyl, isobutyl, sec-butyl, methylthio-$(CH_2)_2$—, benzyl, $C_6H_5$—$CH_2$—$CH_2$—, 3-triptophanyl-$CH_2$—, $NH_2$—CO—$CH_2$—, $NH_2$—CO—$(CH_2)_2$—, 4-imidazolyl-$CH_2$—;

b) HS—$CH_2$—, c) $R_xO$—$CH_2$—, $R_xO$—$CH(CH_3)$—, $(R_xO)$-p-$C_6H_4$—$CH_2$—, wherein $R_x$ is H, d) $R_gC(O)CH_2$, $R_gC(O)(CH_2)_2$—, wherein $R_g$ is OH, $(CH_3)_3CO$—, or the group $R_{gg}$:

$R_{gg}$ e) $R_hNH(CH_2)_p$— or $R_iNH(=NH)NH$—$(CH_2)_3$—, wherein p is an integer equal to 3 or 4, $R_h$ is H or $(CH_3)_3C$—OC(O)—, $R_i$ is H;

$R_c$ of formula (IIc) is selected from the group comprising:

H, $CH_3$, isopropyl, isobutyl, sec-butyl, methylthio-$(CH_2)_2$—, benzyl, 3-triptophanyl-$CH_2$—, 4-imidazolyl-$CH_2$—, $NH_2$—CO—$CH_2$—, $NH_2$—CO—$(CH_2)_2$—;

$R_L$ of formula (Ill) is H,

Y of the group (Y—$ONO_2$) is selected from:

A)
  a straight or branched $C_2$-$C_{10}$ alkylene
  a straight or branched $C_2$-$C_{10}$ alkylene substituted with a —$ONO_2$ group;

B)

(IB)

wherein in formula (IB)
$n^0$ is from 0 to 5 and $n^1$ is an integer from 1 to 10;

C)

(IC)

wherein in formula (IC)
$n^1$ is an integer from 1 to 10,
$n^2$ is 1 and $R^2$ is $CH_3$, $X_1$ is —C(O)O—;

D)

(ID)

wherein in formula (ID):
$n^2$ is 1 and $R^2$ is $CH_3$,
$Y^1$ is —CH=CH—$(CH_2)_n{}^{2a}$— wherein $n^{2a}$ is 0,
$X_1$ is —C(O)O— and $n^1$ is an integer from 1 to 10;

E)

(IE)

—[$(CH_2)_{n3}$CH—$(CH_2)_{n4}$—$X_2$]$_{n3}$—[$(CH_2)_{n3'}$—CH—$(CH_2)_{n4'}$]—
         |                                    |
         $R^2$                                $R^2$ wherein in formula (IE)
$n^3$ is from 1 to 5,
$n_3$ is 0 and $n_4$ is from 1 to 4,
$n_{3'}$ is 0 and $n_{4'}$ is from 1 to 4,
$X_2$ is —O— or —NH—,
$R^2$ is H,
preferably the group —(Y—$ONO_2$) is selected from:

-continued
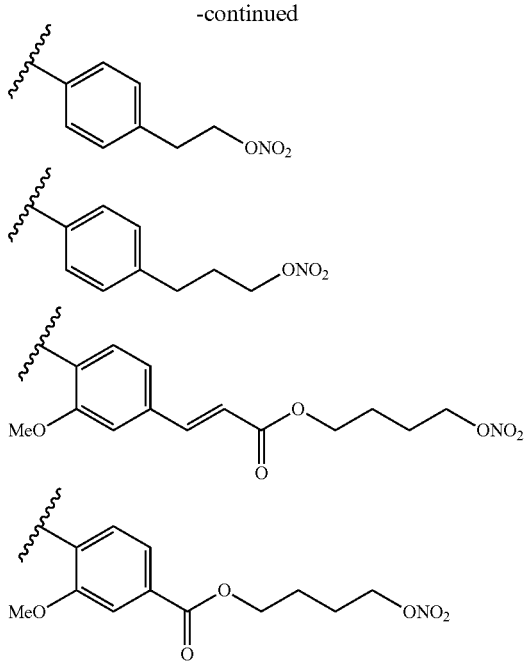
the following are preferred compounds according to the present invention:
-continued

(14)
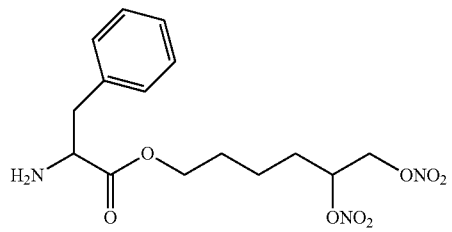
(15)
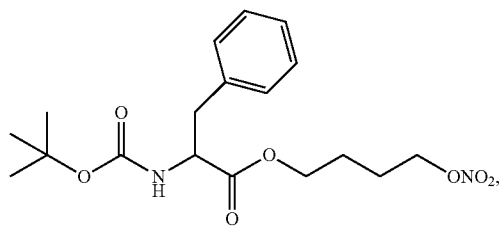
(16)
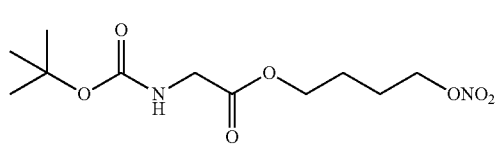
(17)
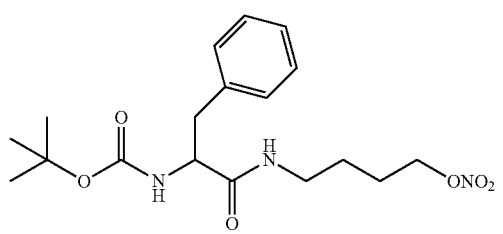
(18)
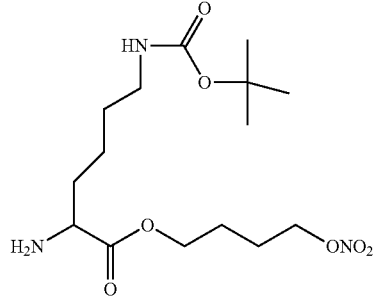
(19)
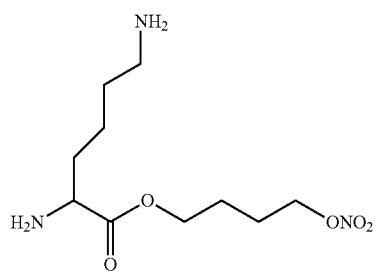
(20)
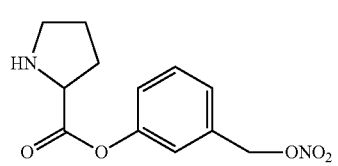
(21)
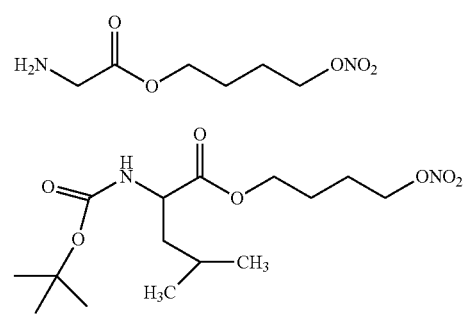
(22)
(23)
(24)
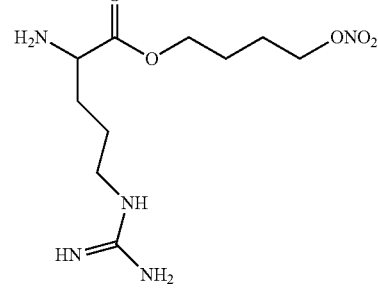
(25)
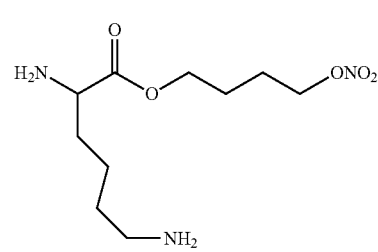
(26)
(27)

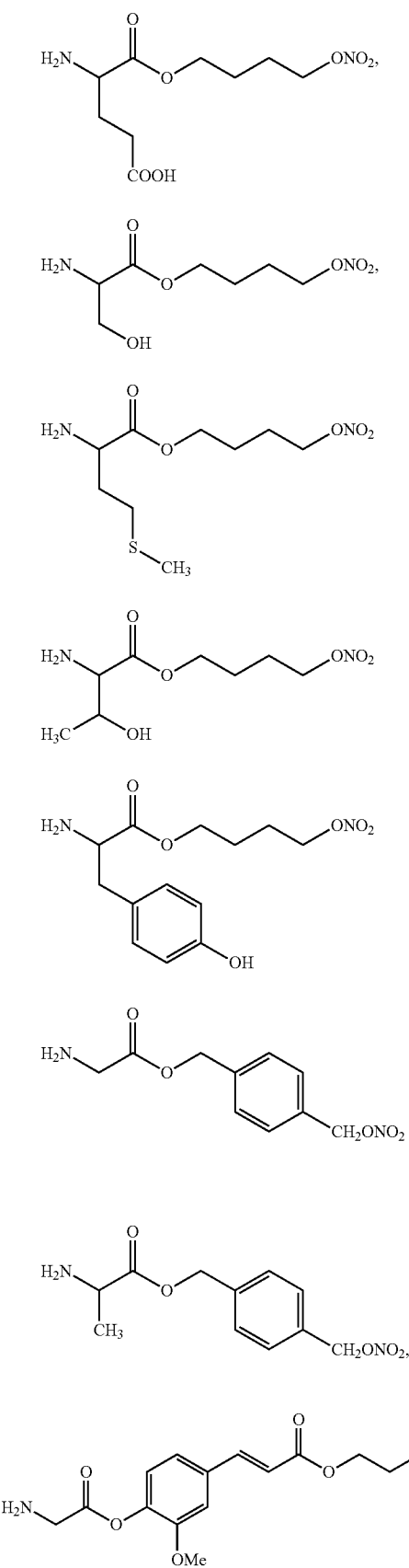
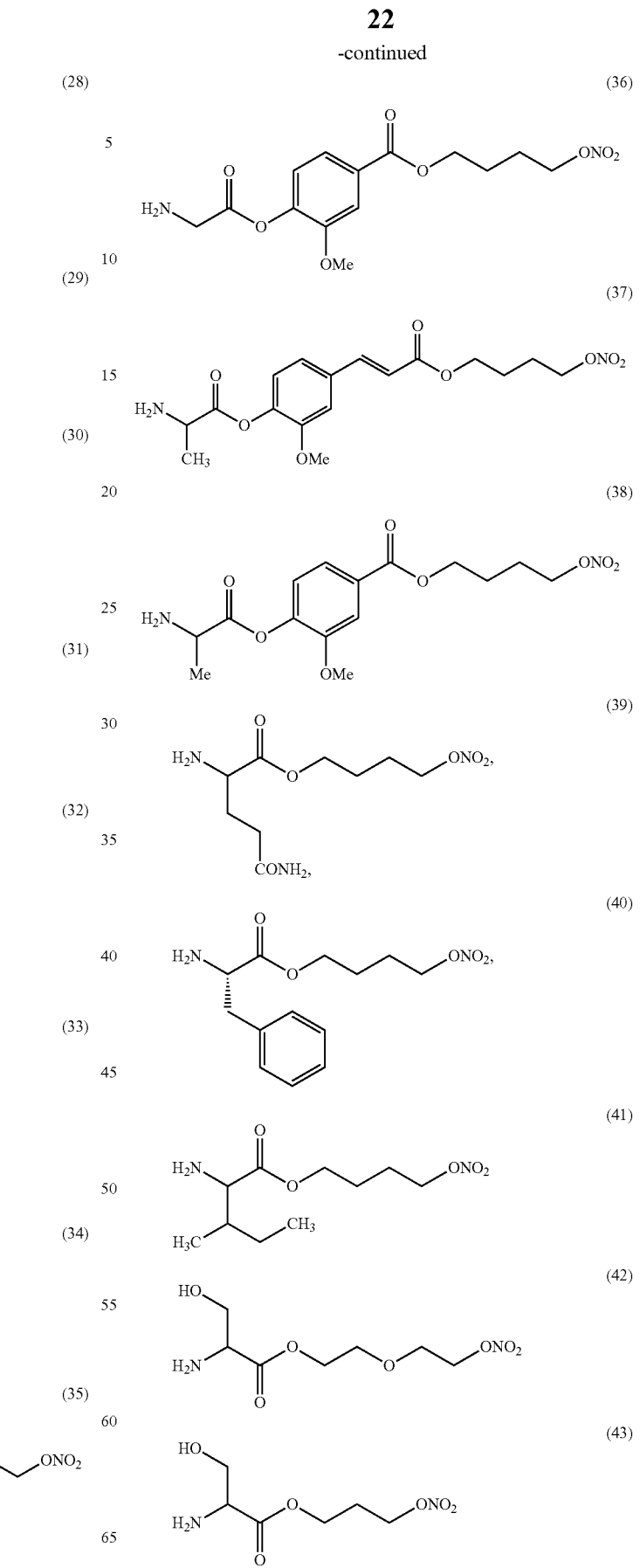

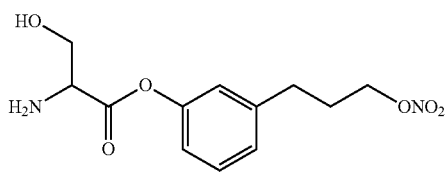
(44)
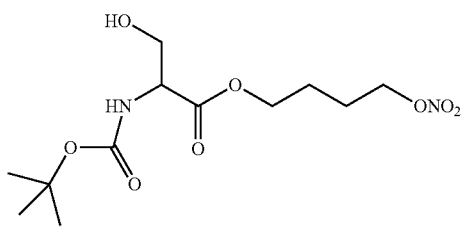
(45)
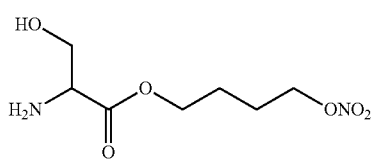
(46)
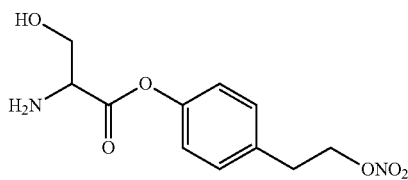
(47)
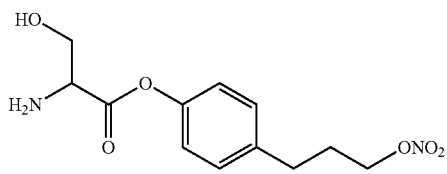
(48)
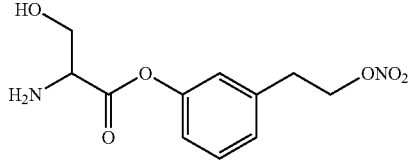
(49)
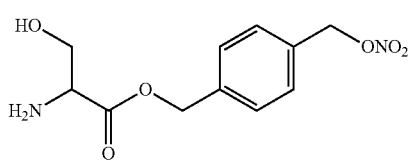
(50)
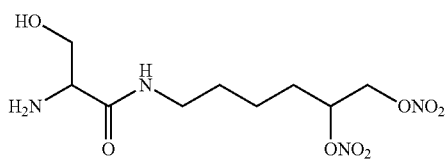
(51)
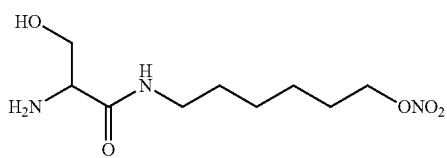
(52)
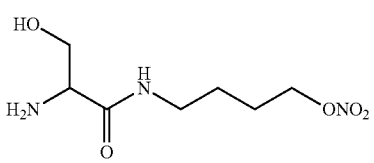
(53)
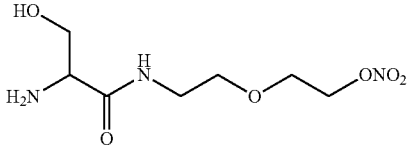
(54)
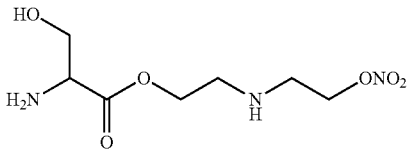
(55)
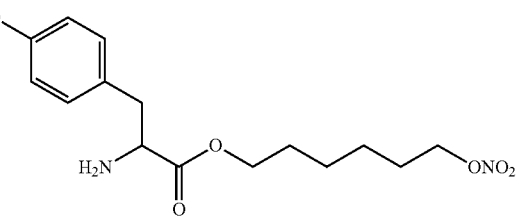
(56)
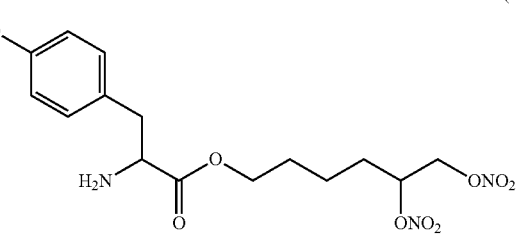
(57)
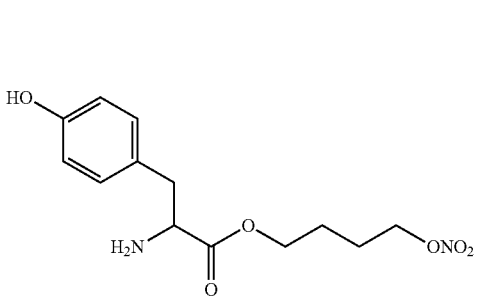
(58)
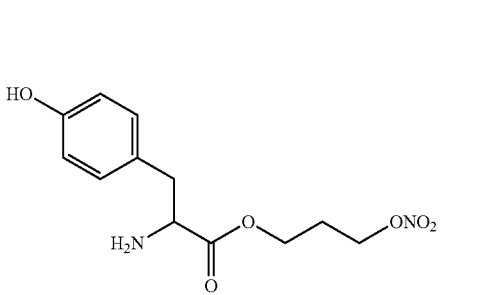
(59)

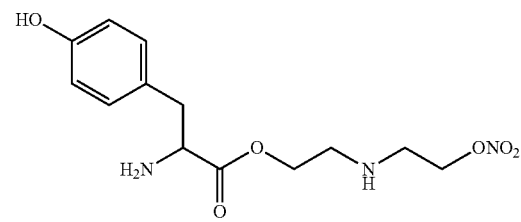
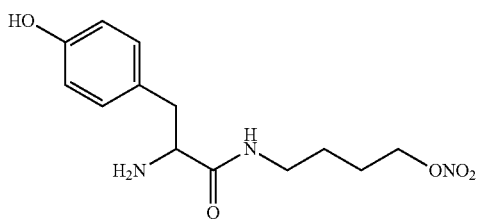
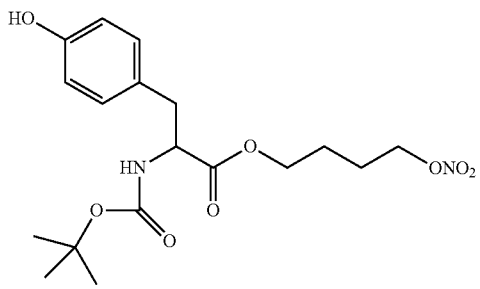
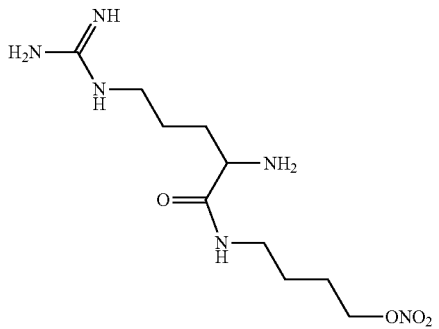
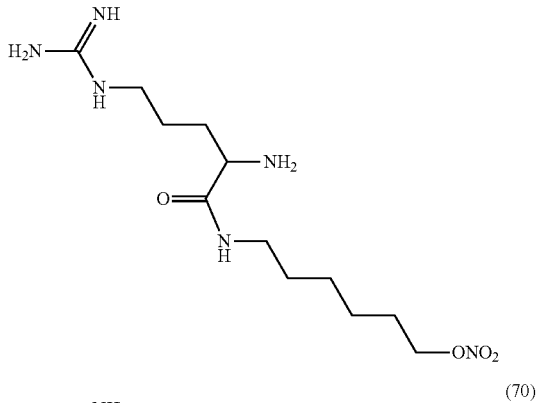
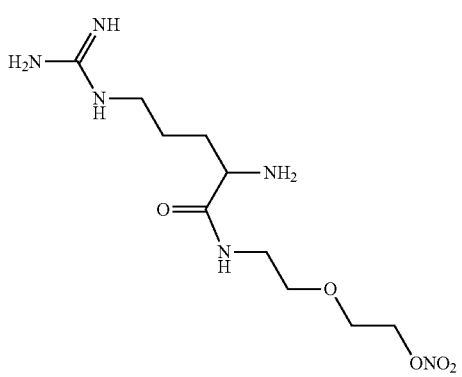

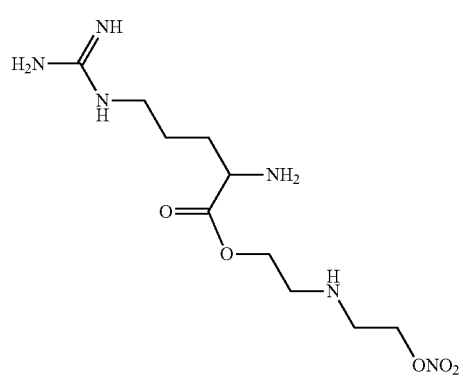
(71)
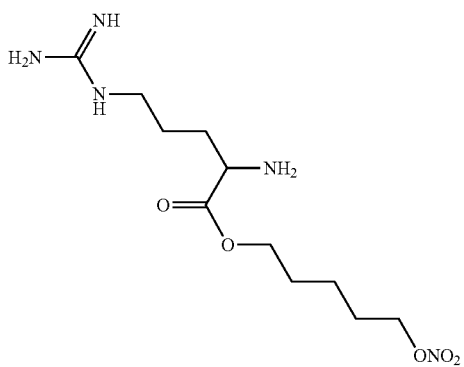
(75)
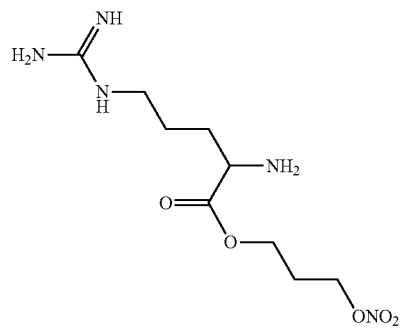
(72)
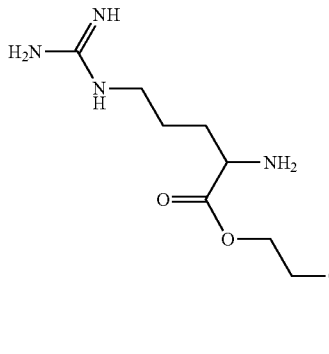
(76)
(73)
(77)
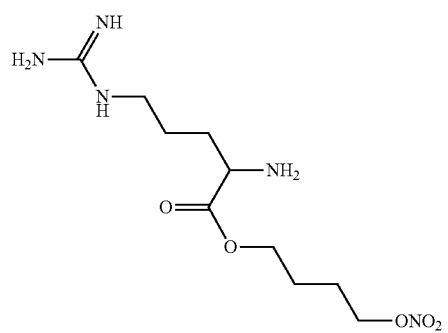
(74)
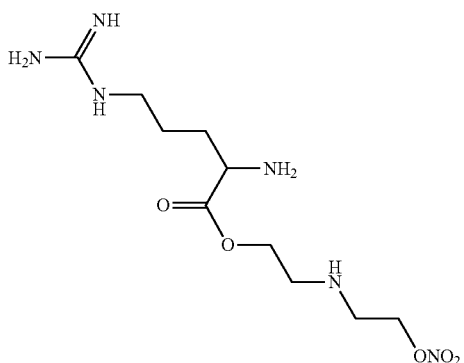
(78)

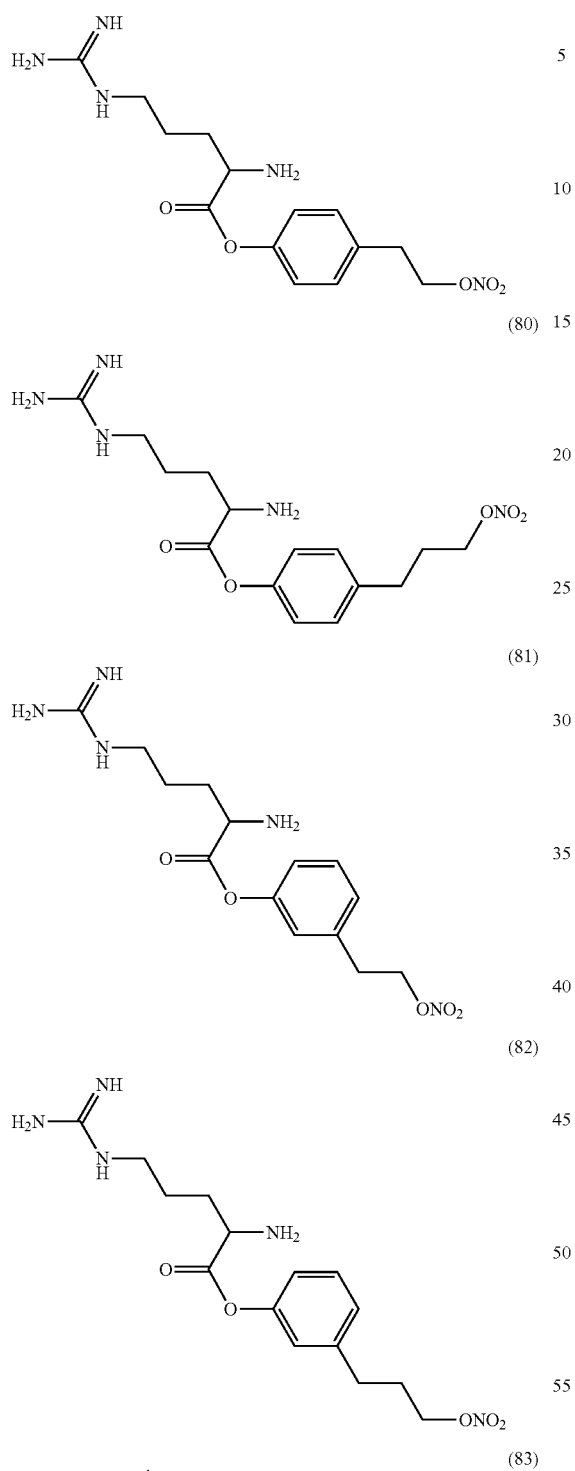
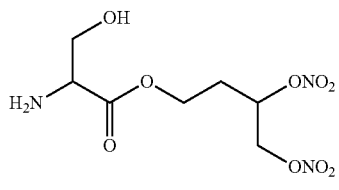
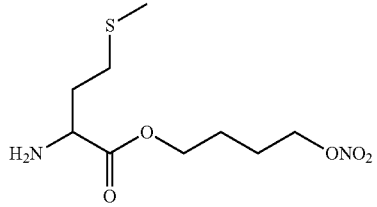
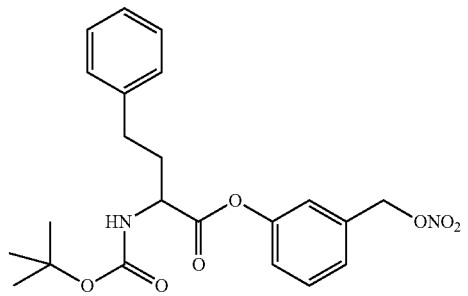
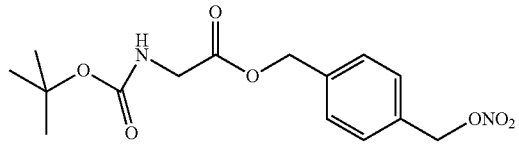
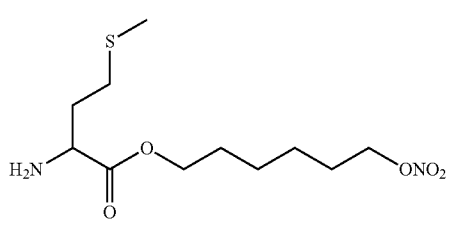
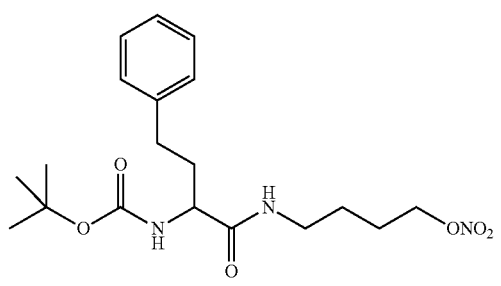

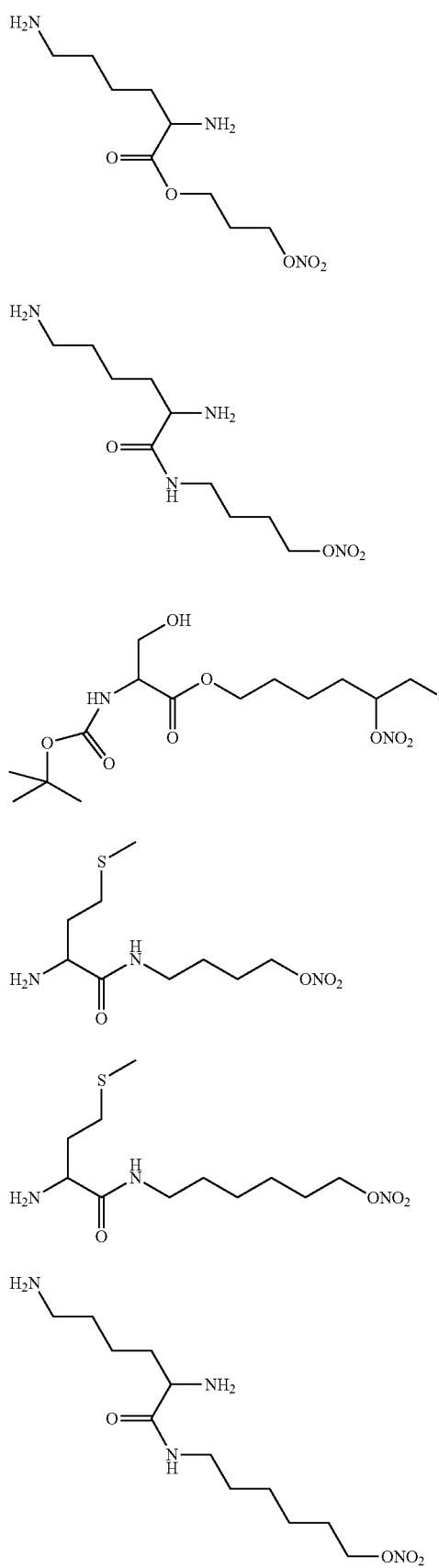
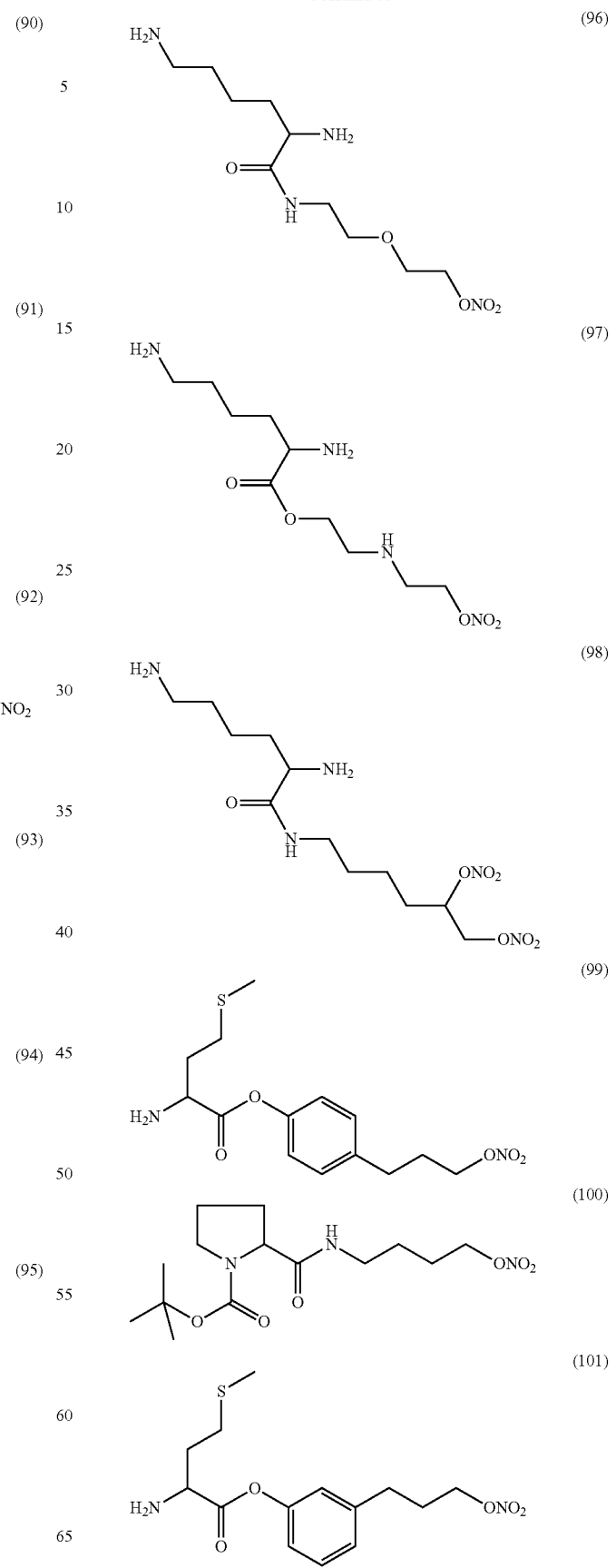

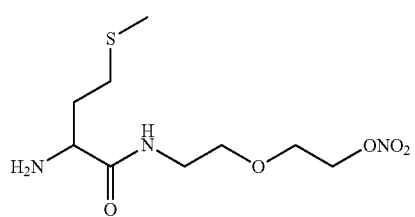 (102)
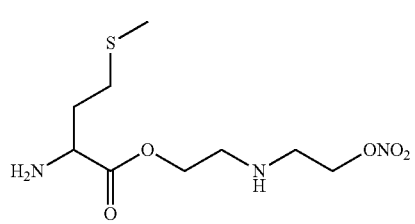 (103)
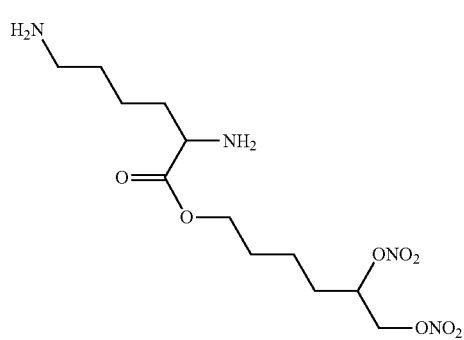 (104)
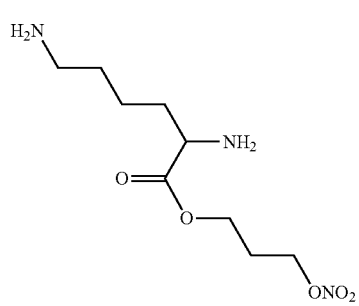 (105)
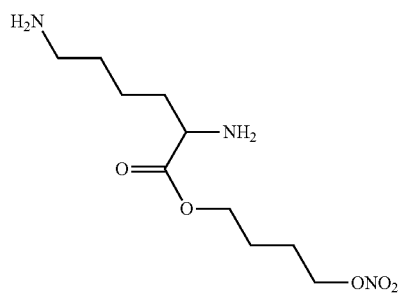 (106)
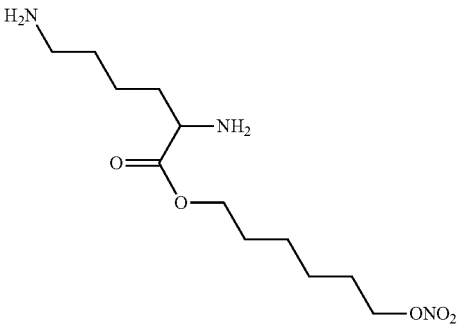 (107)
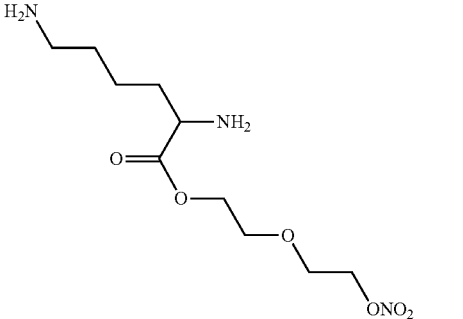 (108)
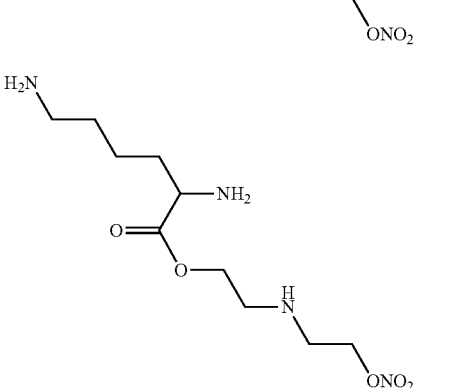 (109)
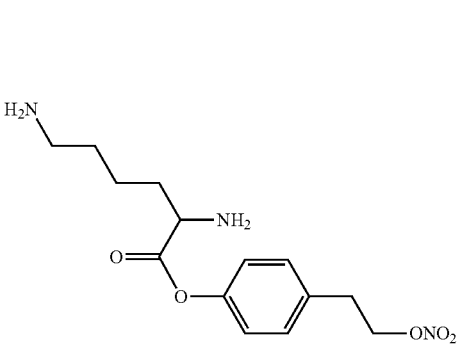 (110)
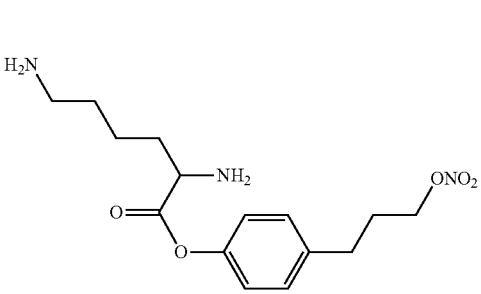 (111)

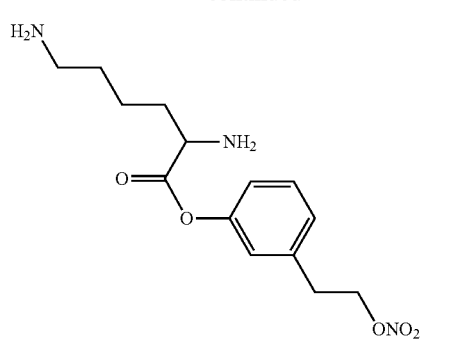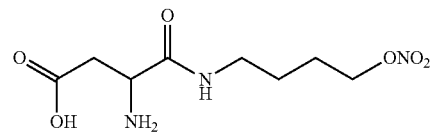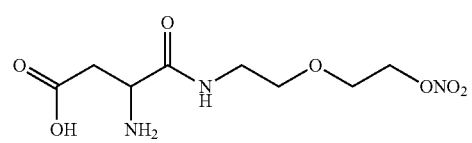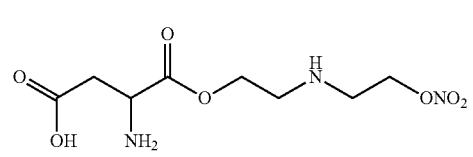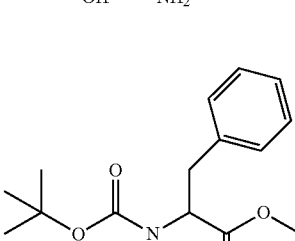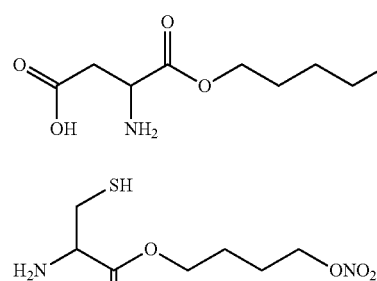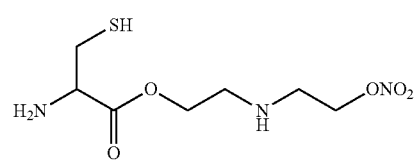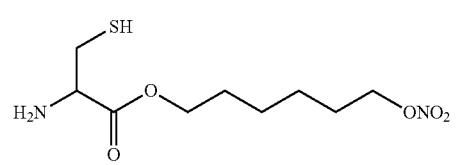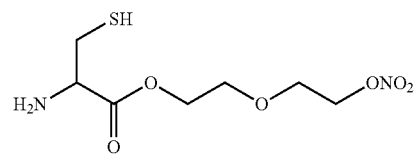

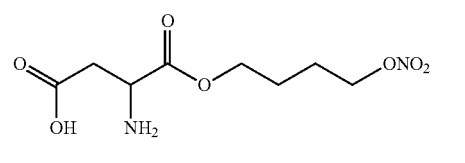 (129)
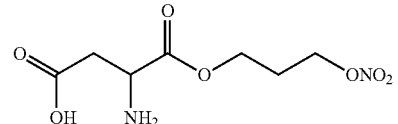 (130)
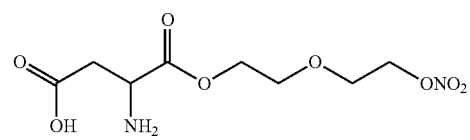 (131)
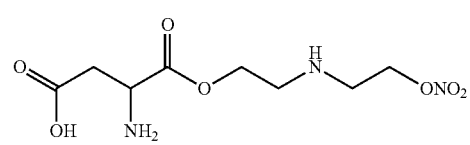 (132)
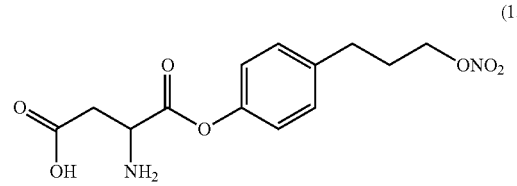 (133)
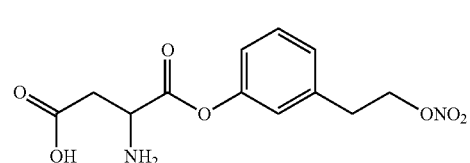 (134)
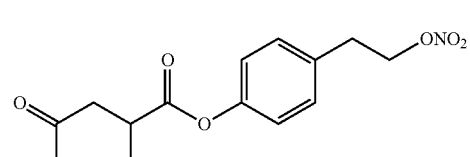 (135)
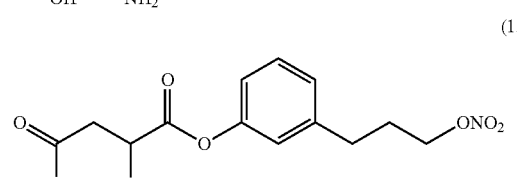 (136)
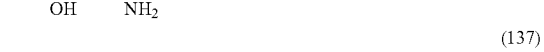 (137)
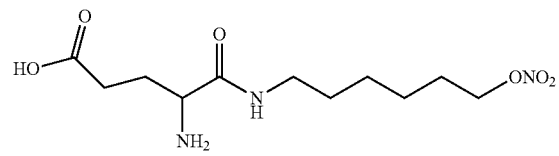 (138)
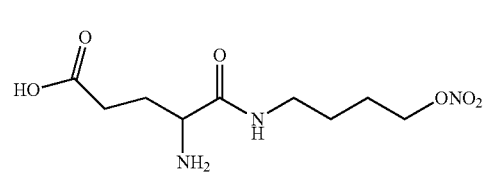 (139)
 (140)
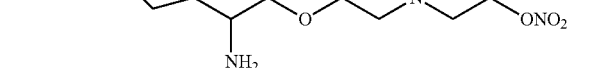 (141)
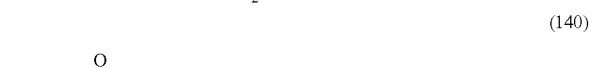 (142)
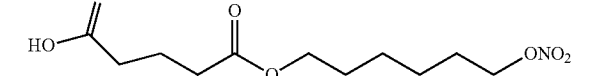 (143)
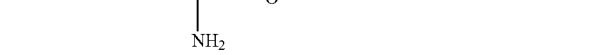 (144)
 (145)
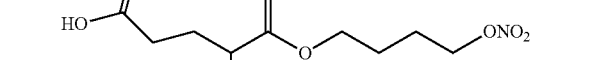 (146)
 (147)

-continued
(148) 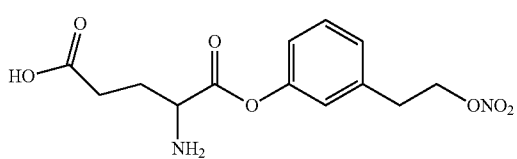
(149) 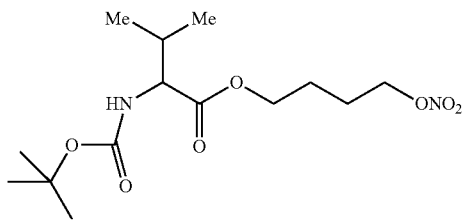
(150) 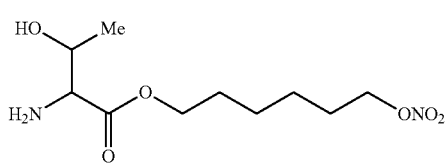
(151) 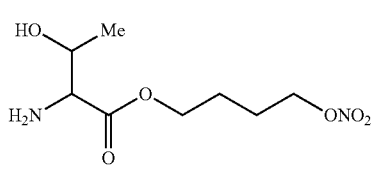
(152) 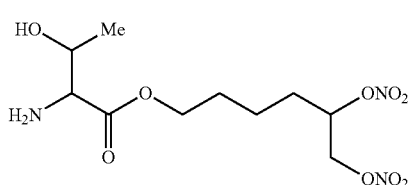
(153) 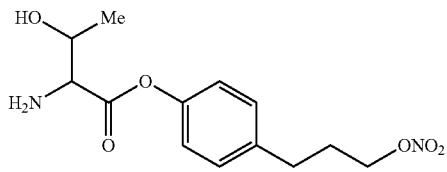
(154) 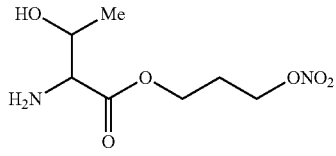
(155) 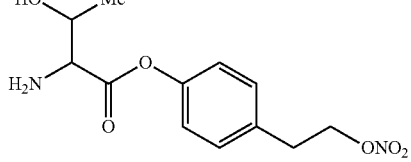
(156) 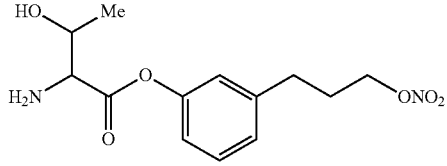
-continued
(157) 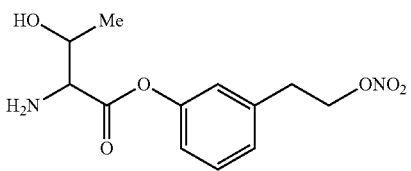
(158) 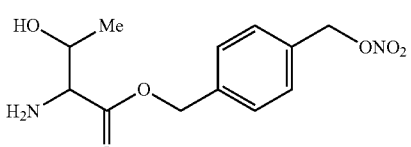
(159) 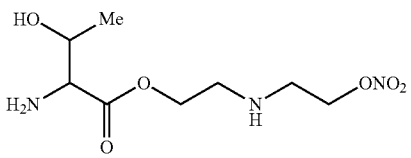
(160) 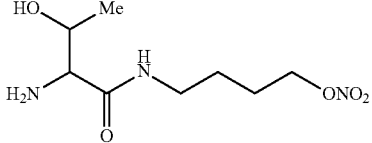
(161) 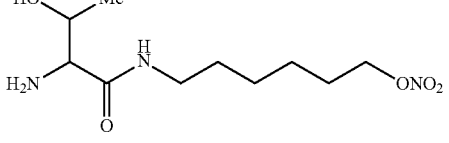
(162) 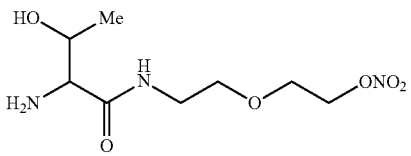
(163) 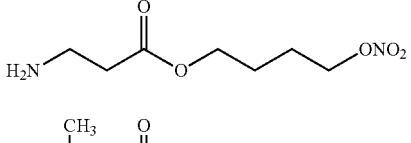
(164) 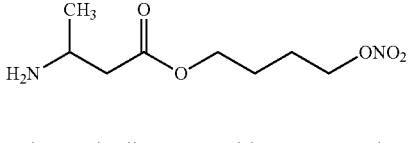
Another embodiment provides compounds of formula (I)
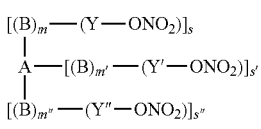
(I)

wherein s and m are 1,
s' and s" are 0,
B is selected from:

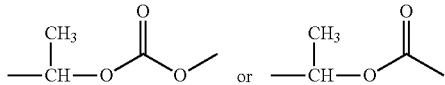

more preferably B is

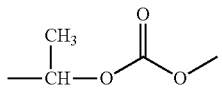

A is a radical selected from:

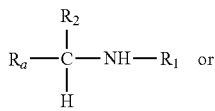

wherein
$R_1$ is H or —C(O)O—C(CH$_3$)$_3$,
$R_2$ is —C(O)OR$_{2x}$ wherein $R_{2x}$ is the group —[(B)—(Y—ONO$_2$)] of formula (I) wherein B is as above defined and Y is below defined,
$R_a$ of formula (IIa) is selected from:
a) H, CH$_3$, isopropyl, isobutyl, sec-butyl, methylthio-(CH$_2$)$_2$—, benzyl, C$_6$H$_5$—CH$_2$—CH$_2$—, 3-triptophanyl-CH$_2$—, NH$_2$—CO—CH$_2$—, NH$_2$—CO—(CH$_2$)$_2$—, 4-imidazolyl-CH$_2$—;
b) HS—CH$_2$—;
c) R$_x$O—CH$_2$—, R$_x$O—CH(CH$_3$)— or (R$_x$O)-p-C$_6$H$_4$—CH$_2$—, wherein R$_x$ is H;
d) R$_g$C(O)CH$_2$, R$_g$C(O)(CH$_2$)$_2$—, wherein R$_g$ is OH or (CH$_3$)$_3$C—O—, or the group R$_{gg}$:

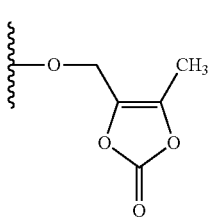

e) R$_h$NH(CH$_2$)$_p$— or R$_i$NH(=NH)NH—(CH$_2$)$_3$— wherein p is an integer equal to 3 or 4, R$_h$ is H or (CH$_3$)$_3$C—OC(O)—, R$_i$ is H;

$R_L$ of formula (III) is H;
Y of the group —(Y—ONO$_2$) is selected from:
A)
 a straight or branched C$_2$-C$_{10}$ alkylene,
 a straight or branched C$_2$-C$_{10}$ alkylene substituted with a —ONO$_2$ group;
E)

$$—[(CH_2)n_3CH—(CH_2)n_4—X_2]_{n^3}—[(CH_2)n_3'—CH—(CH_2)n_4']— \atop \quad\quad R^2 \quad\quad\quad\quad\quad\quad\quad\quad R^2$$ (IE)

wherein in formula (IE)
$n^3$ is from 1 to 5
$n_3$ is 0 and $n_4$ is from 1 to 4,
$n_{3'}$ is 0 and $n_{4'}$ is from 1 to 4,
$X_2$ is —O— or —NH—,
$R^2$ is H;
preferably —(Y—ONO$_2$) is selected from:

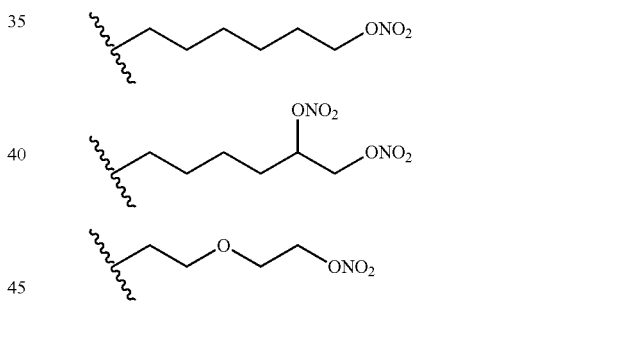

The following are preferred compounds according to the present invention:

(165)

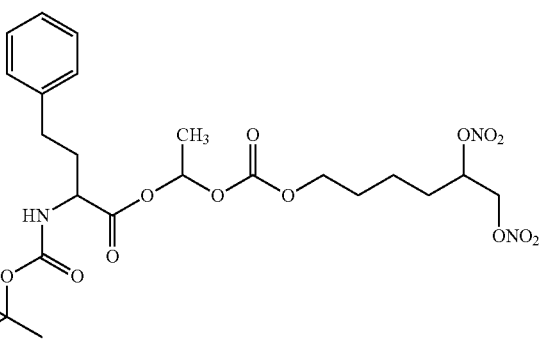

-continued

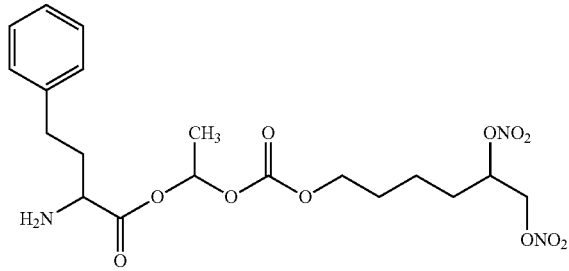
(166)

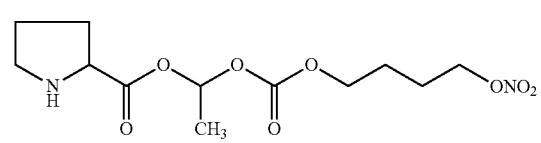
(167)

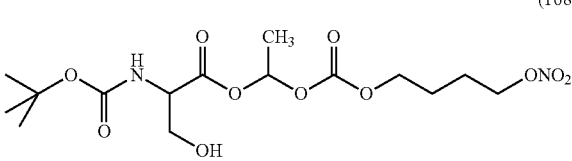
(168)

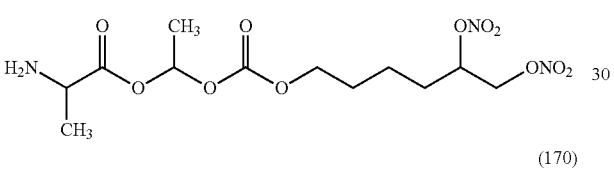
(169)

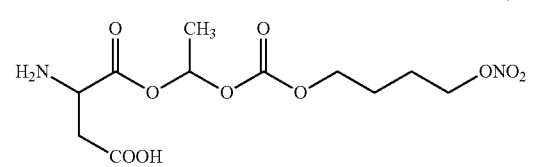
(170)

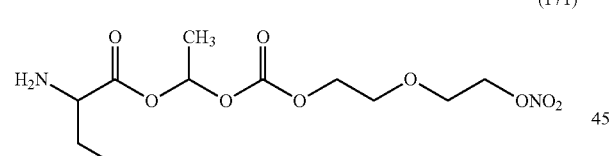
(171)

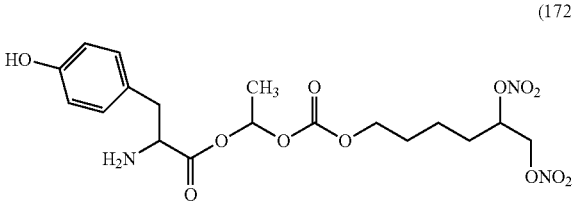
(172)

Another embodiment relates to compounds of formula (I)

$$[(B)_m-(Y-ONO_2)]_s$$
$$A-[(B)_{m'}-(Y'-ONO_2)]_{s'}$$
$$[(B)_{m''}-(Y''-ONO_2)]_{s''}$$
(I)

wherein s is 1 and m is 0,
s' and s'' are 0,
A is a radical selected from

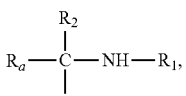
(IIa)

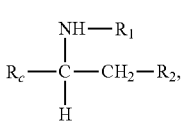
(IIc)

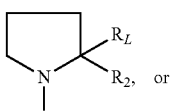
(III)

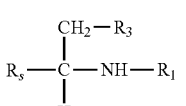
(IIs)

wherein is $R_1$ is —C(O)$R_{1x}$, —C(O)O$R_{1x}$ wherein $R_{1x}$ is the group —(Y—ONO$_2$) of formula (I) wherein Y is below reported, $R_2$ in formulas (IIa) (IIc) and (III) is —C(O)OH, —C(O)—OC(CH$_3$)$_3$ or $R_2$ is the group $R_4$:

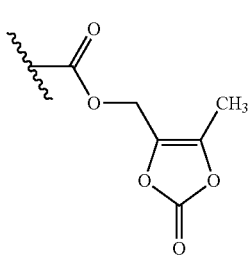

$R_3$ in formula (IIs) is OH;
$R_a$ of formula (IIa) is selected from:
a) H, CH$_3$, isopropyl, isobutyl, sec-butyl, methylthio-(CH$_2$)$_2$—, benzyl, C$_6$H$_5$—CH$_2$—CH$_2$—, 3-triptophanyl-CH$_2$—, NH$_2$—CO—CH$_2$—, NH$_2$—CO—(CH$_2$)$_2$—, 4-imidazolyl-CH$_2$—;
b) HS—CH$_2$—;
c) R$_x$O—CH$_2$—, R$_x$O—CH(CH$_3$)—, (R$_x$O)-p-C$_6$H$_4$—CH$_2$— wherein R$_x$ is H;
d) R$_g$C(O)CH$_2$ or R$_g$C(O)(CH$_2$)$_2$—, wherein R$_g$ is OH or (CH$_3$)$_3$C—O—, or R$_g$ is the group R$_{gg}$:

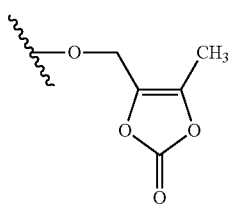

e) $R_hNH(CH_2)_p$— or $R_iNH(=NH)NH(CH_2)_3$—, wherein p is an integer equal to 3 or 4, $R_h$ is H or $(CH_3)_3C$—OC(O)—, $R_i$ is H;

$R_c$ of formula (IIc) is selected from:
H, $CH_3$, isopropyl, isobutyl, sec-butyl, methylthio-$(CH_2)_2$—, benzyl, 3-triptophanyl-$CH_2$—, 4-imidazolyl-$CH_2$—, $NH_2$—CO—$CH_2$—, $NH_2$—CO—$(CH_2)_2$—;

$R_L$ of formula (III) is H;

$R_s$ of formula (IIs) is H, $CH_3$, isopropyl, isobutyl, sec-butyl, methylthio-$(CH_2)_2$—, benzyl, 3-triptophanyl-$CH_2$—, 4-imidazolyl-$CH_2$—, $NH_2$—CO—$CH_2$—, $NH_2$—CO—$(CH_2)_2$—;

Y of the groups (Y—$ONO_2$ is selected from:

A)
a straight or branched $C_2$-$C_{10}$ alkylene
a straight or branched $C_2$-$C_{10}$ alkylene substituted with a —$ONO_2$ group;

B)

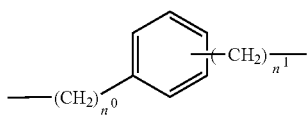
(IB)

wherein in formula (IB)
$n^0$ is from 0 to 5 and $n^1$ is an integer from 1 to 10;

C)

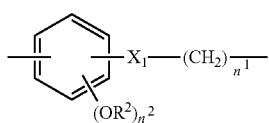
(IC)

wherein in formula (IC)
$n^1$ is an integer from 1 to 10,
$n^2$ is 1 and $R^2$ is $CH_3$, $X_1$ is —C(O)O—;

D)

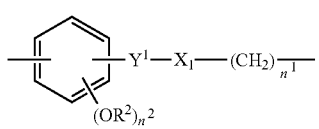
(ID)

wherein in formula (ID):
$n^2$ is 1 and $R^2$ is $CH_3$,
$Y^1$ is —CH=CH—$(CH_2)_{n^{2a}}$ wherein $n^{2a}$ is 0,
$X_1$ is —C(O)O— and $n^1$ is an integer from 1 to 10;

E)

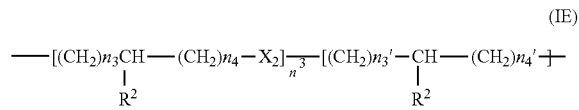
(IE)

wherein in formula (IE)
$n^3$ is from 1 to 5,
$n_3$ is 0 and $n_4$ is from 1 to 4,
$n_{3'}$ is 0 and $n_{4'}$ is from 1 to 4,
$X_2$ is —O— or —NH—,
$R^2$ is H, preferably —(Y—$ONO_2$) is selected from:

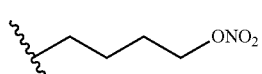

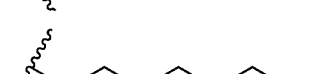

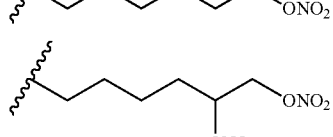

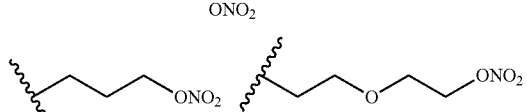

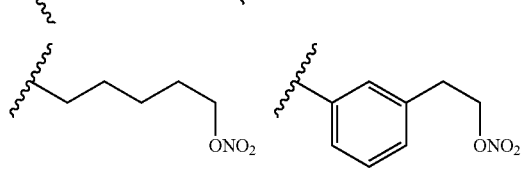

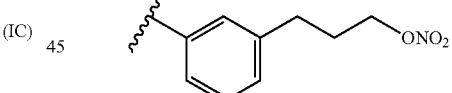

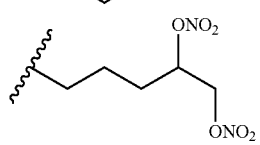

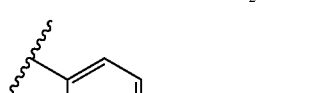

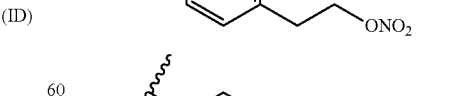

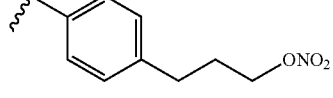

the following are preferred compounds according to the present invention:

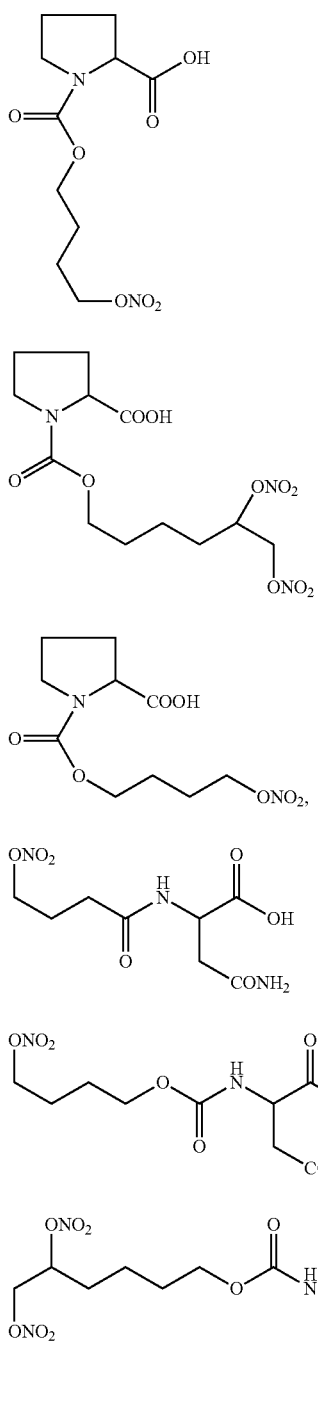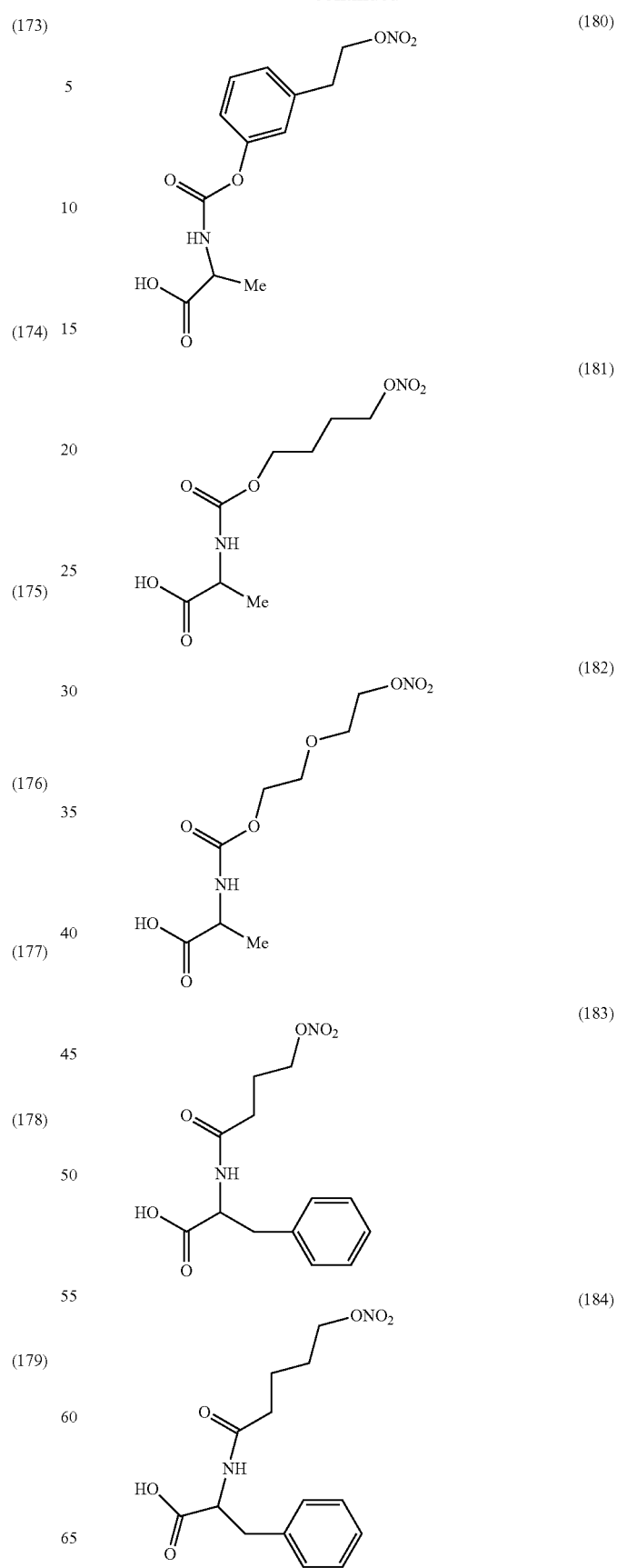

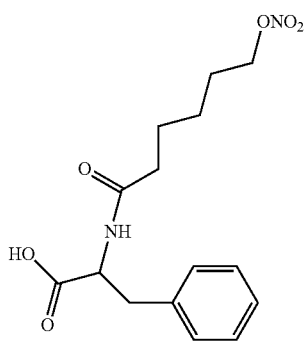
(185)
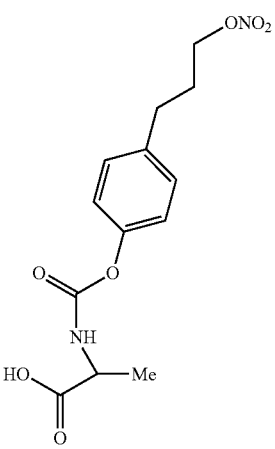
(189)
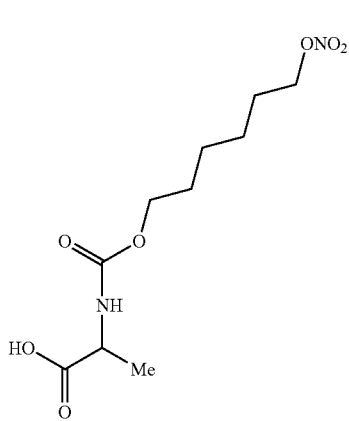
(186)
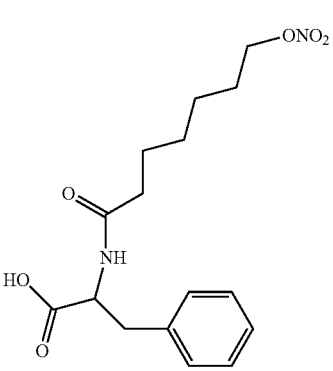
(190)
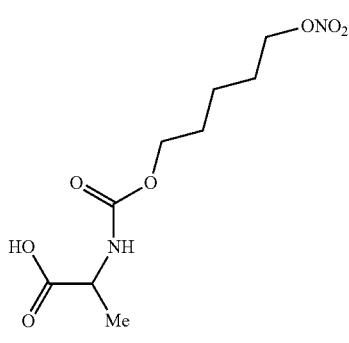
(187)
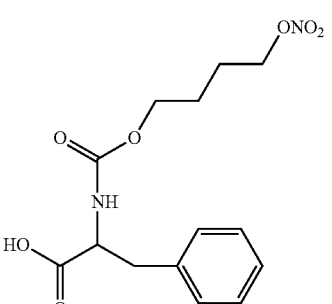
(191)
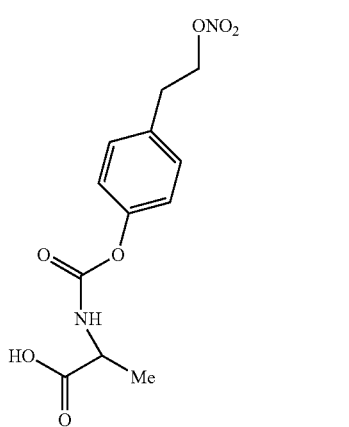
(188)
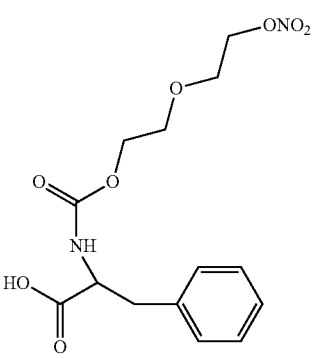
(192)

(193)
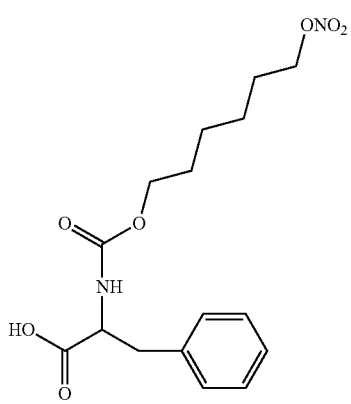
(194)
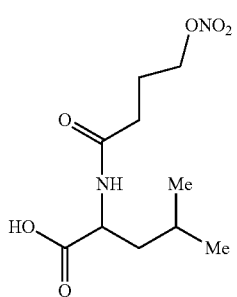
(195)
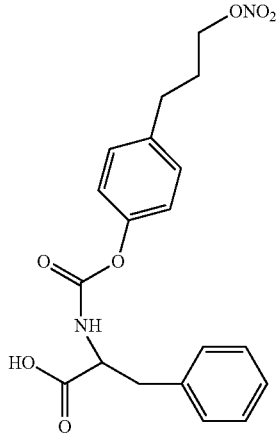
(196)
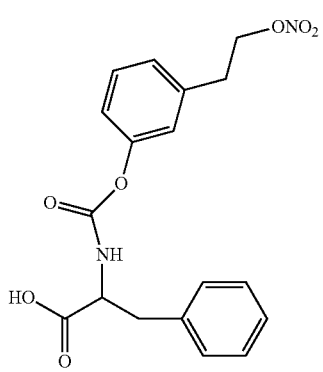
(197)
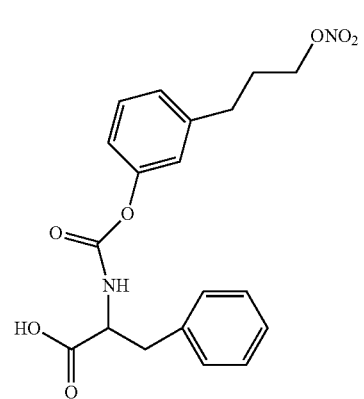
(198)
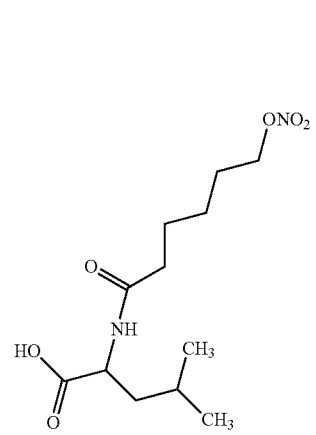
(199)
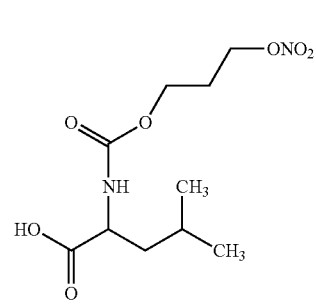
(200)
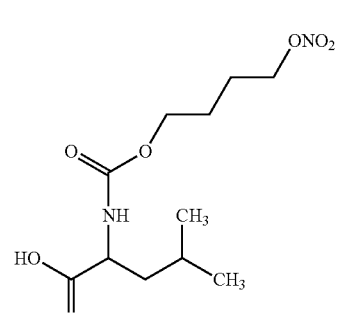

(201) 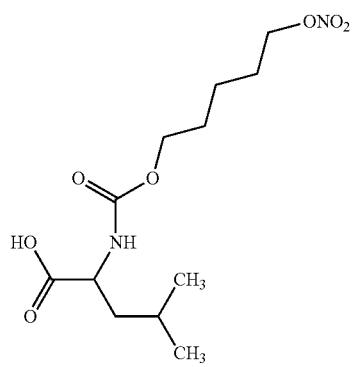
(202) 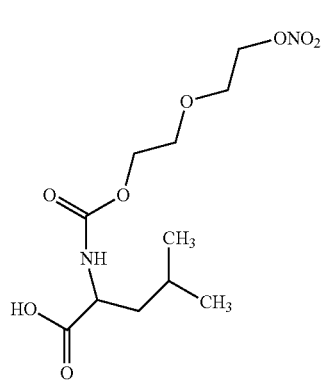
(203) 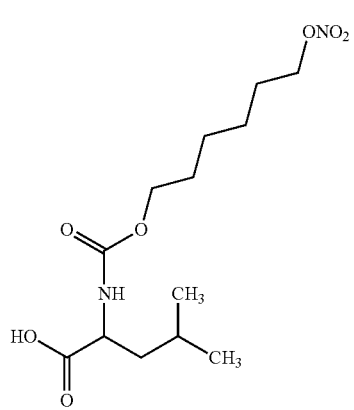
(204) 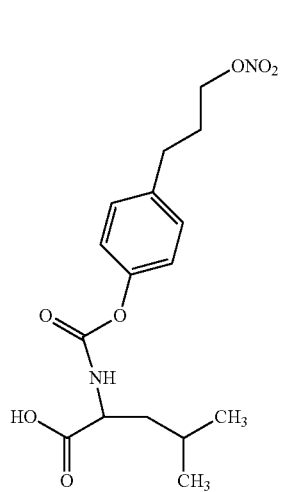
(205) 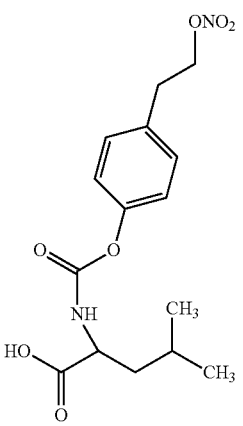
(206) 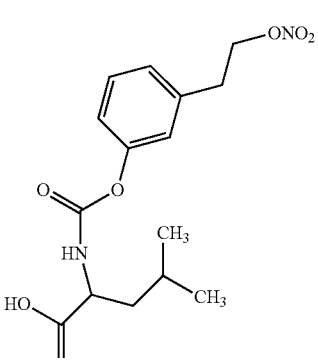
(207) 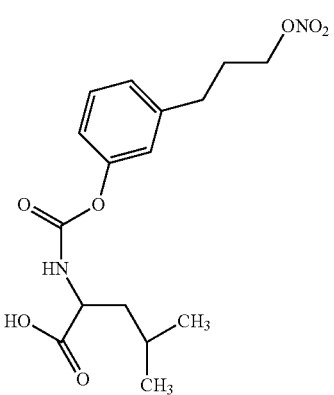
(208) 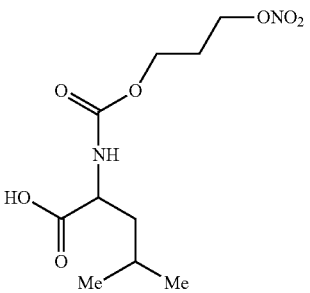

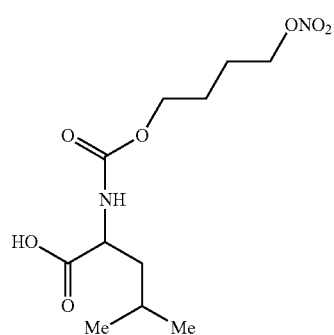
(209)
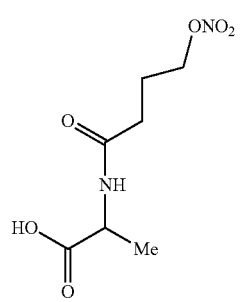
(210)
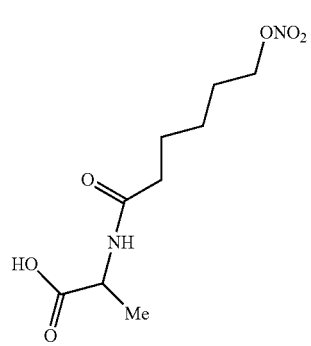
(211)
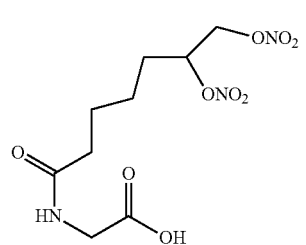
(212)
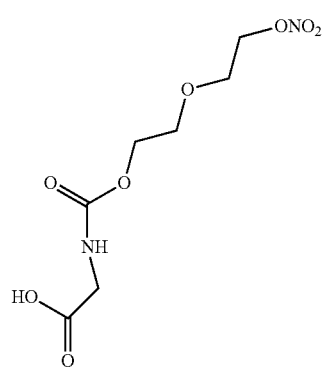
(213)
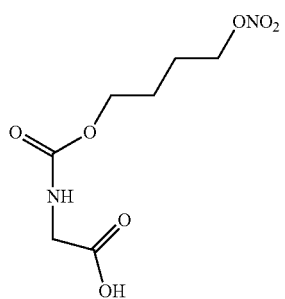
(214)
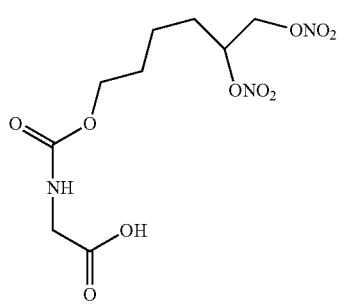
(215)
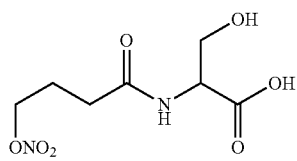
(216)
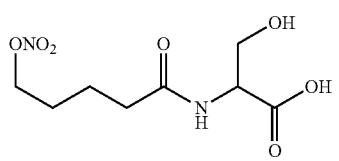
(217)
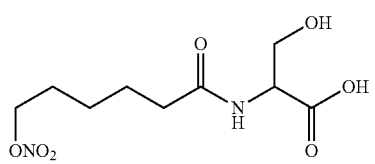
(218)
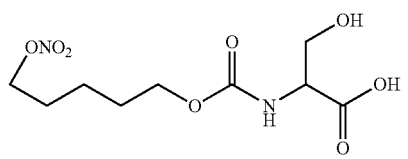
(219)
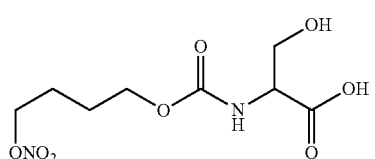
(220)
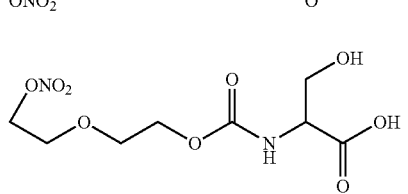
(221)

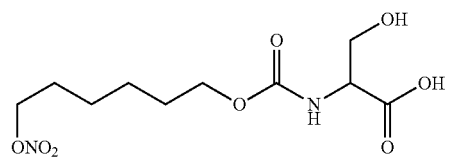
(222)
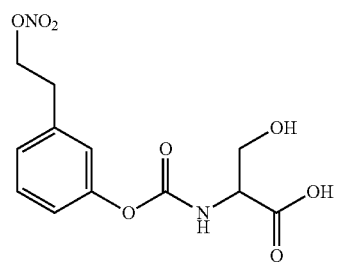
(223)
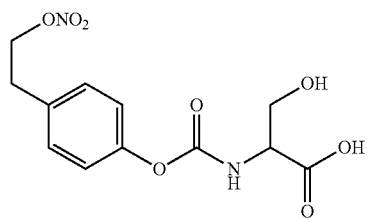
(224)
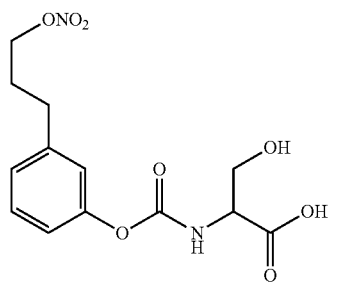
(225)
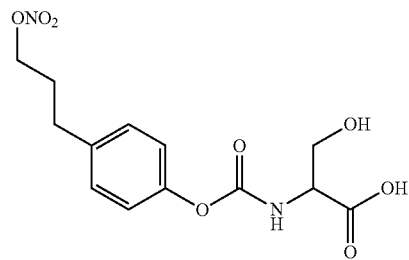
(226)
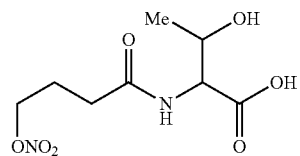
(227)
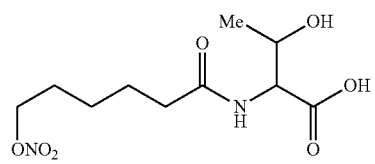
(228)
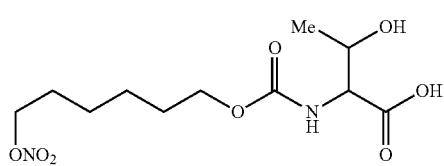
(229)
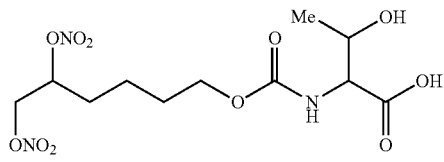
(230)
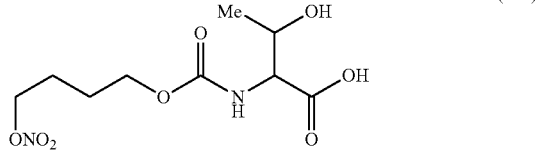
(231)
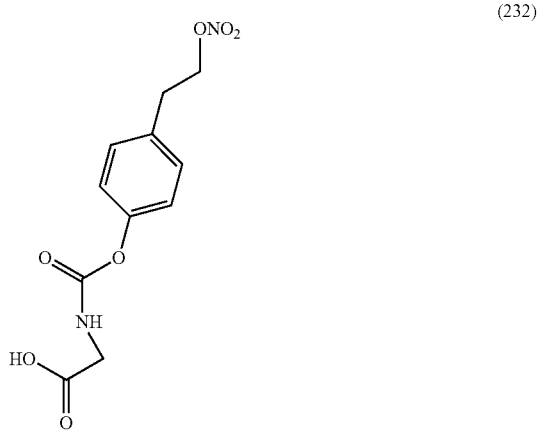
(232)
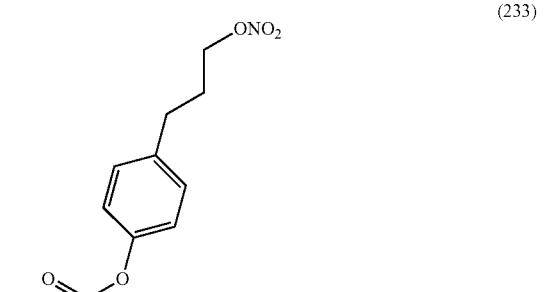
(233)
(234)
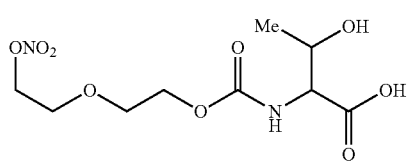

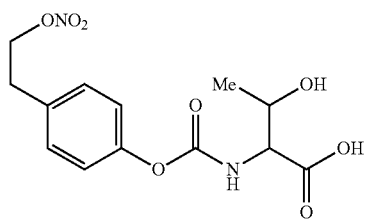 (235)
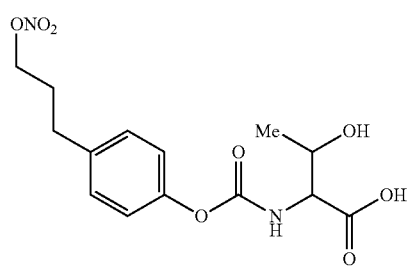 (236)
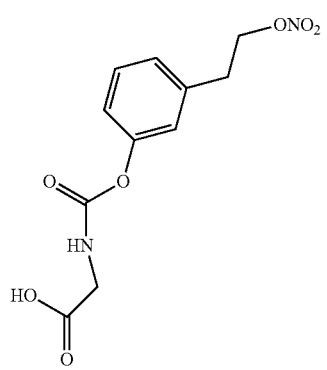 (237)
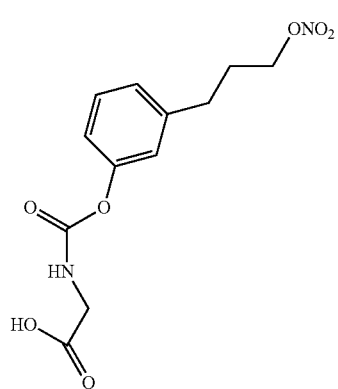 (238)
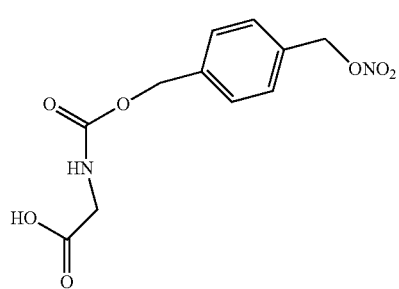 (239)
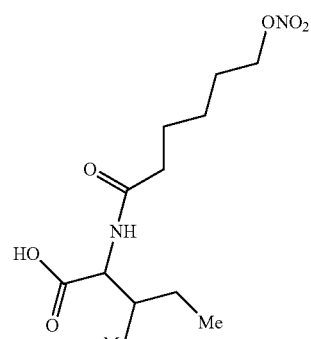 (240)
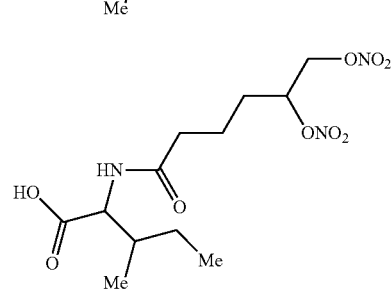 (241)
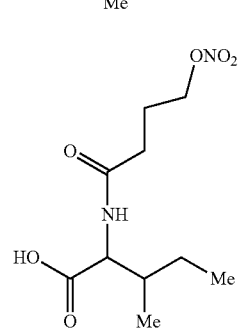 (242)
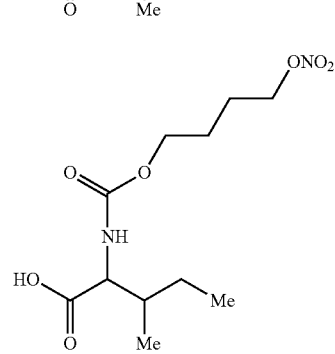 (243)
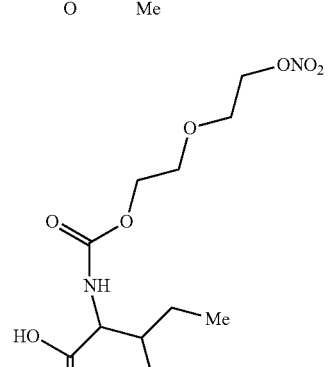 (244)

(245) 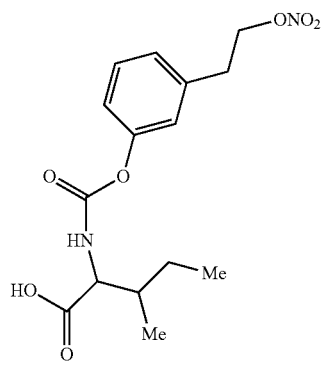
(246) 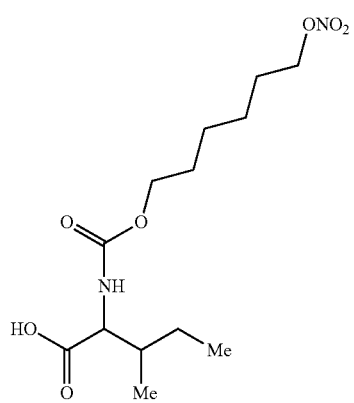
(247) 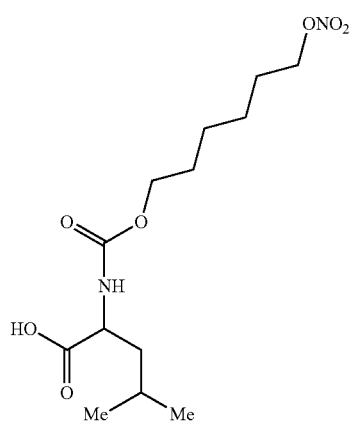
(248) 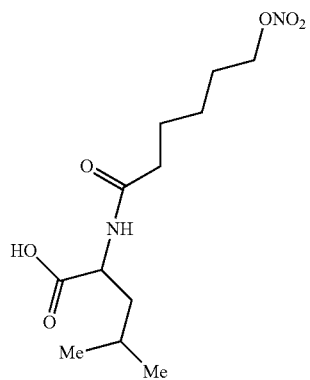
(249) 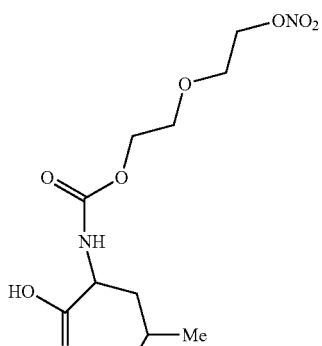
(250) 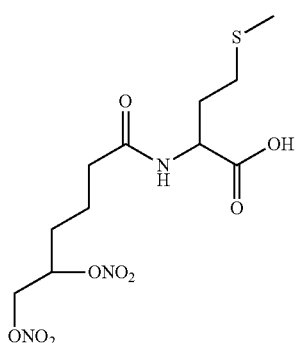
(251) 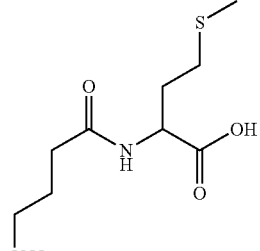
(252) 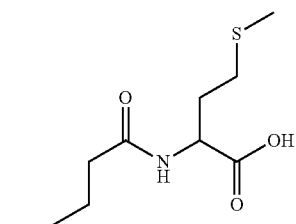
(253) 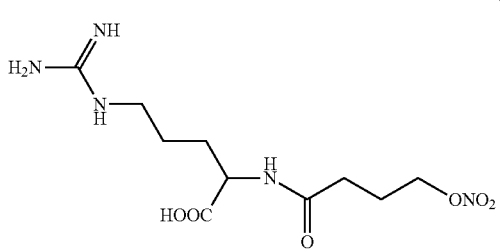

(254)
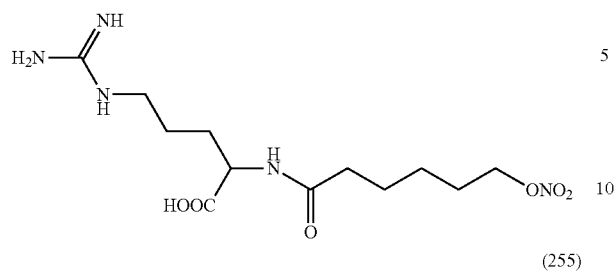
(255)
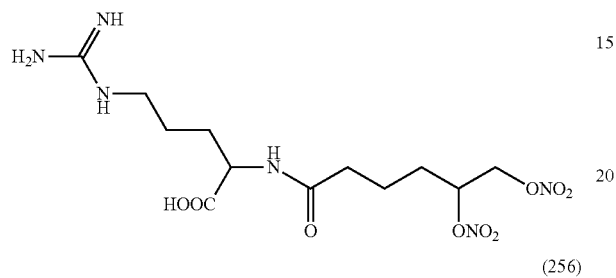
(256)
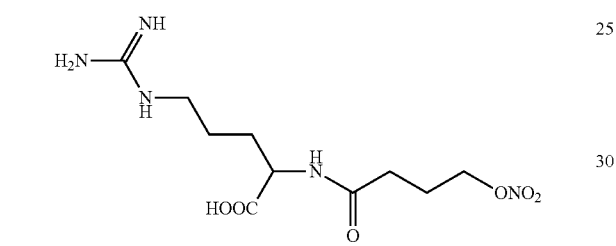
(257)
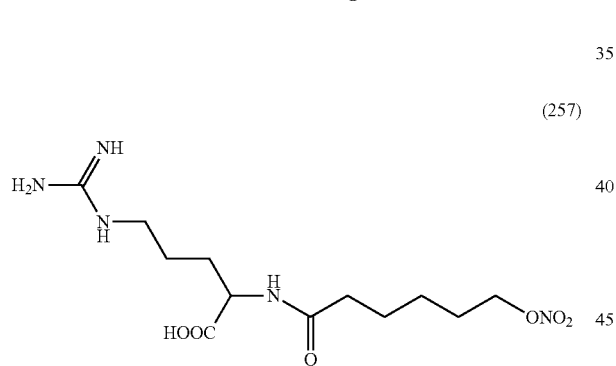
(258)
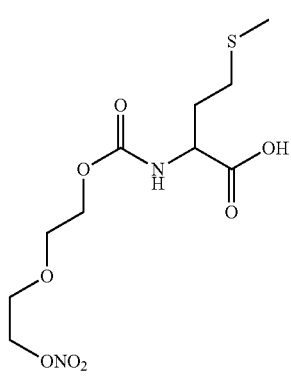
(259)
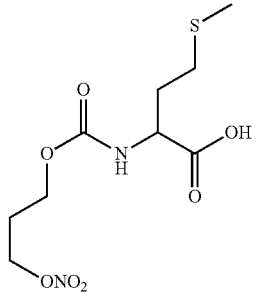
(260)
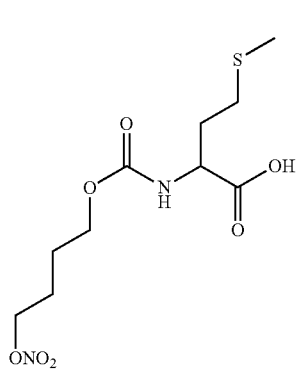
(261)
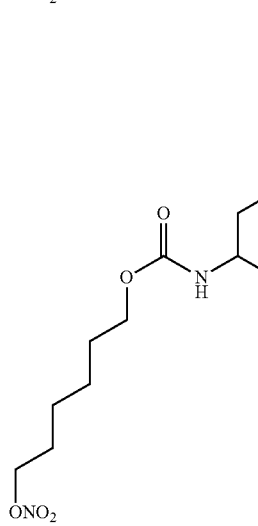
(262)

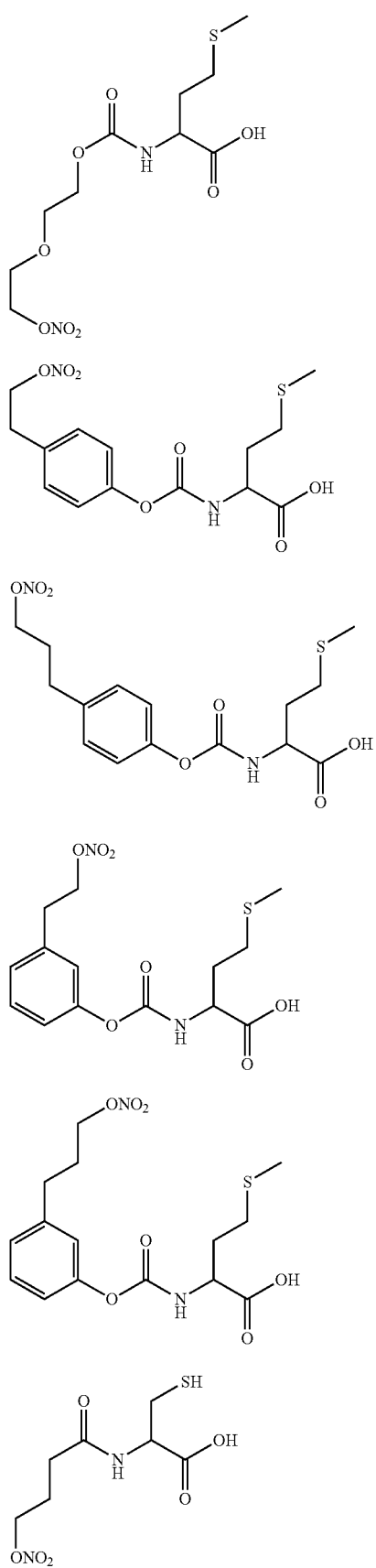
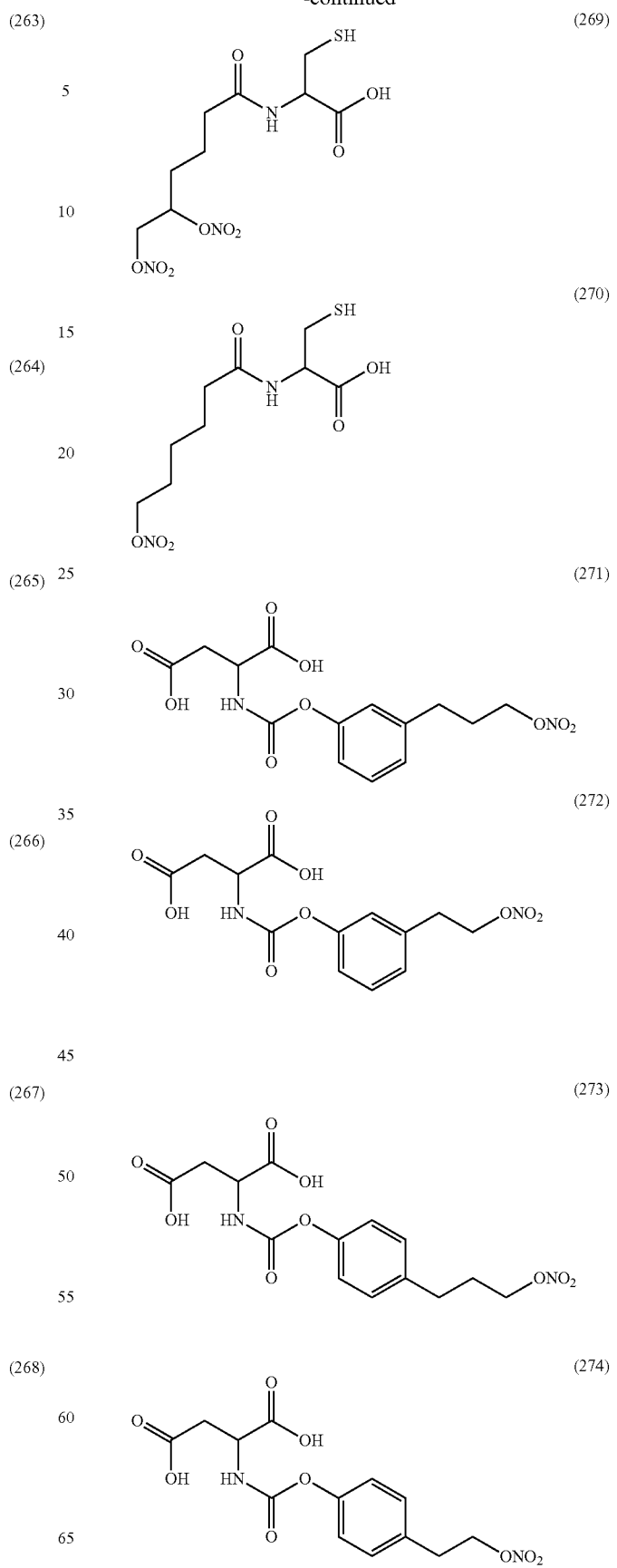

(275) 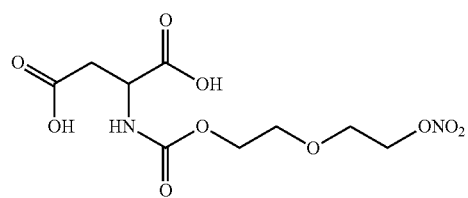
(276) 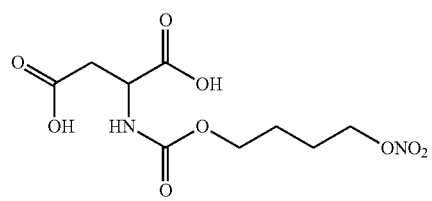
(277) 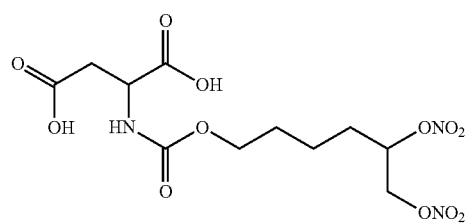
(278) 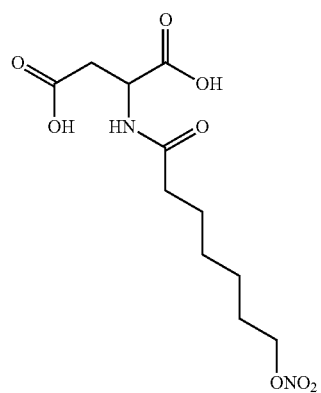
(279) 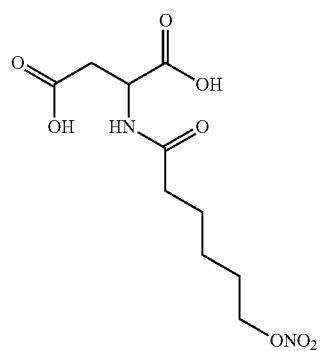
(280) 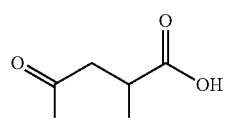
(281) 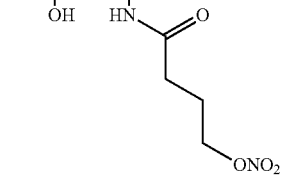
(282) 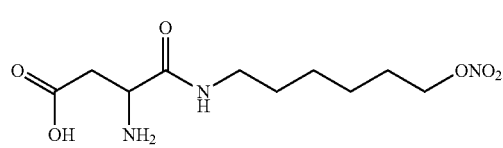
(283) 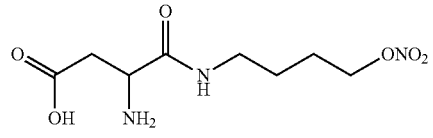
(284) 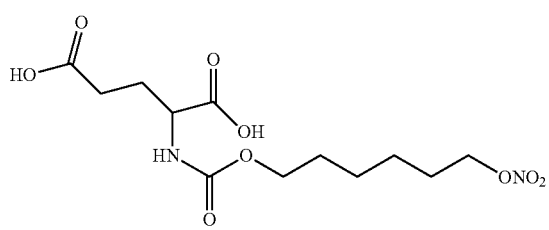
(285) 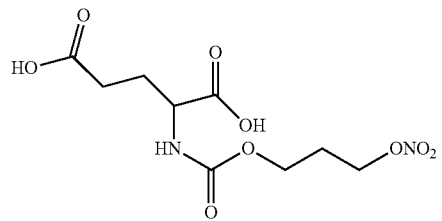
(286) 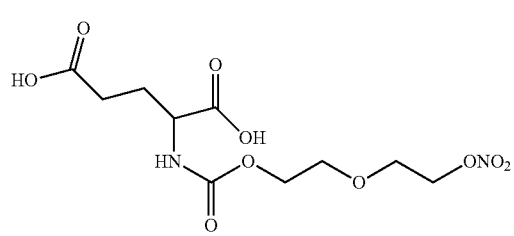

(287)
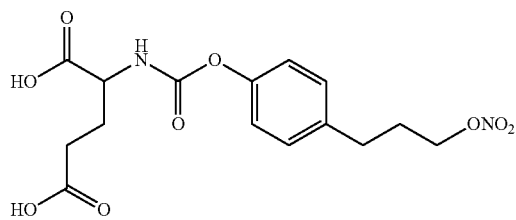
(288)
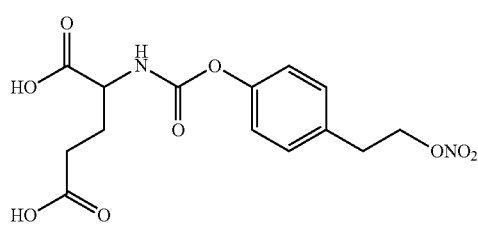
(289)
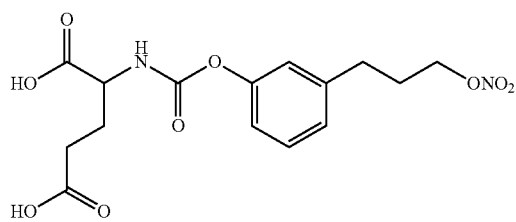
(290)
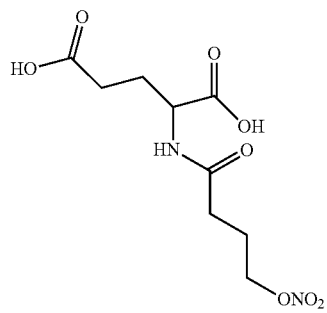
(291)
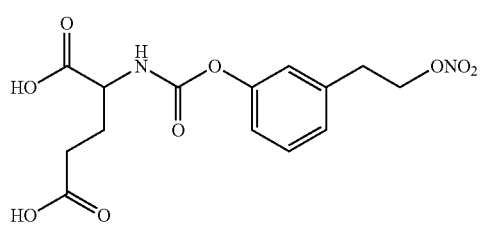
(292)
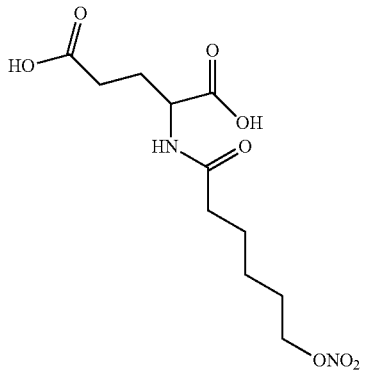
(293)
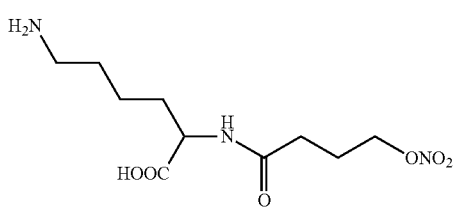
(294)
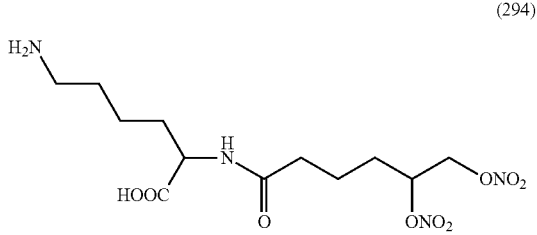
(295)
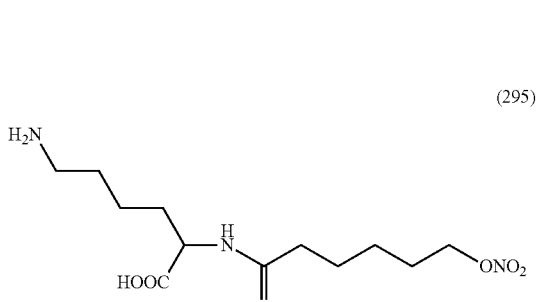
(296)
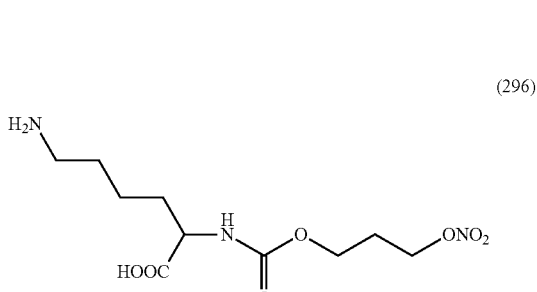
(297)
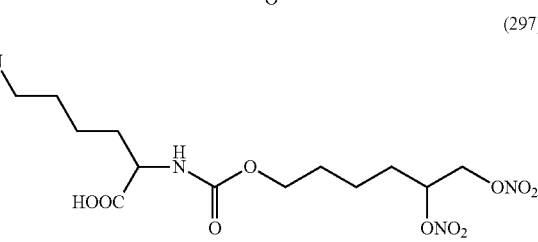

(298) 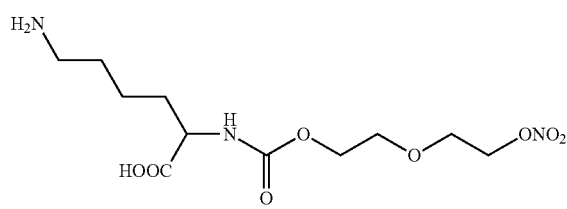

(299) 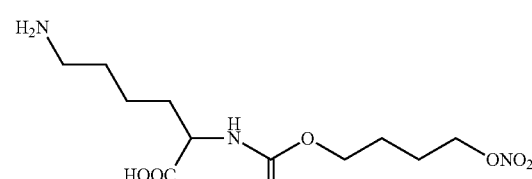

(300) 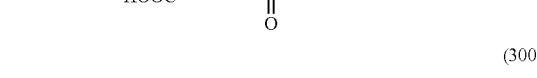

(301) 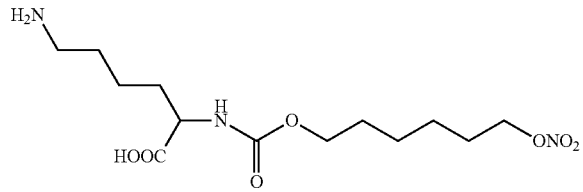

(302) 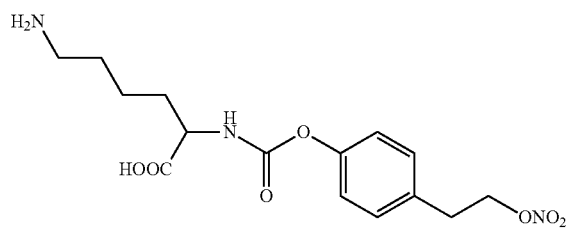

(303) 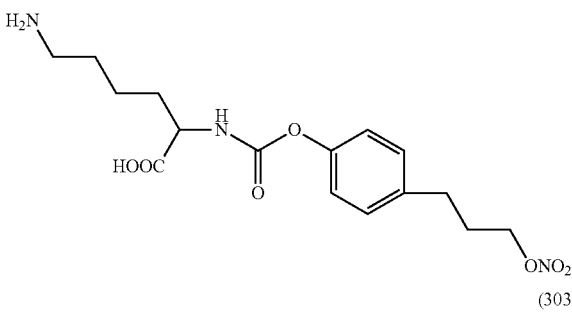

(304) 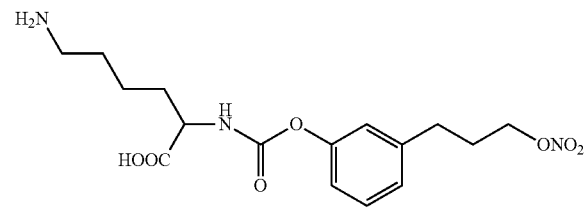

(305) 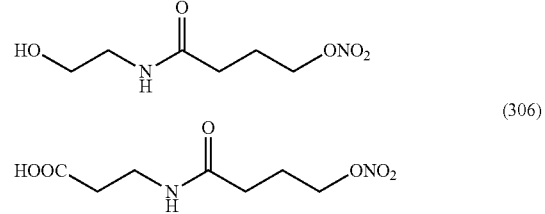

(306) 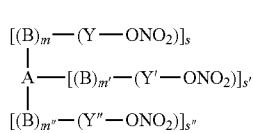

Another embodiment relates to compounds of formula (I)

$$[(B)_m-(Y-ONO_2)]_s$$
$$A-[(B)_{m'}-(Y'-ONO_2)]_{s'} \quad (I)$$
$$[(B)_{m''}-(Y''-ONO_2)]_{s''}$$

wherein s and s' are 1 and m, m' are 0,
s" is 0,
A is a radical of formula (IIa)

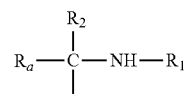 (IIa)

wherein $R_1$ is $-C(O)R_{1x}$, or $-C(O)OR_{1x}$ wherein $R_{1x}$ is one of the groups $-(Y-ONO_2)$ or $-(Y'-ONO_2)$ of formula (I) wherein Y and Y' are below reported,
$R_2$ is $-C(O)OH$, $-C(O)-OC(CH_3)_3$ or $R_2$ is the group $R_4$:

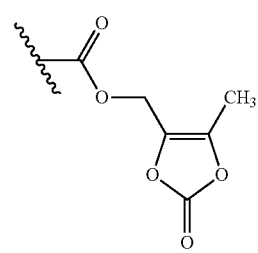 $R_4$ $R_a$ is selected from:
b) $R_{bx}C(O)-S-CH_2-$, $R_{bx}-OC(O)-S-CH_2-$, $R_{bx}-NH-C(O)S-CH_2-$ wherein $R_{bx}$ is one of the groups $-(Y-ONO_2)$ or $-(Y'-ONO_2)$;
c) $R_xO-CH_2-$, $R_xO-CH(CH_3)-$, $(R_xO)-p-C_6H_4-CH_2-$, wherein $R_x$ is $R_{xx}C(O)-$, $R_{xx}OC(O)-$ or $R_{xx}NHC(O)-$ wherein $R_{xx}$ is one of the groups $-(Y-ONO_2)$ or $-(Y'-ONO_2)$ of formula (I) wherein Y and Y' are below defined;

d) $R_gC(O)CH_2$—, $R_gC(O)(CH_2)_2$—, wherein $R_g$ is $R_{gx}$—O—, $R_{gxx}$—NH—, wherein $R_{gx}$ and $R_{gxx}$ are one of the groups —(Y—ONO$_2$) or —(Y'—ONO$_2$) of formula (I) wherein Y and Y' are below defined;

e) $R_hNH(CH_2)_p$— wherein p is an integer equal to 3 or 4, $R_h$ is $R_{hh}$—C(O)— or $R_{hh}$—OC(O)— wherein $R_{hh}$ is one of the groups —(Y—ONO$_2$) or —(Y'—ONO$_2$) of formula (I) wherein Y and Y' are below defined, or $R_iNH$(=NH)NH—(CH$_2$)$_3$— wherein $R_i$ is $R_{ii}$C(O)— or $R_{ii}$OC(O)— wherein $R_{ii}$ is one of the groups —(Y—ONO$_2$) or —(Y'—ONO$_2$) of formula (I) wherein Y and Y' are below defined;

Y and Y' of the groups —(Y—ONO$_2$) or —(Y'—ONO$_2$) are each independently selected from:

A)
a straight or branched $C_2$-$C_{10}$ alkylene
a straight or branched $C_2$-$C_{10}$ alkylene substituted with a —ONO$_2$ group;

B)

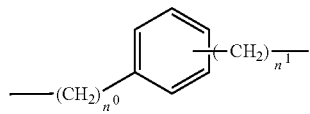
(IB)

wherein in formula (IB)
$n^0$ is from 0 to 5 and $n^1$ is an integer from 1 to 10;

C)

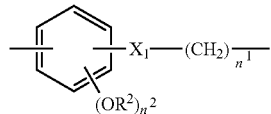
(IC)

wherein in formula (IC)
$n^1$ is an integer from 1 to 10,
$n^2$ is 1 and $R^2$ is $CH_3$, $X_1$ is —C(O)O—;

D)

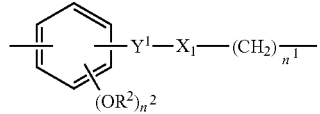
(ID)

wherein in formula (ID):
$n^2$ is 1 and $R^2$ is $CH_3$,
$Y^1$ is —CH=CH(CH$_2$)$_n{}^{2a}$— wherein $n^{2a}$ is 0,
$X_1$ is —C(O)O— and $n^1$ is an integer from 1 to 10;

E)

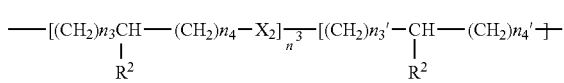
(IE)

wherein in formula (IE)
$n^3$ is from 1 to 5,
$n_3$ is 0 and $n_4$ is from 1 to 4, $n_{3'}$ is 0 and $n_{4'}$ is from 1 to 4,
$X_2$ is —O— or —NH—,
$R^2$ is H, preferably (Y—ONO$_2$) and (Y'—ONO$_2$) are each independently selected from:

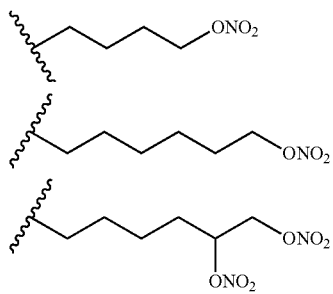

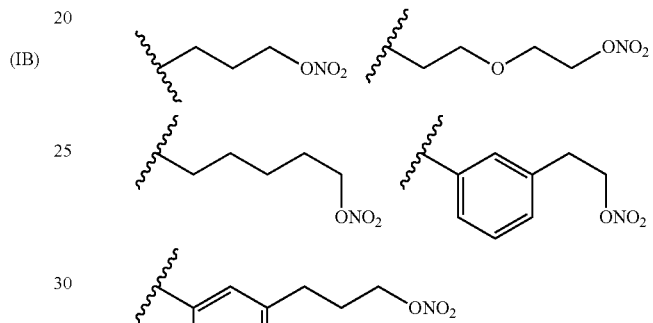

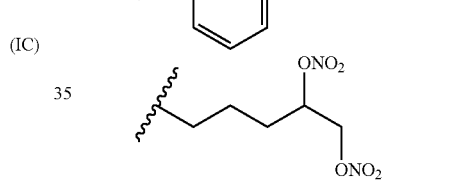

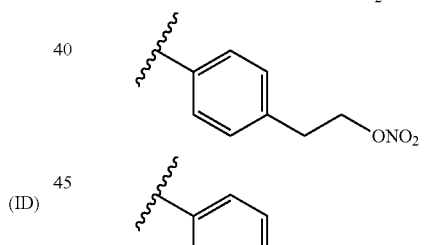

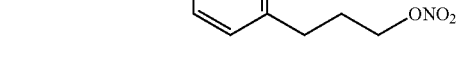

more preferably (Y—ONO$_2$) and (Y'—ONO$_2$) are equal.

The following are preferred compounds according to the present invention:

(307)

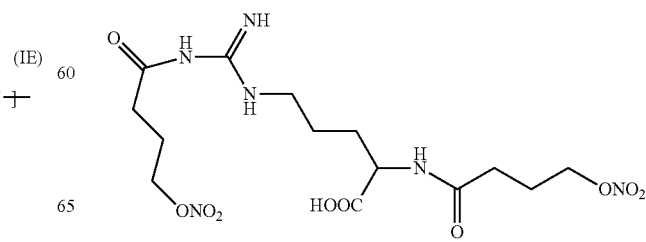

(308) 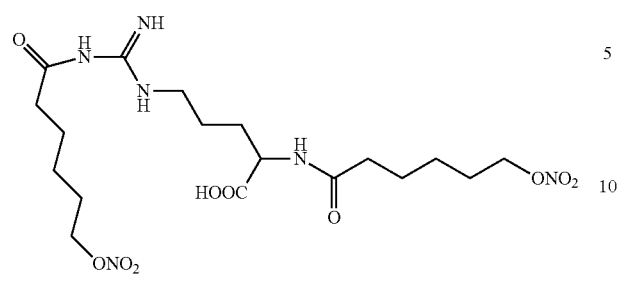
(309) 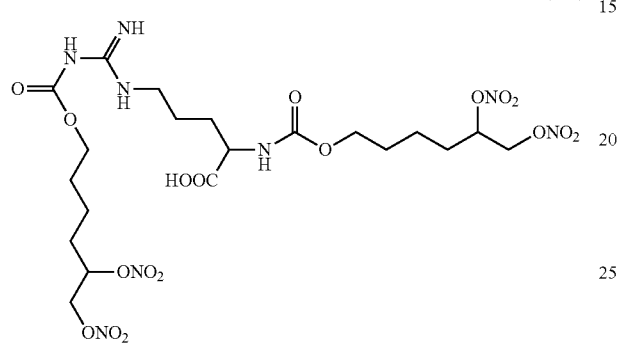
(310) 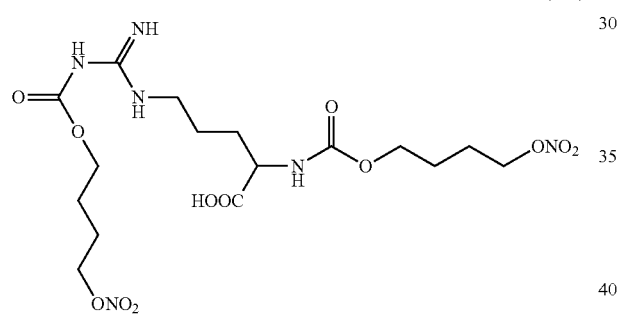
(311) 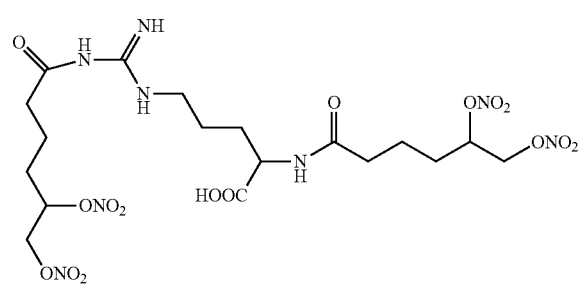
(312)
(313) 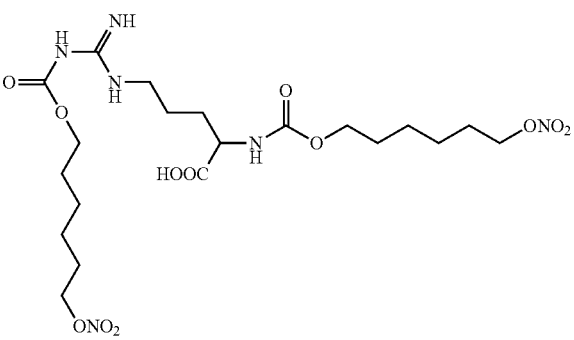
(314) 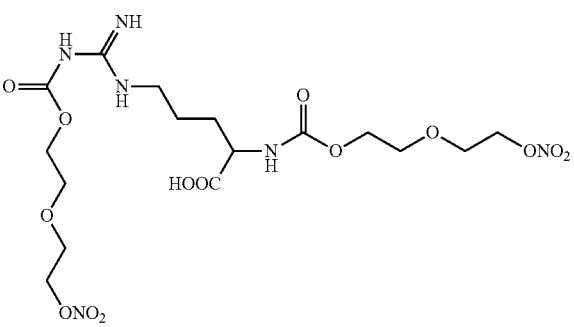
(315) 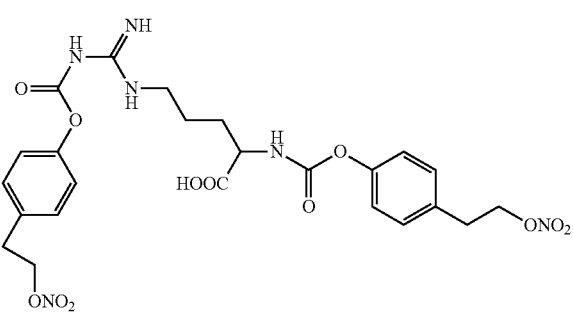
(316) 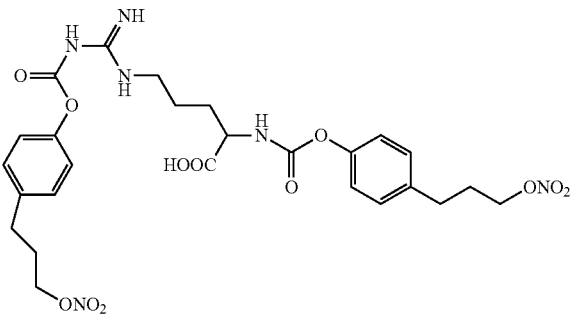

(317)
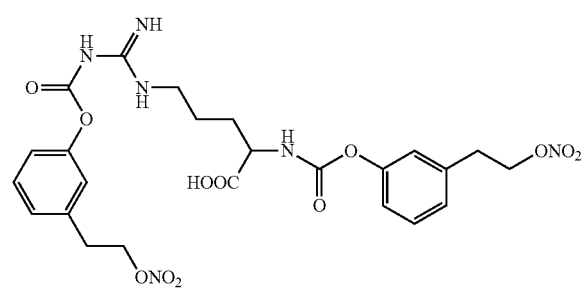
(318)
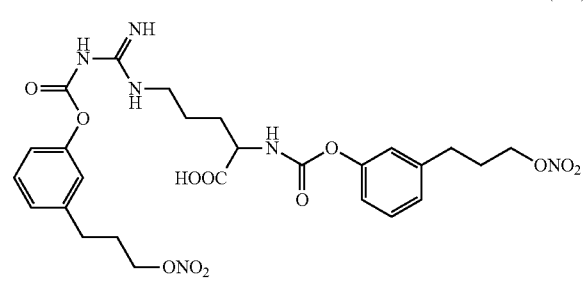
(319)
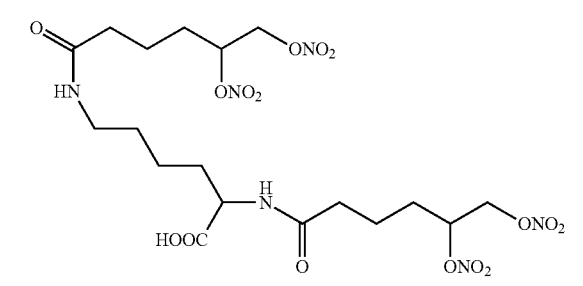
(320)
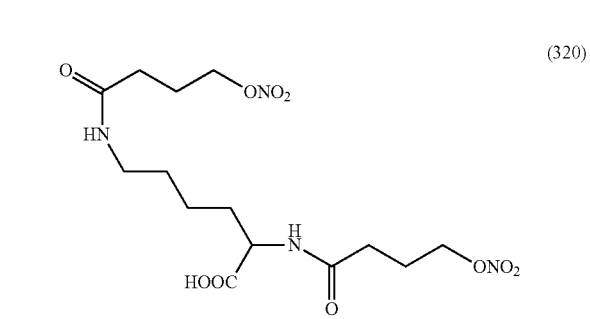
(322)
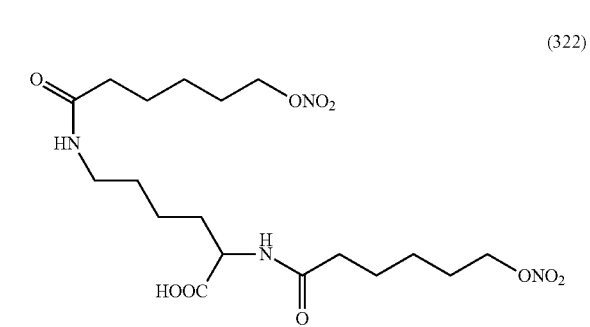
(323)
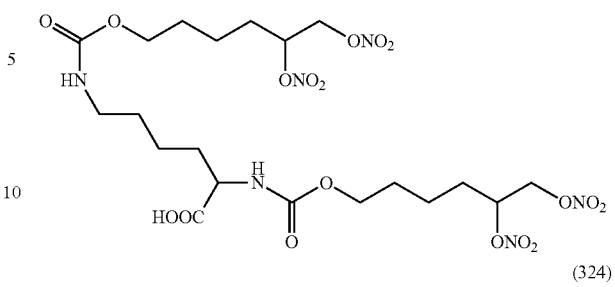
(324)
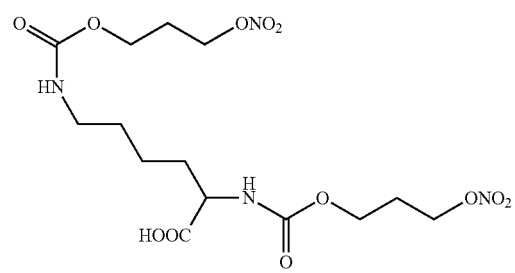
(325)
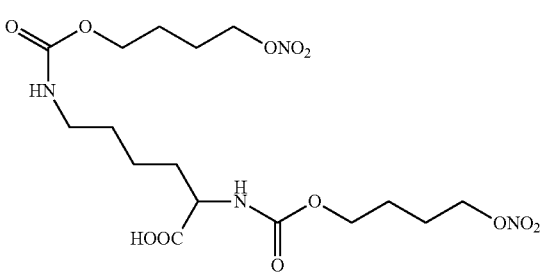
(326)
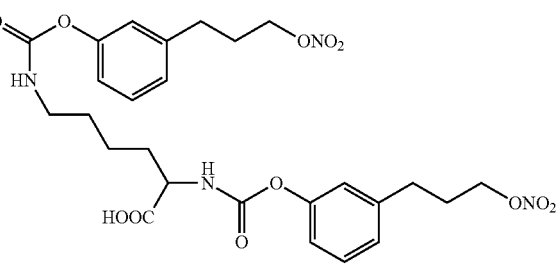
(327)
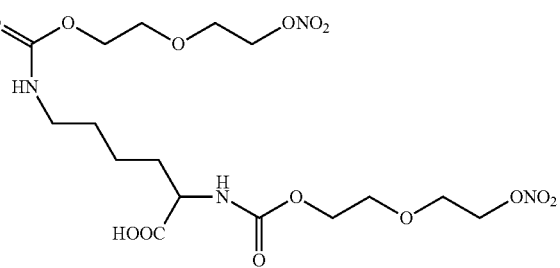

(328) 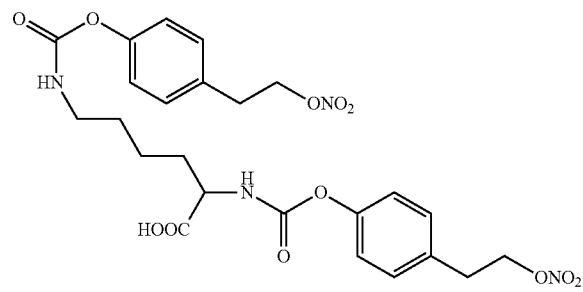
(329) 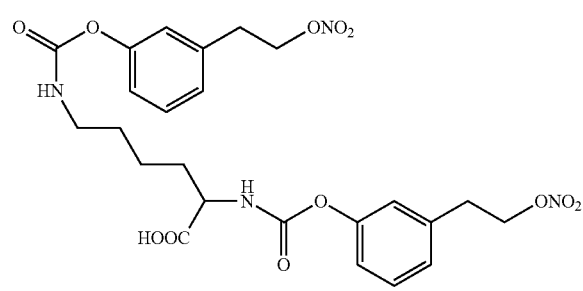
(330) 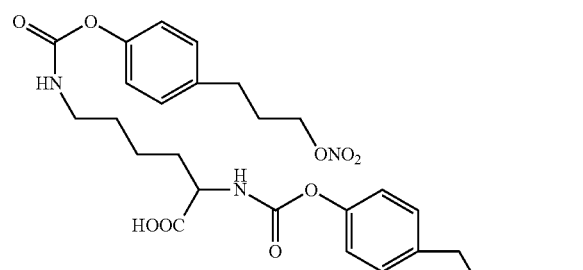
(331) 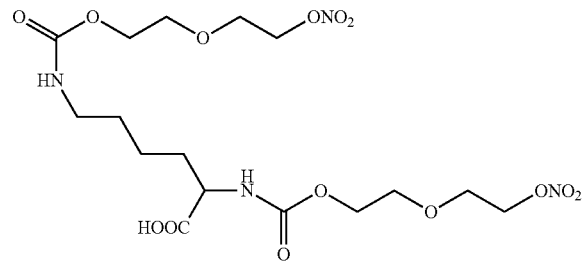
(332) 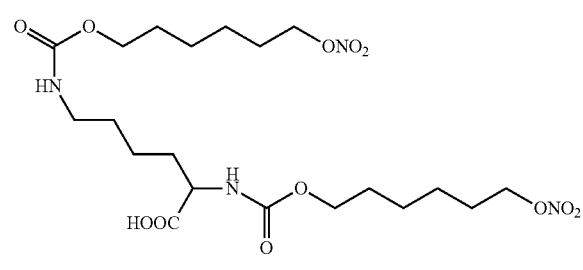
(333) 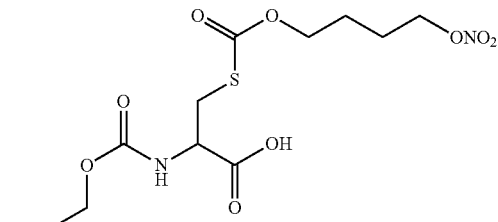
(334) 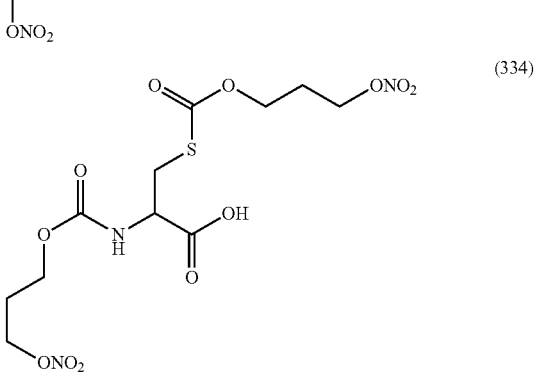
(335) 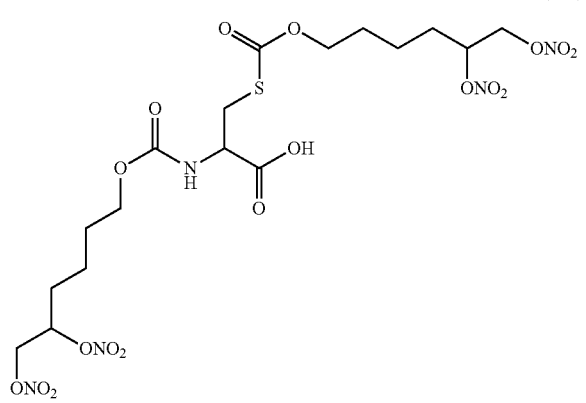
(336) 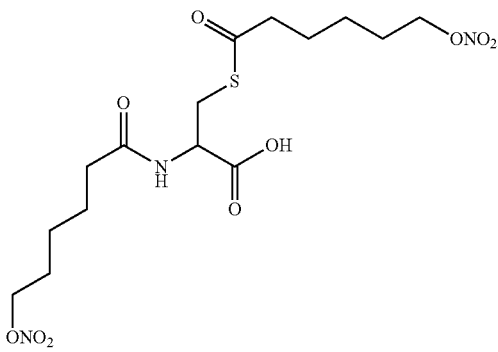

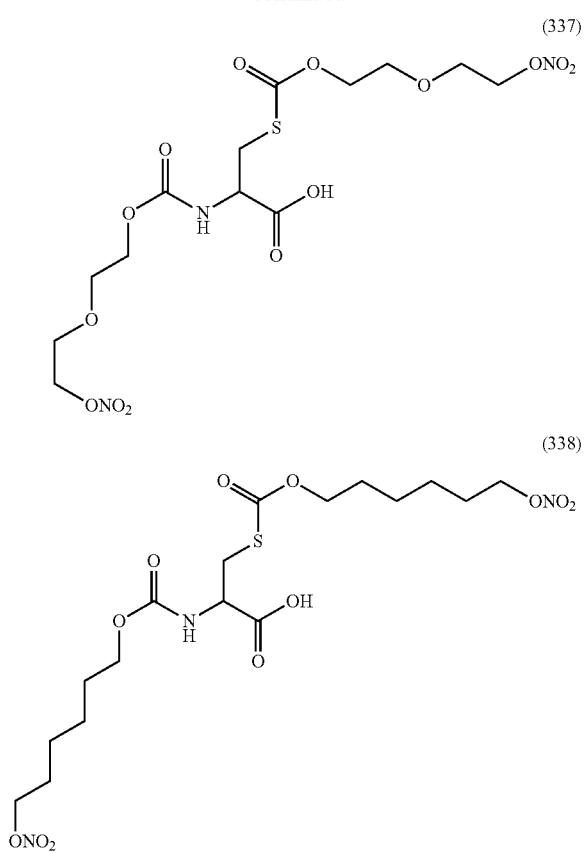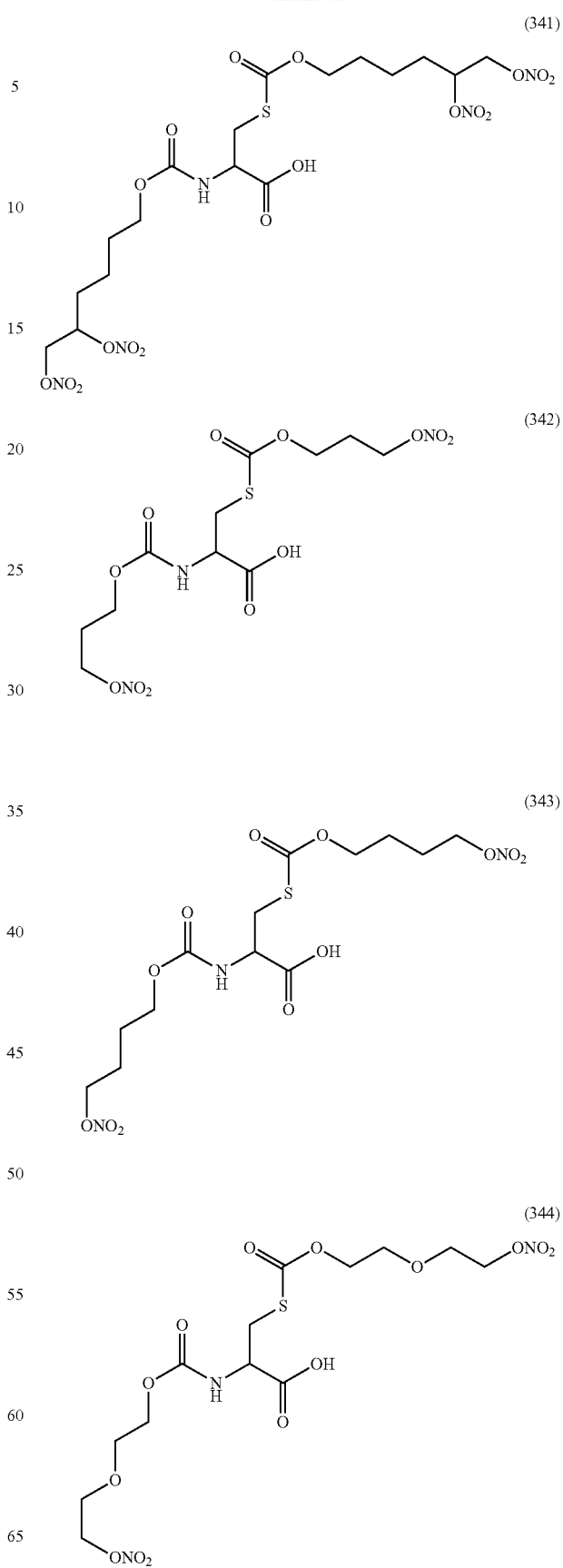

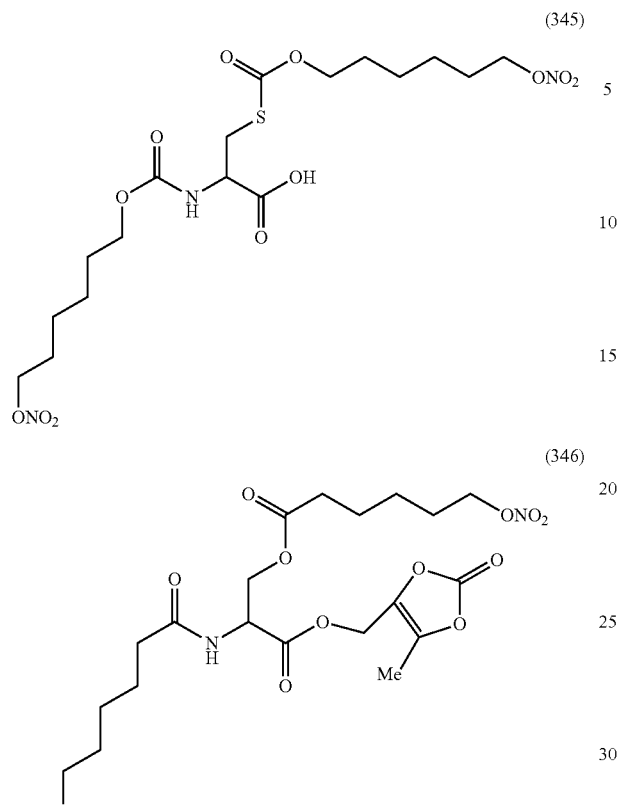
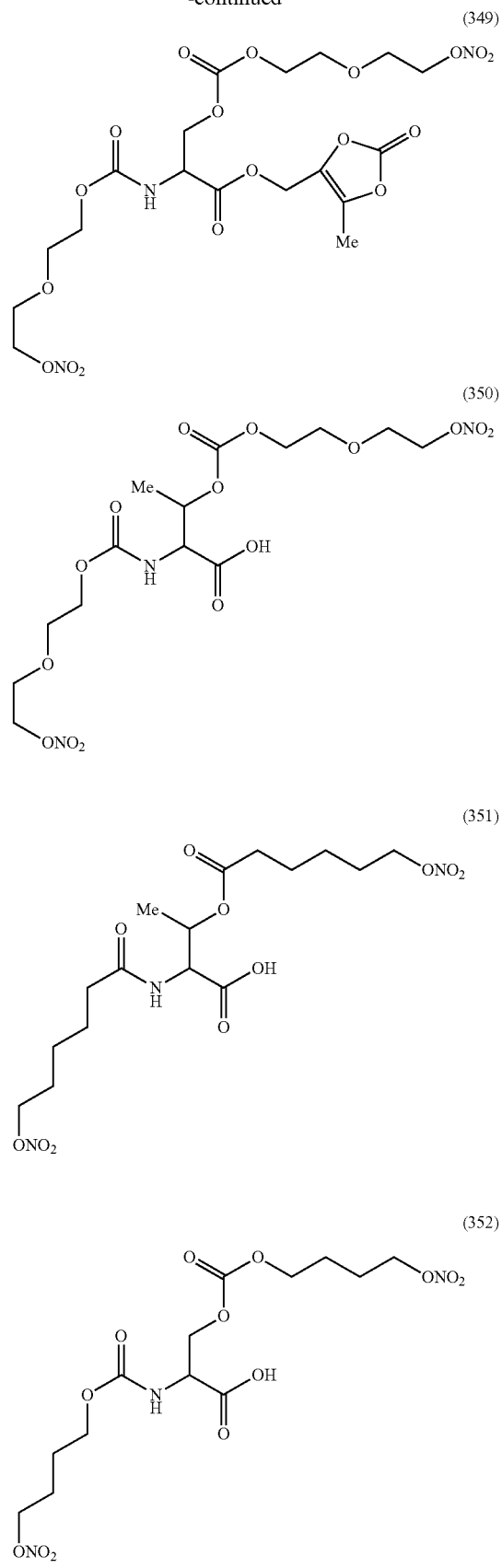

Another embodiment provides compounds of formula (I)

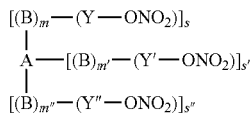 (I)

wherein s is 1 and m is 0,
s' and s" are 0,
A is a radical of formula (IIa) or (III)

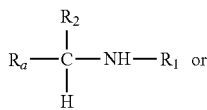 (IIa)

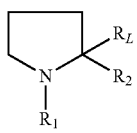 (III)

wherein $R_1$ is —C(O)$R_{1x}$ or —C(O)O$R_{1x}$ wherein $R_{1x}$ is the group —(Y—ONO$_2$) of formula (I) wherein Y is below defined, $R_2$ in formulas (IIa) and (III) is the group $R_4$

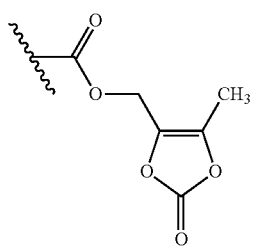 $R_4$ $R_a$ of formula (IIa) is selected from:
a) H, CH$_3$, isopropyl, isobutyl, sec-butyl, methylthio-(CH$_2$)$_2$—, benzyl, C$_6$H$_5$—CH$_2$—CH$_2$—, 3-triptophanyl-CH$_2$—, NH$_2$—CO—CH$_2$—, NH$_2$—CO—(CH$_2$)$_2$—, 4-imidazolyl-CH$_2$—;
b) HS—CH$_2$—;
c) $R_x$O—CH$_2$—, $R_x$O—CH(CH$_3$)—, ($R_x$O)-p-C$_6$H$_4$—CH$_2$—, wherein $R_x$ is H;
d) $R_g$C(O)CH$_2$ or $R_g$C(O)(CH$_2$)$_2$—, wherein $R_g$ is OH, (CH$_3$)$_3$O— or the group $R_{gg}$

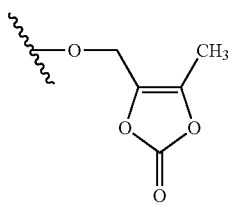 $R_{gg}$ e) $R_h$NH(CH$_2$)$_p$— or $R_t$NH(=NH)NH—(CH$_2$)$_3$—, wherein p is an integer equal to 3 or 4, $R_h$ is H or (CH$_3$)$_3$C—OC(O)—, $R_t$ is H;

$R_L$ of formula (III) is H;

Y of the group —(Y—ONO$_2$) is selected from:

A)
  a straight or branched C$_2$-C$_{10}$ alkylene
  a straight or branched C$_2$-C$_{10}$ alkylene substituted with a —ONO$_2$ group;

B)

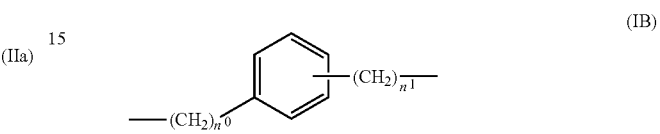 (IB)

wherein in formula (IB)
$n^0$ is from 0 to 5 and $n^1$ is an integer from 1 to 10;

C)

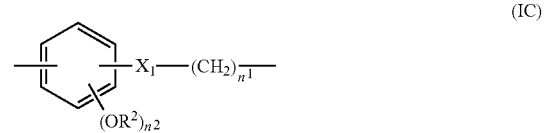 (IC)

wherein in formula (IC)
$n^1$ is an integer from 1 to 10,
$n^2$ is 1 and $R^2$ is CH$_3$, $X_1$ is —C(O)O—;

D)

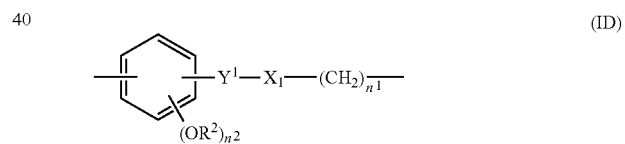 (ID)

wherein in formula (ID):
$n^2$ is 1 and $R^2$ is CH$_3$,
$Y^1$ is —CH=CH—(CH$_2$)$_n^{2a}$— wherein $n^{2a}$ is 0,
$X_1$ is —C(O)O— and $n^1$ is an integer from 1 to 10;

E)

—[(CH$_2$)$_{n_3}$CH—(CH$_2$)$_{n_4}$—X$_2$]$_{\overline{n^3}}$—[(CH$_2$)$_{n_3'}$—CH—(CH$_2$)$_{n_4'}$]— (IE)
          |                                              |
          R$^2$                                          R$^2$ wherein in formula (IE)
$n^3$ is from 1 to 5,
$n_3$ is 0 and $n_4$ is from 1 to 4,
$n_{3'}$ is 0 and $n_{4'}$ is from 1 to 4,
$X_2$ is —O— or —NH—,
$R^2$ is H, preferably (Y—ONO₂) is selected from:
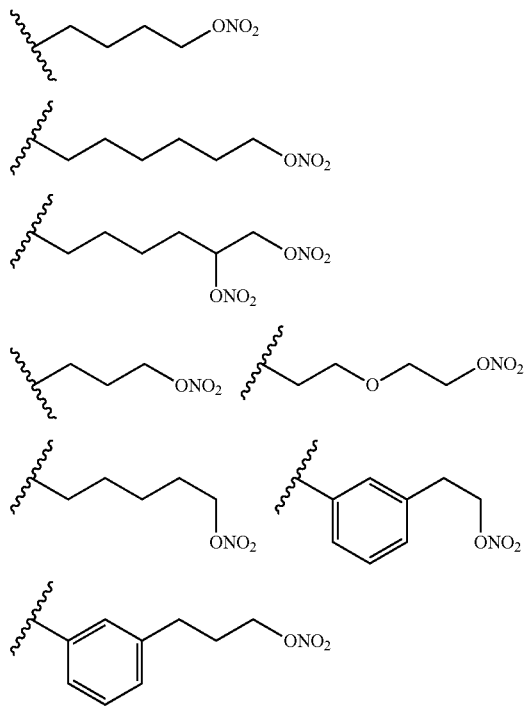
The following are preferred compounds according to the present invention:
(354)
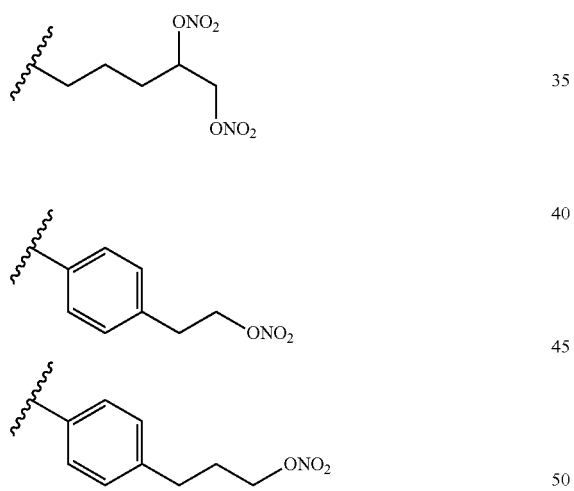
-continued
(355)
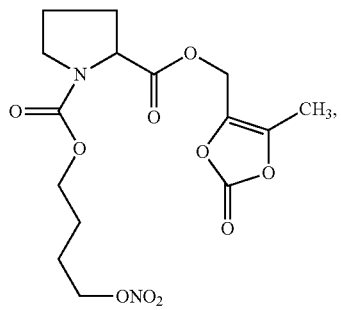
(356)
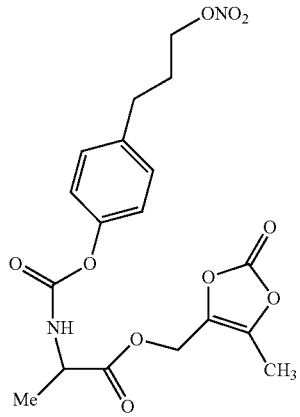
(357)
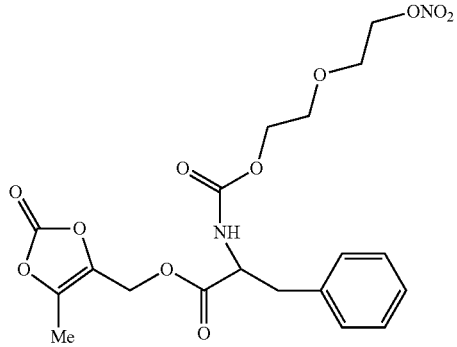
(358)
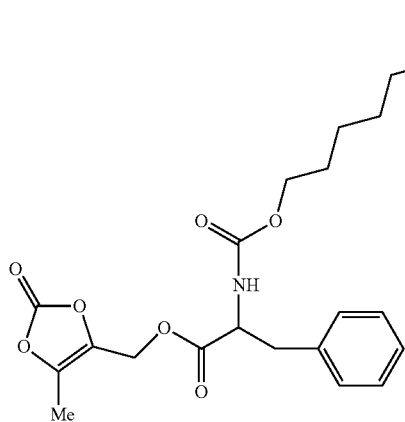

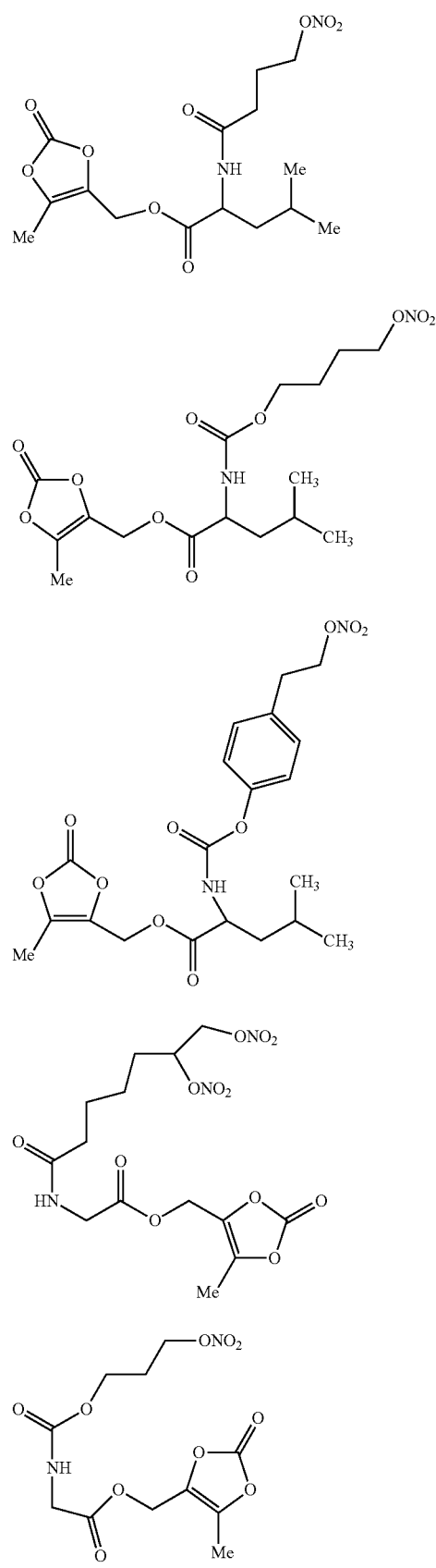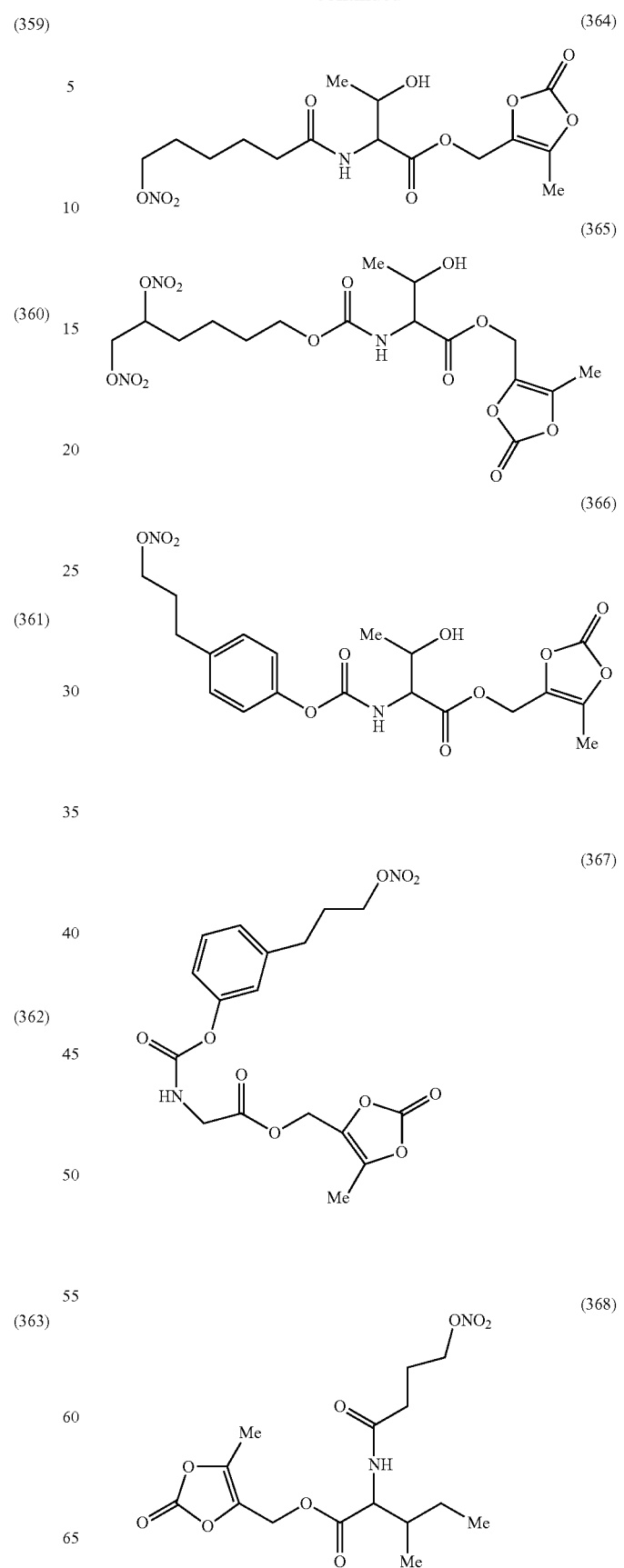

-continued (369)
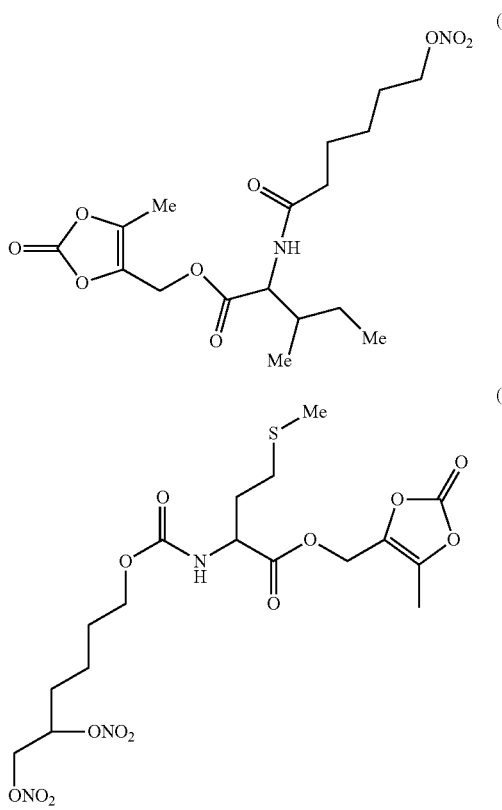

(370)

(371)
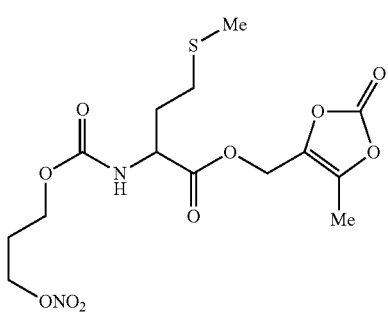

Another embodiment relates to compounds of formula (I)

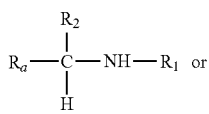  (I)

wherein s and s' are 1 and m, m' are 0, s'' is 0,
A is a radical of formula (IIa) or (III)

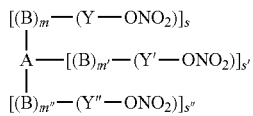  (IIa)

-continued

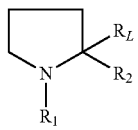  (III)

wherein
$R_1$ is —C(O)$R_{1x}$, —C(O)O$R_{1x}$ wherein $R_{1x}$ is one of the groups —(Y—ONO$_2$) or —(Y'—ONO$_2$) of formula (I) wherein Y and Y' are below defined;
$R_2$ is —C(O)O$R_{2x}$, —C(O)NH$R_{2x}$, —C(O)N(CH$_3$)$R_{2xx}$, wherein $R_{2x}$ and $R_{2xx}$ are one of the groups —(Y—ONO$_2$) or —(Y'—ONO$_2$) of formula (I) wherein Y and Y' are below defined, more preferably $R_2$ is —C(O)O$R_{2x}$ or —C(O)NH$R_{2xx}$;
$R_a$ is selected from:
a) H, CH$_3$, isopropyl, isobutyl, sec-butyl, methylthio-(CH$_2$)$_2$—, benzyl, C$_6$H$_5$—CH$_2$—CH$_2$—, 3-triptophanyl-CH$_2$—, NH$_2$—CO—CH$_2$—, NH$_2$—CO—(CH$_2$)$_2$—, 4-imidazolyl-CH$_2$—;
$R_L$ in formula (III) is H;
Y and Y' of the groups (Y—ONO$_2$) or (Y'—ONO$_2$) are each independently selected from
A)
a straight or branched C$_2$-C$_{10}$ alkylene
a straight or branched C$_2$-C$_{10}$ alkylene substituted with a —ONO$_2$ group;
B)

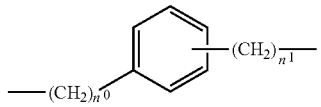  (IB)

wherein in formula (IB)
$n^0$ is from 0 to 5 and $n^1$ is an integer from 1 to 10;
C)

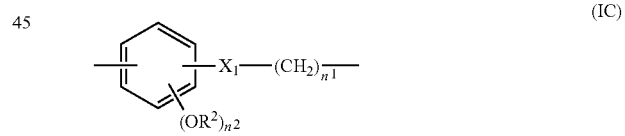  (IC)

wherein in formula (IC)
$n^1$ is from 1 to 10,
$n^2$ is 1 and $R^2$ is CH$_3$, $X_1$ is —C(O)O—;
D)

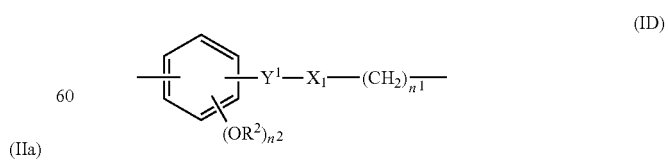  (ID)

wherein in formula (ID):
$n^2$ is 1 and $R^2$ is CH$_3$,
$Y^1$ is —CH=CH—(CH$_2$)$_{n^{2a}}$— $n^{2a}$ is 0,
$X_1$ is —C(O)O— and $n_1$ is an integer from 1 to 10;

E)
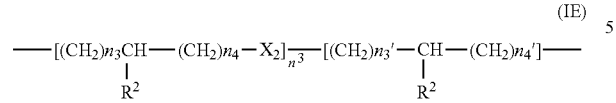
(IE)
wherein in formula (IE)
$n^3$ is from 1 to 5,
$n_3$ is 0 and $n_4$ is from 1 to 4,
$n_{3'}$ is 0 and $n_{4'}$ is from 1 to 4,
$X_2$ is —O— or —NH—,
$R^2$ is H,
preferably (Y—ONO$_2$) and (Y'—ONO$_2$) are each independently selected from:
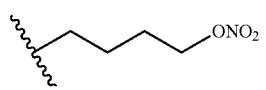
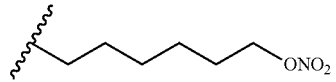
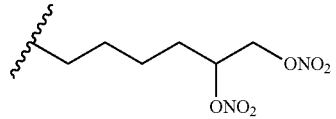
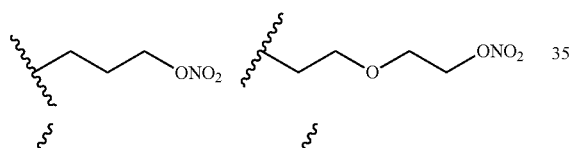
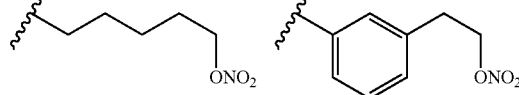
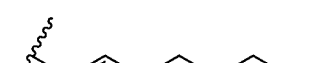
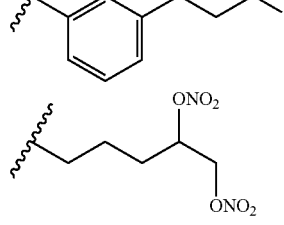
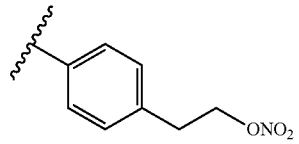
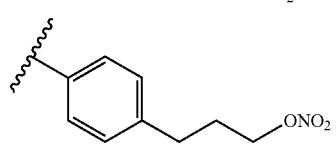
The following are preferred compounds according to the present invention:
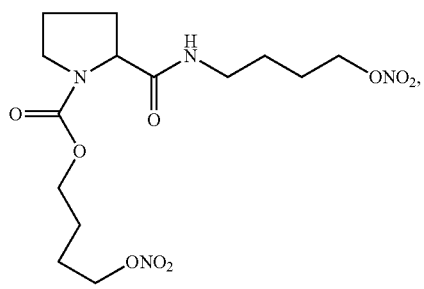
(372)
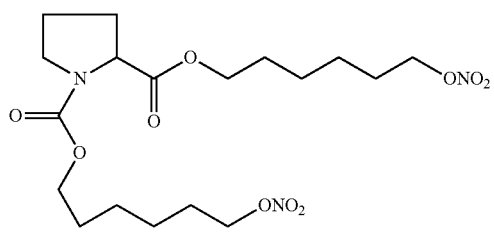
(373)
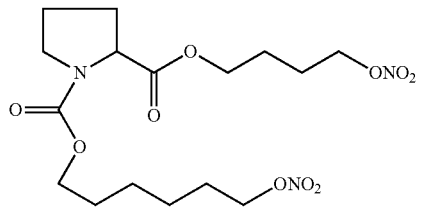
(374)
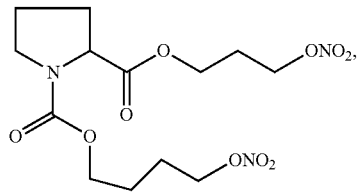
(375)
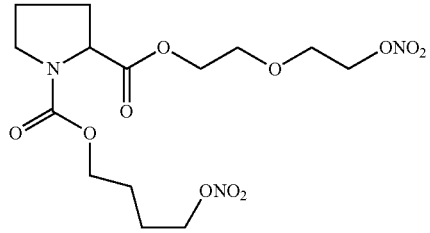
(376)
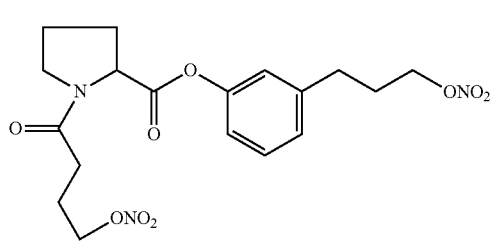
(377)

(378) 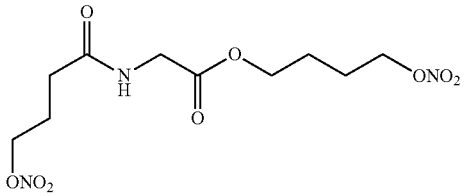
(383) 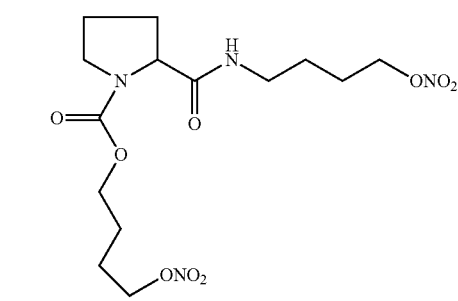
(384) 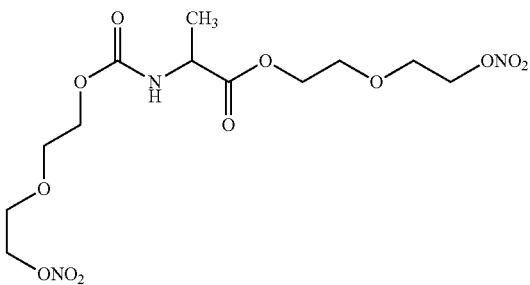
(379) 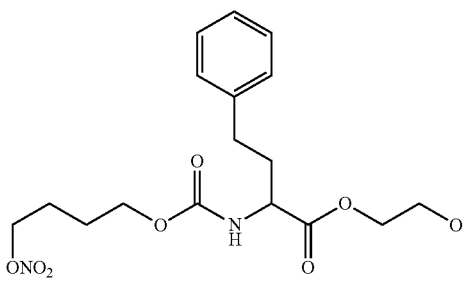
(385) 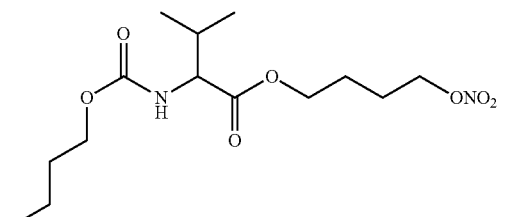
(380) 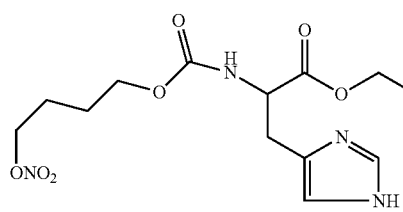
(386) 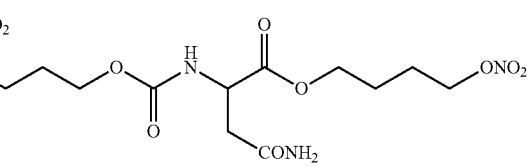
(381) 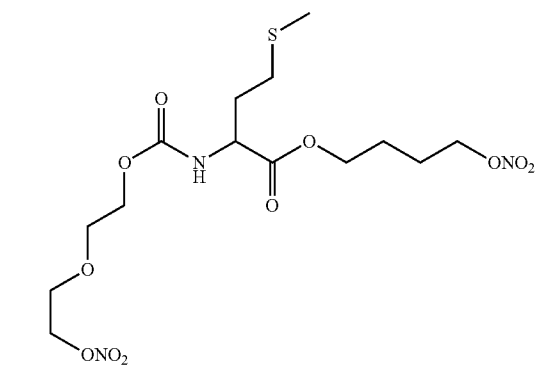
(387) 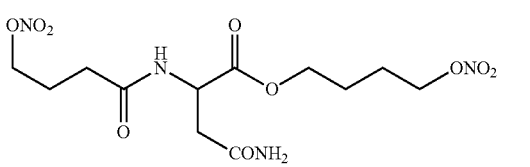
Another embodiment relates to compounds of formula (I)
(382) 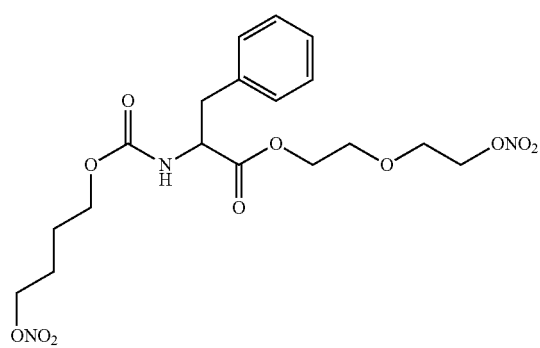
$$[(B)_m-(Y-ONO_2)]_s$$
$$A-[(B)_{m'}-(Y'-ONO_2)]_{s'}$$
$$[(B)_{m''}-(Y''-ONO_2)]_{s''}$$ (I)
wherein s and s' are 1, m is 1, m' is 0, s" is 0,
B at each occurrence is independently selected from:
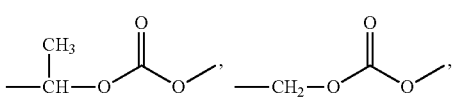

-continued

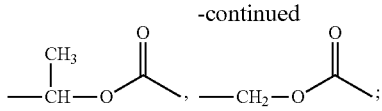

preferably B is

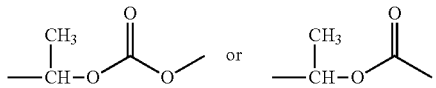

more preferably B is:

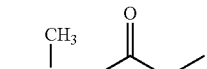

A is a radical of formula

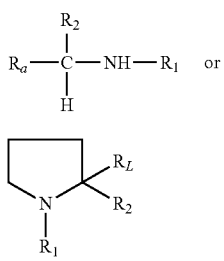

wherein
$R_1$ is —C(O)$R_{1x}$, —C(O)O$R_{1x}$ wherein $R_{1x}$ is —(Y—ONO$_2$) of formula (I) wherein Y is below defined;
$R_2$ is —C(O)O$R_{2x}$, wherein $R_{2x}$ is the group —[B—(Y'—ONO$_2$)] of formula (I) wherein B is as above reported and Y' is below reported,
$R_a$ is selected from:
H, CH$_3$, isopropyl, isobutyl, sec-butyl, methylthio-(CH$_2$)$_2$—, benzyl, C$_6$H$_5$—CH$_2$—CH$_2$—, 3-triptophanyl-CH$_2$—, NH$_2$—CO—CH$_2$—; NH$_2$—CO—(CH$_2$)$_2$—, 4-imidazolyl-CH$_2$—;
$R_L$ in formula (III) is H,
Y and Y' of the groups (Y—ONO$_2$) and —(Y'—ONO$_2$) are each independently selected from:

A)
 a straight or branched $C_2$-$C_{10}$ alkylene
 a straight or branched $C_2$-$C_{10}$ alkylene substituted with a —ONO$_2$ group;
E)

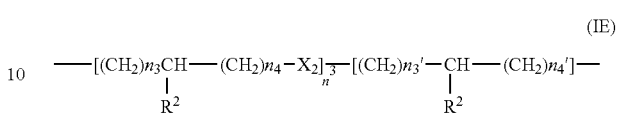

wherein in formula (IE)
$n^3$ is from 1 to 5,
$n_3$ is 0 and $n_4$ from 1 to 4,
$n_{3'}$ is 0 and $n_{4'}$ is from 1 to 4,
$X_2$ is —O— or —NH—,
$R^2$ is H,
preferably (Y—ONO$_2$) and —(Y'—ONO$_2$) are each independently selected from:

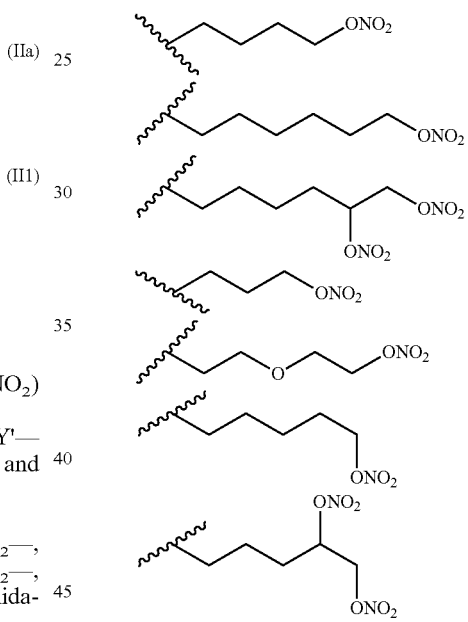

The following are preferred compounds according to the present invention:

(388)
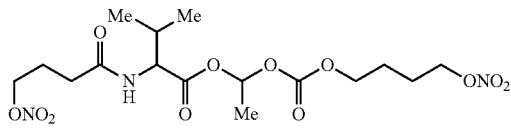

(389)
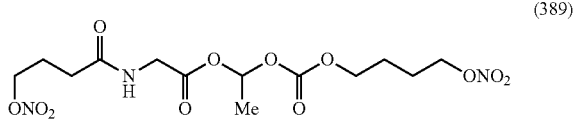

(390)
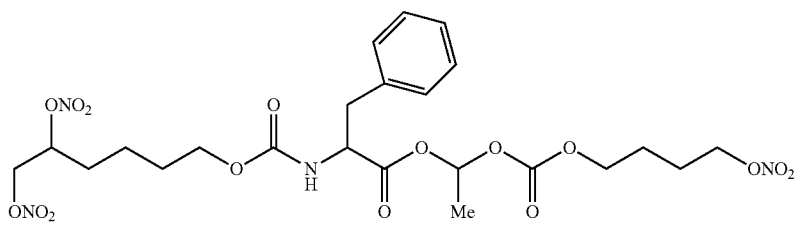

(391)
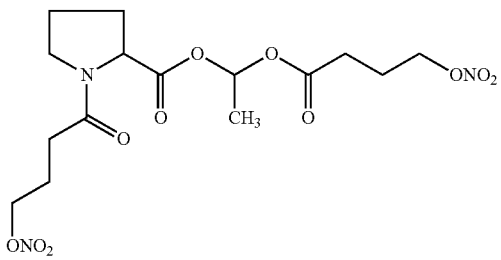

(392)
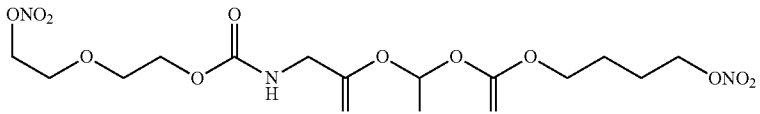

(393)
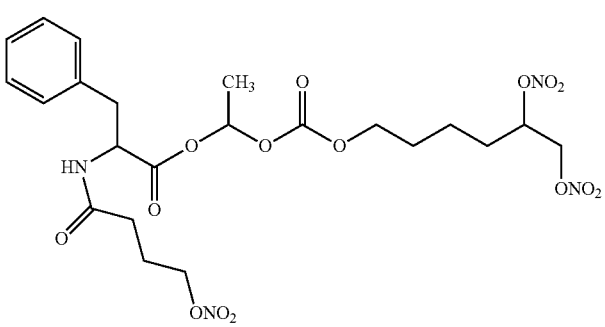

Another embodiment relates to compounds of formula (I)

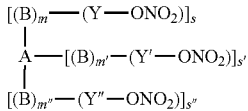 (I)

wherein s and s' are 1, and s" are 0, m and m' are 0,
A is a radical of formula

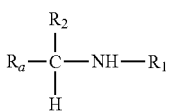 (IIa)

wherein $R_1$ is —C(O)$R_{1x}$ or —C(O)O$R_{1x}$ wherein $R_{1x}$ is one of the groups —(Y—ONO$_2$) or (Y'—ONO$_2$) of formula (I) wherein Y and Y' are below defined;

$R_2$ is —C(O)O$R_{2x}$, —C(O)NH$R_{2xx}$ or —C(O)N(CH$_3$)$R_{2xx}$, wherein $R_{2xx}$ and $R_{2x}$ are one of the groups —(Y—ONO$_2$) or —(Y'—ONO$_2$) of formula (I) wherein Y and Y' are below defined, more preferably $R_2$ is —C(O)O$R_{2x}$, —C(O)NH$R_{2xx}$;

$R_a$ is selected from:
b) HS—CH$_2$—;
c) $R_x$O—CH$_2$—, $R_x$O—CH(CH$_3$)—, ($R_x$O)-p-C$_6$H$_4$—CH$_2$—, wherein $R_x$ is H,
d) $R_g$C(O)CH$_2$— or $R_g$C(O)(CH$_2$)$_2$—, wherein $R_g$ is OH, (CH$_3$)$_3$CO—, or the group $R_{gg}$

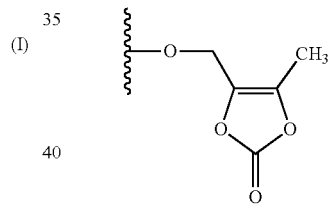 $R_{gg}$ e) $R_h$NH(CH$_2$)$_p$— or $R_i$NH(=NH)NH—(CH$_2$)$_3$—, wherein p is an integer equal to 3 or 4, $R_h$ is H, (CH$_3$)$_3$C—OC(O)—, $R_i$ is H;

Y and Y' of the groups (Y—ONO$_2$), —(Y'—ONO$_2$) are each independently selected from:
A)
a straight or branched C$_2$-C$_{10}$ alkylene
a straight or branched C$_2$-C$_{10}$ alkylene substituted with a —ONO$_2$ group;
E)

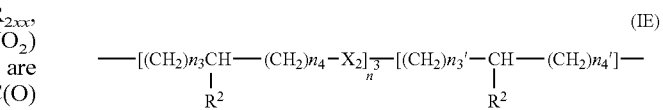 (IE)

wherein in formula (IE)
$n^3$ is from 1 to 5,
$n_3$ is 0 and $n_4$ is from 1 to 4,
$n_{3'}$ is 0 and $n_{4'}$ is from 1 to 4,
$X_2$ is —O— or —NH—,
$R^2$ is H, preferably (Y—ONO$_2$) and (Y'—ONO$_2$) are each independently selected from:

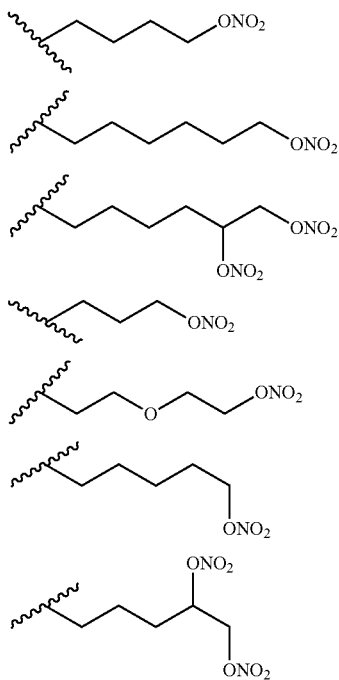

The following are preferred compounds according to the present invention:

(394)

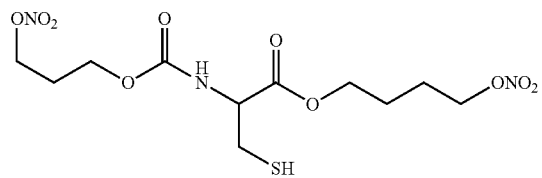

(395)

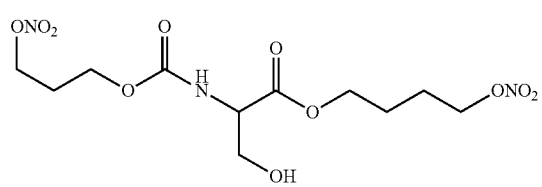

(396)

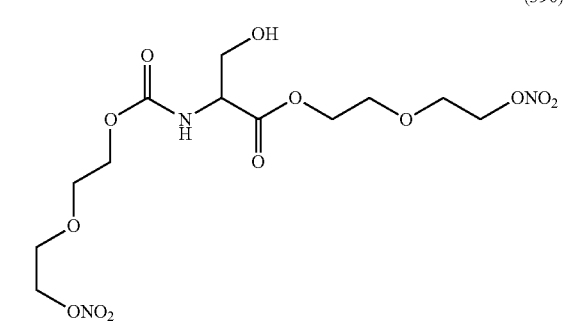

-continued (397)

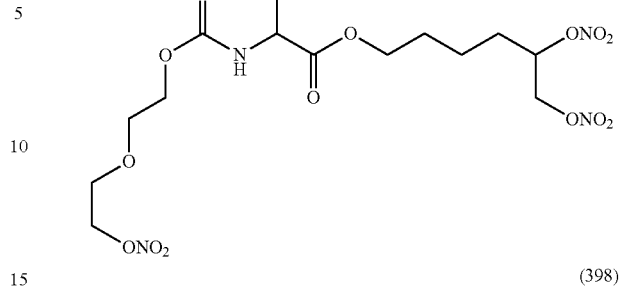

(398)

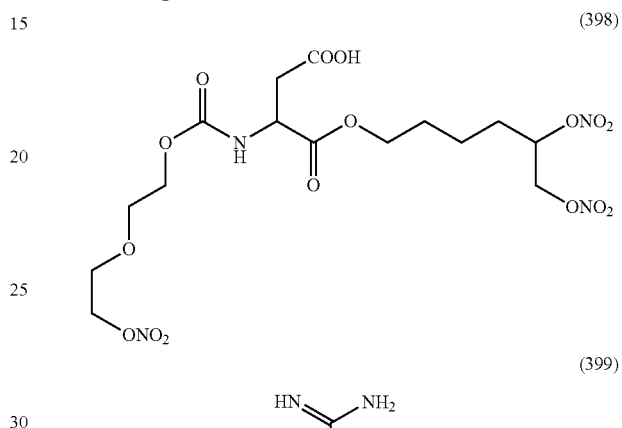

(399)

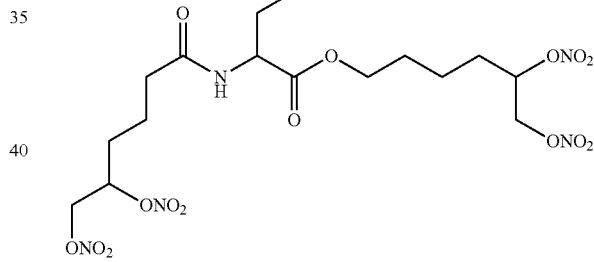

Another embodiment provides compounds of formula (I)

$$[(B)_m-(Y-ONO_2)]_s$$
$$A-[(B)_{m'}-(Y'-ONO_2)]_{s'}$$
$$[(B)_{m''}-(Y''-ONO_2)]_{s''}$$

(I)

wherein s is 1 and m is 0, s' and s" are 0,
A is a radical of formula

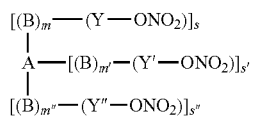

(IIa)

wherein R$_1$ is H or —C(O)O—C(CH$_3$)$_3$,
R$_2$ is —C(O)OH or R$_2$ is equal to the group R$_4$

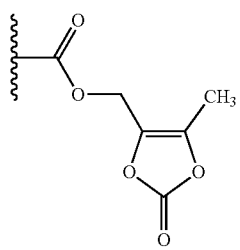

$R_a$ is selected from:
b) $R_{bx}C(O)$—S—$CH_2$—, $R_{bx}OC(O)$—S—$CH_2$—, $R_{bx}NH$—C(O)S—$CH_2$— wherein $R_{bx}$ is the group —(Y—$ONO_2$) of formula (I) wherein Y is below defined,
c) $R_xO$—$CH_2$—, $R_xO$—$CH(CH_3)$—, $(R_xO)$-p-$C_6H_4$—$CH_2$—, wherein $R_x$ is $R_{xx}C(O)$—, $R_{xx}OC(O)$— or $R_{xx}NHC(O)$— wherein $R_{xx}$ is the group —(Y—$ONO_2$) of formula (I) wherein Y is below defined;
d) $R_gC(O)CH_2$, $R_gC(O)(CH_2)_2$— wherein $R_g$ is $R_{gx}O$—, $R_{gxx}$—NH—, or $Rg_{xx}$—$N(CH_3)$—, wherein $R_{gx}$ and $R_{gxx}$ are the group —(Y—$ONO_2$) of formula (I) wherein Y is below defined, more preferably $R_g$ is $R_{gx}O$—, $R_{gxx}$—NH—
e) $R_hNH(CH_2)_p$— wherein p is 3 or 4, and $R_h$ is $R_{hh}C(O)$— or $R_{hh}OC(O)$— wherein $R_{hh}$ is the group —(Y—$ONO_2$) of formula (I) wherein Y is below defined;
or $R_iNH(=NH)NH$—$(CH_2)_2$— wherein $R_i$ is $R_{ii}C(O)$— or $R_{ii}OC(O)$— wherein $R_{ii}$ is the group —(Y—$ONO_2$) of formula (I) wherein Y is below defined;
Y of the group (Y—$ONO_2$) is selected from:
A)
    a straight or branched $C_2$-$C_{10}$ alkylene
    a straight or branched $C_2$-$C_{10}$ alkylene substituted with a —$ONO_2$ group;
E)

(IE)

—[$(CH_2)_{n3}$CH—$(CH_2)_{n4}$—$X_2$]$_{\overline{n}}$—[$(CH_2)_{n3'}$—CH—$(CH_2)_{n4'}$]—
        |                                                    |
        $R^2$                                           $R^2$ wherein in formula (IE)
$n^3$ is from 1 to 5,
$n_3$ is 0 and $n_4$ is from 1 to 4,
$n_{3'}$ is 0 and $n_{4'}$ is from 1 to 4,
$X_2$ is —O— or —NH—,
$R^2$ is H,
preferably (Y—$ONO_2$) is selected from:

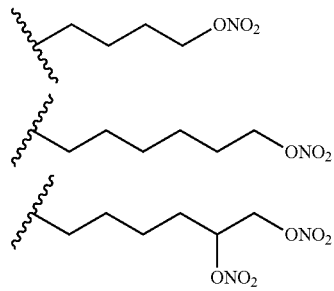

The following are preferred compounds according to the present invention:

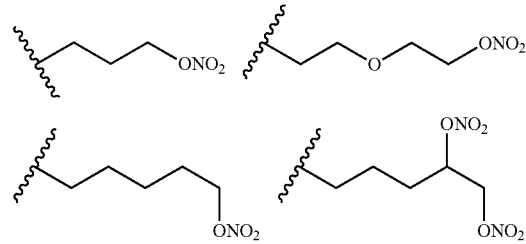

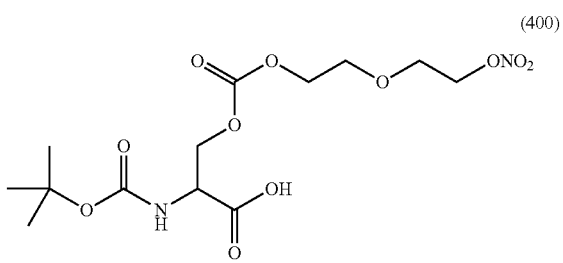

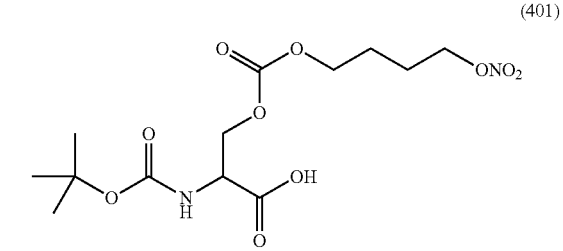

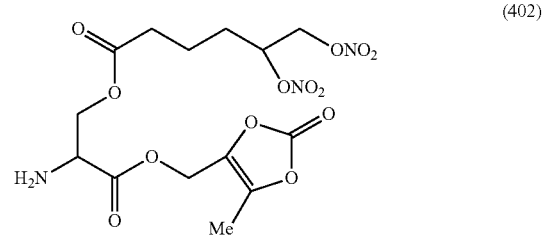

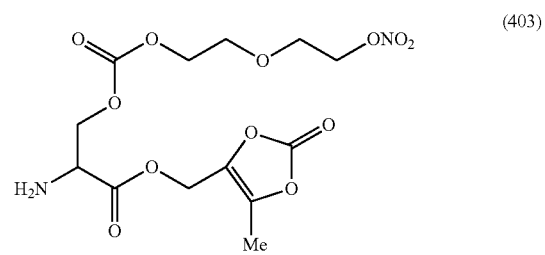

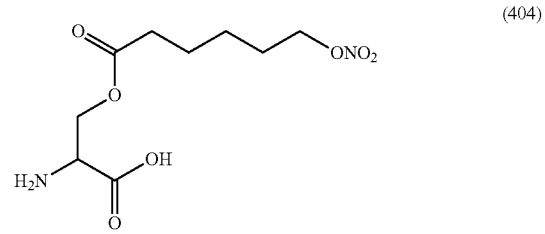

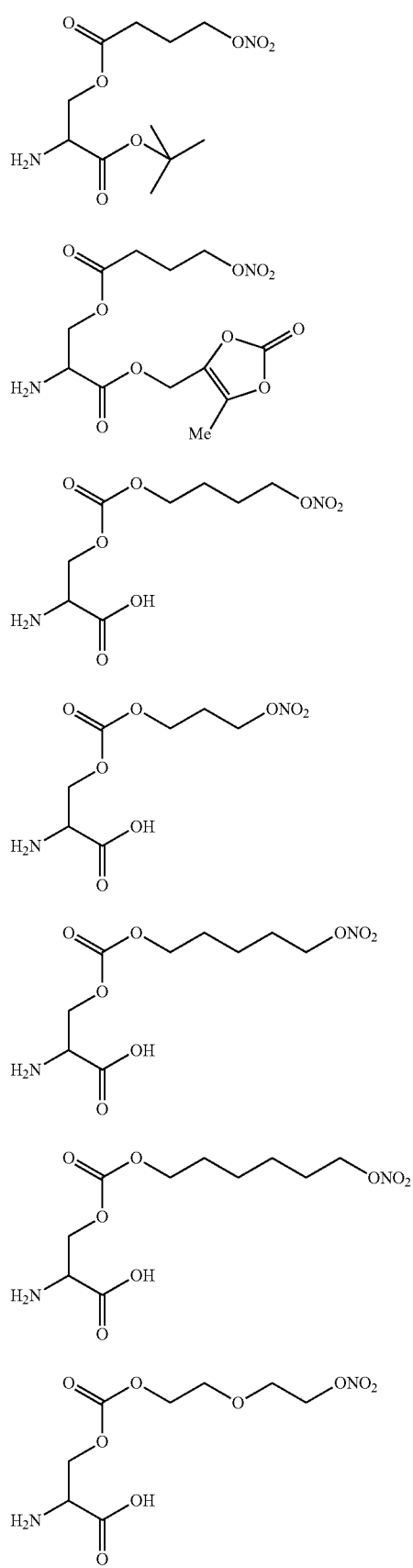
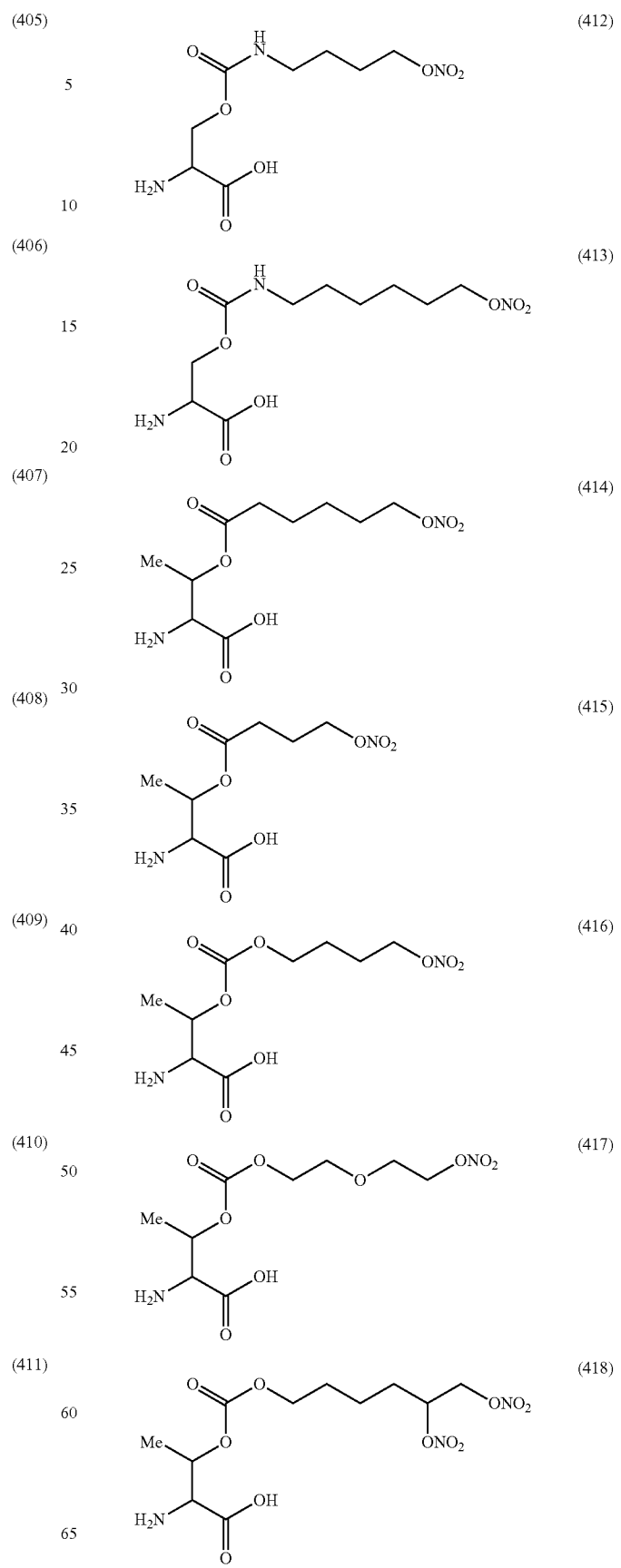

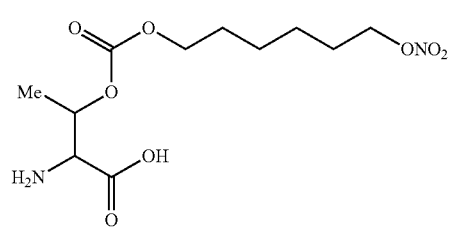
(419)
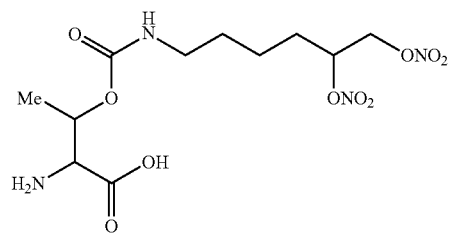
(420)
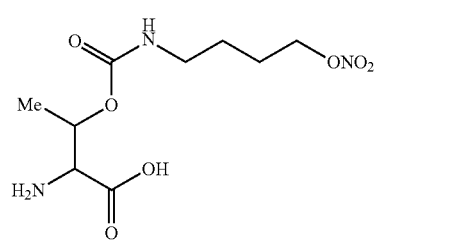
(421)
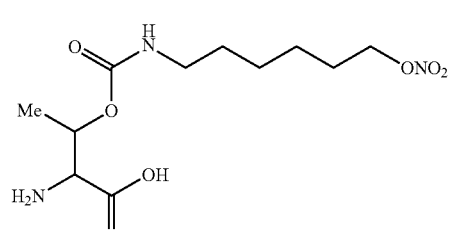
(422)
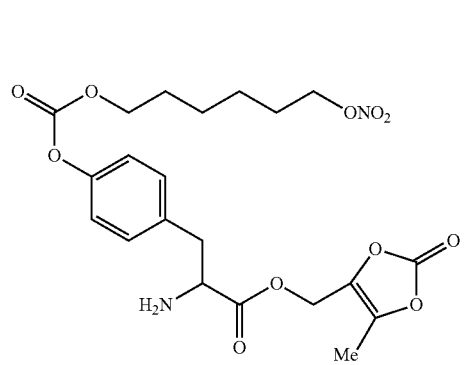
(423)
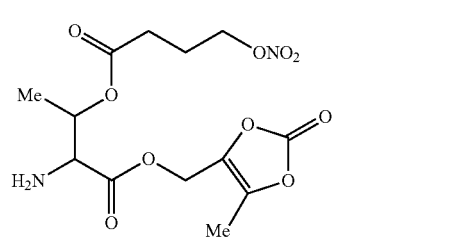
(424)
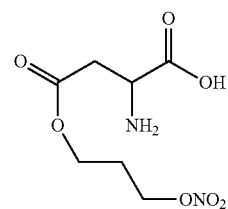
(425)
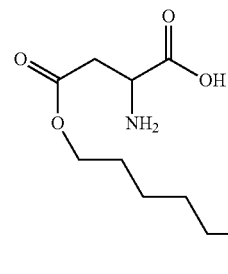
(426)
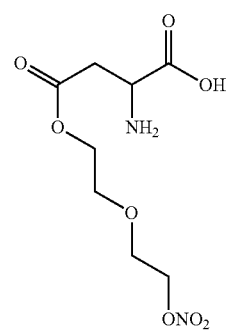
(427)
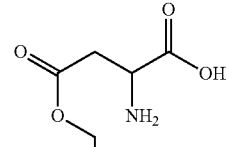
(428)
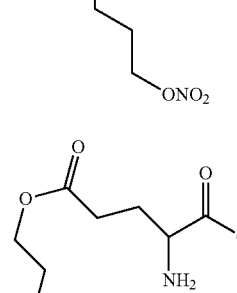
(429)
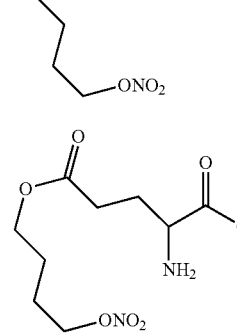
(430)

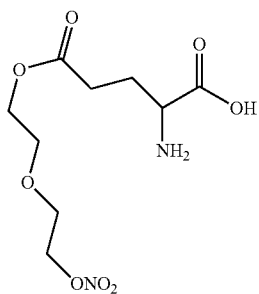
(431)
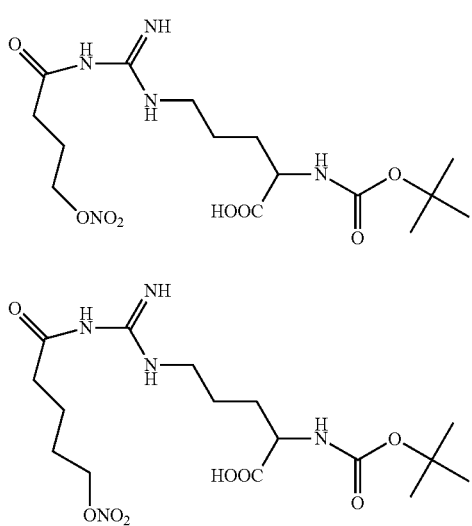
(432)
(433)
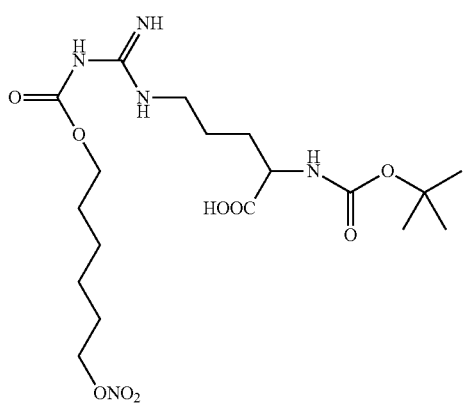
(434)
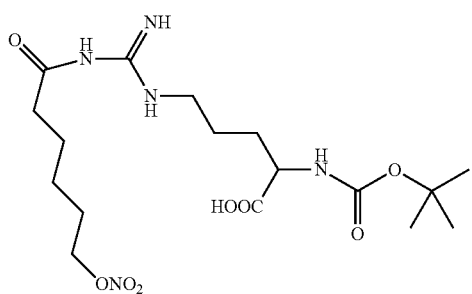
(435)
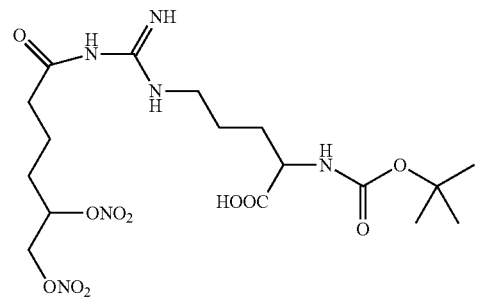
(436)
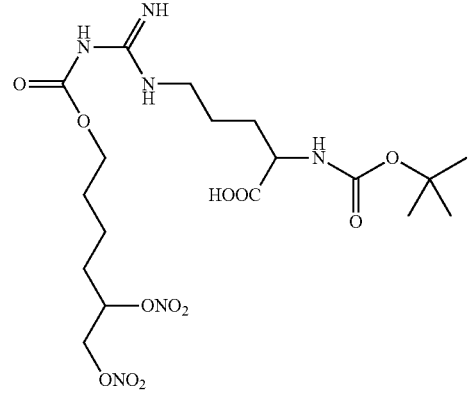
(437)
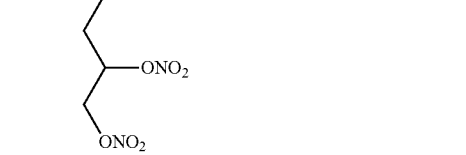
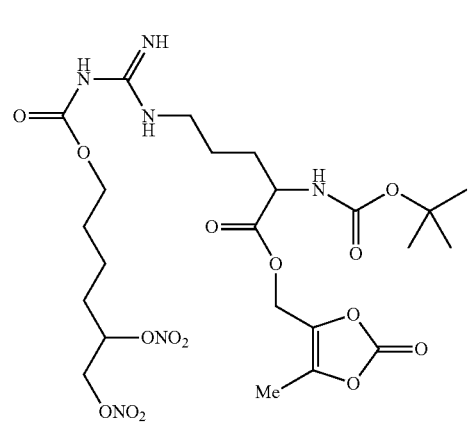
(438)
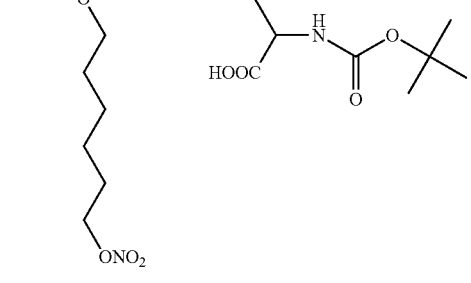
(439)

111
-continued
(440)
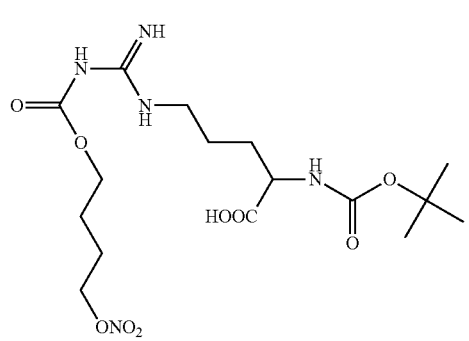
(441)
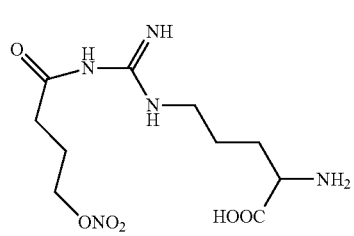
(442)
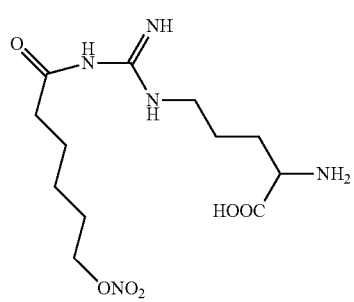
(443)
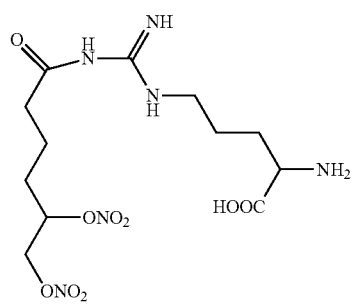
(444)
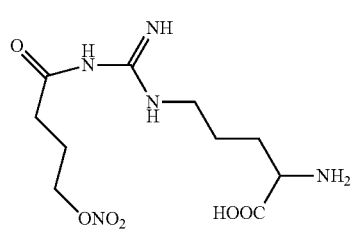
112
-continued
(445)
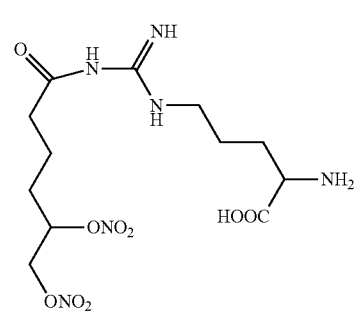
(446)
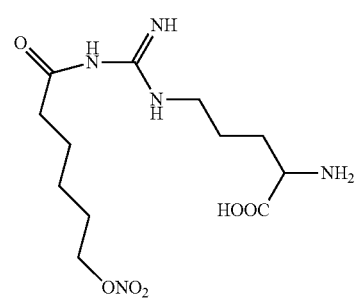
(447)
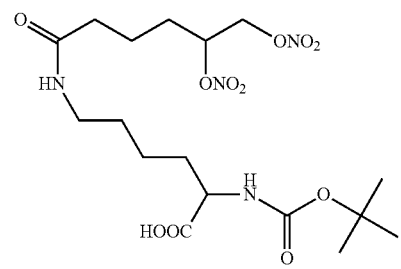
(448)
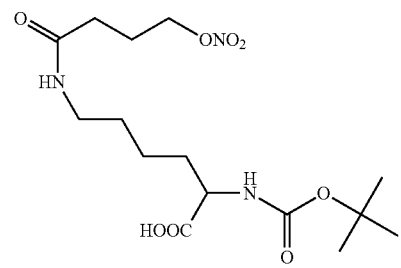
(449)
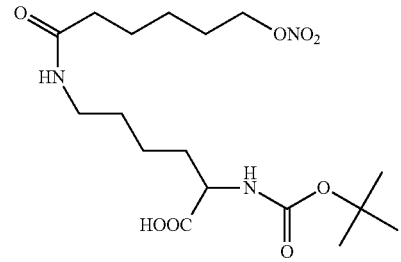

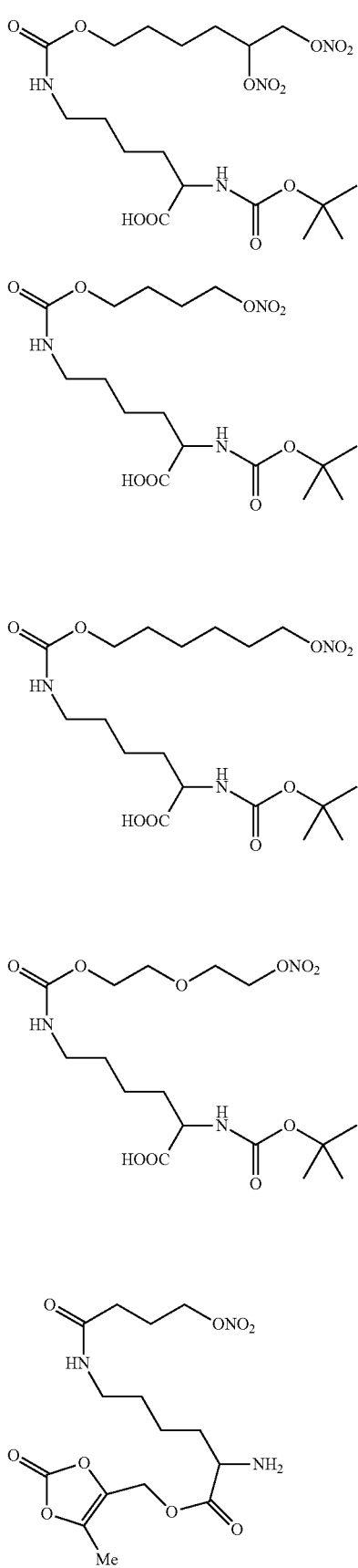
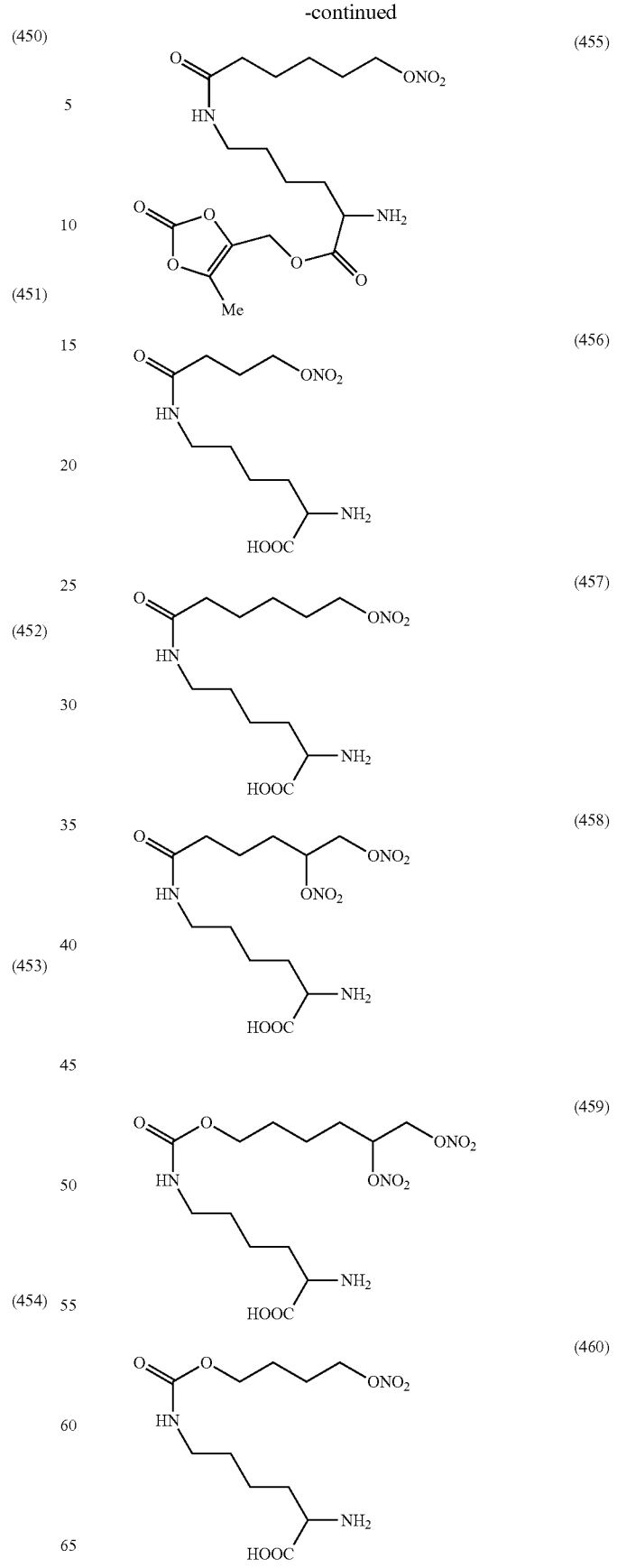

-continued

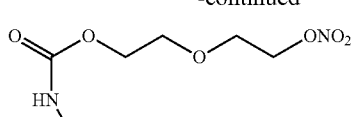
(461)

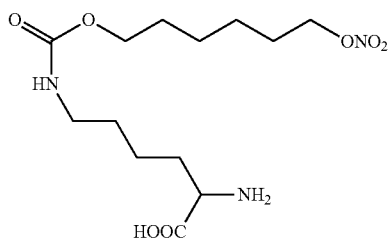
(462)

Another embodiment provides compounds of formula (I)

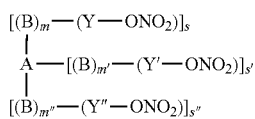
(I)

wherein s and s' are 1 and m, m' are 0, s" is 0,
A is a radical of formula

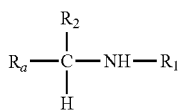
(IIa)

wherein $R_1$ is H or —C(O)O—C(CH$_3$)$_3$—,
$R_2$ is —C(O)OR$_{2x}$, —C(O)NHR$_{2xx}$, —C(O)N(CH$_3$)R$_{2xx}$ wherein R$_{2x}$ and R$_{2xx}$ are one of the groups —(Y—ONO$_2$) or —(Y'—ONO$_2$) of formula (I) wherein Y and Y' are below defined, more preferably $R_2$ is —C(O)OR$_{2x}$, —C(O)NHR$_{2x}$;
$R_a$ is selected from:
b) R$_{bx}$C(O)—S—CH$_2$—, R$_{bx}$OC(O)—S—CH$_2$—, R$_{bx}$NH—C(O)S—CH$_2$— wherein R$_{bx}$ is one of the groups —(Y—ONO$_2$) or —(Y'—ONO$_2$) wherein Y and Y' are below defined;
c) R$_x$O—CH$_2$—, R$_x$O—CH(CH$_3$)—, (R$_x$O)-p-C$_6$H$_4$—CH$_2$—, wherein R$_x$ is R$_{xx}$C(O)—, R$_{xx}$OC(O)— or R$_{xx}$-NHC(O)— wherein R$_{xx}$ is one the groups —(Y—ONO$_2$) or —(Y'—ONO$_2$) of formula (I) wherein Y and Y' are below reported;
e) R$_h$NH(CH$_2$)$_p$— wherein p is 3 or 4, and R$_h$ is R$_{hh}$C(O)— or R$_{hh}$OC(O)— wherein R$_{hh}$ is one the groups —(Y—ONO$_2$) or —(Y'—ONO$_2$) of formula (I) wherein Y and Y' are below reported;
or $R_a$ is R$_i$NH(=NH)NH—(CH$_2$)$_2$— wherein R$_i$ is R$_{ii}$C(O)— or R$_{ii}$OC(O)— wherein R$_{ii}$ is one the groups —(Y—ONO$_2$) or —(Y'—ONO$_2$) of formula (I) wherein Y and Y' are below defined;
Y and Y' of the groups (Y—ONO$_2$) or —(Y'—ONO$_2$) are each independently selected from:

A)
a straight or branched C$_2$-C$_{10}$ alkylene
a straight or branched C$_2$-C$_{10}$ alkylene substituted with a —ONO$_2$ group;

E)

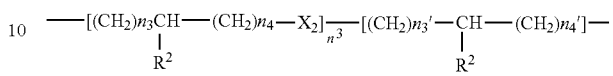
(IE)

wherein in formula (IE)
$n^3$ is from 1 to 5,
$n_3$ is 0 and $n_4$ is from 1 to 4,
$n_{3'}$ is 0 and $n_{4'}$ is from 1 to 4,
X$_2$ is —O— or —NH—,
R$^2$ is H,
preferably —(Y—ONO$_2$) and —(Y'—ONO$_2$) are each independently selected from:

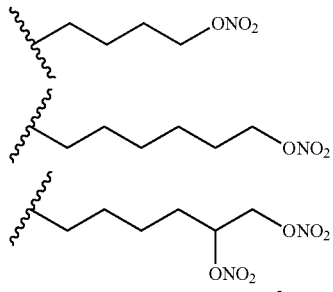

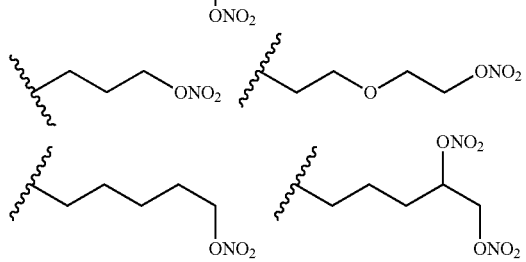

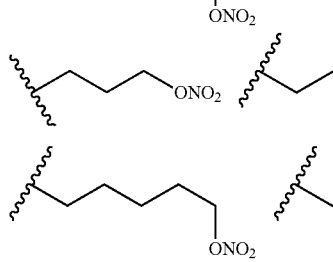

The following are preferred compounds according to the present invention:

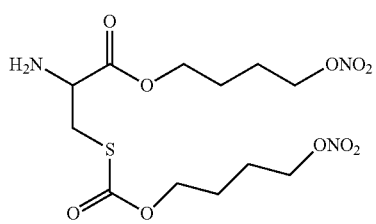
(463)

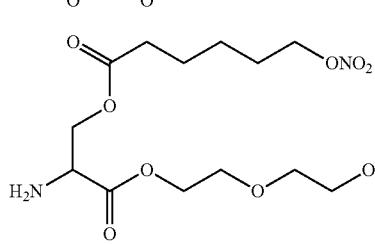
(464)

-continued (465)
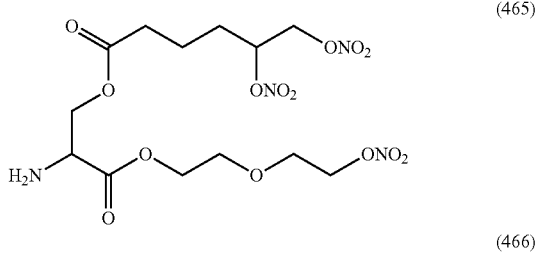

(466)
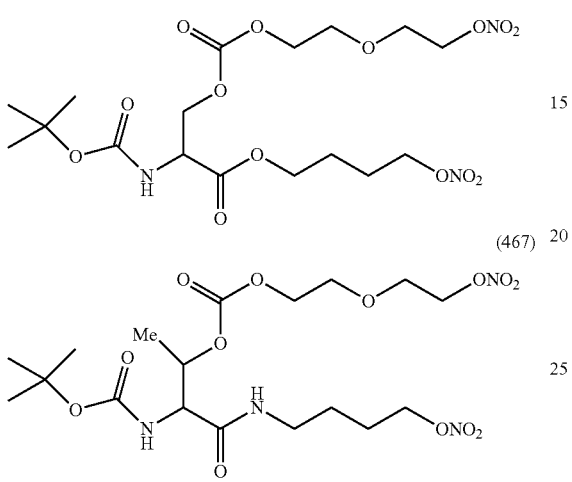

(467)

Another embodiment provides compounds of formula (I)

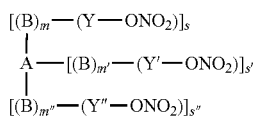 (I)

wherein s and s' are 1 and m, m' are 0, s" is 0,
A is a radical of formula

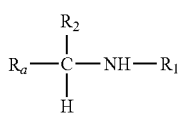 (IIa)

wherein $R_1$ is H or —C(O)O—C(CH$_3$)$_3$,
$R_2$ is —C(O)O$R_{2x}$, —C(O)NH$R_{2xx}$, —C(O)N(CH$_3$)$R_{2xx}$ wherein $R_{2x}$ and $R_{2xx}$ are one of the groups —(Y—ONO$_2$) or —(Y'—ONO$_2$) of formula (I) wherein Y and Y' are below defined, more preferably $R_2$ is —C(O)O$R_{2x}$, —C(O)NH$R_{2xx}$;
$R_a$ is selected from:
d) $R_gC(O)CH_2$—, $R_gC(O)(CH_2)_2$—, wherein $R_g$ is $R_{gx}O$—, $R_{gxx}$—NH—, $R_{gxx}N(CH_3)$—, wherein $R_{gx}$ and $R_{gxx}$ are one of the groups —(Y—ONO$_2$) or —(Y'—ONO$_2$) of formula (I) wherein Y and Y' are below defined, more preferably $R_g$ is $R_{gx}O$— or $R_{gxx}$—NH—;
Y and Y' of the groups (Y—ONO$_2$) and —(Y'—ONO$_2$) are each independently selected from:
A)
  a straight or branched C$_2$-C$_{10}$ alkylene
  a straight or branched C$_2$-C$_{10}$ alkylene substituted with a —ONO$_2$ group;

E)

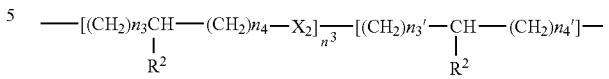 (IE)

wherein in formula (IE)
$n^3$ is from 1 to 5,
$n_3$ is 0 and $n_4$ is from 1 to 4,
$n_{3'}$ is 0 and $n_{4'}$ is from 1 to 4,
$X_2$ is —O— or —NH—,
$R^2$ is H,
preferably (Y—ONO$_2$) and (Y'—ONO$_2$) are each independently selected from:

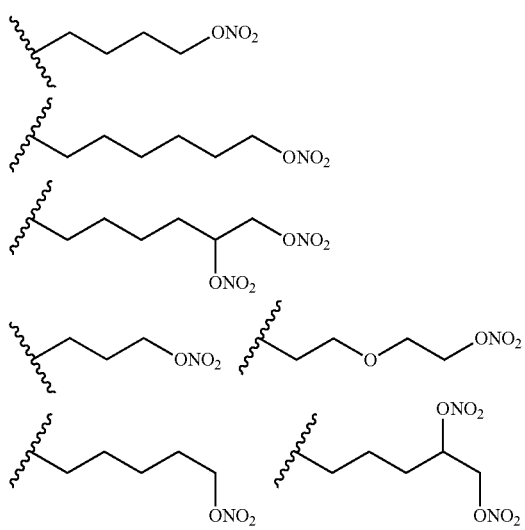

The following are preferred compounds according to the present invention:

(468)
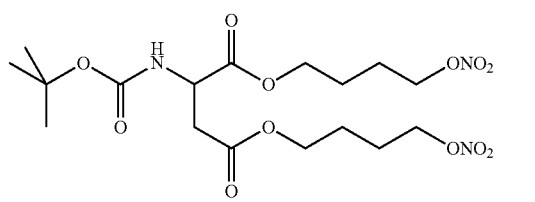

(469)
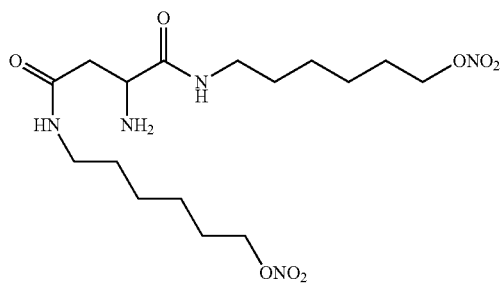

119
-continued
(470)
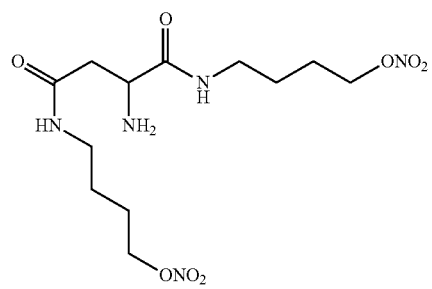
(471)
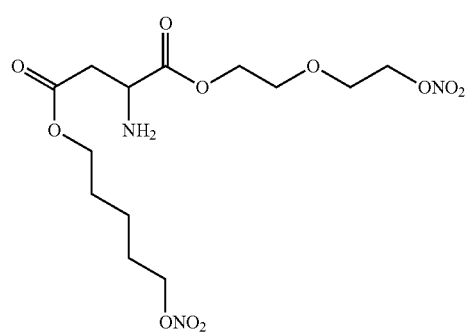
(472)
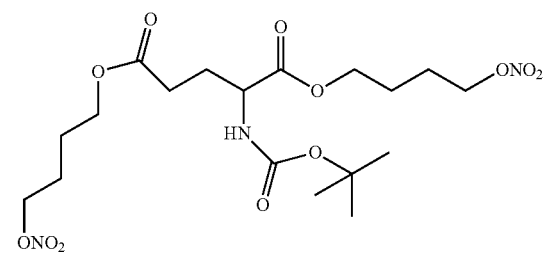
(473)
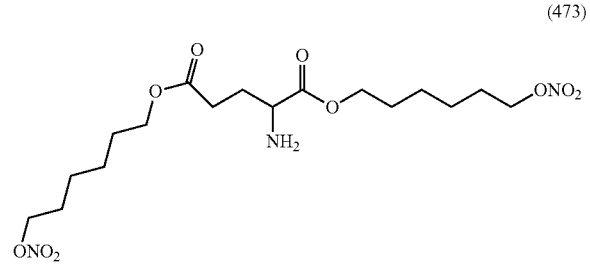
(474)
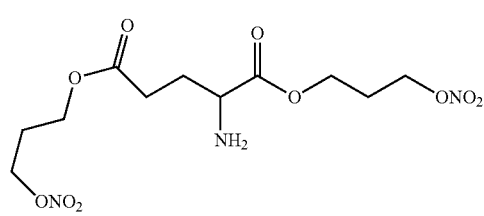
120
-continued
(475)
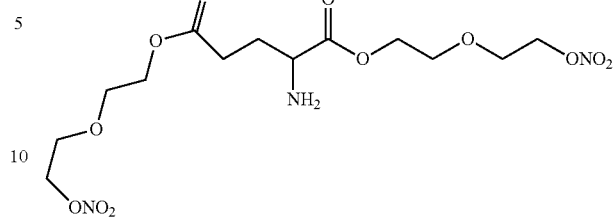
(476)
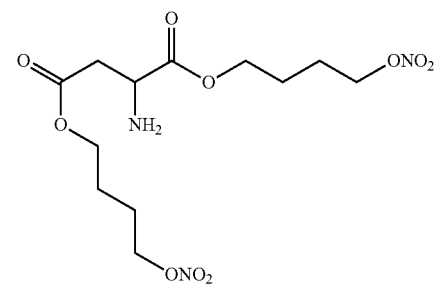
(477)
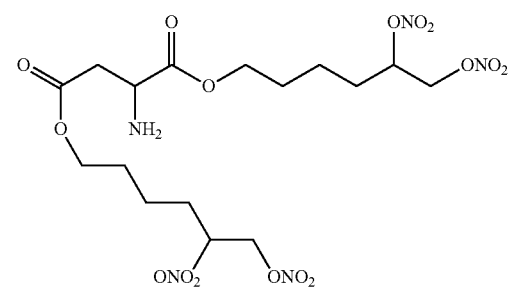
(478)
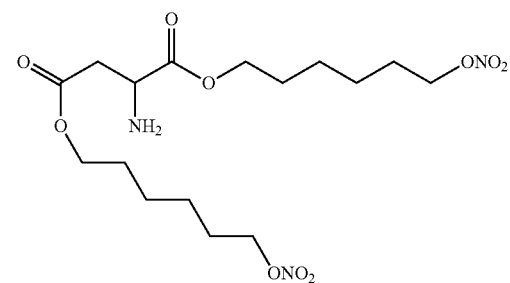
(479)
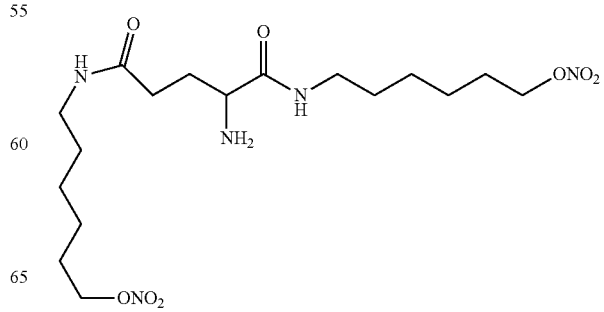

(480)

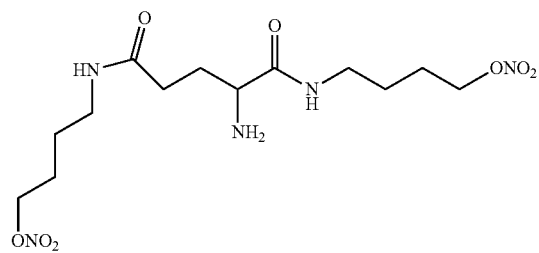

(481)

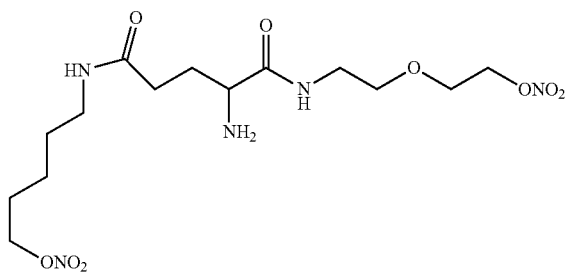

Another embodiment provides compounds of formula (I)

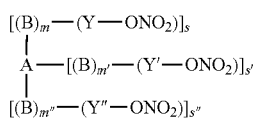
(I)

wherein s, s' and s" are 1, m, m' and m" are 0,
A is a radical of formula

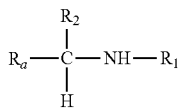
(IIa)

wherein $R_1$ is $-C(O)R_{1x}$, $-C(O)OR_{1x}$ wherein $R_{1x}$ is one of the groups $-(Y-ONO_2)$ or $-(Y'-ONO_2)$ or $-(Y"-ONO_2)$ of formula (I) wherein Y, Y' and Y" are below defined;
$R_2$ is $-C(O)OR_{2x}$, $-C(O)NHR_{2xx}$, $-C(O)N(CH_3)R_{2xx}$ wherein $R_{2x}$ and $R_{2xx}$ are one of the groups $-(Y-ONO_2)$ or $-(Y'-ONO_2)$ or $-(Y"-ONO_2)$ of formula (I) wherein Y, Y' and Y" are below reported, and more preferably $R_2$ is $-C(O)OR_{2x}$, $-C(O)NHR_{2x}$;
$R_a$ is selected from:
b) $R_{bx}C(O)-CH_2-$, $R_{bx}OC(O)-S-CH_2-$, $R_{bx}NH-C(O)S-CH_2-$ wherein $R_{bx}$ is one of the groups $-(Y-ONO_2)$ or $-(Y'-ONO_2)$ or $-(Y"-ONO_2)$ of formula (I) wherein Y, Y' and Y" are below reported;
c) $R_xO-CH_2-$, $R_xO-CH(CH_3)-$, $(R_xO)-p-C_6H_4-CH_2-$, wherein $R_x$ is $R_{xx}C(O)-$, $R_{xx}OC(O)-$ or $R_{xx}NHC(O)-$ wherein $R_{xx}$ is one of the groups $-(Y-ONO_2)$ or $-(Y'-ONO_2)$ or $-(Y"-ONO_2)$ of formula (I) wherein Y, Y' and Y" are below reported;
d) $R_gC(O)CH_2$, $R_gC(O)(CH_2)_2-$, wherein $R_g$ is $R_{gx}O-$, $R_{gxx}-NH-$, $R_{gxx}-N(CH_3)-$, wherein $R_{gx}$ and $R_{gxx}$ are one of the groups $-(Y-ONO_2)$ or $-(Y'-ONO_2)$ or $-(Y"-ONO_2)$ of formula (I) wherein Y, Y' and Y" are below defined, more preferably $R_g$ is $R_{gx}O-$ or $R_{gxx}NH-$,
e) $R_hNH(CH_2)_p-$ wherein p is 3 or 4, and $R_h$ is $R_{hh}C(O)-$ or $R_{hh}OC(O)-$ wherein $R_{hh}$ is one of the groups $-(Y-ONO_2)$ or $-(Y'-ONO_2)$ or $-(Y"-ONO_2)$ of formula (I) wherein Y, Y' and Y" are below defined,
or $R_a$ is $R_iNH(=NH)NH-(CH_2)_3-$ wherein $R_i$ is $R_{ii}C(O)-$ or $R_{ii}OC(O)-$ wherein $R_{ii}$ is one of the groups $-(Y-ONO_2)$ or $-(Y'-ONO_2)$ or $-(Y"-ONO_2)$ of formula (I) wherein Y, Y' and Y" are below reported;
Y, Y' and Y" of the groups $(Y-ONO_2)$ or $-(Y'-ONO_2)$ or $-(Y"-ONO_2)$ are each independently selected from:
A)
  a straight or branched $C_2-C_{10}$ alkylene
  a straight or branched $C_2-C_{10}$ alkylene substituted with a $-ONO_2$ group;
E)

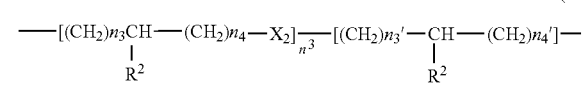
(IE)

wherein in formula (IE)
$n^3$ is from 1 to 5,
$n_3$ is 0 and $n_4$ is from 1 to 4,
$n_{3'}$ is 0 and $n_{4'}$ is from 1 to 4,
$X_2$ is $-O-$ or $-NH-$,
$R^2$ is H,
preferably $-(Y-ONO_2)$, $-(Y'-ONO_2)$ and $-(Y"-ONO_2)$ are each independently selected from:

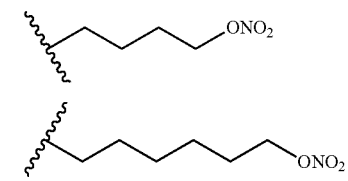

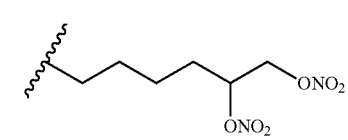

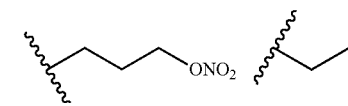

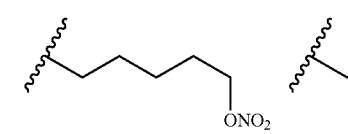

The following are preferred compounds according to the present invention:
(482)
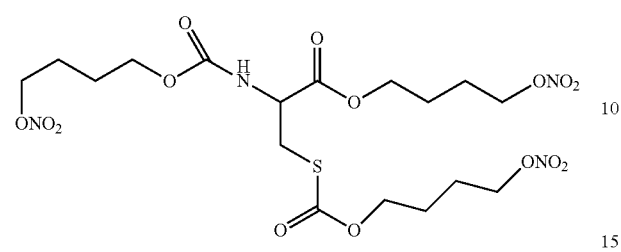
(483)
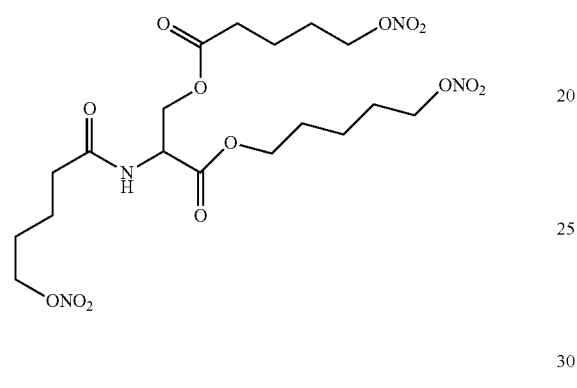
(484)
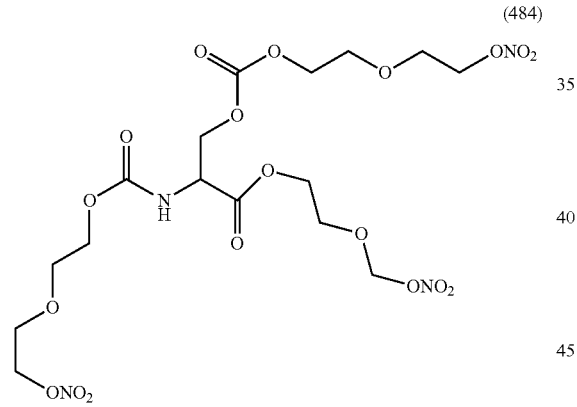
(485)
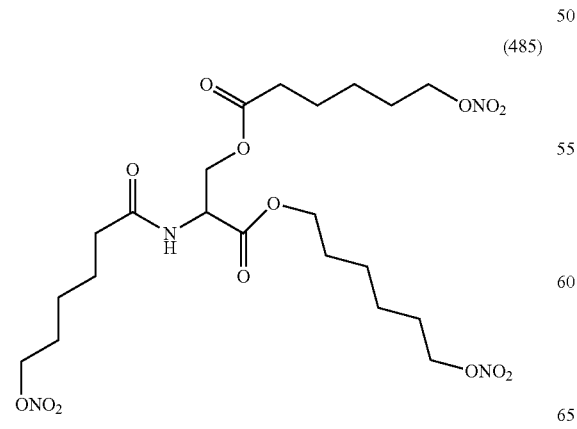
(486)
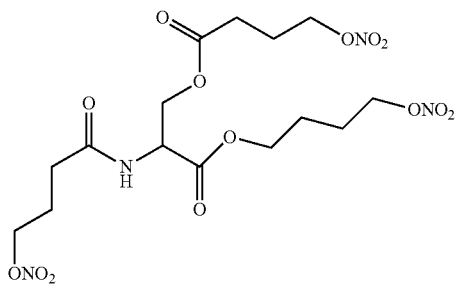
(487)
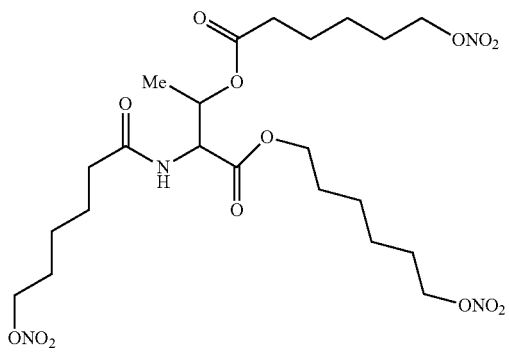
(488)
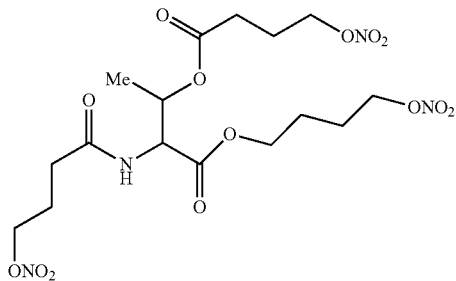
(489)
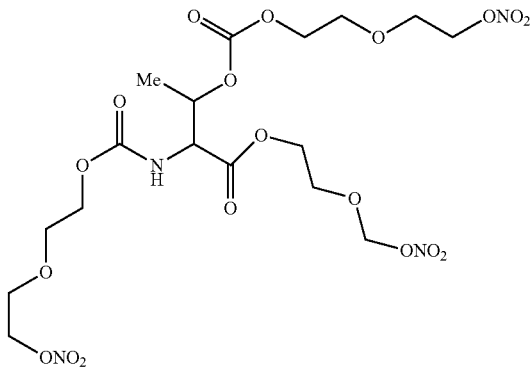

-continued
(490)
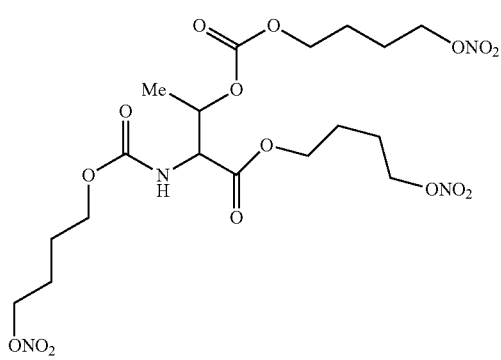
(491)
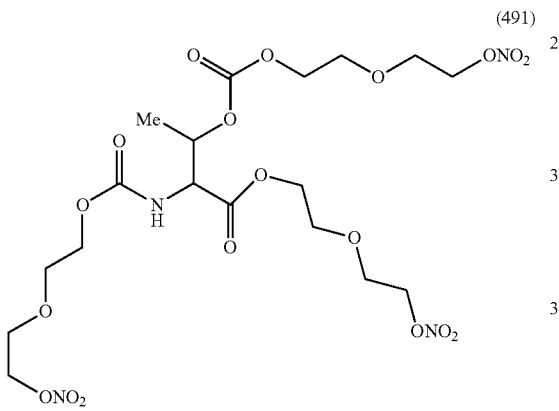
(492)
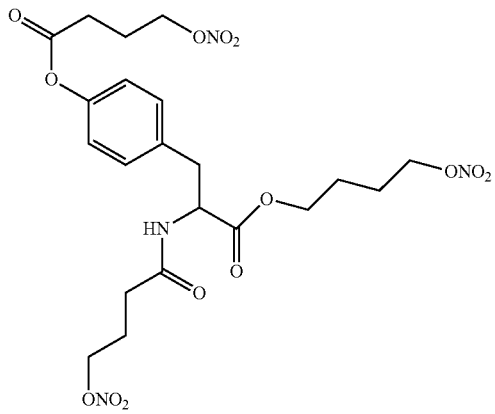
(493)
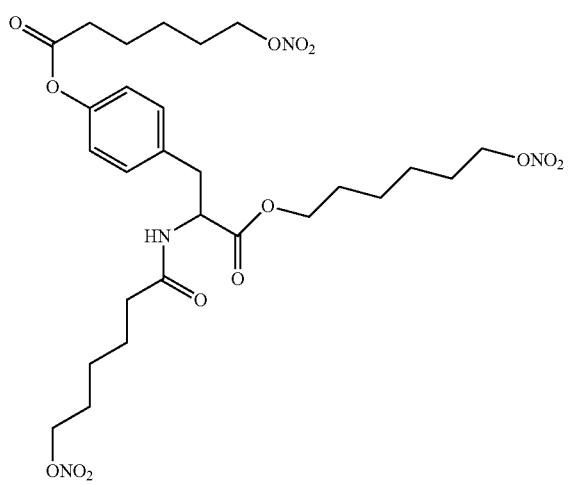
(494)
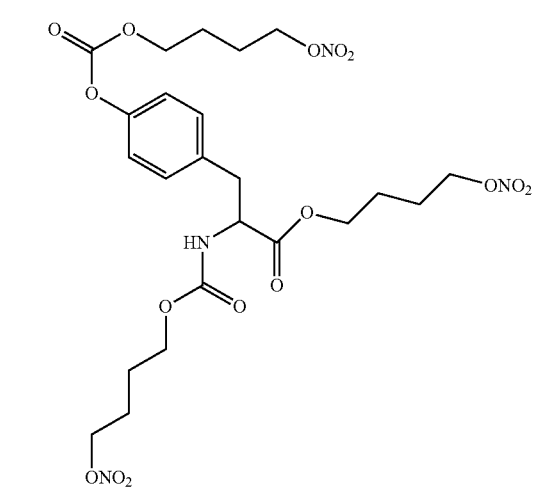
(495)
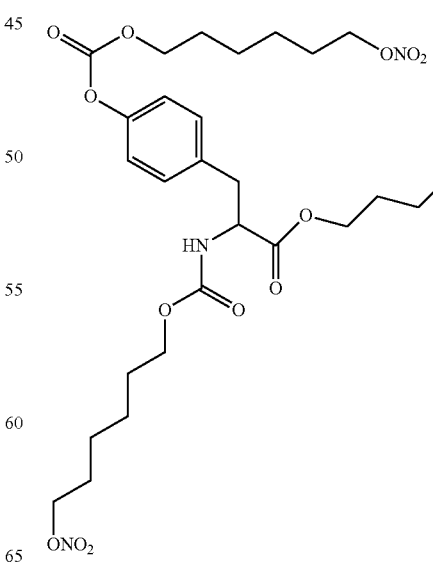

(496) 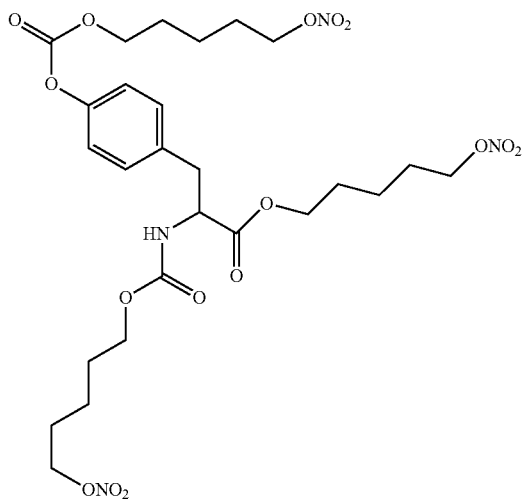

(497) 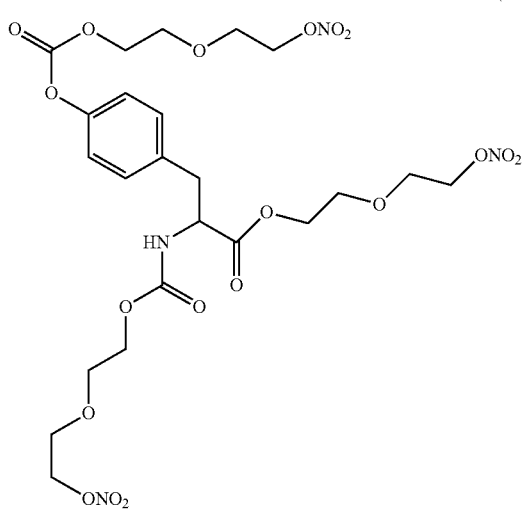

(498) 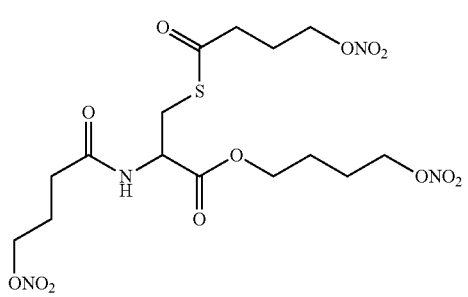

(499) 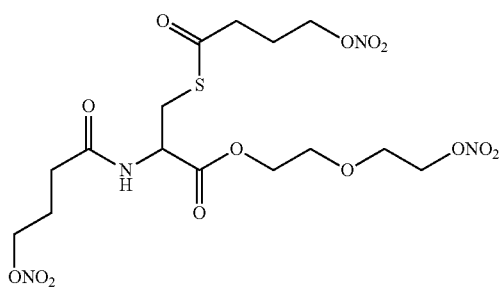

(500) 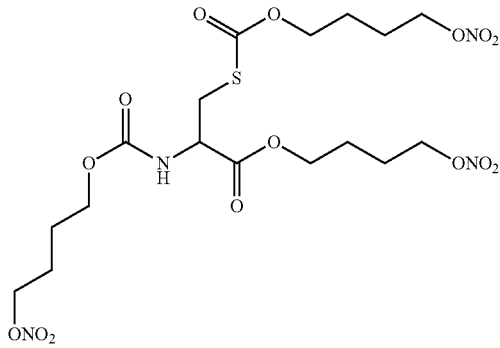

(501) 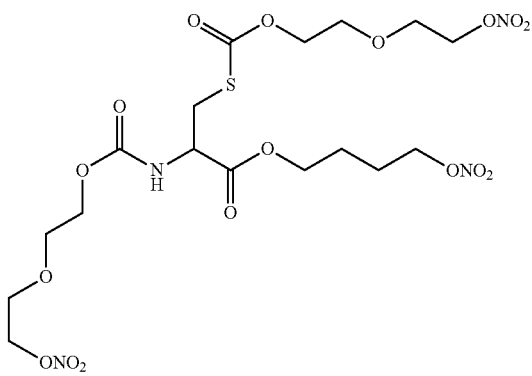

Another embodiment provides compounds or formula (I)

$$A \begin{matrix} [(B)_m-(Y-ONO_2)]_s \\ [(B)_{m'}-(Y'-ONO_2)]_{s'} \\ [(B)_{m''}-(Y''-ONO_2)]_{s''} \end{matrix} \qquad (I)$$

wherein s and s' are 1, m and m' are 0, s'' is 0,
A is a radical of formula $$H-\underset{R_s}{\overset{NH-R_1}{\underset{|}{C}}}-CH_2-R_3 \qquad (IIs)$$

wherein $R_1$ is H or —C(O)—OC(CH$_3$)$_3$—;

$R_3$ is —OC(O)R$_{3x}$, OC(O)OR$_{3x}$, —OC(O)—NHR$_{3x}$, wherein R$_{3x}$ is one of the groups —(Y—ONO$_2$) or —(Y'—ONO$_2$) of formula (I) wherein Y and Y' are below defined;

$R_3$ is selected from:

b") R$_{bx}$—C(O)—S—CH$_2$—, R$_{bx}$—OC(O)—S—CH$_2$—, R$_{bx}$—NH—C(O)S—CH$_2$— wherein R$_{bx}$ is one of the groups —(Y—ONO$_2$) or —(Y'—ONO$_2$) of formula (I) wherein Y and Y' are below defined;

c") R$_x$O—CH$_2$—, R$_x$O—CH(CH$_3$)—, (R$_x$O)-p-C$_6$H$_4$—CH$_2$—, wherein R$_x$ is R$_{xx}$C(O)—, R$_{xx}$OC(O)—, R$_{xx}$NHC(O)— wherein R$_{xx}$ is one of the groups —(Y—ONO$_2$) or —(Y'—ONO$_2$) of formula (I) wherein Y and Y' are below defined;

d") $R_gC(O)CH_2$, $R_gC(O)(CH_2)_2$—, wherein $R_g$ is $R_{gx}O$— or $R_{gxx}NH$— wherein $R_{gx}$ and $R_{gxx}$ are one of the groups —(Y—$ONO_2$) or —(Y'—$ONO_2$) of formula (I) wherein Y and Y' are below defined;

e''') $R_hNH(CH_2)_p$— wherein p is 3 or 4 and $R_h$ is $R_{hh}C(O)$— or $R_{hh}OC(O)$— wherein $R_{hh}$ is one of the groups —(Y—$ONO_2$) or —(Y'—$ONO_2$) of formula (I) wherein Y and Y' are below defined, or $R_iNH(=NH)NH$—$(CH_2)_3$—, wherein $R_i$ is $R_{ii}C(O)$— or $R_{ii}OC(O)$— wherein $R_{ii}$ is one of the groups —(Y—$ONO_2$) or —(Y'—$ONO_2$) of formula (I) wherein Y and Y' are below defined;

Y and Y' of the groups (Y—$ONO_2$) or —(Y'—$ONO_2$) are each independently selected from:

A)
 a straight or branched $C_2$-$C_{10}$ alkylene
 a straight or branched $C_2$-$C_{10}$ alkylene substituted with a —$ONO_2$ group;

E)

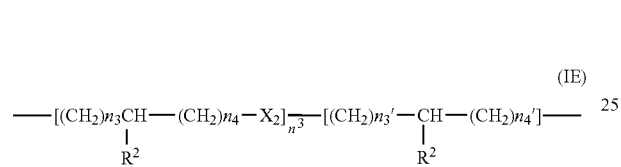

wherein in formula (IE)
$n^3$ is from 1 to 5,
$n_3$ is 0 and $n_4$ is from 1 to 4,
$n_{3'}$ is 0 and $n_{4'}$ is from 1 to 4,
$X_2$ is —O— or —NH—,
$R^2$ is H,
preferably (Y—$ONO_2$) and (Y'—$ONO_2$) are each independently selected from:

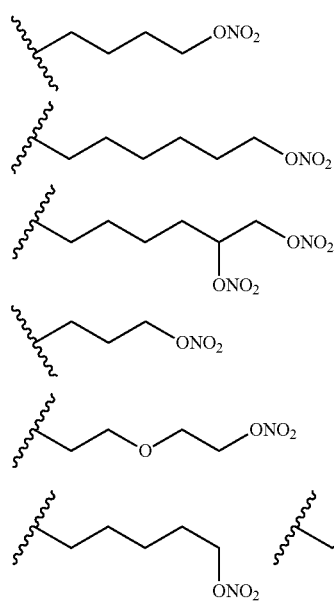

The following are preferred compounds according to the present invention:

(502)

(503)

(504)

(505)

(506)

Another embodiment provides compounds of formula (I)

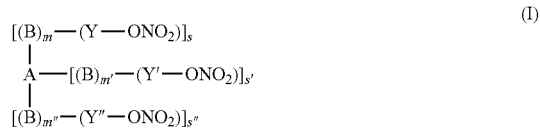
(I)

wherein s is 1, m is 0, s' and s" are 0,
A is a radical of formula

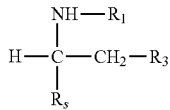 (IIs)

wherein $R_1$ is H or —C(O)—OC(CH$_3$)$_3$;
$R_3$ is —OC(O)$R_{3x}$, OC(O)O$R_{3x}$, —OC(O)—NH$R_{3x}$, wherein $R_{3x}$ is the group —(Y—ONO$_2$) of formula (I) wherein Y is below reported;
$R_s$ is selected from:
a") H, CH$_3$, isopropyl, isobutyl, sec-butyl, methylthio-(CH$_2$)$_2$—, benzyl, C$_6$H$_5$—CH$_2$—CH$_2$—, 3-triptophanyl-CH$_2$—, NH$_2$—CO—CH$_2$—, NH$_2$—CO—(CH$_2$)$_2$—, 4-imidazolyl-CH$_2$—;
Y of the group (Y—ONO$_2$) is selected from:
A)
    a straight or branched C$_2$-C$_{10}$ alkylene
    a straight or branched C$_2$-C$_{10}$ alkylene substituted with a —ONO$_2$ group;
E)

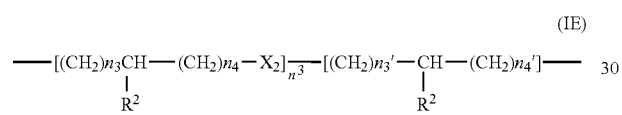 (IE)

wherein in formula (IE)
$n^3$ is from 1 to 5,
$n_3$ is 0 and $n_4$ is from 1 to 4,
$n_{3'}$ is 0 and $n_{4'}$ is from 1 to 4,
$X_2$ is —O— or —NH—,
$R^2$ is H,
preferably (Y—ONO$_2$) is selected from:

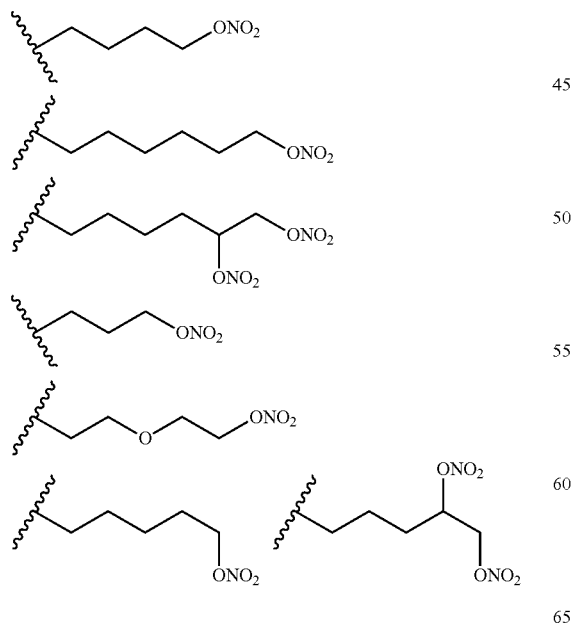

The following are preferred compounds according to the present invention:

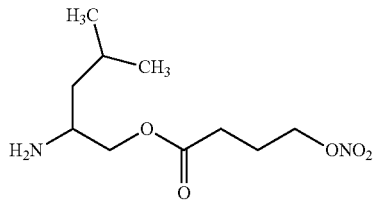 (507)

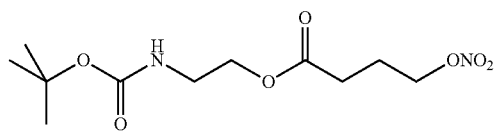 (508)

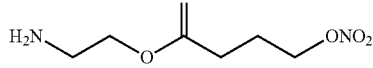 (509)

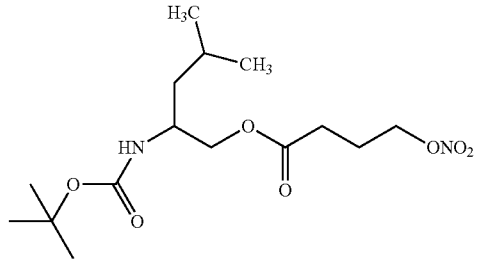 (510)

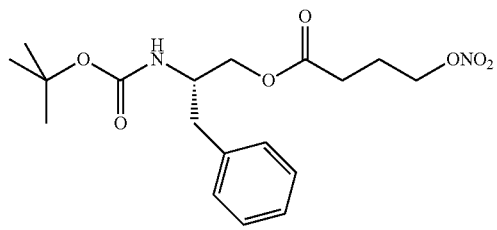 (511)

Another embodiment provides compounds or formula (I)

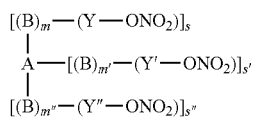 (I)

wherein s is 1 and m is 0, s' and s" are 0,
A is a radical of formula (IIq)

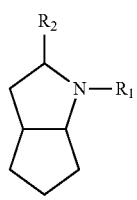 (IIq)

$R_1$ is H or —C(O)O—C(CH$_3$)$_3$—,
$R_2$ is —C(O)OR$_{2x}$, —C(O)NHR$_{2x}$ —C(O)N(CH$_3$) wherein R$_{2x}$ is the group —(Y—ONO$_2$) of formula (I) wherein Y is below reported, more preferably R$_2$ is —C(O)OR$_{2x}$ or —C(O)NHR$_{2x}$;
Y of the group (Y—ONO$_2$) is selected from:

A)
   a straight or branched C$_2$-C$_{10}$ alkylene
   a straight or branched C$_2$-C$_{10}$ alkylene substituted with a —ONO$_2$ group;

E)

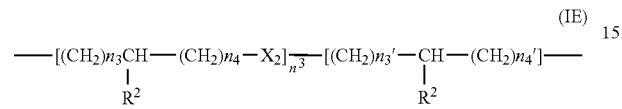
(IE)

wherein in formula (IE)
$n^3$ is from 1 to 5,
$n_3$ is 0 and $n_4$ is from 1 to 4,
$n_{3'}$ is 0 and $n_{4'}$ is from 1 to 4,
X$_2$ is —O— or —NH—,
R$^2$ is H,
preferably (Y—ONO$_2$) is selected from:

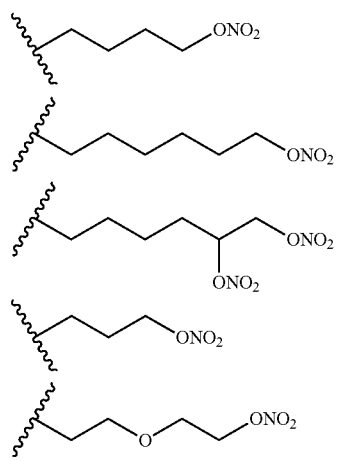

The following are preferred compounds according to the present invention:

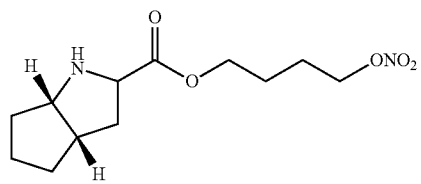
(512)

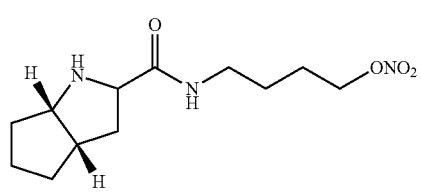
(513)

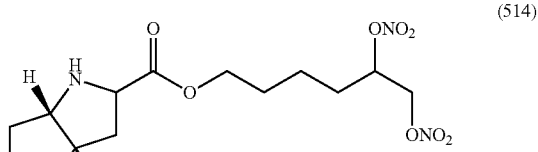
(514)

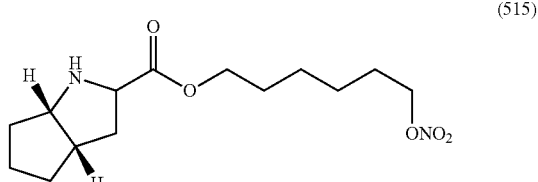
(515)

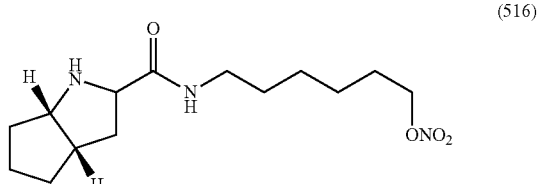
(516)

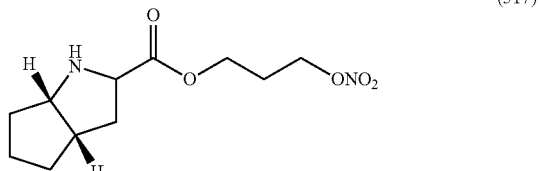
(517)

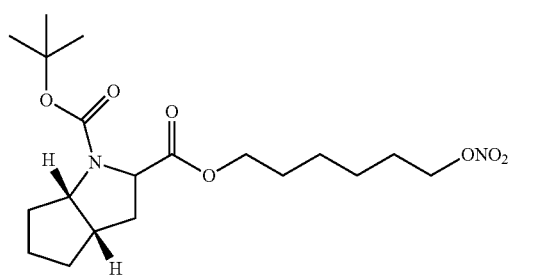
(518)

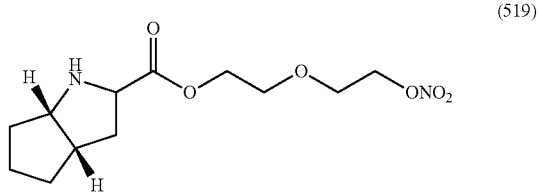
(519)

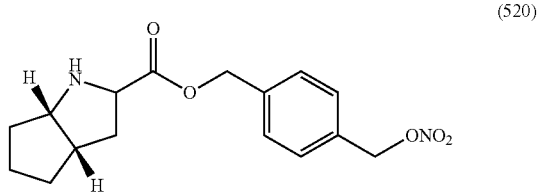
(520)

Another embodiment relates to compounds of formula (I)

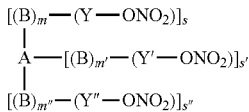  (I)

wherein s is 1 and m is 0, s' and s" are 0,
A is a radical of formula (IIu)

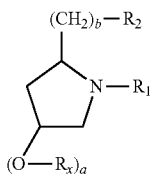  (IIu)

wherein a is 1 and b is 0;
$R_1$ is H or —C(O)O—C(CH$_3$)$_3$,
$R_2$ is —C(O)OR$_{2x}$, —C(O)NHR$_{2x}$—C(O)N(CH$_3$)R$_{2x}$ wherein R$_{2x}$ is the group —(Y—ONO$_2$) of formula (I) wherein Y is below reported, more preferably R$_2$ is —C(O)OR$_{2x}$, or —C(O)NHR$_{2x}$,
$R_x$ is H,
Y of the group (Y—ONO$_2$) is selected from:
A)
 a straight or branched C$_2$-C$_{10}$ alkylene
 a straight or branched C$_2$-C$_{10}$ alkylene substituted with a —ONO$_2$ group;
E)

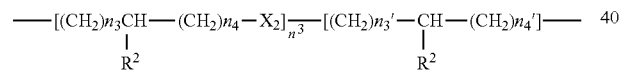  (IE)

wherein in formula (IE)
$n^3$ is from 1 to 5,
$n_3$ is 0 and $n_4$ is from 1 to 4,
$n_{3'}$ is 0 and $n_{4'}$ is from 1 to 4,
$X_2$ is —O— or —NH—,
$R^2$ is H,
preferably (Y—ONO$_2$), is selected from:

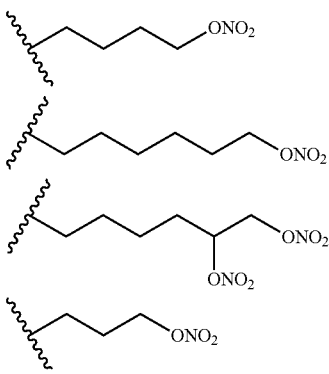

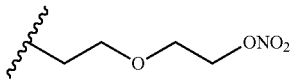

The following are preferred compounds according to the present invention:

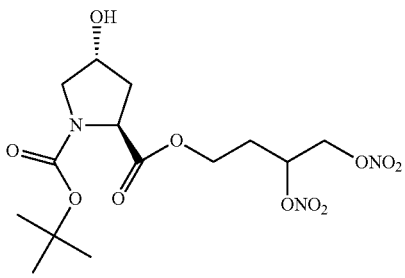  (521)

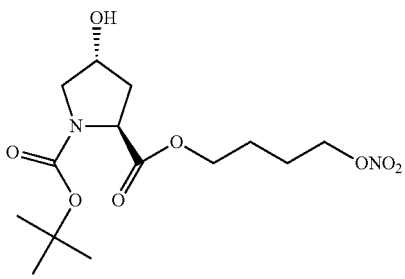  (522)

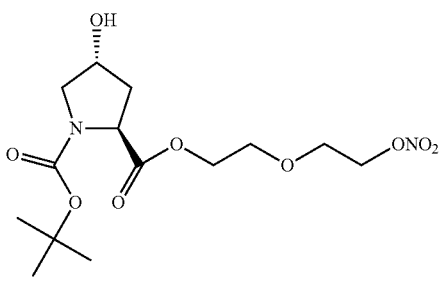  (523)

The compound's of the present invention show significant advantages over the other known nitric oxide donor compounds, they release nitric oxide (NO) slower, they do not induce hypotension in normotensive subjects and moreover they do not induce increasing of heart rate in hypertensive patients.

The term "C$_1$-C$_{20}$ alkylene" as used herein refers to branched or straight chain C$_1$-C$_{20}$ hydrocarbon, preferably having from 1 to 10 carbon atoms such as methylene, ethylene, propylene, isopropylene, n-butylene, pentylene, n-hexylene and the like.

The term "C$_1$-C$_{10}$ alkyl" as used herein refers to branched or straight chain alkyl groups comprising one to ten carbon atoms, including methyl, ethyl, n-propyl, isopropyl, n-butyl, isobutyl, t-butyl, pentyl, hexyl, octyl and the like.

One term "cycloalkylene" as used herein refers to ring having from 5 to 7 carbon atoms including, but not limited to, cyclopentylene, cyclohexylene optionally substituted with side chains such as straight or branched (C$_1$-C$_{10}$)-alkyl, preferably CH$_3$.

The term "heterocyclic" as used herein refers to saturated, unsaturated or aromatic 5 or 6 members ring, containing one or more heteroatoms selected from nitrogen, oxygen, sulphur, such as for example pyridine, pyrazine, pyrimidine, pyrrolidine, morpholine, imidazole and the like.

As stated above, the invention includes also the pharmaceutically acceptable salts of the compounds of formula (I) and stereoisomers thereof.

Examples of pharmaceutically acceptable salts are either those with inorganic bases, such as sodium, potassium, calcium and aluminium hydroxides, or with organic bases, such as lysine, arginine, triethylamine, dibenzylamine, piperidine and other acceptable organic amines.

The compounds according to the present invention, when they contain in the molecule one salifiable nitrogen atom, can be transformed into the corresponding salts by reaction in an organic solvent such as acetonitrile, tetrahydrofuran with the corresponding organic or inorganic acids.

Examples of organic acids are: oxalic, tartaric, maleic, succinic, citric acids. Examples of inorganic acids are: nitric, hydrochloric, sulphuric, phosphoric acids. Salts with nitric acid are preferred.

The compounds of the invention which have one or more asymmetric carbon atoms can exist as optically pure enantiomers, pure diastereomers, enantiomers mixtures, diastereomers mixtures, enantiomer racemic mixtures, racemates or racemate mixtures. Within the object of the invention are also all the possible isomers, stereoisomers and their mixtures of the compounds of formula (I).

The invention also relates to the use of the compounds of formula (I) or their salts for treating cardiovascular diseases, inflammation, pain, fever, gastrointestinal disorders, ophthalmic diseases including glaucoma, hepatic disorders, renal diseases, respiratory disorders, immunological diseases, bone metabolism dysfunctions, central and peripheral nervous system diseases, sexual dysfunctions, infectious diseases, for the inhibition of platelet aggregation and platelet adhesion, for treating pathological conditions resulting from abnormal cell proliferation and vascular diseases.

Another embodiment of the present invention relates to compositions comprising at least a compound of formula (I) or its salt and at least one therapeutic agent selected from anti-inflammatory drugs, drugs used to treat cardiovascular diseases, drugs for treating ocular diseases, drugs for treating respiratory disorders.

Anti-inflammatory drugs include, but are not limited to, non steroidal anti-inflammatory drugs and steroidal anti-inflammatory drugs Drugs used to treat cardiovascular diseases refers to any therapeutic compound, or a pharmaceutically acceptable salt thereof, used to treat any cardiovascular disease. Suitable compounds include, but are not limited to aspirin and derivatives thereof, anti-thrombotic drugs, angiotensin-converting enzyme inhibitors (ACE inhibitors), beta-adrenergic blockers, calcium, channel blockers, angiotensin II receptor antagonists, endothelin antagonists, renin inhibitors, β-adrenergic receptor agonists, cholesterol reducers such as, for example, HMG-CoA reductase inhibitors, including, but not limited to, lovastatin, simvastatin, pravastatin, fluvastatin, cerivastatin, atorvastatin.

Drugs for treating ocular diseases include, but are not limited to, prostaglandins.

In another object of the invention the two components of the composition above defined are administered simultaneously or sequentially wherein the two components may be administered by the same or different administration pathways.

Another object of the invention provide the use of the composition above reported for the treatment of cardiovascular diseases, inflammation, pain, fever, gastrointestinal disorders, ophthalmic diseases including glaucoma, hepatic disorders, renal diseases, respiratory disorders, immunological diseases, bone metabolism dysfunctions, central and peripheral nervous system diseases, sexual dysfunctions, infectious diseases, for the inhibition of platelet aggregation and platelet adhesion, for treating pathological conditions resulting from abnormal cell proliferation and vascular diseases.

Generally the treatment of cardiovascular disease and/or peripheral vascular disorders is a long-term therapy, and it is directed to patients suffering from cardiovascular disease and/or peripheral vascular disorders or inflammatory diseases which suffer from hypertension or diabetes.

Long term treatment ranges from about one month to over two years of chronic/maintenance administration.

Another object of the present invention relates to pharmaceutical compositions comprising the composition above reported and non toxic adjuvants and/or carriers usually employed in the pharmaceutical field.

An object of the present invention relates to pharmaceutical compositions comprising at least a compound of formula (I) together with non toxic adjuvants and/or carriers usually employed in the pharmaceutical field.

The invention also relates to the use of the following compounds 3-(nitrooxy)propyl 2-(tert-butoxycarbonylamino)-4-phenyl butanoate, 3-(nitrooxy)propyl 2-amino-4-phenylbutanoate, 3-(nitrooxy)propyl 2-amino-4-phenylbutanoate hydrochloride, 4-(nitrooxy)butyl 2-(tert-butoxycarbonylamino)-4-phenylbutanoate, 4-(nitrooxy)butyl 2-amino-4-phenylbutanoate, 4-(nitrooxy)butyl 2-amino-4-phenylbutanoate hydrochloride, (2-(nitrooxy)ethoxy)methyl 2-(tert-butoxycarbonylamino)-4-phenyl butanoate, (2-(nitrooxy)ethoxy)methyl 2-amino-4-phenylbutanoate, (2-(nitrooxy)ethoxy)methyl 2-amino-4-phenylbutanoate hydrochloride, 1-tert-butyl 2-(4-(nitrooxy)butyl)pyrrolidine-1,2-dicarboxylate 4-(nitrooxy)butyl pyrrolidine-2-carboxylate, 4-(nitrooxy)butyl pyrrolidine-2-carboxylate hydrochloride, 1-tert-butyl 2-(3-(nitrooxy)propyl)pyrrolidine-1,2-dicarboxylate, 3-(nitrooxy)propyl pyrrolidine-2-carboxylate, 3-(nitrooxy)propyl pyrrolidine-2-carboxylate hydrochloride, for treating cardiovascular diseases, inflammation, pain, fever, gastrointestinal disorders, ophthalmic diseases including glaucoma, hepatic disorders, renal diseases, respiratory disorders, immunological diseases, bone metabolism dysfunctions, central and peripheral nervous system diseases, sexual dysfunctions, infectious diseases, for the inhibition of platelet aggregation and platelet adhesion, for treating pathological conditions resulting from abnormal cell proliferation and vascular diseases.

Another object of the present invention relates to compositions comprising at least one of the following compounds:

3-(nitrooxy)propyl 2-(tert-butoxycarbonylamino)-4-phenyl butanoate, 3-(nitrooxy)propyl 2-amino-4-phenylbutanoate, 3-(nitrooxy)propyl 2-amino-4-phenylbutanoate hydrochloride, 4-(nitrooxy)butyl 2-(tert-butoxycarbonylamino)-4-phenyl butanoate, 4-(nitrooxy)butyl 2-amino-4-phenylbutanoate, 4-(nitrooxy)butyl 2-amino-4-phenylbutanoate hydrochloride,
(2-(nitrooxy)ethoxy)methyl 2-(tert-butoxycarbonylamino)-4-phenyl butanoate,
(2-(nitrooxy)ethoxy)methyl 2-amino-4-phenylbutanoate,
(2-(nitrooxy)ethoxy)methyl 2-amino-4-phenylbutanoate hydrochloride,
1-tert-butyl 2-(4-(nitrooxy)butyl)pyrrolidine-1,2-dicarboxylate,
4-(nitrooxy)butylpyrrolidine-2-carboxylate,
4-(nitrooxy)butylpyrrolidine-2-carboxylate hydrochloride,
1-tert-butyl 2-(3-(nitrooxy)propyl)pyrrolidine-1,2-dicarboxylate,
3-(nitrooxy)propylpyrrolidine-2-carboxylate,
3-(nitrooxy)propylpyrrolidine-2-carboxylate hydrochloride,
and at least one therapeutic agent selected from anti-inflammatory drugs, drugs used to treat cardiovascular diseases, drugs for treating ocular diseases, drugs for treating respiratory disorders.

Anti-inflammatory drugs include, but are not limited to, non steroidal anti-inflammatory drugs and steroidal anti-inflammatory drugs Drugs used to treat cardiovascular diseases refers to any therapeutic compound, or a pharmaceutically acceptable salt thereof, used to treat any cardiovascular disease. Suitable compounds include, but are not limited to aspirin and derivatives thereof, anti-thrombotic drugs, angiotensin-converting enzyme inhibitors (ACE inhibitors), beta-adrenergic pinchers, calcium channel blockers, angiotensin II receptor antagonists, endothelin antagonists, renin inhibitors, β-adrenergic receptor agonists, cholesterol reducers such as, for example, HMG-CoA reductase inhibitors, including, but not limited to, lovastatin, simvastatin, pravastatin, fluvastatin, cerivastatin, atorvastatin.

Drugs for treating ocular diseases include, but are not limited to, prostaglandins.

In another object of the invention the two components of the composition above defined are administered simultaneously or sequentially wherein the two components may be administered by the same or different administration pathways.

Another object of the invention provides the use of the composition comprising at least one of the following compounds:
3-(nitrooxy)propyl 2-(tert-butoxycarbonylamino)-4-phenyl Butanoate,
3-(nitrooxy)propyl 2-amino-4-phenylbutanoate,
3-(nitrooxy)propyl 2-amino-4-phenylbutanoate hydrochloride,
4-(nitrooxy)butyl 2-(tert-butoxycarbonylamino)-4-phenyl butanoate,
4-(nitrooxy)butyl 2-amino-4-phenylbutanoate,
4-(nitrooxy)butyl 2-amino-4-phenylbutanoate hydrochloride,
(2-(nitrooxy)ethoxy)methyl 2-(tert-butoxycarbonylamino)-4-phenyl butanoate,
(2-(nitrooxy)ethoxy)methyl 2-amino-4-phenylbutanoate,
(2-(nitrooxy)ethoxy)methyl 2-amino-4-phenylbutanoate hydrochloride,
1-tert-butyl 2-(4-(nitrooxy)butyl)pyrrolidine-1,2-dicarboxylate,
4-(nitrooxy)butyl pyrrolidine-2-carboxylate,
4-(nitrooxy)butyl pyrrolidine-2-carboxylate hydrochloride,
1-tert-butyl 2-(3-(nitrooxy)propyl)pyrrolidine-1,2-dicarboxylate,
3-(nitrooxy)propyl pyrrolidine-2-carboxylate,
3-(nitrooxy)propyl pyrrolidine-2-carboxylate hydrochloride
and at least one therapeutic agent selected from anti-inflammatory drugs, drugs used to treat cardiovascular diseases, drugs for treating ocular diseases, drugs for treating respiratory disorders, for the treatment of cardiovascular diseases, inflammation, pain, fever, gastrointestinal disorders, ophthalmic diseases including glaucoma, hepatic disorders, renal disease, respiratory disorders, immunological diseases, bone metabolism dysfunctions, central and peripheral nervous system diseases, sexual dysfunctions, infectious diseases, for the inhibition of platelet aggregation and platelet adhesion, for treating pathological conditions resulting from abnormal cell proliferation and vascular diseases.

An object of the present invention relates to pharmaceutical compositions comprising the composition above reported together with non toxic adjuvants and/or carriers usually employed in the pharmaceutical field.

The daily dose of the active ingredient that should be administered can be a single dose or it can be an effective amount divided into several smaller doses that are to be administered throughout the day. The dosage regimen and administration frequency for treating the mentioned diseases with the compound of the invention and/or with the pharmaceutical compositions of the present invention will be selected in accordance with a variety of factors, including for example age, body weight, sex and medical condition of the patient as well as severity of the disease, route of administration, pharmacological considerations and eventual concomitant therapy with other drugs. In some instances, dosage levels below or above the aforesaid range and/or more frequent may be adequate, and this logically will be within the judgment of the physician and will depend on the disease state.

The compounds of the invention may be administered orally, parenterally, rectally or topically, by inhalation or aerosol, in formulations eventually containing conventional non-toxic pharmaceutically acceptable carriers, adjuvants and vehicles as desired. Topical administration may also involve the use of transdermal administration such as transdermal patches or iontophoresis devices. The term "parenteral" as used herein, includes subcutaneous injections, intravenous, intramuscular, intrasternal injection or infusion techniques.

Injectable preparations, for example sterile injectable aqueous or oleaginous suspensions may be formulated according to known art using suitable dispersing or wetting agents and suspending agents. The sterile injectable preparation may also be a sterile injectable solution or suspension in a non-toxic parenterally acceptable diluent or solvent. Among the acceptable vehicles and solvents are water, Ringer's solution and isotonic sodium chloride. In addition, sterile, fixed oils are conventionally employed as a solvent or suspending medium. For this purpose any bland fixed oil may be employed including synthetic mono or diglycerides, in addition fatty acids such as oleic acid find use in the preparation of injectables.

Suppositories for rectal administration of the drug can be prepared by mixing the active ingredient with a suitable non-irritating excipient, such as cocoa butter and polyethylene glycols.

Solid dosage forms for oral administration may include capsules, tablets, pills, powders, granules and gels. In such solid dosage forms, the active compound may be admixed with at least one inert diluent such as sucrose, lactose or starch. Such dosage forms may also comprise, as in normal practice, additional substances other than inert diluents, e.g. lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavouring and the like.

Synthesis Procedure

1. The Compounds of General Formula (I)

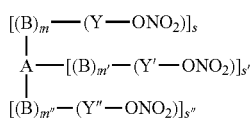
(I)

wherein:
s is equal to 1;
m, m', m", s' and s" are 0
Y is as above defined,
A is a radical of formula (IIa)-(IIm), (IIo)-(IIr), (IIt)-(IIu) and (IIn) wherein $R_1$ is —C(O)—$R_{1x}$ and it binds the group —Y—$ONO_2$, $R_2$ is —COOH;
in formula (IIn) $R_n$ is —C(O)—$R_{nx}$, or is —$(CH_2)_2$—NH—$R_h$ wherein $R_h$ is —C(O)$R_{hh}$ and it binds the group —Y—$ONO_2$
$R_a$ of formula (IIa) is selected in group a)
$R_c$ of formula (IIc) is selected in group a')
in formula (IIt) d is an integer from 3 to 5, d' is 0;
can be prepared as follows 1a) by reacting a compound of formula (I) wherein s, s', s", m, m', m", Y, Y', Y" are as above defined in 1., A is a radical of formula (IIa)-(IIm), (IIo)-(IIr), (IIt)-(IIu) and (IIn) wherein $R_2$ is —C(O)OC($CH_3$)$_3$; $R_1$, $R_a$, $R_c$, $R_h$, $R_n$, d, and d' are as defined in 1., with anhydrous or aqueous organic or inorganic acid to hydrolyze the t-butyl ester following procedure well known in the literature.

1b) by reacting a compound of formula A with a compound of formula (IIIa)

A+HOOC—Y—$ONO_2$ (IIIa)

wherein Y is as above defined and A is selected from (IIa)-(IIm), (IIo)-(IIr), (IIt)-(IIu) and (IIn) wherein $R_1$, is —H and $R_2$ is —C(O)O($CH_3$)$_3$;
in formula (IIn) $R_n$ is H, or is —$(CH_2)_2$—NH—$R_h$ wherein $R_h$ is H;
$R_a$ of formula (IIa) is selected in group a);
$R_c$ of formula (IIc) is selected in group a');
in formula, (IIt) d and d' are as above defined;
in the presence of a condensing agent such as dicyclohexylcarbodiimide (DCC) or N,N'-carbonyldiimidazol (CDI) or other known condensing reagents such as O-(7-azabenzotriazol-1-yl)-N,N,N',N'-tetramethyluronium hexafluorophosphate (HATU), in the presence or not of 1-Hydroxybenzotriazole (HOBT) in solvent such as DMF, THF, chloroform at a temperature in the range from −5° C. to 80° C. in the presence or not of a base as for example DMAP.

The nitric acid ester compounds of formula (IIIa) can be obtained from the corresponding alcohols of formula HOOC—Y—OH (IIIb), that are commercially available, by reaction with nitric acid and acetic anhydride in a temperature range from −51° C. to 0° C. or reacting the corresponding halogen derivatives of formula HOOC—Y—Hal (IIIc) wherein Hal is an halogen atom preferably Cl, Br, I, that are commercially available, with $AgNO_3$ as known in the literature. Alternatively the reaction with $AgNO_3$ can be performed under microwave irradiation in solvents such acetonitrile or THF at temperatures in the range between about 100-180° C. for time range about 1-60 min.

Dinitrated compounds of formula (IIIa) can be also directly prepared with $I_2$ and $AgNO_3$ starting from carboxylic acids with a double bond in the chain as described in WO 2005/070868.

Compounds (IIIa) can be also prepared from the corresponding Tosyl derivative (IIId) HOOC—Y—OTs by reacting with $AgNO_3$ or MetalNO$_3$ wherein Metal is $Li^+$, $Na^+$, $K^+$, in solvents such acetonitrile or DMF at refluxing temperature or under microwave irradiation at temperatures in the range between about 100-180° C. for time range about 1-120 min.

1b') alternatively compound A reported in 1b) can be reacted with a compound of formula (IIIe):

A+Act-CO—Y—$ONO_2$ (IIIe)

wherein Y is as above defined; Act is an Halogen atom or a carboxylic acid activating group used in peptide chemistry such as:

Act = 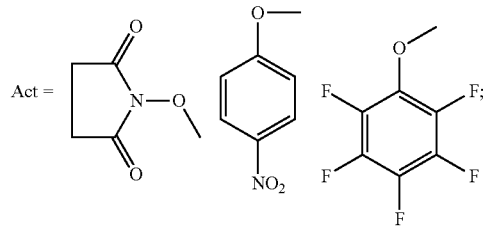

the reaction is generally carried out in presence of a inorganic or organic base in an aprotic polar/non-polar solvent such as DMF, THF or $CH_2Cl_2$ at temperatures range between 0°-80° C. or in a double phase system $H_2O/Et_2O$ at temperatures range between 20°-40° C.; or in the presence of DMAP and a Lewis acid such as Sc(OTf)$_3$ or Bi(OTf)$_3$ in solvents such as DMF, $CH_2Cl_2$.

The compounds of formula (IIIe) can be obtained as described in WO 2006/008196.

1c) compounds A reported in 1b) are commercially available or can be prepared by reacting a compound of formula $A_1$ wherein $A_1$ is a radical of formula (IIa)-(IIm), (IIo)-(IIr), (IIt)-(IIu) and (IIn) wherein $R_2$ is —COOH, $R_1$ and $R_6$ are substituted by the Fmoc protective group and $R_a$, $R_c$, d and d' are as defined in 1., with tert-butyl alcohol and sulphuric acid or other methods to obtain a tert-butyl ester well known in the literature. Eventually removing the Fmoc protective group using methods known in the literature.

Compounds $A_1$ are commercially available or can be prepared by the correspondent compounds $A_2$:

$A_2 \rightarrow A_1$ wherein $A_2$ is a radical of formula (IIa)-(IIm), (IIo)-(IIr), (IIt)-(IIu) and (IIn) wherein $R_2$ is —COOH, and $R_1$ is —C(O)OC($CH_3$)$_3$, $R_n$ is —C(O)OC($CH_3$)$_3$ or is —$(CH_2)_2$—NH—C(O)OC($CH_3$)$_3$, $R_a$, $R_c$ d and d' are as defined in 1., by converting the —BOC protective group into the Fmoc protective group as described in the literature.

Compounds $A_2$ are commercially available.

2. Alternatively compounds of formula (I) described in 1. can be obtained:

2a) by reacting a compound of formula (IVa)

A-(Y—X) (IVa)

wherein X is an halogen atom or tosyl group, Y is as above defined and A is as above defined in 1b), with AgNO$_3$ or MetalNO$_3$ as above described in 1b).

Compounds (IVa) can be obtained by reacting compound A as above defined in 1b), with compounds (IIIc) as above described in 1b), with a condensing reagent such as DCC or CDI as above described in 1b);

or

2a') alternatively compounds of formula (I) described in 1a) can be obtained by reacting a compound of formula (Va):

A—(Y—OH)  (Va)

wherein A and Y are as above defined in 1a), with triflic anhydride/tetraalkylammonium nitrate salt in an aprotic polar/non-polar solvent such as DMF, THF or CH$_2$Cl$_2$ at temperatures range between −78° to 80° C.

Compounds (Va) can be obtained by reacting compound A as defined in 1b), with compounds (IIIb) with a condensing reagent as above described for (IIIa) in 1b).

3. The compounds of general formula (I) wherein:
s is equal to 1;
m, m', m'', s' and s'' are 0
Y is as above defined,
A is a radical of formula (IIa)-(IIm), (IIo)-(IIr), (IIt)-(IIu) and (IIn) wherein R$_1$ is —C(O)O—R$_{1x}$ and it binds the group —Y—ONO$_2$,
R$_2$ is —COOH;
in formula (IIn) R$_n$ is —C(O)O—R$_{nx}$ or —(CH$_2$)$_2$—NH—R$_h$ wherein R$_h$ is —C(O)O—R$_{hh}$, and it binds the group —Y—ONO$_2$
R$_a$ of formula (IIa) is selected in group a)
R$_c$ of formula (IIc) is selected in group a')
in formula (IIt) d is an integer from 3 to 5, d' is 0;
can be prepared as follows 3a) by reacting a compound of formula (I) wherein s, s', s'', m, m', m'', Y, Y', Y'' are as above defined in 3., A is a radical of formula (IIa)-(IIm), (IIo)-(IIr), (IIt)-(IIu) and (IIn) wherein R$_2$ is —C(O)OC(CH$_3$)$_3$; R$_1$, R$_a$, R$_c$, R$_n$, R$_h$, d and d' are as defined in 3. with anhydrous or aqueous organic or inorganic acid to hydrolyze the t-butyl ester following procedure well known in the literature.

3b) by reacting a compound of formula A with a compound of formula (IIIf)

A+Act-(O)C—O—Y—ONO$_2$  (IIIf)

wherein A is as above reported in 1b), Y is as above reported and Act is as above defined in 1b').

The reaction is generally carried out in presence of a inorganic or organic base in an aprotic polar/non-polar solvent such as DMF, THF or CH$_2$Cl$_2$ at temperatures range between 0°-80° C. or in a double phase system H$_2$O/Et$_2$O at temperatures range between 20°-40° C.; or in the presence of DMAP and a Lewis acid such as Sc(OTf)$_3$ or Bi(OTf)$_3$ in solvents such as DMF, CH$_2$Cl$_2$. Compounds (IIIf) are obtained as described in WO 2006/008196.

4. The compounds of general formula (I) wherein:
s and m are equal to 1;
s', s'', m', m'' are equal to 0;
Y is as above defined;
B is:

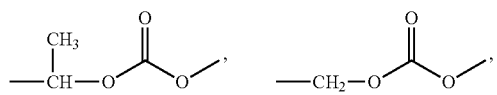

A is a radical of formula (IIa)-(IIm), (IIo)-(IIr), (IIt)-(IIu) and (IIn) wherein R$_1$ is —H and R$_2$ is —C(O)OR$_{2x}$ and binds the group —B—Y—ONO$_2$
in formula (IIn) R$_n$ is —H or is —(CH$_2$)$_2$—NH$_2$;
R$_a$ of formula (IIa) is selected in group a),
R$_c$ of formula (IIc) is selected in group a'),
in formula (IIt) d is an integer from 3 to 5, d' is 0;
can be obtained as follows:

4a) reacting a compound of formula (I) wherein B, s, s', s'', m, m', m'', Y, Y' and Y'' are as above defined in 4., A is a radical of formula (IIa)-(IIm), (IIo)-(IIr), (IIt)-(IIu) and (IIn) wherein R$_2$, R$_a$, R$_c$, d and d' and of are as defined in 4., R$_1$ is —C(O)OC(CH$_3$)$_3$; R$_n$ or is —C(O)OC(CH$_3$)$_3$ or is —(CH$_2$)$_2$—NH—C(O)OC(CH$_3$)$_3$;
with anhydrous or aqueous organic or inorganic acid as well known in the literature to remove all the —BOC protective groups.

4b) by reacting a compound of formula A with compounds of formula (IIIg)

A+Hal-W$_1$—OC(O)O—Y—ONO$_2$  (IIIg)

wherein Y is as above described, Hal is an halogen atom and W$_1$ is —CH$_2$— or —CH(CH$_3$)—, and A is a compound of formula (IIa)-(IIm), (IIo)-(IIr), (IIt)-(IIu) and (IIn) wherein R$_1$ is —C(O)OC(CH$_3$)$_3$ and R$_2$ is —COOH;
R$_a$ of formula (IIa) is selected in group a),
R$_c$ of formula (IIc) is selected in group a'),
in formula (IIt) d and d' are as above defined;
in formula (IIn) R$_n$ is —C(O)OC(CH$_3$)$_3$ or is —(CH$_2$)$_2$—NH—C(O)OC(CH$_3$)$_3$;
in the presence of a inorganic or organic base in an aprotic polar/non-polar solvent such as DMF, THF or CH$_2$Cl$_2$ at temperatures range between 0° to 100° C. or in a double phase system H$_2$O/Et$_2$O at temperatures range between 20°-40° C. Compounds A as above defined are commercially available.

The compounds of formula (IIIg) are obtained by reacting the commercially available haloalkylhalocarbonate of formula (IIIh)

Hal-W$_1$—OC(O)Hal  (IIIh)

wherein Hal and W$_1$ are as above defined, with a compound of formula (IIIi)

HO—Y—ONO$_2$  (IIIi)

wherein Y is as above defined, in the presence of a inorganic or organic base in an aprotic polar or in an aprotic non-polar solvent such as DMF, THF or CH$_2$Cl$_2$ at temperatures range between 0° to 80° C.

Dinitrated compounds of formula (IIIi) can be also prepared with I$_2$ and AgNO$_3$ or by Sharpless oxidation and then Nitration with Acetic anhydride and nitric acid starting from a double bond in the chain as described in WO 2005/070868.

The compounds of formula (IIIi) are obtained by reacting compounds of formula HO—Y-Hal (IIIj) wherein Y and Hal are as above defined or compounds of formula HO—Y—OTs (IIIk) wherein Ts is the tosyl group, with AgNO$_3$ on MetalNO$_3$ in a suitable organic solvent such as acetonitrile or tetrahydrofuran (THF) under nitrogen in the dark at temperatures range between 20°-80° C.; alternatively the reaction with AgNO$_3$ or MetalNO$_3$ can be performed under microwave irradiation in solvents such acetonitrile or THF at temperatures in the range between about 100°-180° C. for time range about 1-120 min as already described in 1b)

The compounds of formula (IIIj) and (IIIk) are commercially available or can be obtained from commercially available compounds HO—Y—OH (IIIl) with methods well known in the literature.

5. Alternatively compounds (I) described in 4a) can be obtained 5a) by reacting compounds of formula (VIa) wherein A, B and Y have been already defined in 4. with tetraalkylammonium nitrate and triflic anhydride as previously described A-(B)—(Y—OH)  (VIa)

Compounds (VIa) can be obtained by reacting compounds A as defined in 4b) with compounds (IIIm):

Hal-W$_1$—OC(O)O—Y—OH  (IIIm)

Using the same procedure described in 4b). Compounds (IIIm) are prepared from commercially available compounds Hal-W$_1$—OC(O)Hal (IIIh) by reacting with compounds HO—Y—OH (IIII) in the presence of a inorganic or organic base in an aprotic polar or in an aprotic non-polar solvent such as DMF, THF or CH$_2$Cl$_2$ at temperatures range between 0°-80° C., using a ratio (IIIh)/(IIII) 1:1.

6. The compounds of general formula (I) wherein:
s and m are equal to 1
s', s", m', m" are equal to 0;
Y is as above defined;
B is:

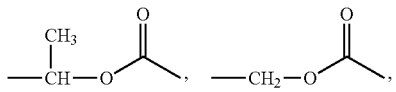

A is a radical of formula (IIa)-(IIm), (IIo)-(IIr), (IIt)-(IIu) and (IIn) wherein R$_1$ is —H and R$_2$ is —C(O)OR$_{2x}$ and binds the group —B—Y—ONO$_2$
in formula (IIn) R$_n$ is —H or is —(CH$_2$)$_2$—NH$_2$;
R$_a$ of formula (IIa) is selected in group a)
R$_c$ of formula (IIc) is selected in group a'),
in formula (IIt) d is an integer from 3 to 5, d' is 0;
can be obtained as follows:
6a) reacting a compound of formula (I) wherein s, s', s", m, m', m", Y, Y' and Y" are as above defined in 6., A is a radical of formula (IIa)-(IIm), (IIo)-(IIr), (IIt)-(IIu) and (IIn) wherein R$_2$, R$_a$, and R$_c$, d and d' as defined in 6., R$_1$ or R$_n$ is —C(O)OC(CH$_3$)$_3$ or —(CH$_2$)$_2$—NH—C(O)OC(CH$_3$)$_3$;
with anhydrous or aqueous organic or inorganic acid as well known in the literature to remove all the —BOC protective groups.
6b) by reacting a compound of formula A with compounds of formula (IIIn)

A+Hal-W$_1$—OC(O)—Y—ONO$_2$  (IIIn)

wherein Y is as above described, Hal is an halogen atom and W$_1$ is —CH$_2$— or —CH(CH$_3$)—, and A is a compound of formula (IIa)-(IIm), (IIo)-(IIr), (IIt)-(IIu) and (IIn) wherein R$_1$ is —C(O)OC(CH$_3$)$_3$ and R$_2$ is —COOH;
R$_a$ of formula (IIa) is selected in group a),
R$_c$ of formula (IIc) is selected in group a'),
in formula (IIn) R$_n$ is —C(O)OC(CH$_3$)$_3$ or is —(CH$_2$)$_2$—NHR$_h$ wherein R$_h$ is —C(O)OC(CH$_3$)$_3$;
in formula (IIt) d is an integer from 3 to 5, d' is 0;
in the presence of a inorganic or organic base in an aprotic polar/non-polar solvent such as DMF, THF or CH$_2$Cl$_2$ at temperatures range between 0°-100° C. or in a double phase system H$_2$O/Et$_2$O at temperatures range between 20°-40° C.
The compounds of formula (IIIn) are obtained by reacting a compound W$_2$—CHO, wherein W$_2$ is H—, CH$_3$— with compounds of formula (IIIe), wherein Y and Act are as above defined, and ZnCl$_2$ as described in the literature (Steven K. Davidsen and al., *J. Med Chem.*, 37(26), 4423, 1994).

W$_2$—CHO+ZnCl$_2$+Act-(O)C—Y—ONO$_2$  (IIIe)

7. The compounds of general formula (I) wherein:
s is equal to 1;
s', s", m, m', m" are equal to 0;
Y is as above defined;
A is a radical of formula (IIa)-(IIm), (IIo)-(IIr), (IIt)-(IIu) and (IIn) wherein R$_1$ is —H and R$_2$ is —C(O)NHR$_{2xx}$ or —C(O)N(CH$_2$)R$_{2xx}$ and R$_2$ binds the group —Y—ONO$_2$
in formula (IIn) R$_n$ is —H or is —(CH$_2$)$_2$—NH$_2$;
R$_a$ of formula (IIa) is selected in group a);
R$_c$ of formula (IIc) is selected in group a');
in formula (IIt) d is an integer from 3 to 5, d' is 0;
can be obtained as follows:
7a) reacting a compound of formula (I) wherein s, s', s", m, m', m", Y, Y' and Y" are as above defined in 7., A is a radical of formula (IIa)-(IIm), (IIo)-(IIr), (IIt)-(IIu) and (IIn) wherein R$_2$, R$_a$ R$_c$, d and d' are as defined in 7., R$_1$ is —C(O)OC(CH$_3$)$_3$; R$_n$ is —C(O)OC(CH$_3$)$_3$ or is —(CH$_2$)$_2$—NHR$_h$ wherein R$_h$ is —C(O)OC(CH$_3$)$_3$;
with anhydrous or aqueous organic or inorganic acid as well known in the literature to remove all the —BOC protective groups.
7b) by reacting a compound of formula A with compounds of formula (IIIo)

W$_3$NH—Y—ONO$_2$  (IIIo)

wherein Y is as above described, W$_3$ is H or —CH$_3$, A has been already defined in 4b), in the presence of a condensing agent like dicyclohexylcarbodiimide (DCC) or N,N'-carbonyldiimidazol (CDI) or other known condensing reagents such as O-(7-Azabenzotriazol-1-yl)-N,N,N',N'-tetramethyluronium hexafluorophosphate (HATU) in the presence or not of 1-Hydroxybenzotriazole (HOBT) in solvent such as DMF, THF, chloroform at a temperature in the range from −5° C. to 60° C. in the presence or not of a base as for example DMAP.
Compounds (IIIo) can be prepared from compounds (IIIp), wherein Y and W$_3$ are as above defined by hydrolysing the BOC protecting group as known in the literature:

(CH$_3$)$_3$CO(O)C—NW$_3$—Y—ONO$_2$  (IIIp)

Compounds (IIIp) can be prepared from compounds (IIIq) or (IIIr) wherein W$_3$, Y, Hal and Ts are as above described, by reacting with AgNO$_3$ as already described for analogous compounds:

(CH$_3$)$_3$CO(O)C—NW$_3$—Y-Hal  (IIIq)

(CH$_3$)$_3$CO(O)C—NW$_3$—Y—OTs  (IIIr)

Alternatively compounds (IIIp) can be prepared from compounds (IIIs) by reacting with tetraalkylammonium nitrate as already described for analogous compounds.

(CH$_3$)$_3$CO(O)C—NW$_3$—Y—OH  (IIIs)

Compounds (IIIq) and (IIIr) can be prepared from compounds (IIIs) by halogenation or tosylation as known an the literature. Compounds (IIIs) are obtained by known methods from compounds (IIIt) that are commercially available.

W$_3$NH—Y—OH  (IIIt)

8. The compounds of general formula (I) wherein:
s is equal to 1;
s', s", m, m', m" are equal to 0;
Y is as above defined;

A is a radical of formula ((IIa)-(IIm), (IIo)-(IIr), (IIt)-(IIu) and (IIn) wherein $R_1$ is —H and $R_2$ is —C(O)O$R_{2x}$ and binds the group —Y—ONO$_2$ in formula (IIn) $R_n$ is —H or is —(CH$_2$)$_2$—NH$_2$;

$R_a$ of formula (IIa) is selected in group a);

$R_c$ of formula (IIc) is selected in group a');

in formula (IIt) d is an integer from 3 to 5, d' is 0;

can be obtained as follows:

8a) reacting a compound of formula (I) wherein s, s', s", m, m', m", Y, Y' and Y" are as above defined in 8., A is a radical of formula (IIa)-(IIm), (IIo)-(IIr), (IIt)-(IIu) and (IIn) wherein $R_2$, $R_a$, $R_c$ d and d' are as defined in 8., $R_1$ is —C(O)OC(CH$_3$)$_3$; $R_n$ is —C(O)OC(CH$_3$)$_3$ or is —(CH$_2$)$_2$—NHR—C(O)OC(CH$_3$)$_3$;

with anhydrous or aqueous organic or inorganic acid as well known in the literature to remove all the —BOC protective groups.

8b) by reacting a compound of formula A with compounds of formula (IIIi)

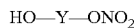  HO—Y—ONO$_2$    (IIIi)

wherein Y is as above described, A is a radical of formula (IIa)-(IIm), (IIo)-(IIr), (IIt)-(IIu) and (IIn) wherein $R_1$ is —C(O)OC(CH$_3$)$_3$; $R_2$ is —COOH or is equal to $R_{2a}$ wherein $R_{2a}$ is the group —COAct wherein Act is as above described in 1b') and is a carboxylic acid activating group, $R_a$, $R_c$ d and d' are as defined in 8., $R_n$ is —C(O)OC(CH$_3$)$_3$ or is —(CH$_2$)$_2$—NHR—C(O)OC(CH$_3$)$_3$;

in the presence of a condensing agent such as dicyclohexylcarbodiimide (DCC) or N,N'-carbonyldiimidazol (CDI) or other known condensing reagents such as O-(7-Azabenzotriazol-1-yl)-N,N,N',N'-tetramethyluronium hexafluorophosphate (HATU), in the presence or not or 1-Hydroxybenzotriazole (HOBT) in solvent such as DMF, THF or chloroform at a temperature in the range from −5° C. to 60° C. in the presence or not of a base as for example DMAP when $R_2$ is —COOH; or in the presence of equimolar amount of DMAP in solvent such as DMF, THF, chloroform at a temperature in the range from −5° C. to 60° C. when $R_2$ is equal to $R_{2a}$.

9. Alternatively the compounds of formula (I) as defined in 8a) can be obtained as follow:

9a) reacting a compound of formula (IVb)

A-Y—X    (IVb)

wherein Y is as above defined and A is as above defined in 8a) and X is an halogen atom or a tosyl group, by reacting with AgNO$_3$ or MetalNO$_3$ as above described. Compounds (IVb) can be obtained by reacting compound A defined as above in 6b), with compounds (IIIj) or (IIIk)

HO—Y-Hal    (IIIj)

HO—Y—OTs    (IIIk)

with a condensing reagent such as DCC or CDI or HATU as shove defined in 6b).

10. Alternatively the compounds of formula (I) as defined in 8a) can be obtained 10a) by reacting a compound of formula (Vb)

A-Y—OH    (Vb)

wherein Y is as above defined, and A is as already defined in 8) with triflic anhydride/tetraalkylammonium nitrate as already described. Compounds (Vb) can be obtained by reacting components A as above described in 8b) with a compound of formula HO—Y—OH (IIIl) with a condensing reagent such as DCC or CDI or HATU as above defined in 8b) using a ratio A/(IIIl) 1:1.

11. The compounds of general formula (I) wherein:

s and s' are equal to 1;

s", m, m', m", are 0

Y, Y' can be equal or different and are as above defined,

A is selected from (IIa)-(IIm), (IIo)-(IIr), (IIt)-(IIu) and (IIn) wherein:

$R_1$ is —C(O)$R_{1x}$ and binds the group —Y—ONO$_2$, $R_2$ is —C(O)O$R_{2x}$ and binds the group —Y'—ONO$_2$;

in formula (IIn) $R_n$ is —C(O)—$R_{nx}$ or —(CH$_2$)$_2$—NH—$R_h$ wherein $R_h$ is —C(O)—$R_{hh}$, $R_n$ or $R_h$ binds the group —Y—ONO$_2$;

$R_a$ of formula (IIa) is selected in group a);

$R_c$ of formula (IIc) is selected in group a');

in formula (IIt) d is an integer from 3 to 5, d' is 0;

can be prepared as follows:

11a) by reacting compounds of formula (I) as defined in 1., obtained with the procedure described in 1. with compounds (IIIi)

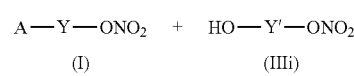

Wherein Y and Y' are equal or different and are as above defined and A has the following meanings:

A is a radical of formula (IIa)-(IIm), (IIo)-(IIr), (IIt)-(IIu) and (IIn) wherein $R_1$ is —C(O)—$R_{1x}$ and binds the group —Y—ONO$_2$, $R_2$ is —COOH;

in formula (IIn) $R_n$ is —C(O)—$R_{nx}$ or —(CH$_2$)$_2$—NH—$R_h$ wherein $R_h$ is —C(O)—$R_{hh}$, $R_n$ or $R_h$ binds the group —Y—ONO$_2$;

$R_a$ of formula (IIa) is selected in group a);

$R_c$ of formula (IIc) is selected in group a');

in formula (IIt) d is an integer from 3 to 5, d' is 0;

using the same procedure described in 8b).

12. The compounds of general formula (I) wherein:

s and s' are equal to 1;

s", m, m', m", are 0

Y, Y' can be equal or different and are as above defined,

A is a radical of formula (IIa)-(IIm), (IIo)-(IIr), (IIt)-(IIu) and (IIn) wherein $R_1$ is —C(O)O—$R_{1x}$ and binds the group —Y—ONO$_2$; $R_2$ is —C(O)O$R_{2x}$ and $R_2$ binds the group —Y—ONO$_2$;

in formula (IIn) $R_n$ is —C(O)O—$R_{nx}$ or —(CH$_2$)$_2$—NH—$R_h$ wherein $R_h$ is —C(O)O—$R_{hh}$, $R_n$ or $R_h$ binds the group —Y—ONO$_2$;

$R_a$ of formula (IIa) is selected in group a), $R_c$ of formula (IIc) is selected in group a');

in formula (IIt) d is an integer from 3 to 5, d' is 0;

can be prepared as follows:

12a) by reacting compounds of formula (I) obtained with the procedure described in 3. with compounds (IIIi)

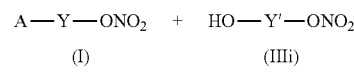

Wherein Y and Y' are equal or different and are as above defined and A has the following meanings:

A is a radical of formula (IIa)-(IIm), (IIo)-(IIr), (IIt)-(IIu) and (IIn) wherein $R_1$ is —C(O)O—$R_{1x}$ and binds the group —Y—ONO$_2$, $R_2$ is —COOH;

in formula (IIn) $R_n$ is —C(O)O—$R_{nx}$ or —(CH$_2$)$_2$—NH—$R_h$ wherein $R_h$ is —C(O)O—$R_{hh}$, $R_n$ or $R_h$ binds the group —Y—ONO$_2$;

$R_a$ of formula (IIa) is selected in group a);
$R_c$ of formula (IIc) is selected in group a');
in formula (IIt) d is an integer from 3 to 5, d' is 0;
using the same procedure described in 8b).
13. The compounds of general formula (I) wherein:
s and s' are equal to 1;
s", m, m', m", are 0
Y, Y' can be equal or different and are as above defined,
A is selected from (IIa)-(IIm), (IIo)-(IIr), (IIt)-(IIu) and (IIn) wherein:
$R_1$ is —C(O)—$R_{1x}$ and binds the group —Y—$ONO_2$, $R_2$ is —C(O)$NHR_{2xx}$ or —C(O)N($CH_3$)$R_{2xx}$ and binds the group —Y—$ONO_2$;
in formula (IIn) $R_n$ is —C(O)—$R_{nx}$ or —($CH_2$)$_2$—NH—$R_h$ wherein $R_h$ is —C(O)—$R_{hh}$, $R_n$ or $R_h$ binds the group —Y—$ONO_2$;
$R_a$ of formula (IIa) is selected in group a);
$R_c$ of formula (IIc) is selected in group a');
in formula (IIt) d is an integer from 3 to 5, d' is 0;
can be prepared as follows:
13a) by reacting compounds of formula (I) obtained with the procedure described in 1. with compounds (IIIo)

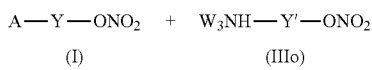

Wherein Y and Y' are equal or different and are as above defined, $W_3$ is as above defined and A has the following meanings:
A is a radical of formula (IIa)-(IIm), (IIo)-(IIr), (IIt)-(IIu) and (IIn) wherein $R_1$ is —C(O)—$R_{1x}$ and binds the group —Y—$ONO_2$, $R_2$ is —COOH;
in formula (IIn) $R_n$ is —C(O)—$R_{nx}$ or —($CH_2$)$_2$—NH—$R_h$ wherein $R_h$ is —C(O)—$R_{hh}$, $R_n$ or $R_h$ binds the group —Y—$ONO_2$;
$R_a$ of formula (IIa) is selected in group a);
$R_c$ of formula (IIc) is selected in group a');
in formula (IIt) d is an integer from 3 to 5, d' is 0;
using the same procedure described in 7b).
14. The compounds of general formula (I) wherein:
s and s' are equal to 1;
s", m, m', m", are 0
Y, Y' can be equal or different and are as above defined,
A is a radical of formula (IIa)-(IIm), (IIo)-(IIr), (IIt)-(IIu) and (IIn) wherein $R_1$ is —C(O)O—$R_{1x}$ and $R_1$ binds the group —Y—$ONO_2$, $R_2$ is —C(O)$NHR_{2xx}$ or —C(O)N($CH_3$)$R_{2xx}$ and $R_2$ binds the group —Y—$ONO_2$;
in formula (IIn) $R_n$ is —C(O)O—$R_{nx}$ or —($CH_2$)$_2$—NH—$R_n$ wherein $R_h$ is —C(O)O—$R_{hh}$, $R_n$ or $R_h$ binds the group —Y—$ONO_2$;
$R_a$ of formula (IIa) is selected in group a),
$R_c$ of formula (IIc) is selected in group a');
in formula (IIt) d is an integer from 3 to 5, d' is 0;
can be prepared as follows:
14a) by reacting compounds of formula (I) obtained with the procedure described in 3. with compounds (IIIo)

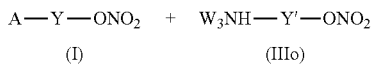

Wherein Y and Y' are equal or different and are as above defined, $W_3$ is as above defined and A has the following meanings:
A is a radical of formula (IIa)-(IIm), (IIo)-(IIr), (IIt)-(IIu) and (IIn) wherein $R_1$ is —C(O)O—$R_{1x}$ and binds the group —Y—$ONO_2$, $R_2$ is —COOH;
in formula (IIn) $R_n$ is —C(O)O—$R_{nx}$ or —($CH_2$)$_2$—NH—$R_h$ wherein $R_h$ is —C(O)O—$R_{hh}$, $R_n$ or $R_h$ binds the group —Y—$ONO_2$;
$R_a$ of formula (IIa) is selected in group a);
$R_c$ of formula (IIc) is selected in group a');
in formula (IIt) d is an integer from 3 to 5, d' is 0;
using the same procedure described in 7b).
15. The compounds of general formula (I) wherein:
s, s' and m' are equal to 1;
s", m, m", are 0
Y, Y' can be equal or different and are as above defined;
B is:

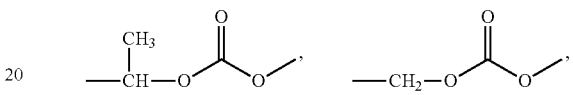

A is selected from (IIa)-(IIm), (IIo)-(IIr), (IIt)-(IIu) and (IIn) wherein:
$R_1$ is —C(O)—$R_{1x}$ and binds the group —Y—$ONO_2$, $R_2$ is —C(O)$OR_{2x}$ and $R_2$ binds the group —B—Y'—$ONO_2$;
in formula (IIn) $R_n$ is —C(O)—$R_{nx}$ or —($CH_2$)$_2$—NH—$R_h$ wherein $R_h$ is —C(O)—$R_{hh}$, $R_n$ or $R_h$ binds the group —Y—$ONO_2$;
$R_a$ of formula (IIa) is selected in group a);
$R_c$ of formula (IIc) is selected in group a');
in formula (IIt) d is an integer from 3 to 5, d' is 0;
can be prepared as follows:
15a) By reacting compounds of formula (I) obtained with the procedure described in 1. with compounds (IIIg)

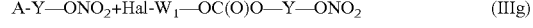

wherein Y is as above described, Hal is an halogen atom and $W_1$ is —$CH_2$— or —CH($CH_3$)—, and A has the following meanings:
A is a radical of formula (IIa)-(IIm), (IIo)-(IIr), (IIt)-(IIu) and (IIn) wherein $R_1$ is —C(O)—$R_{1x}$— and binds the group —Y—$ONO_2$, $R_2$ is —COOH;
in formula (IIn) $R_n$ is —C(O)—$R_{nx}$ or —($CH_2$)$_2$—NH—$R_h$ wherein $R_h$ is —C(O)—$R_{hh}$, $R_n$ or $R_h$ binds the group —Y—$ONO_2$;
$R_a$ of formula (IIa) is selected in group a);
$R_c$ of formula (IIc) is selected in group a');
in formula (IIt) d is an integer from 3 to 5, d' is 0;
using the same procedure described in 4b).
16. The compounds of general formula (I) wherein:
s, s' and m' are equal to 1;
s", m, m", are 0
Y, Y' can be equal or different and are as above defined;
B is:

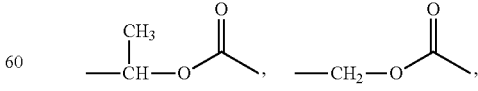

A is selected from (IIa)-(IIm), (IIo)-(IIr), (IIt)-(IIu) and (IIn) wherein:
$R_1$ is —C(O)—$R_{1x}$ and binds the group —Y—$ONO_2$, is $R_2$ is —C(O)$OR_{2x}$ and binds the group —B—Y'—$ONO_2$;
in formula (IIn) $R_n$ is —C(O)—$R_{nx}$ or —($CH_2$)$_2$—NH—$R_h$ wherein $R_h$ is —C(O)—$R_{hh}$, $R_n$ or $R_h$ binds the group —Y—ONO$_2$,
$R_a$ of formula (IIa) is selected in group a),
$R_c$ of formula (IIc) is selected in group a'),
in formula (IIt) d is an integer from 3 to 5, d' is 0;
can be prepared as follows
16a) by reacting compounds of formula (I) obtained with the procedure described in 1, with compounds (IIIn)

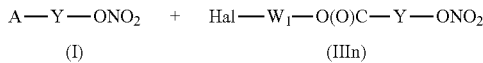

wherein 1 is as above described, Hal is an halogen atom and $W_1$ is —CH$_2$— or —CH(CH$_3$)—, and A has the following meanings:
A is a radical of formula (IIa)-(IIm), (IIo)-(IIr), (IIt)-(IIu) and (IIn) wherein $R_1$ is —C(O)—$R_{1x}$— and binds the group —Y—ONO$_2$,
$R_2$ is —COOH;
in formula (IIn) $R_n$ is —C(O)—$R_{nx}$— or —(CH$_2$)$_2$—NH—$R_h$
wherein $R_h$ is —C(O)—$R_{hh}$, $R_n$ or $R_h$ binds the group —Y—ONO$_2$,
$R_a$ of formula (IIa) is selected in group a),
$R_c$ of formula (IIc) is selected in group a'),
in formula (IIt) d is an integer from 3 to 5, d' is 0;
using the same procedure described in 6b).
17. The compounds of general formula wherein:
s, s' and m' are equal to 1;
s", m, m", are 0
Y, Y' can be equal or different and are as above defined;
B is:

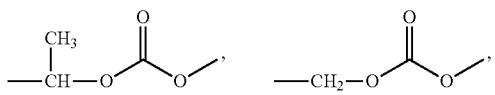

A is a radical of formula (IIa)-(IIm), (IIo)-(IIr), (IIt)-(IIu) and (IIn) wherein $R_1$ is —C(O)O—$R_{1x}$ and $R_2$ is —C(O)O$R_{2x}$
and $R_1$ binds the group —Y—ONO$_2$ and $R_2$ binds the group —B—Y'—ONO$_2$;
in formula (IIn) $R_n$ is —C(O)O—$R_{nx}$ or —(CH$_2$)$_2$—NH—$R_h$
wherein $R_h$ is —C(O)O—$R_{hh}$, $R_n$ or $R_h$ binds the group —Y—ONO$_2$,
$R_a$ of formula (IIa) is selected in group a),
$R_c$ of formula (IIc) is selected in group a'),
in formula (IIt) d is an integer from 3 to 5, d' is 0;
can be prepared as follows:
17a) by reacting compounds of formula (I) obtained with the procedure described in 3. with compounds (IIIg)

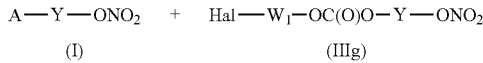

wherein Y is as above described, Hal is an halogen atom and $W_1$ is —CH$_2$— or —CH(CH$_3$)—, and A has the following meanings:
A is a radical of formula (IIa)-(IIm), (IIo)-(IIr), (IIt)-(IIu) and (IIn) wherein $R_1$ is —C(O)O—$R_{1x}$— binds the group —Y—ONO$_2$, $R_2$ is —COOH;
in formula (IIn) $R_n$ is —C(O)O—$R_{nx}$, or is —(CH$_2$)$_2$—NH—$R_h$ wherein $R_h$ is —C(O)O—$R_{hh}$, $R_n$ or $R_h$ binds the group —Y—ONO$_2$;
$R_a$ of formula (IIa) is selected in group a),
$R_c$ of formula (IIc) is selected in group a'),
in formula (IIt) d is an integer from 3 to 5, d' is 0;
using the same procedure described in 4b).
18. The compounds of general formula (I) wherein:
s, s' and m' are equal to 1;
s", m, m", are 0
Y, Y' can be equal or different and are as above defined;
B is:

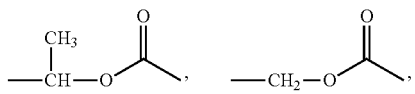

A is a radical of formula (IIa)-(IIm), (IIo)-(IIr), (IIt)-(IIu) and (IIn) wherein $R_1$ is —C(O)O—$R_{1x}$ and $R_2$ is —C(O)O$R_{2x}$
and $R_1$ binds the group —Y—ONO$_2$ and $R_2$ binds the group —B—Y'—ONO$_2$;
in formula (IIn) $R_n$ is —C(O)O—$R_{nx}$ or —(CH$_2$)$_2$—NH—$R_h$
wherein $R_h$ is —C(O)O—$R_{hh}$, $R_n$ or $R_h$ binds the group —Y—ONO$_2$;
$R_a$ of formula (IIa) is selected in group a),
$R_c$ of formula (IIc) is selected in group a');
in formula (IIt) d is an integer from 3 to 5, d' is 0;
can be prepared as follows:
18a) By reacting compounds of formula I obtained with the procedure described in 3. with compounds (IIIn)

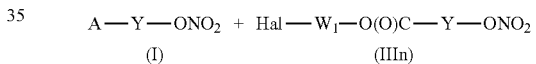

wherein Y is as above described, Hal is an halogen atom and $W_1$ is —CH$_2$— or —CH(CH$_3$)—, and A has the following meanings:
A is a radical of formula (IIa)-(IIm), (IIo)-(IIr), (IIt)-(IIu) and (IIn) wherein $R_1$ is —C(O)O—$R_{1x}$— and binds the group —Y—ONO$_2$, $R_2$ is —COOH;
in formula (IIn) $R_n$ is —C(O)O—$R_{nx}$, or is —(CH$_2$)$_2$—NH—$R_h$ wherein $R_h$ is —C(O)O—$R_{hh}$, $R_n$ or $R_h$ binds the group —Y—ONO$_2$;
$R_a$ of formula (IIa) is selected in group a),
$R_c$ of formula (IIc) is selected in group a'),
in formula (IIt) d is an integer from 3 to 5, d' is 0;
using the same procedure described in 6b).
19. Alternatively the compounds of general formula (I) described in procedure 11. wherein:
s and s' are equal to 1;
s", m, m', m", are 0
Y, Y' can be equal or different and are as above defined,
A is a radical of formula (IIa)-(IIm), (IIo)-(IIr), (IIt)-(IIu) and (IIn) wherein $R_1$ is —C(O)—$R_{1x}$ and $R_2$ is —C(O)O$R_{2x}$
and $R_2$ binds the group —Y—ONO$_2$ and $R_2$ binds the group —Y'—ONO$_2$;
in formula (IIn) $R_n$ is —C(O)—$R_{nx}$, or is —(CH$_2$)$_2$—NH—$R_h$ wherein $R_h$ is —C(O)—$R_{hh}$, $R_n$ or $R_h$ binds the group —Y'—ONO$_2$;
$R_a$ of formula (IIa) is selected in group a),
$R_c$ of formula (IIc) is selected in group a'),
in formula (IIt) d is an integer from 3 to 5, d' is 0;
can be prepared as follows:

19a) By reacting compounds of formula (I) obtained with the procedure described in 8. with compounds (IIIa) or (IIIe)

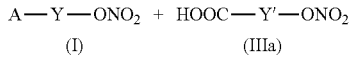
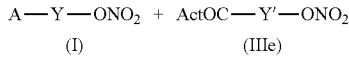

Wherein Y and Y' are equal or different and are as above defined, Act is as above defined and A has the following meanings:
A is a radical of formula (IIa)-(IIm), (IIo)-(IIr), (IIt)-(IIu) and (IIn) wherein $R_2$ is —C(O)O$R_{2x}$ and binds the group —Y—ONO$_2$, $R_1$ is —H;
in formula (IIn) $R_n$ is —H or is —(CH$_2$)$_2$—NH$_2$;
$R_a$ of formula (IIa) is selected in group a),
$R_c$ of formula (IIc) is selected in group a'),
in formula (IIt) d is an integer from 3 to 5, d' is 0;
using the same procedure described in 1b) or 1b').
20. Alternatively the compounds of general formula (I) described in procedure 12., wherein:
s and s' are equal to 1;
s", m, m', m", are 0
Y, Y' can be equal or different and are as above defined;
A is selected from (IIa)-(IIm), (IIo)-(IIr), (IIt)-(IIu) and (IIn) wherein:
$R_1$ is —C(O)O—$R_{1x}$ and $R_2$ is —C(O)O$R_{2x}$ and $R_2$ binds the group —Y—ONO$_2$ and $R_1$ binds the group —Y'—ONO$_2$;
in formula (IIn) $R_n$ is —C(O)O—$R_{nx}$ or —(CH$_2$)$_2$—NH—$R_h$ wherein $R_h$ is —C(O)O—$R_{hh}$, $R_n$ or $R_h$ binds the group —Y'—ONO$_2$;
$R_a$ of formula (IIa) is selected in group a),
$R_c$ of formula (IIc) is selected in group a'),
in formula (IIt) d is an integer from 3 to 5, d' is 0;
can be prepared as follows:
20a) By reacting compounds of formula (I) obtained with the procedure described in 8. with compounds (IIIf)

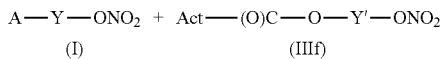

Wherein Y and Y' are equal or different and are as above defined and A has the following meanings:
A is a radical of formula (IIa)-(IIm), (IIo)-(IIr), (IIt)-(IIu) and (IIn) wherein $R_2$ is —C(O)O$R_{2x}$ and binds the group —Y—ONO$_2$, $R_1$ is —H;
in formula (IIn) $R_n$ is —H or is —(CH$_2$)$_2$—NH$_2$;
$R_a$ of formula (IIa) is selected in group a),
$R_c$ of formula (IIc) is selected in group a'),
in formula (IIt) d is an integer from 3 to 5, d' is 0;
using the same procedure described in 3b).
21. Alternatively the compounds of general formula (I) described in procedure 13. wherein:
s and s' are equal to 1;
s", m, m', m", are 0
Y, Y' can be equal or different and are as above defined,
A is selected from (IIa)-(IIm), (IIo)-(IIr), (IIt)-(IIu) and (IIn) wherein:
$R_1$ is —C(O)—$R_{1x}$ and $R_2$ is —C(O)NH$R_{2xx}$ or —C(O)NCH$_3$—$R_{2xx}$ and $R_2$ binds the group —Y—ONO$_2$ and $R_1$ binds the group —Y'—ONO$_2$;
in formula (IIn) $R_n$ is —C(O)—$R_{nx}$ or is —(CH$_2$)$_2$—NH—$R_h$ wherein $R_h$ is —C(O)—$R_{hh}$, $R_n$ or $R_h$ binds the group —Y'—ONO$_2$;
$R_a$ of formula (IIa) is selected in group a),
$R_c$ of formula (IIc) is selected in group a'),
in formula (IIt) d is an integer from 3 to 5, d' is 0;
can be prepared as follows:
21a) By reacting compounds of formula (I) obtained with the procedure described in 7. with compounds (IIIa) or (IIIe)

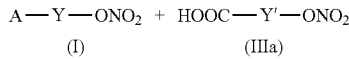
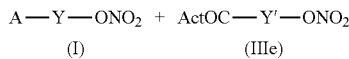

wherein Y and Y' are equal or different and are as above defined, Act is as above defined and A has the following meanings:
A is a radical of formula (IIa)-(IIm), (IIo)-(IIr), (IIt)-(IIu) and (IIn) wherein $R_2$ is —C(O)NH$R_{2xx}$ or —C(O)N(CH$_3$)$R_{2xx}$ and binds the group —Y—ONO$_2$, $R_1$ is —H;
in formula (IIn) $R_n$ is —H or is —(CH$_2$)$_2$—NH$_2$;
$R_a$ of formula (IIa) is selected in group a),
$R_c$ of formula (IIc) is selected in group a'),
in formula (IIt) d is an integer from 3 to 5, d' is 0;
using the same procedure described in 1b) or 1b').
22. Alternatively the compounds of general formula (I) wherein:
s and s' are equal to 1;
s", m, m', m", are 0, Y, Y' can be equal or different and are as above defined;
A is a radical of formula (IIa)-(IIm), (IIo)-(IIr), (IIt)-(IIu) and (IIn) wherein $R_1$ is —C(O)O—$R_{1x}$ and $R_2$ is —C(O)NH$R_{2xx}$ or —C(O)N(CH$_3$)$R_{2xx}$ and $R_2$ binds the group —Y—ONO$_2$ and $R_1$ binds the group —Y'—ONO$_2$;
in formula (IIn) $R_n$ is —C(O)O—$R_{nx}$ or —(CH$_2$)$_2$—NH—$R_h$ wherein $R_h$ is —C(O)O—$R_{hh}$, $R_n$ or $R_h$ binds the group —Y'—ONO$_2$;
$R_a$ of formula (IIa) is selected in group a),
$R_c$ of formula (IIc) is selected in group a'),
in formula (IIt) d is an integer from 3 to 5, d' is 0;
can be prepared as follows:
22a) By reacting compounds of formula (I) obtained with the procedure described in 7. with compounds (IIIf)

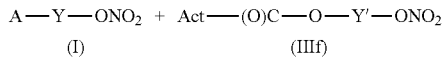

wherein Y and Y' are equal or different and are as above defined and A has the following meanings:
A is a radical of formula (IIa)-(IIm), (IIo)-(IIr), (IIt)-(IIu) and (IIn) wherein $R_2$ is —C(O)NH$R_{2xx}$ or —C(O)N(CH$_3$)$R_{2xx}$ and binds the group —Y—ONO$_2$, $R_1$ is —H;
in formula (IIn) $R_n$ is —H or is —(CH$_2$)$_2$—NH$_2$;
$R_a$ of formula (IIa) is selected in group a),
$R_c$ of formula (IIc) is selected in group a'),
in formula (IIt) d is an integer from 3 to 5, d' is 0;
using the same procedure described in 3b).
23. Alternatively the compounds of general formula (I) wherein:
s, s' and m are equal to 1;
s", m, m", are 0
Y, Y' can be equal or different and are as above defined;

B is:

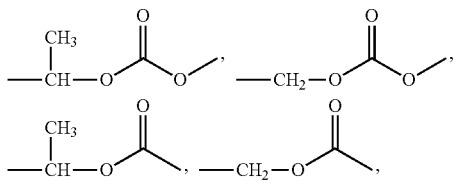

A is selected from (IIa)-(IIm), (IIo)-(IIr), (IIt)-(IIu) and (IIn) wherein:
$R_1$ is —C(O)—$R_{1x}$ and $R_2$ is —C(O)O$R_{2x}$ and $R_2$ binds the group —B—Y—$ONO_2$ and $R_1$ binds the group —Y'—$ONO_2$;
in formula (IIn) $R_n$ is —C(O)—$R_{nx}$, or is —$(CH_2)_2$—NH—$R_h$ wherein $R_h$ is —C(O)—$R_{hh}$, $R_n$ or $R_h$ binds the group —Y'—$ONO_2$;
$R_a$ of formula (IIa) is selected in group a),
$R_c$ of formula (IIc) is selected in group a'),
in formula (IIt) d is an integer from 3 to 5, d' is 0;
can be prepared as follows:
23a) By reacting compounds of formula (I) obtained with the procedure described in 4. or 6. with compounds (IIIa) or (IIIe)

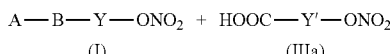
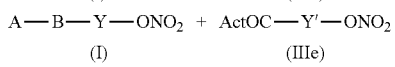

wherein Y, and Y' are equal or different and are as above defined, Act and B are as above described and A has the following meanings:
A is a radical of formula (IIa)-(IIm), (IIo)-(IIr), (IIt)-(IIu) and (IIn) wherein $R_1$ is —H, $R_2$ is —C(O)O$R_{2x}$ and $R_2$ binds the group —B—Y—$ONO_2$
in formula (IIn) $R_n$ is —H or is —$(CH_2)_2$—$NH_2$;
$R_a$ of formula (IIa) is selected in group a),
$R_c$ of formula (IIc) is selected in group a'),
in formula (IIt) d is an integer from 3 to 5, d' is 0;
using the same procedure described in 1b) or 1b').
24. Alternatively the compounds of general formula (I) wherein:
s, s' and m are equal to 1;
s'', m, m'', are 0
Y, Y' can be equal or different and are as above defined;
B is:

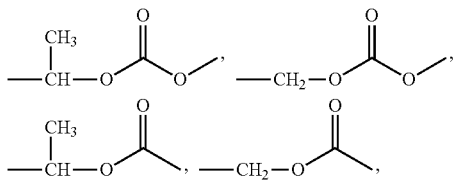

A is a radical of formula (IIa)-(IIm), (IIo)-(IIr), (IIt)-(IIu) and (IIn) wherein $R_1$ is —C(O)O—$R_{1x}$ and $R_2$ is —C(O)O$R_{2x}$ and $R_2$ binds the group —B—Y—$ONO_2$ and $R_1$ binds the group —Y'—$ONO_2$;
in formula (IIn) $R_n$ is —C(O)O—$R_{nx}$ or —$(CH_2)_2$—NH—$R_h$ wherein $R_h$ is —C(O)O—$R_{hh}$, $R_n$ or $R_h$ binds the group —Y'—$ONO_2$;
$R_a$ of formula (IIa) is selected in group a),
$R_c$ of formula (IIc) is selected in group a'),
in formula (IIt) d is an integer from 3 to 5, d' is 0;
can be prepared as follows:
24a) by reacting compounds of formula (I) obtained with the procedure described in 4. or 6. depending on the meanings of B with compounds (IIIf)

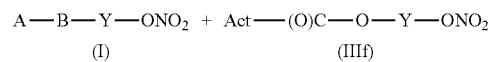

wherein Y, and Y' are equal or different and are as above defined, Act is as above described and A has the following meanings:
A is a radical of formula (IIa)-(IIm), (IIo)-(IIr), (IIt)-(IIu) and (IIn) wherein $R_1$ is —H, $R_2$ is —C(O)O$R_{2x}$ and binds the group —B—Y—$ONO_2$
B is:

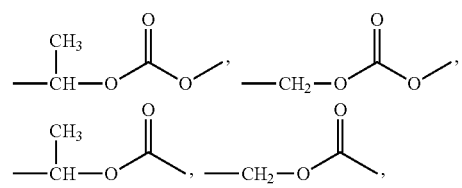

in formula (IIn) $R_n$ is —H or is —$(CH_2)_2$—$NH_2$;
$R_a$ of formula (IIa) is selected in group a),
$R_c$ of formula (IIc) is selected in group a'),
in formula (IIt) d is an integer from 3 to 5, d' is 0;
using the same procedure described in 3b).
25. The compounds of general formula (I) wherein:
s, is equal to 1;
s' s'', m, m', m'', are 0
Y is as above defined;
A is a radical of formula (IIs) wherein $R_1$ is —C(O)—$R_{1x}$ and it binds the group —Y—$ONO_2$, $R_3$ is —OH and $R_s$ is selected in group a''), can be prepared as follows
25a) by reacting compounds of formula A with a compound of formula (IIIa) or (IIIe):

HOOC—Y—$ONO_2$ (IIIa)

ActOC—Y—$ONO_2$ (IIIe)

wherein Y is as above defined, Act is as above described and A is a compound of formula (IIs) wherein $R_1$ is —H, $R_3$ is —OH and $R_s$ is selected in group a''), using the same procedure described in 1b) or 1b') using a ratio A/(IIIa) or A/(IIIe) 1:1.
Compounds A are commercially available.
26. The compounds of general formula (I) wherein:
s is equal to 1;
s', s'', m, m', m'', are 0
Y is as above defined;
A is a radical of formula (IIs) wherein $R_1$ is —C(O)O—$R_{1x}$ and it binds the group —Y—$ONO_2$, $R_3$ is —OH and $R_s$ is selected in group a''), can be prepared as follows:
26a) by reacting compounds of formula A with a compound of formula (IIIf):

Act-(O)C—O—Y—$ONO_2$ (IIIf)

wherein Y is as above defined, Act is as above described and A is a compound of formula (IIs) described, in 25a) wherein $R_1$ is —H, $R_3$ is —OH and $R_s$ is selected in group a"), using the same procedure described, in 3b) using a ratio A/(IIIf) 1:1.

27. The compounds of general formula (I) wherein:
s is equal to 1;
s', s", m, m', m", are 0
Y is as above defined;
A is a radical of formula (IIs) wherein $R_3$ is —OC(O)—$R_{3x}$ and it binds the group —Y—ONO$_2$; $R_1$ is —H and $R_s$ is selected in group a"), can be prepared as follows:
27a) by reacting compounds of formula (I) wherein s, s', s", m, m', m", Y, Y', Y" are as above defined in 27., A is a radical of formula (IIs) $R_1$ is —C(O)OC(CH$_3$)$_3$; $R_3$ and $R_s$ are as defined in 27.; with anhydrous or aqueous organic or inorganic acid to hydrolyze the —BOC protective groups following procedure well known in the literature.
27b) by reacting a compound of formula A with a compound of formula (IIIe)

Act-(O)C—Y—ONO$_2$     (IIIe)

wherein Y and Act are as above defined; A is a compound of formula (IIs) wherein $R_1$ is —C(O)OC(CH$_3$)$_3$, $R_3$ is —OH and $R_s$ is selected in group a"), using the same procedure described in 1b'). Compounds A are commercially available.

28. The compounds of general formula (I) wherein:
s is equal to 1;
s', s", m, m', m", are 0
Y is as above defined;
A is a radical of formula (IIs) wherein $R_3$ is —OC(O)O—$R_{3x}$ and it binds the group —Y—ONO$_2$; $R_1$ is —H and $R_s$ is selected in group a"), can be prepared as follows:
28a) by reacting compounds of formula (I) wherein s, s', s", m, m', m", Y, Y', Y" are as above defined in 28., A is a radical of formula (IIs) $R_1$ is —C(O)OC(CH$_3$)$_3$; $R_3$ and $R_s$ are as defined in 28. with anhydrous or aqueous organic or inorganic acid to hydrolyze the —BOC protective groups following procedure well known in the literature.
28b) By reacting a compound of formula A with a compound of formula (IIf)

Act-(O)C—O—Y—ONO$_2$     (IIIf)

wherein Y and Act are as above defined; A is a compound of formula (IIs) described in 27a) wherein $R_1$ is —C(O)OC(CH$_3$)$_3$, $R_3$ is —OH and $R_s$ is selected in group a"), using the same procedure described in 3b)

29. The compounds of general formula (I) wherein:
s is equal to 1;
s', s", m, m', m", are 0
Y is as above defined;
A is a radical of formula (IIs) wherein $R_3$ is —OC(O)—NH—$R_{3x}$— and it binds the group —Y—ONO$_2$; $R_1$ is —H and $R_s$ is selected in group a"), can be prepared as follows:
29a) by reacting compounds of formula (I) wherein s, s', s", m, m', m", Y, Y', Y" are as above defined in 29., A is a radical of formula (IIs) $R_1$ is —C(O)OC(CH$_3$)$_3$; $R_3$ and $R_s$ are as defined in 29. with anhydrous or aqueous organic or inorganic acid to hydrolyze the —BOC protective groups following procedure well known in the literature.
29b) by reacting a compound of formula A with a compound of formula (IIIu)

Act-(O)C—NH—Y—ONO$_2$     (IIIu)

wherein Y and Act are as above defined; A is a compound of formula (IIs) described in 27b) wherein $R_1$ is —C(O)OC(CH$_3$)$_3$, $R_3$ is —OH and $R_s$ is selected in group a"), in the presence of a inorganic or organic base in an aprotic polar/non-polar solvent such as DMF, THF, or CH$_2$Cl$_2$ at temperatures range between 0°-100° C. for time range of 1-60 hrs, or under microwave irradiation in the presence of DMAP and a Lewis acid such as Sc(OTf)$_3$ or Bi(OTf)$_3$ in solvents such as DMF, CH$_2$Cl$_2$ at temperatures range between 60°-120° C. for time range of 1-120 min;

Compounds (IIIu) can be prepared from compounds Act-(O)C—NH—Y—OH (IIIv) by nitrating reactions with tetraalkylammonium nitrate as already described. Compounds (IIIv) can be prepared from commercially available Act-CO-Hal (IIIw) and compounds W$_3$NH—Y—OH (IIIt) with the proviso that in (IIIt) W$_3$ has only the meaning of —H.

30. The compounds of general formula (I) wherein:
s and s' are equal to 1;
s", m, m', m", are 0
Y, Y' can be equal or different and are as above defined;
A is a radical of formula (IIs) wherein $R_3$ is —OC(O)—$R_{3x}$ and it binds the group —Y—ONO$_2$ or the group —Y—ONO$_2$; $R_1$ is —C(O)—$R_{1x}$ and it binds the group —Y—ONO$_2$ or the group —Y'—ONO$_2$;
$R_s$ is selected in group a"), can be prepared as follows:
30a) Y and Y' are equal
by reacting compounds of formula A described in 25a) with a compound of formula (IIIe)

Act-(O)C—Y—ONO$_2$     (IIIe)

wherein Y and Act are as above defined; A is a compound of formula (IIs) wherein $R_1$ is —H, $R_3$ is —OH and $R_s$ is selected in group a"), using a ratio A/(IIIe) 1:2 and applying the same procedure described in 1b').
30a') Y and Y' are equal or different
by reacting compounds of formula (I) prepared in 25. with a compound of formula (IIIe)

A-Y—ONO$_2$+Act-(O)C—Y'—ONO$_2$     (IIIe)

wherein Y, Y' and Act are as above defined; A is a compound of formula (IIs) wherein $R_1$ is —C(O)—$R_{1x}$ and binds the group —Y—ONO$_2$, $R_3$ is —OH and $R_s$ is selected in group a"), applying the same procedure described in 1b').
30a") Y and Y' are equal or different
by reacting compounds of formula (I) prepared in 27. with a compound of formula (IIIe)

A-Y—ONO$_2$+Act-(O)C—Y'—ONO$_2$     (IIIe)

wherein Y, Y' and Act are as above defined; A is selected from (IIs) wherein $R_1$ is —H, $R_3$ is —OC(O)—$R_{3x}$ and $R_s$ is selected in group a"), applying the same procedure described in 1b').

31. The compounds of general formula (I) wherein:
s and s' are equal to 1;
s", m, m', m", are 0
Y and Y' can be equal or different and are as above defined;
A is a radical of formula (IIs) wherein $R_3$ is —OC(O)O—$R_{3x}$— and it binds the group —Y—ONO$_2$ or the group —Y'—ONO$_2$; $R_1$ is —C(O)—$R_{1x}$ and it binds the group —Y—ONO$_2$ or the group —Y'—ONO$_2$, $R_s$ is selected in group a"), can be prepared as follows:
31a) by reacting compounds of formula (I) obtained in procedure 25. with a compound of formula (IIIf)

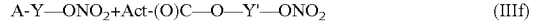

A-Y—ONO$_2$+Act-(O)C—O—Y'—ONO$_2$     (IIIf)

wherein Y, Y' and Act are as above defined; A is a radical of formula (IIs) wherein $R_1$ is —C(O)—$R_{1x}$ and it binds the group —Y—ONO$_2$, $R_3$ is —OH and $R_s$ is selected in group a"), applying the same procedure described in 28b).

31a') alternatively by reacting compounds of formula (I) prepared as described in 28. with a compound of formula (IIIe)

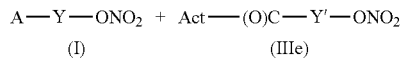
A—Y—ONO₂+Act-(O)C—Y'—ONO₂ (IIIe)

wherein Y, Y' and Act are as above defined; A is the radical of formula (IIs) wherein $R_1$ is —H, $R_3$ is —OC(O)O—$R_{3x}$ and $R_3$ binds the group —Y—ONO₂, $R_s$ is selected in group a"), applying the same procedure described in 25a).

32. The compounds of general formula (I) wherein:
s and s' are equal to 1;
s", m, m', m", are 0
Y and Y' can be equal or different and are as above defined;
A is a radical of formula (IIs) wherein $R_3$ is —OC(O)—NH—$R_{3x}$ and it binds the group —Y—ONO₂; $R_1$ is —C(O)—$R_{1x}$ and it binds the group —Y'—ONO₂, $R_s$ is selected in group a"), can be prepared as follows:
32a) by reacting compounds of formula (I) obtained in procedure 29. with a compound of formula (IIIe)

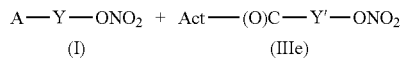
A—Y—ONO₂ + Act—(O)C—Y'—ONO₂
(I)               (IIIe)

wherein Y, Y' and Act are as above defined; A is a radical of formula (IIs) wherein $R_1$ is —H, $R_3$ is —OC(O)—NH—$R_{3x}$ it binds the group —Y—ONO₂, $R_s$ is selected in group a"), applying the same procedure described in 25a).

33. The compounds of general formula (I) wherein:
s and s' are equal to 1;
s", m, m', m", are 0
Y and Y' can be equal or different and are as above defined;
A is a radical of formula (IIs) wherein $R_3$ is —OC(O)—$R_{3x}$ and it binds the group —Y'—ONO₂; $R_1$ is —C(O)O—$R_{1x}$ and it binds the group —Y—ONO₂, $R_s$ is selected in group a"), can be prepared as follows:
33a) by reacting compounds of formula (I) obtained in procedure 26. with a compound of formula (IIIe)

A—Y—ONO₂ + Act—(O)C—Y'—ONO₂
(I)               (IIIe)

wherein Y, Y' and Act are as above defined; A is a radical of formula (IIs) wherein $R_1$ is —C(O)O—$R_{1x}$ and it binds the group —Y—ONO₂, $R_3$ is —OH and $R_s$ is selected in group a"),
applying the same procedure described in 27b).

34. The compounds of general formula (I) wherein:
s and s' are equal to 1;
s", m, m', m", are 0
Y and Y' can be equal or different and are as above defined;
A is a radical of formula (IIs) wherein $R_3$ is —OC(O)O—$R_{3x}$ and it binds the group —Y—ONO₂ or the group —Y'—ONO₂, $R_1$ is —C(O)O—$R_{1x}$ and it binds the group —Y—ONO₂ or the group —Y'—ONO₂, $R_s$ is selected in group a"), can be prepared as follows:
34a) Y and Y' are equal;
by reacting compounds of formula A described in 25a) with a compound of formula (IIIf)

A+Act-(O)C—O—Y'—ONO₂ (IIIf)

wherein Y, Y' and Act are as above defined; A is a compound of formula (IIs) wherein $R_1$ is —H, $R_3$ is —OH and $R_s$ is selected in group a"), using a ratio A/(IIIf) 1:2 and applying the same procedure described in 3b).

34a') Y and Y' are equal or different
by reacting compounds of formula (I) prepared in 26. with a compound of formula (IIIf)

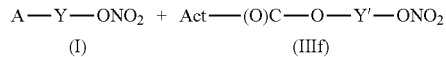
A—Y—ONO₂ + Act—(O)C—O—Y'—ONO₂
(I)                    (IIIf)

wherein Y, Y' and Act are as above defined; A is a radical of formula (IIs) wherein $R_1$ is —C(O)O—$R_{1x}$ and it binds the group —Y—ONO₂ and $R_3$ is —OH, $R_3$ is selected in group a");
applying the same procedure described in 3b).

34a") Y and Y' are equal or different
by reacting compounds of formula (I) prepared in 28. with a compound of formula (IIIf)

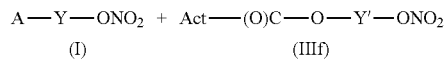
A—Y—ONO₂ + Act—(O)C—O—Y'—ONO₂
(I)                    (IIIf)

wherein Y, Y' and Act are as above defined; A is a radical of formula (IIs) wherein $R_1$ is —H, $R_3$ is —OC(O)O—$R_{3x}$ and $R_3$ binds the group —Y—ONO₂, $R_s$ is selected in group a"), applying the same procedure described in 3b).

35. The compounds of general formula (I) wherein:
s and s' are equal to 1;
s", m, m', m", are 0
Y and Y' can be equal or different and are as above defined;
A is a radical of formula (IIs) wherein $R_3$ is —OC(O)—NH—$R_{3x}$ and it binds the group —Y'—ONO₂; $R_1$ is —C(O)O—$R_{1x}$ and it binds the group —Y—ONO₂, $R_s$ is selected in group a"),
can be prepared as follows:
35a) by reacting compounds of formula (I) obtained in procedure 26. with a compound of formula (IIIu)

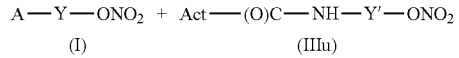
A—Y—ONO₂ + Act—(O)C—NH—Y'—ONO₂
(I)                    (IIIu)

wherein Y, Y' and Act are as above defined; A is a radical of formula (IIs) wherein $R_1$ is —C(O)O—$R_{1x}$ and it binds the group —Y—ONO₂, $R_3$ is —OH and $R_s$ is selected in group a"),
using the same procedure described in 29b).

35a") alternatively by reacting compound of formula (I) prepared in 29. with a compound of formula (IIIf)

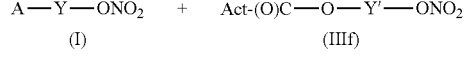
A—Y—ONO₂  +  Act-(O)C—O—Y'—ONO₂
(I)                    (IIIf)

wherein Y, Y' and Act are as above defined; A is a radical of formula (IIs) wherein $R_1$ is —H, $R_3$ is —OC(O)—NH—$R_{3x}$ and it binds the group —Y—ONO₂, $R_s$ is selected in group a"),
applying the same procedure described in 3b).

36. The compounds of general formula (I) wherein:
s is equal to 1;
s' can be 0 or 1; with the proviso that s' is 1 when A is the radical (IIs) and (IIs) is as defined in iii) below reported,
s", m, m', m", are 0
Y and Y' when presents are equal and are as above defined;

A is selected among:
i) (IIa) wherein $R_1$ is —H, $R_2$ is —COOH and $R_a$ is selected from $R_{bx}$—C(O)—S—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ —C(O)— and $R_a$ binds a group —Y—$ONO_2$;
ii) (IIc) wherein $R_1$ is —H, $R_2$ is —COOH and $R_c$ is selected from $R_{bx}$—C(O)—S—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ —C(O)— and $R_c$ binds a group —Y—$ONO_2$;
iii) (IIs) (s' is 1) wherein $R_1$ is —H, $R_3$ is —OC(O) and $R_s$ is selected from $R_{bx}$—C(O)—S—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ is $R_{xx}$—C(O)—; both $R_3$ and $R_s$ bind a group —Y—$ONO_2$ or a —Y'—$ONO_2$;
vi) (IIs) (s' is 0) wherein $R_1$ is —H, $R_3$ is —OC(O) and $R_3$ binds a group —Y—$ONO_2$; $R_s$ is selected from $R_gC(O)CH_2$—NH—, $R_gC(O)CH_2$, $R_gC(O)(CH_2)_2$—, $R_gC(O)(CH_2)_4$—, wherein $R_g$ is —OH;
v) (IIu) wherein $R_1$ is —H, $R_2$ is —COOH, a is 1; b is 0 or 1; and $R_x$ is $R_{xx}$—C(O)— and $R_x$ binds a group —Y—$ONO_2$;
can be prepared as follows:
36a) by reacting a compound of formula (I) wherein s, s', s", m, m', m", Y, Y', Y" are as above defined in 36., A is a radical of formula (IIa), (IIc), (IIs) or (IIu) wherein; $R_2$, $R_3$, a, b, $R_a$, $R_c$, $R_s$, $R_g$ and $R_x$, are as defined in 36.; $R_1$ is —C(O)OC($CH_3$)$_3$ with anhydrous or aqueous organic or inorganic acid to hydrolyze the —BOC protective groups following procedure well known in the literature.
36b) by reacting a compound of formula A with a compound of formula (IIIa)

A+Act(O)C—Y—$ONO_2$ (IIIe)

wherein Act and Y are as above defined and A has the following meanings:
i') a radical of formula (IIa) wherein $R_1$ is —C(O)OC($CH_3$)$_3$, $R_2$ is —COOH and $R_a$ is selected from HS—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ —H;
ii') a radical of formula (IIc) wherein $R_1$ is —C(O)OC($CH_3$)$_3$, $R_2$ is —COOH and $R_c$ is selected from HS—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ —H;
iii') a radical of formula (IIs) wherein $R_1$ is —C(O)OC($CH_3$)$_3$, $R_3$ is —OH and $R_s$ is selected from HS—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ —H;
iv') a radical of formula (IIs) wherein $R_1$ is —C(O)OC($CH_3$)$_3$, $R_3$ is —OH; $R_s$ is $R_gC(O)CH_2$—NH—, $R_gC(O)CH_2$, $R_gC(O)(CH_2)_2$—, $R_gC(O)(CH_2)_4$—, wherein $R_g$ is —OH;
v') a radical of formula (IIu) wherein $R_1$ is —C(O)OC($CH_3$)$_3$, $R_2$ is —COOH, a is 1; b is 0 or 1 and $R_x$ is —H;
following the same procedure described in 1b') using a ratio A/(IIIe) 1:1 or 1:2 for s' equal to 1.
37. The compounds of general formula (I) wherein:
s is equal to 1;
s' can be 0 or 1; with the proviso that s' is 1 when A is the radical (IIs) and (IIs) is as defined in iii),
s", m, m', m", are 0
Y and Y', when present are equal and are as above defined;
A is selected among:
i) (IIa) wherein $R_1$ is —H, $R_2$ is —COOH and $R_a$ is selected from $R_{bx}$—OC(O)—S—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ is $R_{xx}$—OC(O)— and $R_a$ binds a group —Y—$ONO_2$;
ii) (IIc) wherein $R_1$ is —H, $R_2$ is —COOH and $R_c$ is selected from $R_{bx}$—OC(O)—S—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ is $R_{xx}$—OC(O)— and $R_c$ binds a group —Y—$ONO_2$;
iii) (IIs) (s' is 1) wherein $R_1$ is —H, $R_3$ is —OC(O)O—$R_{3x}$ and $R_s$ is selected from $R_{bx}$—OC(O)—S—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ is $R_{xx}$—OC(O)— both $R_3$ and $R_s$ bind a group —Y—$ONO_2$ or a group —Y'—$ONO_2$;
vi) (IIs) (s' is 0) wherein $R_1$ is —H, $R_3$ is —OC(O)O—$R_{3x}$ and $R_3$ binds a group —Y—$ONO_2$; $R_s$ is selected from $R_gC(O)CH_2$—NH—, $R_gC(O)CH_2$, $R_gC(O)(CH_2)_2$—, $R_gC(O)(CH_2)_4$—, wherein $R_g$ is —OH;
v) (IIu) wherein $R_1$ is —H, $R_2$ is —COOH, a is 1; b is 0 or 1; and $R_x$ is $R_{xx}$—OC(O)— and $R_x$ binds a group —Y—$ONO_2$;
can be prepared as follows:
37a) by reacting a compound of formula (I) wherein s, s', s", m, m', m", Y, Y', Y" are as above defined in 37., A is a radical of formula (IIa), (IIc), (IIs) or (IIu) wherein; $R_2$, $R_3$, a, b, $R_a$, $R_c$, $R_s$, $R_g$ and $R_x$, are as defined in 37.; $R_1$ is —C(O)OC($CH_3$)$_3$ with anhydrous or aqueous organic or inorganic acid to hydrolyze the —BOC protective groups following procedure well known in the literature.
37b) by reacting a compound of formula A with a compound of formula (IIIf)

A+Act(O)C—O—Y—$ONO_2$ (IIIf)

wherein Act and Y are as above defined and A has the same meanings described in 36b);
following the same procedure described in 3b) using a ratio A/(IIIf) 1:1 or 1:2 for s' equal to 1.
38. The compounds of general formula (I) wherein:
s is equal to 1;
s' can be 0 or 1; with the proviso that s' is 1 when A is the radical (IIs) and (IIs) is as defined in iii),
s", m, m', m", are 0
Y and Y', when presents, are equal and are as above defined;
A is selected among:
i) (IIa) wherein $R_1$ is —H, $R_2$ is —COOH and $R_a$ is selected from $R_{bx}$—NH(O)C—S—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ is $R_{xx}$NH—C(O)— and $R_a$ binds a group —Y—$ONO_2$;
ii) (IIc) wherein $R_1$ is —H, $R_2$ is —COOH and $R_c$ is selected from $R_{bx}$—NH(O)C—S—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ is $R_{xx}$NH—C(O)— and $R_c$ binds a group —Y—$ONO_2$;
iii) (IIs) (s' is 1) wherein $R_1$ is —H, $R_3$ is —OC(O)—NH—$R_{3x}$ and $R_s$ is selected from $R_{bx}$—NH(O)C—S—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ is $R_{xx}$NH—C(O)— both $R_s$ and $R_s$ bind a group —Y—$ONO_2$ or a group —Y'—$ONO_2$;
vi) (IIs) (s' is 0) wherein $R_1$ is —H, $R_3$ is —OC(O)—NH—$R_{3x}$ and $R_3$ binds a group —Y—$ONO_2$; $R_s$ is selected from $R_gC(O)CH_2$—NH—, $R_gC(O)CH_2$, $R_gC(O)(CH_2)_2$—, $R_gC(O)(CH_2)_4$—, wherein $R_g$ is —OH;

v) (IIu) wherein $R_1$ is —H, $R_2$ is —COOH, a is 1; b is 0 or 1; and $R_x$ is $R_{xx}$—NHC(O)— and $R_x$ binds a group —Y—ONO$_2$;

can be prepared as follows:

38a) by reacting a compound of formula (I) wherein s, s', s", m, m', m", Y, Y', Y" are as above defined in 38., A is a radical of formula (IIa), (IIc), (IIs) or (IIu) wherein; $R_2$, $R_3$, a, b, $R_a$, $R_c$, $R_s$, $R_g$ and $R_x$, are as defined in 38.; $R_1$ is —C(O)OC(CH$_3$)$_3$ with anhydrous or aqueous organic or inorganic acid to hydrolyze the —BOC protective groups following procedure well known in the literature.

38b) by reacting a compound of formula A with a compound of formula (IIIu)

A+Act(O)C—NH—Y—ONO$_2$     (IIIu)

wherein Act and Y are as above defined and A has the same meanings described in 36b);

following the same procedure described in 29. using a ratio A/(IIIu) 1:1 or 1:2 for s' equal to 1.

39. The compounds of general formula (I) wherein:
s and a' are equal to 1;
s", m, m', m", are 0
Y and Y' are equal or different and are as above defined;
A is selected among:
i) (IIa) wherein $R_1$ is —H, $R_2$ is —C(O)OR$_{2x}$ and $R_2$ binds a group —Y'—ONO$_2$; and $R_a$ is selected from $R_{bx}$—C(O)—S—CH$_2$—, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_x$ is $R_{xx}$—C(O)— and $R_a$ binds a group —Y—ONO$_2$;
ii) (IIc) wherein $R_1$ is —H, $R_2$ is —C(O)OR$_{2x}$ and $R_2$ binds a group —Y'—ONO$_2$; $R_c$ is selected from $R_{bx}$—C(O)—S—CH$_2$—, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_x$ is $R_{xx}$—C(O)— and $R_c$ binds a group —Y—ONO$_2$;
iii) (IIs) wherein $R_1$ is —H, $R_3$ is —OC(O)R$_{3x}$ and $R_3$ binds a group —Y—ONO$_2$; $R_s$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_g$ binds a group —Y'—ONO$_2$;
v) (IIu) wherein $R_1$ is —H, $R_2$ is —C(O)O—R$_{2x}$, $R_2$ binds a group —Y'—ONO$_2$; a is 1; b is 0 or 1; and $R_x$ is $R_{xx}$—C(O)— and $R_x$ binds a group —Y—ONO$_2$;

can be prepared as follows:

39a) by reacting a compound of formula (I) wherein s, s', s", m, m', m", Y, Y', Y" are as above defined in 39., A is a radical of formula (IIa), (IIc), (IIs) or (IIu) wherein; $R_2$, $R_3$, a, b, $R_a$, $R_c$, $R_s$, $R_g$ and $R_x$, as defined in 39.; $R_1$ is —C(O)OC(CH$_3$)$_3$ with anhydrous or aqueous organic or inorganic acid to hydrolyze the —BOC protective groups following procedure well known in the literature.

39b) by reacting a compound of formula (I) obtained in 36b) with a compound of formula (IIIi)

A—Y—ONO$_2$  +  HO—Y'—ONO$_2$
(I)                  (IIIi)

wherein Y and Y' are as above defined and in formula (I) A is a radical of formula (IIa), (IIc), (IIs) or (IIu) wherein $R_1$ is —C(O)OC(CH$_3$)$_3$, $R_2$ is —COOH, $R_3$, $R_a$, $R_c$ $R_x$ a and b are as above defined in 39., $R_s$ is $R_gC(O)CH_2$—NH—, $R_gC(O)CH_2$, $R_gC(O)(CH_2)_2$—, $R_gC(O)(CH_2)_4$—, wherein $R_g$ is —OH;

following the same procedure described in 8b).

40. The compounds of general formula (I) wherein:
s and s' are equal to 1;
s", m, m', m", are 0
Y and Y' are equal or different and are as above defined;
A is selected among:
i) (IIa) wherein $R_1$ is —H, $R_2$ is —C(O)OR$_{2x}$ and $R_2$ binds a group —Y'—ONO$_2$; and $R_a$ is selected from $R_{bx}$—OC(O)—S—CH$_2$—, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_x$ is $R_{xx}$—OC(O)— and $R_a$ binds a group —Y—ONO$_2$;
ii) (IIc) wherein $R_1$ is —H, $R_2$ is —C(O)OR$_{2x}$ and $R_2$ binds a group —Y'—ONO$_2$; $R_c$ is selected from $R_{bx}$—OC(O)—S—CH$_2$—, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_x$ is $R_{xx}$—OC(O)— and $R_c$ binds a group —Y—ONO$_2$;
iii) (IIs) wherein $R_1$ is —H, $R_3$ is —OC(O)O—R$_{3x}$ and $R_3$ binds a group —Y—ONO$_2$; $R_s$ is selected from $R_gC(O)CH_2$—NH—, $R_gC(O)CH_2$, $R_gC(O)(CH_2)_2$—, $R_gC(O)(CH_2)_4$—, $R_g$ is $R_{gx}$—O—, and $R_s$ binds a group —Y'—ONO$_2$;
v) (IIu) wherein $R_1$ is —H, $R_2$ is —C(O)O—R$_{2x}$, $R_2$ binds a group —Y'—ONO$_2$; a is 1; b is 0 or 1 and $R_x$ is $R_{xx}$—OC(O)— and $R_x$ binds a group —Y—ONO$_2$;

can be prepared as follows:

40a) by reacting a compound of formula (I) wherein s, s', s", m, m', m", Y, Y', Y" are as above defined, in 40., A is a radical of formula (IIa), (IIc), (IIs) or (IIu) wherein; $R_2$, $R_3$, a, b, $R_a$, $R_c$, $R_s$, $R_g$ and $R_x$, are as defined in 40.; $R_1$ is —C(O)OC(CH$_3$)$_3$ with anhydrous or aqueous organic or inorganic acid to hydrolyze the —BOC protective groups following procedure well known in the literature.

40b) by reacting a compound of formula (I) obtained in 37b) with a compound of formula (IIIi)

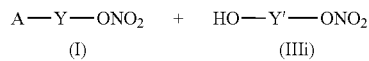

A—Y—ONO$_2$  +  HO—Y'—ONO$_2$
(I)                  (IIIi)

wherein Y and Y' are as above defined and in formula (I) A is a radical of formula (IIa), (IIc), (IIs) or (IIu) wherein $R_1$ is —C(O)OC(CH$_3$)$_3$, $R_2$ is —COOH, $R_3$, $R_a$, $R_c$ $R_x$ a and b are as above defined in 40., $R_s$ is $R_gC(O)CH_2$—NH—, $R_gC(O)CH_2$, $R_gC(O)(CH_2)_2$—, $R_gC(O)(CH_2)_4$—, wherein $R_g$ is —OH;

following the same procedure described in 8b).

41. The compounds of general formula (I) wherein:
s and s' are equal to 1;
s", m, m', m", are 0
Y and Y' are equal or different and are as above defined;
A is selected among:
i) (IIa) wherein $R_1$ is —H, $R_2$ is —C(O)OR$_{2x}$ and $R_2$ binds a group —Y'—ONO$_2$; and $R_a$ is selected from $R_{bx}$—NH(O)C—S—CH$_2$—, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_x$ is $R_{xx}$NH—C(O)— and $R_a$ binds a group —Y—ONO$_2$;
ii) (IIc) wherein $R_1$ is —H, $R_2$ is —C(O)OR$_{2x}$ and $R_2$ binds a group —Y'—ONO$_2$; $R_c$ is selected from $R_{bx}$—NH(O)C—S—CH$_2$—, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_x$ is $R_{xx}$NH—C(O)— and $R_c$ binds a group —Y—ONO$_2$;
iii) (IIs) wherein $R_1$ is —H, $R_3$ is —OC(O)—NH—R$_{3x}$ and $R_3$ binds a group —Y—ONO$_2$; $R_s$ is selected from $R_gC(O)$ $CH_2$—NH—, $R_gC(O)CH_2$, $R_gC(O)(CH_2)_2$—, $R_gC(O)(CH_2)_4$—, wherein $R_g$ is $R_{gx}$—O—, and $R_s$ binds a group —Y'—$ONO_2$;

v) (IIu) wherein $R_1$ is —H, $R_2$ is —C(O)O—$R_{2x}$, $R_2$ binds a group —Y'—$ONO_2$; a is 1; b is 0 or 1 and $R_x$ is $R_{xx}$—NHC(O)— and $R_x$ binds a group —Y—$ONO_2$;

can be prepared as follows:

41a) by reacting a compound of formula (I) wherein s, s', s'', m, m', m'', Y, Y', Y'' are as above defined in 41., A is a radical of formula (IIa), (IIc), (IIs) or (IIu) wherein; $R_2$, $R_3$, a, b, $R_a$, $R_c$, $R_s$, $R_g$ and $R_x$, are as defined in 41.; $R_1$ is —C(O)OC(CH$_3$)$_3$ with anhydrous or aqueous organic or inorganic acid to hydrolyze the —BOC protective groups following procedure well known in the literature.

41b) by reacting a compound of formula (I) obtained in 38b) with a compound of formula (IIIi)

wherein Y and Y' are as above defined and in formula (I) A is a radical of formula (IIa), (IIc), (IIs) or (IIu) wherein $R_1$ is C(O)OC(CH$_3$)$_3$, $R_2$ is —COOH, $R_3$, $R_a$, $R_c$ $R_x$ a and b are as above defined in 41., $R_s$ is $R_gC(O)CH_2$—NH—, $R_gC(O)CH_2$, $R_gC(O)(CH_2)_2$—, $R_gC(O)(CH_2)_4$—, wherein $R_g$ is —OH;

following the same procedure described in 8b).

42. The compounds of general formula (I) wherein:

s and s' are equal to 1;

s'', m, m', m'', are 0

Y and Y' are equal or different and are as above defined;

A is selected among:

i) (IIa) wherein $R_1$ is —H, $R_2$ is —C(O)NHR$_{2xx}$ or —C(O)N(CH$_3$)R$_{2xx}$ and $R_2$ binds a group —Y'—$ONO_2$; and $R_a$ is selected from $R_{bx}$—OC(O)—S—$CH_2$—, or $R_xO$—$CH_2$—, $R_xO$—CH(CH$_3$)—, ($R_xO$)-p-$C_6H_4$—$CH_2$—, 4-($R_xO$)-3,5-diiodobenzyl-4-($R_xO$)-3-nitrobenzyl- wherein $R_x$ is $R_{xx}$—C(O)— and $R_a$ binds a group —Y—$ONO_2$;

ii) (IIc) wherein is $R_1$ is —H, $R_2$ is —C(O)NHR$_{2xx}$ or —C(O)N(CH$_3$)R$_{2xx}$ and $R_2$ binds a group —Y'—$ONO_2$; $R_c$ is selected free $R_{bx}$—C(O)—S—$CH_2$—, or $R_xO$—$CH_2$—, $R_xO$—CH(CH$_3$)—, ($R_xO$)-p-$C_6H_4$—$CH_2$—, 4-($R_xO$)-3,5-diiodobenzyl-4-($R_xO$)-3-nitrobenzyl- wherein $R_x$ is $R_{xx}$—C(O)— and $R_c$ binds a group —Y—$ONO_2$;

iii) (IIs) wherein $R_1$ is —H, $R_3$ is —OC(O)$R_{3x}$ and $R_3$ binds a group —Y—$ONO_2$; $R_s$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— and $R_s$ binds a group —Y'—$ONO_2$;

v) (IIu) wherein $R_1$ is —H, $R_2$ is —C(O)NHR$_{2xx}$ or —C(O)N(CH$_3$)R$_{2xx}$ and $R_2$ binds a group —Y'—$ONO_2$; a is 1; b is 0 or 1 and $R_x$ is $R_{xx}$—C(O)— and $R_x$ binds a group —Y—$ONO_2$;

can be prepared as follows:

42a) by reacting a compound of formula (I) wherein s, s', s'', m, m', m'', Y, Y', Y'' are as above defined, in 42., A is a radical of formula (IIa), (IIc), (IIs) or (IIu) wherein; $R_2$, $R_3$, a, b, $R_a$, $R_c$, $R_s$, $R_g$ and $R_x$, are as defined in 42.; $R_1$ is —C(O)OC(CH$_3$)$_3$ with anhydrous or aqueous organic or inorganic acid to hydrolyze the —BOC protective groups following procedure well known in the literature.

42b) by reacting a compound of formula (I) obtained in 36b) with a compound of formula (IIIo)

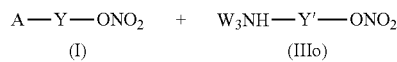

wherein Y and Y' are as above defined, $W_3$ is as above defined and in formula (I) A is a radical of formula (IIa), (IIc), (IIs) or (IIu) wherein $R_1$ is —C(O)OC(CH$_3$)$_3$, $R_2$ is —COOH, $R_3$, $R_a$, $R_c$ $R_x$ a and b are as above defined in 42., $R_s$ is $R_gC(O)CH_2$—NH—, $R_gC(O)CH_2$, $R_gC(O)(CH_2)_2$—, $R_gC(O)(CH_2)_4$—, wherein $R_g$ is —OH;

following the same procedure described in 7b).

43. The compounds of general formula (I) wherein:

s and s' are equal to 1;

s'', m, m', m'', are 0

Y and Y' are equal or different and are as above defined;

A is selected among:

i) (IIa) wherein $R_1$ is —H, $R_2$ is —C(O)NHR$_{2xx}$ or —C(O)N(CH$_3$)R$_{2xx}$ and $R_2$ binds a group —Y'—$ONO_2$; and $R_a$ is selected from $R_{bx}$—OC(O)—S—$CH_2$—, or $R_xO$—$CH_2$—, $R_xO$—CH(CH$_3$)—, ($R_xO$)-p-$C_6H_4$—$CH_2$—, 4-($R_xO$)-3,5-diiodobenzyl-4-($R_xO$)-3-nitrobenzyl- wherein $R_x$ is $R_{xx}$—OC(O)— and $R_a$ binds a group —Y—$ONO_2$;

ii) (IIc) wherein $R_1$ is —H, $R_2$—C(O)NHR$_{2xx}$ or —C(O)N(CH$_3$)R$_{2xx}$ and $R_2$ binds a group —Y'—$ONO_2$; $R_c$ is selected from $R_{bx}$—OC(O)—S—$CH_2$—, or $R_xO$—$CH_2$—, $R_xO$—CH(CH$_3$)—, ($R_xO$)-p-$C_6H_4$—$CH_2$—, 4-($R_xO$)-3,5-diiodobenzyl-4-($R_xO$)-3-nitrobenzyl- wherein $R_x$ is $R_{xx}$—OC(O)— and $R_c$ binds a group —Y—$ONO_2$;

v) (IIu) wherein $R_1$ is —H, $R_2$ is —C(O)NHR$_{2xx}$ or —C(O)NHR$_{2xx}$ and $R_2$ binds a group —Y'—$ONO_2$; a is 1; b is 0 or 1 and $R_x$ is $R_{xx}$—OC(O)— and $R_x$ binds a group —Y—$ONO_2$;

can be prepared as follows:

43a) by reacting a compound of formula (I) wherein s, s', s'', m, m', m'', Y, Y', Y'' are as above defined in 43., A is a radical of formula (IIa), (IIc), (IIs) or (IIu) wherein; $R_2$, $R_3$, a, b, $R_a$, $R_c$, $R_s$, $R_g$ and $R_x$, are as defined, an 43.; $R_1$ is —C(O)OC(CH$_3$)$_3$ with anhydrous or aqueous organic or inorganic acid to hydrolyze the —BOC protective groups following procedure well known in the literature.

43b) by reacting a compound of formula (I) obtained in 37b) with a compound of formula (IIIo)

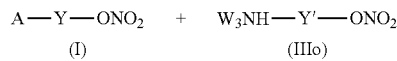

wherein Y and Y' are as above defined, $W_3$ is as above defined and in formula (I) A is a radical of formula (IIa), (IIc), (IIs) or (IIu) wherein $R_1$ is —C(O)OC(CH$_3$)$_3$, $R_2$ is —COOH, $R_3$, $R_a$, $R_c$ $R_x$ a and b are as above defined in 43., $R_g$ is $R_gC(O)CH_2$—NH—, $R_gC(O)CH_2$, $R_gC(O)(CH_2)_2$—, $R_gC(O)(CH_2)_4$—, wherein $R_g$ is —OH;

following the same procedure described in 7b).

44. The compounds of general formula (I) wherein:

s and s' are equal to 1;

s'', m, m', m'', are 0

Y and Y' are equal or different and are as above defined;

A is selected among:
i) (IIa) wherein $R_1$ is —H, $R_2$ is —C(O)NH$R_{2xx}$ or —C(O)N(CH$_3$)$R_{2xx}$ and $R_2$ binds a group —Y'—ONO$_2$; $R_a$ is selected from $R_{bx}$—NH(O)C—S—CH$_2$—, or $R_xO$—CH$_2$—, $R_xO$—CH(CH$_3$)—, ($R_xO$)-p-C$_6$H$_4$—CH$_2$—, 4-($R_xO$)-3,5-$R_{xx}$NH—C(O)— and $R_a$ binds a group —Y—ONO$_2$;
ii) (IIc) wherein $R_1$ is —H, $R_2$ is —C(O)NH$R_{2xx}$ or —C(O)N(CH$_3$)$R_{2xx}$ and $R_2$ binds a group —Y'—ONO$_2$; $R_c$ is selected from $R_{bx}$—NH(O)C—S—CH$_2$—, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_x$ is $R_{xx}$NH—C(O)— and $R_c$ binds a group —Y—ONO$_2$;
iii) (IIs) wherein $R_1$ is —H, $R_3$ is —OC(O)—NH—$R_{3x}$ and $R_3$ binds a group —Y—ONO$_2$; $R_s$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— and $R_s$ binds a group —Y'—ONO$_2$;
v) (IIu) wherein $R_1$ is —H, $R_2$ is —C(O)NH$R_{2xx}$ or —C(O)N(CH$_3$)$R_{2xx}$ $R_2$ binds a group —Y—ONO$_2$; a is 1; b is 0 or 1; and $R_x$ is $R_{xx}$—NHC(O)— and $R_x$ binds a group —Y—ONO$_2$;
can be prepared as follows:
44a) by reacting a compound of formula (I) wherein s, s', s", m, m', m", Y, Y', Y" are as above defined in 44., A is a radical of formula (IIa), (IIc), (IIs) or (IIu) wherein; $R_2$, $R_3$, a, b, $R_a$, $R_c$, $R_s$, $R_g$ and $R_x$, are as defined in 44.; $R_1$ is C(O)OC(CH$_3$)$_3$ with anhydrous or aqueous organic or inorganic acid to hydrolyze the —BOC protective groups following procedure well known in the literature.
44b) by reacting a compound of formula (I) obtained in 38b) with a compound of formula (IIIo)

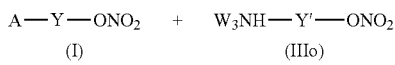

wherein Y and Y' are as above defined, $W_3$ is as above defined and in formula (I) A is a radical of formula (IIa), (IIc), (IIs) or (IIu) wherein $R_1$ is —C(O)OC(CH$_3$)$_3$, $R_2$ is —COOH, $R_3$, $R_a$, $R_c$, $R_x$ a and b are as above defined in 44., $R_s$ is $R_gC(O)CH_2$—NH—, $R_gC(O)CH_2$, $R_gC(O)(CH_2)_2$—, $R_gC(O)(CH_2)_4$—, wherein $R_g$ is —OH;
following the same procedure described in 7b).
45. The compounds of general formula (I) wherein:
s is equal to 1;
s', s", m, m', m", are 0
Y is as above defined;
A is selected among:
i) (IIa) wherein $R_1$ is —H, $R_2$ is —C(O)O$R_{2x}$ and $R_2$ binds a group —Y—ONO$_2$; and $R_a$ is selected from HS—CH$_2$—, $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_x$ —H;
ii) (IIc) wherein $R_1$ is —H, $R_2$ is —C(O)O$R_{2x}$ and $R_2$ binds a group —Y—ONO$_2$; and $R_a$ is selected from HS—CH$_2$—, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_x$ —H;
iii) (IIs) wherein $R_1$ is —H, $R_3$ is —H; $R_s$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_s$ binds a group —Y'—ONO$_2$;
v) (IIu) wherein $R_1$ is —H, $R_2$ is —C(O)O$R_{2x}$, $R_2$ binds a group —Y—ONO$_2$; a is 1; b is 0 or 1 and $R_x$ is —H;
can be prepared as follows:
45a) by reacting a compound of formula (VIIa)

wherein Y is as above defined and $A_{3a}$ is a radical of formula (IIa), (IIc), (IIs) or (IIu) wherein $R_2$, a, b and $R_s$ are as defined in 45.; $R_1$ is —C(O)OC(CH$_3$)$_3$;
in formula (IIs) $R_3$ is equal to $R_{3a}$ wherein $R_{3a}$ is —OTrt, wherein Trt is the trityl protecting group; in formula (IIa) and (IIc) $R_a$ and $R_c$ have the meanings: Trt-S—CH$_2$—, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_{xa}$ is -Trt, the trityl protecting group or the dimethyltertbutylsilyl group;
in formula (IIu) $R_x$ is equal to $R_{xa}$, wherein $R_{xa}$ is as above defined;
with anhydrous or aqueous organic or inorganic acid to hydrolyze the —BOC and the other protective groups following procedure well known in the literature.
45b) by reacting a compound of formula $A_3$ with a compound of formula (IIIi)

$$A_3 + HO-Y-ONO_2 \quad \text{(IIIi)}$$

wherein Y is as above defined and $A_3$ is a radical of formula (IIa), (IIc), (IIs) or (IIu) wherein $R_1$ is —C(O)OC(CH$_3$)$_3$, $R_2$ is —COOH, a is as above defined in 45., $R_3$ is equal to $R_{3a}$ and is —OTrt, $R_a$ and $R_c$ are TrtS—CH$_2$—, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_{xa}$ is as above defined; $R_x$ of formula (IIu) is equal to $R_{xa}$ and is as above defined; $R_s$ is $R_gC(O)CH_2$—NH—, $R_gC(O)CH_2$, $R_gC(O)(CH_2)_2$—, $R_gC(O)(CH_2)_4$—, wherein $R_g$ is —OH;
following the same procedure described in 8b).
Compounds $A_3$ are commercially available or can be prepared from commercially available compounds by simple deprotection/protection steps well known in the literature.
46. The compounds of general formula (I) wherein:
s is equal to 1;
s', s", m, m', m", are 0
Y is as above defined;
A is selected among:
i) (IIa) wherein $R_1$ is —H, $R_2$ is —C(O)NH$R_{2xx}$ or —C(O)N(CH$_3$)$R_{2xx}$ and $R_2$ binds a group —Y—ONO$_2$; and $R_a$ is selected from HS—CH$_2$—, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_x$ —H;
ii) (IIc) wherein $R_1$ is —H, $R_2$ is —C(O)NH$R_{2xx}$ or —C(O)N(CH$_3$)$R_{2xx}$ and $R_2$ binds a group —Y—ONO$_2$; and $R_a$ is selected from HS—CH$_2$—, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_x$ —H;
iii) (IIs) wherein $R_1$ is —H, $R_3$ is —H; $R_s$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— and $R_s$ binds a group —Y'—ONO$_2$;
v) (IIu) wherein $R_1$ is —H, $R_2$ is —C(O)NH$R_{2xx}$ or —C(O)N(CH$_3$)$R_{2xx}$ and $R_2$ binds a group —Y—ONO$_2$; a is 1; b is 0 or 1 and $R_x$ is —H; can be prepared as follows:
46a) by reacting a compound of formula (VIIb)

wherein Y is as above defined and $A_{3b}$ is a radical of formula (IIa), (IIc), (IIs) or (IIu) wherein $R_2$, a, b and $R_s$ are as defined in 46.; $R_1$ is —C(O)OC(CH$_3$)$_3$;
in formula (IIs) $R_3$ is equal to $R_{3a}$ wherein $R_{3a}$ is —OTrt, wherein Trt is the trityl protecting group; in formula (IIa) and (IIc) $R_a$ and $R_c$ have the meanings: Trt-S—CH$_2$—, or $R_xO$—$CH_2$—, $R_xO$—$CH(CH_3)$—, $O$-p-$C_6H_4$—$CH_2$—, 4-($R_xO$)-3,5-diiodobenzyl-4-($R_xO$)-3-nitrobenzyl- wherein $R_{xa}$ is as above defined;

In formula (IIu) $R_x$ is equal to $R_{xa}$ and is as above defined;

with anhydrous or aqueous organic or inorganic acid to hydrolyze the —BOC and the other protective groups following procedure well known in the literature.

46b) by reacting a compound of formula $A_3$ defined in 45b) with a compound of formula (IIIo)

$$A_3 + W_3NH—Y'—ONO_2 \quad (IIIo)$$

following the same procedure described in 7b).

47. The compounds of general formula (I) wherein:
s and m are equal to 1;
s', s'', m', m'', are 0
Y is as above defined;
B is:

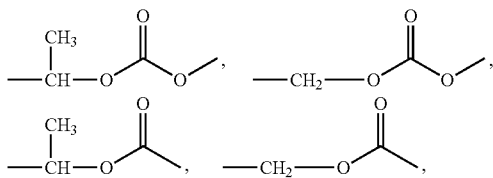

A is selected among:
i) (IIa) wherein $R_1$ is —H, $R_2$ is —$C(O)OR_{2x}$ and $R_2$ binds a group B—Y—$ONO_2$; and $R_a$ is selected from HS—$CH_2$—, or $R_xO$—$CH_2$—, $R_xO$—$CH(CH_3)$—, O-p-$C_6H_4$—$CH_2$—, 4-($R_xO$)-3,5-diiodobenzyl-4-($R_xO$)-3-nitrobenzyl- wherein $R_x$ —H;
ii) (IIc) wherein $R_1$ is —H, $R_2$ is —$C(O)OR_2$ and $R_2$ binds a group B—Y—$ONO_2$; and $R_c$ is selected from HS—$CH_2$—, or $R_xO$—$CH_2$—, $R_xO$—$CH(CH_3)$—, ($R_x$)-p-$C_6H_4$—$CH_2$—, 4-($R_xO$)-3,5-diiodobenzyl-4-($R_xO$)-3-nitrobenzyl- wherein $R_x$ —H;
iii) (IIs) wherein $R_1$ is —H, $R_3$ is —H; $R_s$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_g$ binds a group B—Y—$ONO_2$;
v) (IIu) wherein $R_1$ is —H, $R_2$ is —$C(O)OR_{2x}$, $R_2$ binds a group B—Y—$ONO_2$; a is 1; b is 0 or 1 and $R_x$ is —H; can be prepared as follows:

47a) by reacting a compound of formula (VIIc)

$$A_{3c}\text{-}Y—ONO_2 \quad (VIIc)$$

wherein Y is as above defined and $A_{3c}$ is a radical of formula (IIa), (IIc), (IIs) or (IIu) wherein $R_2$, a, b and $R_s$ are as defined in 47., $R_1$ is —$C(O)OC(CH_3)_3$;

in formula (IIs) $R_3$ is equal to $R_{3a}$ wherein $R_{3a}$ is —OTrt, wherein Trt is the trityl protecting group; in formula (IIa) and (IIc) $R_a$ and $R_c$ have the meanings: Trt-S—$CH_2$—, or $R_{x3}O$—$CH_2$—, $R_{x3}O$—$CH(CH_3)$—, ($R_xO$)-p-$C_6H_4$—$CH_2$—, 4-($R_xO$)-3,5-diiodobenzyl-4-($R_xO$)-3-nitrobenzyl- wherein $R_{xa}$ is above defined;

In formula (IIu) $R_x$ is equal to $R_{xa}$ and is as above defined;

with anhydrous or aqueous organic or inorganic acid to hydrolyze the —BOC and the other protective groups following procedure well known in the literature.

47b) compound (VIIc) can be prepared by reacting a compound of formula $A_3$ defined in 45b) with a compound of formula (IIIg) or (IIIn) depending on the meaning of B $$A_3 + Hal\text{-}W_1—OC(O)O—Y—ONO_2 \quad (IIIg)$$

$$A_3 + Hal\text{-}W_1—OC(O)—Y—ONO_2 \quad (IIIn)$$

following the same procedure described in 4b) or 6b).

48. The compounds of general formula (I) wherein:
s is equal to 1;
s', s'', m, m', m'', are 0
Y is as above defined;
A is selected among:
i) (IIa) wherein $R_1$ is —$C(O)R_{1x}$, and $R_1$ binds a group Y—$ONO_2$; $R_2$ is —COOH; and $R_a$ is selected from HS—$CH_2$—, or $R_xO$—$CH_2$—, $R_xO$—$CH(CH_3)$—, ($R_xO$)-p-$C_6H_4$—$CH_2$—, 4-($R_xO$)-3,5-diiodobenzyl-4-($R_xO$)-3-nitrobenzyl- wherein $R_x$ —H;
ii) (IIc) wherein $R_1$ is —$C(O)R_{1x}$, and $R_1$ binds a group Y—$ONO_2$; $R_2$ is —COOH; and $R_a$ is selected from HS—$CH_2$—, or $R_xO$—$CH_2$—, $R_xO$—$CH(CH_3)$—, ($R_xO$)-p-$C_6H_4$—$CH_2$—, 4-($R_xO$)-3,5-diiodobenzyl-4-($R_xO$)-3-nitrobenzyl- wherein $R_x$ —H;
iii) (IIs) wherein $R_1$ is —$C(O)$—$R_{1x}$ and $R_1$ binds a group Y—$ONO_2$; $R_3$ is —H; $R_s$ is selected from $R_gC(O)CH_2$—NH—, $R_gC(O)CH_2$, $R_gC(O)(CH_2)_2$—, $R_gC(O)(CH_2)_4$—, wherein $R_g$ is —OH;
v) (IIu) wherein and $R_1$ binds a group —Y—$ONO_2$; $R_2$ is —COOH, a is 1, b is 0; $R_x$ is —H;
can be prepared as follows:

48a) by reacting a compound of formula (VIId)

$$A_{4a}\text{-}Y—ONO_2 \quad (VIId)$$

wherein Y, is as above defined and $A_{4a}$ is a radical of formula (IIa), (IIc), (IIs) or (IIu) wherein; $R_1$, $R_2$, a, b and $R_s$ are as defined in 48.; in formula (IIs) $R_3$ is $R_{3a}$ and is —OTrt; in formula (IIa) and (IIc) $R_a$ and $R_c$ are TrtS—$CH_2$—, or $R_xO$—$CH_2$—, $R_{xa}O$—$CH(CH_3)$—, ($R_{xa}O$)-p-$C_6H_4$—$CH_2$—, 4-($R_{xa}O$)-3,5-diiodobenzyl-4-($R_{xa}O$)-3-nitrobenzyl- wherein $R_{xa}$ is -Trt or the group dimethyl-tert-butylsilyl; $R_x$ of formula (IIu) is H or $R_{xa}$ wherein $R_{xa}$ is as above defined;

with anhydrous or aqueous organic or inorganic acid to remove the protective groups following procedure well known in the literature.

48b) compound (VIId) are prepared by reacting a compound of formula $A_4$ with a compound of formula (IIIe)

$$A_4 + Act\text{-}C(O)—Y—ONO_2 \quad (IIIe)$$

Wherein Act and Y are as above defined, $A_4$ is a radical of formula (IIa), (IIc), (IIs) or (IIu) wherein $R_1$ is —H, $R_2$ is —COOH, a and b are as above defined in 48., $R_3$ is $R_{3a}$, $R_a$ and $R_c$ are TrtS—$CH_2$—, or $R_{xa}O$—$CH_2$—, $R_{xa}O$—$CH(CH_3)$—, ($R_{xa}O$)-p-$C_6H_4$—$CH_2$—, 4-($R_{xa}O$)-3,5-diiodobenzyl-4-($R_{xa}O$)-3-nitrobenzyl- wherein $R_{xa}$ is -Trt or dimethyl-tert-butylsilyl; $R_x$ of formula (IIu) is H or $R_{xa}$ wherein $R_{xa}$ is as above defined; $R_s$ is $R_gC(O)CH_2$—NH—, $R_gC(O)CH_2$, $R_gC(O)(CH_2)_2$—, $R_gC(O)(CH_2)_4$—, wherein $R_g$ is OH; following the same procedure described in 1b').

Compounds $A_4$ are commercially available.

49. The compounds of general formula (I) wherein:
s is equal to 1;
s', s'', m, m', m'', are 0
Y is as above defined;
A is selected among:
i) (IIa) wherein $R_1$ is —$C(O)O$—$R_{1x}$, and $R_1$ binds a group —Y—$ONO_2$; $R_2$ is —COOH; and $R_a$ is selected from HS—$CH_2$—, or $OR_x$—$CH_2$—, $R_xO$—$CH(CH_3)$—, ($R_xO$)-p-$C_6H_4$—$CH_2$—, 4-($R_xO$)-3,5-diiodobenzyl-4-($R_xO$)-3-nitrobenzyl- wherein $R_x$ —H;
ii) (IIc) wherein $R_1$ is —$C(O)O$—$R_{1x}$, and $R_1$ binds a group —Y—$ONO_2$; $R_2$ is —COOH; and $R_a$ is selected from HS—$CH_2$—, or $R_xO$—$CH_2$—, $R_xO$—$CH(CH_3)$—, ($R_xO$)-p-$C_6H_4$—$CH_2$—, 4-($R_xO$)-3,5-diiodobenzyl-4-($R_xO$)-3-nitrobenzyl- wherein $R_x$ —H;

iii) (IIs) wherein $R_1$ is —C(O)—$R_{1x}$ and $R_1$ binds a group Y—ONO$_2$; $R_3$ is —H; $R_s$ is selected from $R_gC(O)CH_2$—NH—, $R_gC(O)CH_2$, $R_gC(O)(CH_2)_2$—, $R_gC(O)(CH_2)_4$—, wherein $R_g$ is —OH;

v) (IIu) wherein and $R_1$ binds a group —C(O)O—$R_{1x}$ and $R_1$ binds a group —Y—ONO$_2$; $R_2$ is —COOH, a is 1, b is 0 or 1 and $R_x$ is —H;

can be prepared as follows:

49a) by reacting a compound of formula (VIIf)

$A_{4b}$-Y—ONO$_2$     (VIIf)

wherein Y is as above defined and $A_{4b}$ is a radical of formula (IIa), (IIc), (IIs) or (IIu) wherein; $R_1$, $R_2$, a, b and $R_s$ are as defined in 49.; $R_3$ is $R_{3a}$, $R_a$ and $R_c$ are TrtS—CH$_2$—, or $R_xO$—CH$_2$—, $R_xO$—CH(CH$_3$)—, $(R_{xa}O)$-p-$C_6H_4$—CH$_2$—, 4-($R_xO$)-3,5-diiodobenzyl-4-($R_{xa}O$)-3-nitrobenzyl-wherein $R_{xa}$ is -Trt or dimethyltert-butyl silyl, $R_x$ of formula (IIu) is H or $R_{xa}$ wherein $R_{xa}$ is as above defined;

with anhydrous or aqueous organic or inorganic acid to remove the Trityl or dimethyltert-butyl silyl protective groups following procedure well known in the literature.

49b) by reacting a compound of formula $A_4$ with a compound of formula (IIIf) or (IIIi)

$A_4$+Act-C(O)O—Y—ONO$_2$     (IIf)

$A_4$+HO—Y—ONO$_2$     (IIIi)

Wherein Act and Y are as above defined, $A_4$ is as defined in 48b), following the same procedure described in 3b).

50. The compounds of general formula (I) wherein:
s and s' are equal to 1;
s", m, m', m", are 0
Y and Y' are equal and are as above defined;
A is selected among:

(IIa) wherein $R_1$ is —H, $R_2$ is —C(O)O, and $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, both $R_2$ and $R_a$ bind a group —Y—ONO$_2$ or a group —Y'—ONO$_2$;

(IIc) wherein $R_1$ is —H, $R_2$ is —C(O)O, and $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, both $R_2$ and $R_c$ bind a group —Y—ONO$_2$ or a group —Y'—ONO$_2$;

can be prepared as follows:

50a) by reacting a compound of formula (I) wherein s, s', s", m, m', m", Y, Y', Y" are as above defined in 50., A is a radical of formula (IIa), (IIc), wherein; $R_2$, $R_a$, $R_c$ are as defined in 50.; $R_1$ is —C(O)OC(CH$_3$)$_3$ with anhydrous or aqueous organic or inorganic acid to hydrolyze the —BOC protective groups following procedure well known in the literature.

50b) by reacting a compound of formula A with a compound of formula (IIIi)

A+HO—Y—ONO$_2$     (IIIi)

wherein Y is as above defined and A is a radical of formula (IIa), (IIc) wherein $R_1$ is —C(O)OC(CH$_3$)$_3$, $R_2$ is —COOH, $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is —OH;

following the same procedure described in 8b) using a ratio A/(IIIi) 1:2.

51. The compounds of general formula (I) wherein:
s and s' are equal to 1;
s", m, m', m", are 0
Y and Y' are equal and as above defined;

A is selected among:

(IIa) wherein $R_1$ is —H, $R_2$ is —C(O)NHR$_{2xx}$ or —C(O)N(CH$_3$)R$_{2xx}$ and $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— and both $R_2$ and $R_a$ bind a group —Y—ONO$_2$ or a group —Y'—ONO$_2$;

(IIc) wherein $R_1$ is —H, $R_2$ is —C(O)NHR$_{2xx}$ or —C(O)N(CH$_3$)— and $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— and both $R_2$ and $R_c$ bind a group —Y—ONO$_2$ or a group —Y'—ONO$_2$;

can be prepared as follows:

51a) by reacting a compound of formula (I) wherein s, s', s", m, m', m", Y, Y', Y" are as above defined in 51., A is a radical of formula (IIa), (IIc), wherein $R_2$, $R_a$, $R_c$, are as defined in 51., $R_1$ is —C(O)OC(CH$_3$)$_3$ with anhydrous or aqueous organic or inorganic acid to hydrolyze the —BOC protective groups following procedure well known in the literature.

51b) by reacting a compound of formula A with a compound of formula (IIIo)

A+W$_3$NH—Y—ONO$_2$     (IIIo)

wherein Y is as above defined, W$_3$ is as above defined and A is a radical of formula (IIa), (IIc) wherein $R_1$ is —C(O)OC(CH$_3$)$_3$, $R_2$ is —COOH, $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is —OH;

following the same procedure described in 7b) using a ratio A/(IIIo) 1:2.

52. The compounds of general formula (I) wherein:
s and s' are equal to 1;
m and m' are equal to 1;
m" and s" are 0
B is:

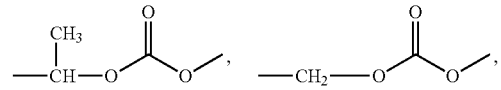

Y and Y' are equal and are as above defined;

A is selected among (IIa) and (IIc) wherein $R_1$ is —H and $R_2$ is —C(O)OR$_{2x}$ and binds a group —B—Y—ONO$_2$ or —B'—Y'—ONO$_2$;

$R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_a$ and $R_c$ bind one of the groups —B—Y—ONO$_2$ or —B'—Y'—ONO$_2$;

Can be prepared as follows:

52a) by reacting a compound of formula (I) wherein B, s, s', s", m, m', m", Y, Y', Y" are as above defined in 52., A is a radical of formula (IIa) or (IIc) wherein $R_1$ is —C(O)OC(CH$_3$)$_3$; $R_2$, $R_a$ and $R_c$ as defined in 52., with anhydrous or aqueous organic or inorganic acid to hydrolyze the —BOC protective groups following procedure well known in the literature.

52b) by reacting a compound of formula A with a compound of formula (IIIg)

A+Hal-W$_1$—OC(O)O—Y—ONO$_2$     (IIIg)

wherein Y is as above defined and A is selected from (IIa) or (IIc) wherein $R_2$ is —COOH and $R_1$ is —C(O)O(CH$_3$)$_3$;

$R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is —OH;

using a ratio A/(IIIg) 1:2 and applying the procedure described on 4b).

33. One compounds of general formula (I) wherein:

s and s' are equal to 1;

m and m' are equal to 1;

m" and s" are 0

B is:

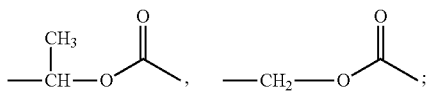

Y and Y' are equal and are as above defined;

A is selected among (IIa) and (IIc) wherein $R_1$ is —H and $R_2$ is —C(O)$OR_{2x}$ and binds a group —B—Y—$ONO_2$ or —B'—Y'—$ONO_2$;

$R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_a$ and $R_c$ bind one of the groups —B—Y—$ONO_2$ or —B'—Y'—$ONO_2$;

Can be prepared as follows:

53a) by reacting a compound of formula (I) wherein B, s, s', s", m, m', m", Y, Y', Y" are as above defined in 53., A is a radical of formula (IIa) or (IIc) wherein $R_1$ is —C(O)OC$(CH_3)_3$;

$R_2$, $R_a$ and $R_c$ are as defined in 53., with anhydrous or aqueous organic or inorganic acid to hydrolyze the —BOC protective groups following procedure well known in the literature.

53b) by reacting a compound of formula A with a compound of formula (IIIn)

$$A + Hal-W_1-O(O)C-B-Y-ONO_2 \quad (IIIn)$$

wherein Y is as above defined and A is selected from (IIa) or (IIc) wherein $R_2$ is —COOH and $R_1$ is —C(O)O$(CH_3)_3$;

$R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is —OH;

Using a ratio A/(IIIn) 1:2 and applying the procedure described in 6b).

54. The compounds of general formula (I) wherein:

s, s' and s" are equal to 1;

m, m', m", are 0

Y, Y' and Y" are as above defined with the proviso that Y is equal to Y'

A is a radical of formula (IIa) or (IIc) wherein $R_1$ is —C(O)—$R_{1x}$ and it binds the group —Y"—$ONO_2$, $R_2$—C(O)$OR_{2x}$ and it binds the group Y—$ONO_2$ or Y'—$ONO_2$;

$R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$O—, and $R_a$ and $R_c$ bind one of the groups —Y—$ONO_2$ or —Y'—$ONO_2$;

can be prepared as follows:

54a) by reacting a compound of formula (I) prepared as described in 49.

with a compound of formula (IIIe):

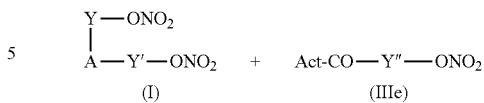

wherein in formula (I) Y and Y' are equal and A is a radical of formula (IIa) or (IIc) wherein $R_1$ is —H; $R_2$, $R_a$ and $R_c$ are as defined in 54., following the same procedure described in 1b').

55. The compounds of general formula (I) wherein:

s, s' and s" are equal to 1;

m, m', m", are 0

Y, Y' and Y" are as above defined with the proviso that Y is equal to Y'

A is a radical of formula (IIa) or (IIc) wherein —C(O)O—$R_{1x}$ and it binds the group —Y"—$ONO_2$, $R_2$ is —C(O)$OR_{2x}$ and it binds the group —Y—$ONO_2$ or —Y'—$ONO_2$;

$R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$O—, and $R_a$ and $R_c$ bind one of the groups —Y—$ONO_2$ or —Y'—$ONO_2$;

can be prepared as follows:

55a) by reacting a compound of formula (I) prepared as described in 49.

with a compound of formula (IIIf):

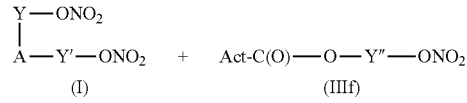

wherein in formula (I) Y and Y' are equal and A has been already defined in 54.;

following the same procedure described in 3b).

56. The compounds of general formula (I) wherein:

s, s' and s" are equal to 1;

m, m', m", are 0

Y, Y' and Y" are as above defined with the proviso that Y is equal to Y'

A is a radical of formula (IIa) or (IIc) wherein $R_1$ is —C(O)—$R_{1x}$ and it binds the group —Y"—$ONO_2$, $R_2$ is —C(O)NH$R_{2xx}$ or —C(O)N$(CH_2)R_{2xx}$ and it binds the group —Y—$ONO_2$ or —Y'—$ONO_2$;

$R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$NH— or $R_{gx}$—N$(CH_3)$— and $R_a$ and $R_c$ bind one of the groups —Y—$ONO_2$ or —Y'—$ONO_2$;

can be prepared as follows:

56a) by reacting a compound of formula (I) prepared as described in 51.

with a compound of formula (IIIe):

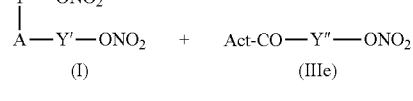

wherein in formula (I) Y and Y' are equal and A is a radical of formula (IIa) or (IIc) wherein $R_1$ is —H; $R_2$, $R_a$ and $R_c$ are as defined in 56., following the same procedure described in 1b').

57. The compounds of general formula (I) wherein:
s, s' and s" are equal to 1;
m, m', m", are 0
Y, Y' and Y" are as above defined with the proviso that Y is equal to Y'
A is a radical of formula (IIa) or (IIc) wherein $R_1$ is —C(O)O—$R_{1x}$ and it binds the group —Y"—$ONO_2$, $R_2$ is —C(O)NH$R_{2xx}$ or —C(O)N($CH_3$)$R_{2xx}$ and it binds the group —Y—$ONO_2$ or —Y'—$ONO_2$;
$R_a$ and $R_c$ are selected from $R_g$C(O)$CH_2$—NH—, $R_g$C(O)$CH_2$, $R_g$C(O)($CH_2$)$_2$—, $R_g$C(O)($CH_2$)$_4$—, wherein $R_g$ is $R_{gx}$NH— or $R_{gx}$N($CH_3$)— and $R_a$ and $R_c$ bind one of the groups —Y—$ONO_2$ or —Y'—$ONO_2$;
can be prepared as follows:
57a) by reacting a compound of formula (I) prepared as described in 51.
with a compound of formula (IIIf):

$$A{-}Y'{-}ONO_2 \quad\text{with}\quad Y{-}ONO_2 \text{ substituent} \quad + \quad \text{Act-C(O)}{-}O{-}Y''{-}ONO_2$$

(I)      (IIIf)

wherein in formula (I) Y and Y' are equal and A has been already defined in 56.,
following she same procedure described in 3b).

58. The compounds of general formula (I) wherein:
s, s' and s" are equal to 1;
m and m' are equal to 1
m" is 0;
B is:

[structures showing four variants with CH3/CH group and CH2 group attached to carbonate and acetate-like moieties]

Y, Y' and Y" are as above defined with the proviso that Y is equal to Y'
A is a radical of formula (IIa) or (IIc) wherein $R_1$ is —C(O)—$R_{1x}$ and it binds the group —Y"—$ONO_2$, $R_2$ is —C(O)O$R_{2x}$ and it binds the group B—Y—$ONO_2$ or B—Y'—$ONO_2$ wherein B—Y—$ONO_2$ or B—Y'—$ONO_2$ are equal;
$R_a$ and $R_c$ are selected from $R_g$C(O)$CH_2$—NH—, $R_g$C(O)$CH_2$, $R_g$C(O)($CH_2$)$_2$—, $R_g$C(O)($CH_2$)$_4$—, wherein $R_g$ is $R_{gx}$O—, and $R_a$ and $R_c$ bind one of the groups B—Y—$ONO_2$ or B—Y'—$ONO_2$ wherein in B—Y—$ONO_2$ or B—Y'—$ONO_2$ are equal;
can be prepared as follows:
58a) by reacting a compound of formula (I) prepared as described in 52. if B is:

[two carbonate structure variants]

or prepared in 53. if B is:

[two ester structure variants]

with a compound of formula (IIIe):

$$\begin{array}{c} B{-}Y{-}ONO_2 \\ | \\ A{-}B_1{-}Y'{-}ONO_2 \end{array} \quad + \quad \text{Act-CO}{-}Y''{-}ONO_2$$

(I)      (IIIe)

wherein in formula (I) B, Y and Y' are as defined in 58.; and A is a radical of formula (IIa) or (IIc) wherein $R_1$ is —H; $R_2$, $R_a$ and $R_c$ are as defined in 58.,
following the same procedure described in 1b').

59. The compounds of general formula (I) wherein:
s, s' and s" are equal to 1;
m and m' are equal to 1;
m" is 0
B is:

[four structure variants]

Y, Y' and Y" are as above defined with the proviso that Y is equal to Y'
A is a radical of formula (IIa) or (IIc) wherein $R_1$ is —C(O)O—$R_{1x}$ and it binds the group —Y"—$ONO_2$, $R_2$ is —C(O)O$R_{2x}$ and it binds the group B—Y—$ONO_2$ or B—Y'—$ONO_2$ wherein B—Y—$ONO_2$ or B—Y'—$ONO_2$ are equal;
$R_a$ and $R_c$ are selected from $R_g$C(O)$CH_2$—NH—, $R_g$C(O)$CH_2$, $R_g$C(O)($CH_2$)$_2$—, $R_g$C(O)($CH_2$)$_4$—, wherein $R_g$ is $R_{gx}$—O—, and $R_a$ and $R_c$ bind one of the groups B—Y—$ONO_2$ or B—Y'—$ONO_2$ wherein B—Y—$ONO_2$ or B—Y'—$ONO_2$ are equal;
can be prepared as follows:
59a) by reacting a compound of formula (I) prepared as described in 52. if B is:

[two carbonate structure variants]

or prepared in 53. if B is:

[two ester structure variants]

with a compound of formula (IIIf):

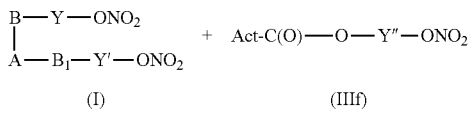

wherein in formula (I) B, Y and Y' are as defined in 59.; A is a radical of formula (IIa) or (IIc) wherein $R_1$ is —H; $R_2$, $R_a$ and $R_c$ are as defined in 59.,
following the same procedure described in 3b).

60. The compounds of general formula (I) wherein:
s, is equal to 1;
s', s", m, m' and m" are equal to 0;
Y is as above defined;
A is selected from (IIa) and (IIc) wherein $R_1$ is —C(O)—$R_{1x}$ and binds a group —Y—$ONO_2$, $R_2$ is —COOH;
$R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is —OH; can be prepared as follows:

60a) by reacting a compound of formula A with a compound of formula (IIIe)

A+Act-(O)C—Y—$ONO_2$      (IIIe)

wherein Y is as above defined and A is a commercially available compound of formula (IIa) or (IIc) wherein $R_2$ is —COOH and $R_1$ is —H;
$R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is —OH;
applying the procedure described in 1b').

61. The compounds of general formula (I) wherein:
s, is equal to 1;
s', s", m, m' and m" are 0;
Y is as above defined;
A is selected among (IIa) and (IIc) wherein $R_1$ is —C(O)O—$R_{1x}$ and binds a group —Y—$ONO_2$, $R_2$ is —COOH;
$R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is —OH; can be prepared as follows:

61a) by reacting a compound of formula A with a compound of formula (IIIf)

A+Act-(O)C—O—Y—$ONO_2$      (IIIf)

wherein Y is as above defined and A is as defined in 60a) applying the procedure described in 3b).

62. Alternatively compounds (I) described in 54. can be prepared starting from compounds (I) prepared as described in 60. and compounds (IIIi) applying the same procedure described in 8b) using a ratio (I)/(IIIi) 1:2. In this case Y' and Y" are equal.

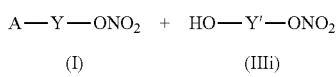

63. Alternatively compounds (I) described in 55. can be prepared starting from compounds (I) prepared as described in 61. and compounds (IIIi) applying the same procedure described in 8b) using a ratio (I)/(IIIi) 1:2. In this case Y' and Y" are equal.

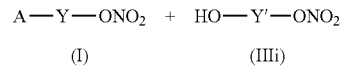

64. Alternatively compounds (I) described in 56. can be prepared starting from compounds (I) prepared as described in 60. and compounds (IIIo) applying the same procedure described in 7b) using a ratio (I)/(IIIo) 1:2. In this case Y' and Y" are equal.

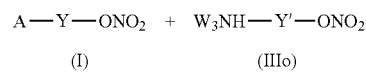

65. Alternatively compounds (I) described in 57. can be prepared starting from compounds (I) prepared as described in 61. and compounds (IIIo) applying the same procedure described in 7b) using a ratio (I)/(IIIo) 1:2. In this case Y' and Y" are equal.

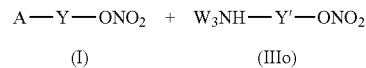

66. Alternatively compounds (I) described in 58. can be prepared starting from compounds (I) prepared as described in 60. and compounds (IIIg) or (IIIn) depending on the meaning of B, and applying the same procedure described in 4b) or 6b) using a ratio (I)/(IIIg) or (I)/(IIIn) 1:2. In this case Y' and Y" are equal.

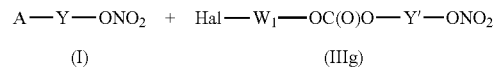
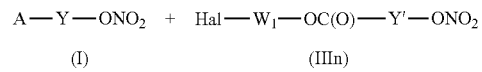

67. Alternatively compounds (I) described in 59. can be prepared starting from compounds (I) prepared as described in 61. and compounds (IIIg) or (IIIn) depending on the meaning of B, and applying the same procedure described in 4b) or 6b) using a ratio (I)/(IIIg) or (I)/(IIIn) 1:2. In this case Y' and Y" are equal.

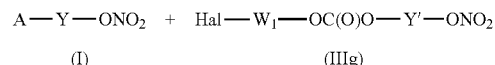
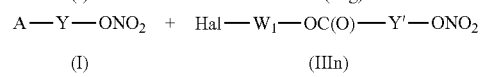

68. The compounds of general formula (I) wherein:
s is equal to 1;
s', s", m, m', m", are 0
Y is as above defined;
A is selected among:
(IIa) wherein $R_1$ is —H, $R_2$ is —C(O)$OR_{2x}$ and $R_2$ binds a group —Y—$ONO_2$; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is —OH;
(IIc) wherein $R_1$ is —H, $R_2$ is —C(O)$OR_{2x}$ and $R_2$ binds a group —Y—$ONO_2$; $R_c$ is selected from $R_gC(O)CH_2$—

NH—, $R_gC(O)CH_2$, $R_gC(O)(CH_2)_2$—, $R_gC(O)(CH_2)_4$—, wherein $R_g$ is —OH; can be prepared as follows:

68a) by reacting a compound of formula (I) wherein s, s', s", m, m', m", Y, Y', Y" are as above defined in 68., A is a radical of formula (IIa), (IIc), wherein $R_2$ is as above defined in 68.; $R_1$ is —C(O)OC(CH$_3$)$_3$; $R_a$ and $R_c$ are $R_gC(O)CH_2$—NH—, $R_gC(O)CH_2$, $R_gC(O)(CH_2)_2$—, $R_gC(O)(CH_2)_4$—, wherein $R_g$ is —C(O)OC(CH$_3$)$_3$;

with anhydrous or aqueous organic or inorganic acid to hydrolyze the tert-butyl esters and the —BOC protective groups following procedure well known in the literature.

68b) by reacting a compound of formula A with a compound of formula (IIIi)

A+HO—Y—ONO$_2$            (IIIi)

wherein Y is as above defined and A is a compound of formula (IIa) or (IIc) wherein $R_1$ is —C(O)OC(CH$_3$)$_3$, $R_2$ is —COOH, $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is —C(O)OC(CH$_3$)$_3$;

following the same procedure described in 8b). Compounds A are commercially available.

69. The compounds of general formula (I) wherein:
s is equal to 1;
s', s", m, m', m", are 0
Y is as above defined;
A is a radical of formula
(IIa) wherein $R_1$ is —H, $R_2$ is —C(O)NHR$_{2xx}$ or —C(O)N(CH$_3$)R$_{2xx}$ and $R_2$ binds a group —Y—ONO$_2$; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is —OH; or
(IIc) wherein $R_1$ is —H, $R_2$ is —C(O)NHR$_{2xx}$ or —C(O)N(CH$_3$)R$_{2xx}$ and $R_2$ binds a group —Y—ONO$_2$; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is —OH; can be prepared as follows:

69a) by reacting a compound of formula (I) wherein s, s', s", m, m', m", Y, Y', Y" are as above defined in 69., A is a radical of formula (IIa), (IIc), wherein $R_2$ is as above defined in 69.; $R_1$ is —C(O)OC(CH$_3$)$_3$); $R_a$ and $R_c$ are $R_gC(O)CH_2$—NH—, $R_gC(O)CH_2$, $R_gC(O)(CH_2)_2$—, $R_gC(O)(CH_2)_4$—, wherein $R_g$ is —C(O)OC(CH$_3$)$_3$;

with anhydrous or aqueous organic or inorganic acid to hydrolyze the tert-butyl esters and the —BOC protective groups following procedure well known in the literature.

69b) by reacting a compound of formula A with a compound of formula (IIIo)

A+W$_3$NH—Y—ONO$_2$            (IIIo)

wherein Y is as above defined, W$_3$ is as above defined and A is as defined in 68b),
following the sane procedure described in 7b).

70. The compounds of general formula (I) wherein:
s and m are equal to 1;
s', s", m', m", are 0
Y is as above defined;
B is:

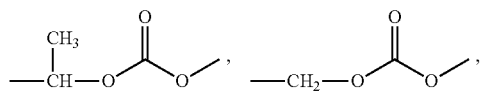

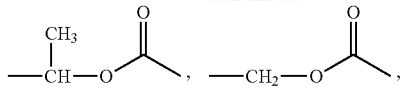

A is a radical selected among:
(IIa) wherein $R_1$ is —H, $R_2$ is —C(O)OR$_{2x}$ and $R_2$ binds a group —B—Y—ONO$_2$; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is —OH;
(IIc) wherein $R_1$ is —H, $R_2$ is —C(O)OR$_{2x}$ and $R_2$ binds a group —B—Y—ONO$_2$; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is —OH; can be prepared as follows:

70a) by reacting a compound of formula (I) wherein s, s', s", m, m', m", B, Y, Y', Y" are as above defined in 70., A is a radical of formula (IIa), (IIc), wherein $R_2$ is as above defined in 70.; $R_1$ is —C(O)OC(CH$_3$)$_3$); $R_a$ and $R_c$ are $R_gC(O)CH_2$—NH—, $R_gC(O)CH_2$, $R_gC(O)(CH_2)_2$—, $R_gC(O)(CH_2)_4$—, wherein $R_g$ is —C(O)OC(CH$_3$)$_3$;

with anhydrous or aqueous organic or inorganic acid to hydrolyze the tert-butyl esters and the —BOC protective groups following procedure well known in the literature.

70b) by reacting a compound of formula A with a compound of formula (IIIg) or (IIIn) depending on the meaning of B A+Hal-W$_1$—OC(O)O—Y—ONO$_2$            (IIIg)

A+Hal-W$_1$—OC(O)—Y—ONO$_2$            (IIIn)

wherein Y, Hal, W$_1$ are as above defined and A is as defined in 68b),
following the same procedures described in 4b) or 6b).

71. The compounds of general formula (I) wherein:
s is equal to 1;
s', s", m, m', m", are 0
Y is as above defined;
A is selected among:
(IIa) wherein $R_1$ is —H, $R_2$ is —COOH; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_g$ binds a group —Y—ONO$_2$;
(IIc) wherein $R_1$ is —H, $R_2$ is —COOH; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_c$ binds a group —Y—ONO$_2$;
can be prepared as follows:

71a) by reacting a compound of formula (I) wherein s, s', s", m, m', m", Y, Y', Y" are as above defined in 71., A is a radical of formula (IIa), (IIc), wherein $R_a$ and $R_c$ are as above defined in 71.; $R_1$ is —C(O)OC(CH$_3$)$_3$; $R_2$ is —C(O)OC(CH$_3$)$_3$;

with anhydrous or aqueous organic or inorganic acid to hydrolyze the tert-butyl esters and the —BOC protective groups following procedure well known in the literature.

68b) by reacting a compound of formula A with a compound of formula (IIIi)

A+HO—Y—ONO$_2$            (IIIi)

wherein Y is as above defined and A is a radical of formula (IIa), (IIc) wherein $R_1$ is —C(O)OC(CH$_3$)$_3$, $R_2$ is —C(O)OC(CH$_3$)$_3$, $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is —OH;
following the same procedure described in 8b).
Compounds A are commercially available.

72. The compounds of general formula (I) wherein:
s is equal to 1;
s', s", m, m', m", are 0
Y is as above defined;
A is selected among:
(IIa) wherein $R_1$ is —H, $R_2$ is —COOH; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— and $R_a$ binds a group —Y—ONO$_2$;
(IIc) wherein $R_1$ is —H, $R_2$ is —COOH; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— and $R_c$ binds a group —Y—ONO$_2$;
can be prepared as follows:
72a) by reacting a compound of formula (I) wherein s, s', s", m, m', m", Y, Y', Y" are as above defined in 72., A is a radical of formula (IIa), (IIc), wherein $R_a$ and $R_c$ are as above defined in 71.; $R_1$ is —C(O)OC(CH$_3$)$_3$; $R_2$ is —C(O)OC(CH$_3$)$_3$;
with anhydrous or aqueous organic or inorganic acid to hydrolyze the tert-butyl esters and the —BOC protective groups following procedure well known in the literature.
72b) by reacting a compound of formula A with a compound of formula (IIIo):

A+W$_3$NH—Y—ONO$_2$      (IIIo)

wherein Y and W$_3$ are as above defined and A is as defined in 71b) following the same procedure described in 7b).

73. One compounds of general formula (I) wherein:
s and m are equal to 1;
s', s", m', m", are 0
Y is as above defined;
B is:

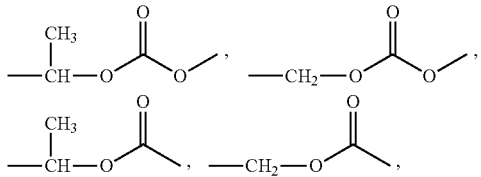

A is selected among:
(IIa) wherein $R_1$ is —H, $R_2$ is —COOH; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_a$ binds a group —B—Y—ONO$_2$;
(IIc) wherein $R_1$ is —H, $R_2$ is —COOH; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_c$ binds a group B—Y—ONO$_2$;
can be prepared as follows:
73a) by reacting a compound of formula (I) wherein s, s', s", m, m', m", B, Y, Y', Y" are as above defined in 73., A is a radical of formula (IIa), (IIc), wherein $R_a$ and $R_c$ are as above defined in 71.; $R_1$—C(O)OC(CH$_3$)$_3$); $R_2$ is —C(O)OC(CH$_3$)$_3$;
with anhydrous or aqueous organic or inorganic acid to hydrolyze the tert-butyl esters and the —BOC protective groups following procedure well known in the literature.
73b) by reacting a compound of formula A with a compound of formula (IIIg) or (IIIn) depending on the meaning of B A+Hal-W$_1$—OC(O)O—Y—ONO$_2$      (IIIg)

A+Hal-W$_1$—OC(O)—Y—ONO$_2$      (IIIn)

wherein Y, Hal, W$_1$ are as above defined and A is as defined in 71b),
following the same procedures described in 4b) or 6b).

74. The compounds of general formula (I) wherein:
s and s' are equal to 1;
s", m, m', m", are 0
Y and Y' can be equal or different and are as above defined;
A is selected among:
(IIa) wherein $R_1$ is —C(O)—$R_{1x}$ and binds a group —Y'—ONO$_2$; $R_2$ is —C(O)OR$_{2x}$ and binds a group —Y—ONO$_2$; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is —OH;
(IIc) wherein $R_1$ is —C(O)—$R_{1x}$ and binds a group —Y'—ONO$_2$; $R_2$ is —C(O)OR$_{2x}$ and binds a group —Y—ONO$_2$; $R_s$ is selected from $R_gC(O)CH_2$—NH—, $R_gC(O)CH_2$, $R_gC(O)(CH_2)_2$—, $R_gC(O)(CH_2)_4$—, wherein $R_g$ is —OH;
can be prepared as follows:
74a) by reacting a compound of formula (I) prepared as described in 68. with a compound of formula (IIIe):

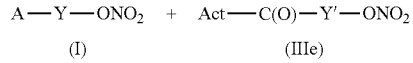

wherein Act, Y and Y' are as above defined and A is a radical of formula (IIa), (IIc), wherein $R_1$ is —H, $R_2$ is —C(O)OR$_{2x}$ and binds a group —Y—ONO$_2$; $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is —OH;
following the same procedures described in 1b').

75. The compounds of general formula (I) wherein:
s and s' are equal to 1;
s", m, m', m", are 0
Y and Y' can be equal or different and are as above defined;
A is selected among:
(IIa) wherein $R_1$ is —C(O)—$R_{1x}$ and binds a group —Y'—ONO$_2$; $R_2$ is —C(O)OR$_{2x}$ and binds a group —Y—ONO$_2$; wherein $R_g$ is —OH;
(IIc) wherein $R_1$ is —C(O)O—$R_{1x}$ and binds a group —Y'—ONO$_2$; $R_2$ is —C(O)OR$_{2x}$ and binds a group —Y—ONO$_2$; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is —OH;
can be prepared as follows:
75a) by reacting a compound of formula (I) prepared as described in 68. with a compound of formula (IIIf):

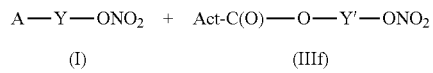

wherein Act, Y and Y' are as above defined and A is as defined in 74a);
following the same procedures described in 3b).

76. The compounds of general formula (I) wherein:
s and s' are equal to 1;
s", m, m', m", are 0
Y and Y' can be equal or different and are as above defined;
A is selected among:
(IIa) wherein $R_1$ is —C(O)—$R_1$ and binds a group —Y'—ONO$_2$; $R_2$ is —C(O)NHR$_{2xx}$ or —C(O)N(CH$_3$)R$_{2xx}$ and binds a group —Y—ONO$_2$; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is —OH;
(IIc) wherein $R_1$ is —C(O)—$R_{1x}$ and binds a group —Y'—ONO$_2$; $R_2$ is —C(O)NHR$_{2xx}$ or —C(O)N(CH$_2$)R$_{2xx}$ and binds a group —Y—ONO$_2$; R$_c$ is selected from R$_g$C(O)CH$_2$—NH—, R$_g$C(O)CH$_2$, R$_g$C(O)(CH$_2$)$_2$—, R$_g$C(O)(CH$_2$)$_4$—, wherein R$_g$ is —OH; can be prepared as follows:

76a) by reacting a compound of formula (I) prepared as described in 69. with a compound of formula (IIIe):

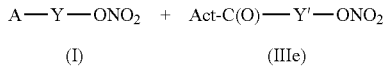

(I)  (IIIe)

wherein Act, Y and Y' are as above defined and A is a radical of formula (IIa), (IIc), wherein R$_1$ is —H, R$_2$ is —C(O)NHR$_{2xx}$ or —C(O)N(CH$_3$)R$_{2xx}$ and binds a group —Y—ONO$_2$; R$_a$ and R$_c$ are selected from R$_g$C(O)CH$_2$—NH—, R$_g$C(O)CH$_2$, R$_g$C(O)(CH$_2$)$_2$—, R$_g$C(O)(CH$_2$)$_4$—, wherein R$_g$ is —OH;

following the same procedures described in 1b').

77. The compounds of general formula (I) wherein:
s and s' are equal to 1;
s", m, m', m", are 0
Y and Y' can be equal or different and are as above defined;
A is selected among:
(IIa) wherein R$_1$ is —C(O)—R$_{1x}$ and binds a group —Y'—ONO$_2$; R$_2$ is —C(O)NHR$_{2xx}$ or —C(O)N(CH$_3$)R$_{2xx}$ and binds a group —Y—ONO$_2$; R$_a$ is selected from R$_g$C(O)CH$_2$—NH—, R$_g$C(O)CH$_2$, R$_g$C(O)(CH$_2$)$_2$—, R$_g$C(O)(CH$_2$)$_4$—, wherein R$_g$ is —OH;
(IIc) wherein R$_1$ is —C(O)O—R$_{1x}$ and binds a group —Y'—ONO$_2$; R$_2$ is —C(O)NHR$_{2xx}$ or —C(O)N(CH$_2$)R$_{2xx}$ and binds a group —Y—ONO$_2$; R$_c$ is selected from R$_g$C(O)CH$_2$—NH—, R$_g$C(O)CH$_2$, R$_g$C(O)(CH$_2$)$_2$—, R$_g$C(O)(CH$_2$)$_4$—, 77a) by reacting a compound of formula (I) prepared as described in 69. with a compound of formula (IIIf):

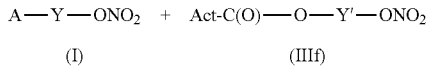

(I)  (IIIf)

wherein Act, Y and Y' are as above defined and A is as above defined in 76., following the same procedures described in 3b).

78. The compounds of general formula (I) wherein:
s, s' and m are equal to 1;
s", m', m", are 0
Y and Y' can be equal or different and are as above defined;
B is:

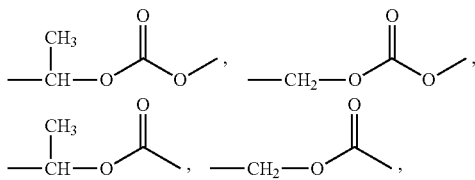

A is selected among:
(IIa) wherein R$_1$ is —C(O)—R$_{1x}$ and binds a group —Y'—ONO$_2$; R$_2$ is —C(O)OR$_{2x}$ and binds a group —B—Y—ONO$_2$; R$_a$ is selected from R$_g$C(O)CH$_2$—NH—, R$_g$C(O)CH$_2$, R$_g$C(O)(CH$_2$)$_2$—, R$_g$C(O)(CH$_2$)$_4$—, wherein R$_g$ is —OH; can be prepared as follows:

78a) by reacting a compound of formula (I) prepared as described in 70. with a compound of formula (IIIe):

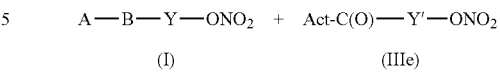

(I)  (IIIe)

wherein Act, B, Y and Y' are as above defined and A is a radical of formula (IIa), (IIc), wherein R$_1$ is —H, R$_2$ is —C(O)OR$_{2x}$ and binds a group B—Y—ONO$_2$; R$_a$ and R$_c$ are selected from R$_g$C(O)CH$_2$—NH—, R$_g$C(O)CH$_2$, R$_g$C(O)(CH$_2$)$_2$—, R$_g$C(O)(CH$_2$)$_4$—, wherein R$_g$ is —OH;

79. The compounds of general formula (I) wherein:
s, s' and m are equal to 1;
s", m', m", are 0
Y and Y' can be equal or different and are as above defined;
B is:

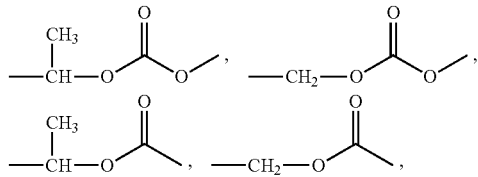

A is selected among:
(IIa) wherein R$_1$ is —C(O)O—R$_{1x}$ and binds a group —Y'—ONO$_2$; R$_2$ is —C(O)OR$_{2x}$ and binds a group —B—Y—ONO$_2$; R$_a$ is selected from R$_g$C(O)CH$_2$—NH—, R$_g$C(O)CH$_2$, R$_g$C(O)(CH$_2$)$_2$—, R$_g$C(O)(CH$_2$)$_4$—, wherein R$_g$ is —OH;
(IIc) wherein R$_1$ is —C(O)O—R$_{1x}$ and binds a group —Y'—ONO$_2$; R$_2$ is —C(O)OR$_{2x}$ and binds a group —B—Y—ONO$_2$; R$_c$ is selected from R$_g$C(O)CH$_2$—NH—, R$_g$C(O)CH$_2$, R$_g$C(O)(CH$_2$)$_2$—, R$_g$C(O)(CH$_2$)$_4$—, wherein R$_g$ is —OH; can be prepared as follows:

79a) by reacting a compound of formula (I) prepared as described in 70. with a compound of formula (IIIf):

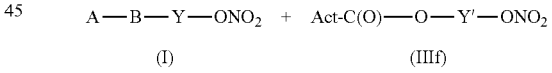

(I)  (IIIf)

wherein Act, B, Y and Y' are as above defined and A is as defined in 78a), following the same procedures described in 3b).

80. The compounds of general formula (I) wherein:
s and s' are equal to 1;
s", m, m', m", are 0
Y and Y' can be equal or different and are as above defined;
A is selected among:
(IIa) wherein R$_1$ is —C(O)—R$_{1x}$ and binds a group —Y'—ONO$_2$; R$_2$ is —COOH; R$_a$ is selected from R$_g$C(O)CH$_2$—NH—, R$_g$C(O)CH$_2$, R$_g$C(O)(CH$_2$)$_2$—, R$_g$C(O)(CH$_2$)$_4$—, wherein R$_g$ is R$_{gx}$—O—, and R$_a$ binds a group —Y—ONO$_2$
(IIc) wherein R$_1$ is —C(O)—R$_{1x}$ and binds a group —Y'—ONO$_2$; R$_2$ is —COOH; R$_c$ is selected from R$_g$C(O)CH$_2$—NH—, R$_g$C(O)CH$_2$, R$_g$C(O)(CH$_2$)$_2$—, R$_g$C(O)(CH$_2$)$_4$—, wherein R$_{gx}$ is R$_{gx}$—O—, and R$_c$ binds a group —Y—ONO$_2$;

can be prepared as follows:

80a) by reacting a compound, of formula (I) prepared as described in 71. with a compound of formula (IIIe):

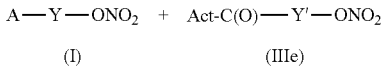

wherein Act, Y and Y' are as above defined and A is a radical of formula (IIa), (IIc), wherein $R_1$ is —H, $R_2$ is —COOH; $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_a$ and $R_c$ bind a group —Y—$ONO_2$
following the same procedures described in 1b').

81. The compounds of general formula (I) wherein:
s and s' are equal to 1;
s", m, m', m", are 0
Y and Y' can be equal or different and are as above defined;
A is selected among:
(IIa) wherein $R_1$ is —C(O)O—$R_{1x}$ and it binds a group —Y'—$ONO_2$; $R_2$ is —COOH; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_a$ binds a group —Y—$ONO_2$
(IIc) wherein $R_1$ is —C(O)O—$R_{1x}$ and binds a group —Y'—$ONO_2$; $R_2$ is —COOH; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_c$ binds a group —Y—$ONO_2$;
can be prepared as follows:
81a) by reacting a compound of formula (I) prepared as described in 71. with a compound of formula (IIIf):

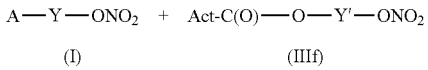

wherein Act, Y and Y' are as above defined and A is a radical of formula (IIa), (IIc), wherein $R_1$ is —H, $R_2$ is —COOH; $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$O— and $R_a$ and $R_c$ bind a group —Y—$ONO_2$, following the same procedures described in 3b).

82. The compounds of general formula (I) wherein:
s and s' are equal to 1;
s", m, m', m", are 0
Y and Y' can be equal or different and are as above defined;
A is selected among:
(IIa) wherein $R_1$ is —C(O)—$R_{1x}$ and it binds a group —Y'—$ONO_2$; $R_2$ is —COOH; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— and $R_a$ binds a group —Y'—$ONO_2$
(IIc) wherein $R_1$ is —C(O)—$R_{1x}$ and it binds a group —Y'—$ONO_2$; $R_2$ is —COOH; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— and $R_c$ binds a group —Y—$ONO_2$;
can be prepared as follows:
82a) by reacting a compound of formula (I) prepared as described in 72. with a compound of formula (IIIe):

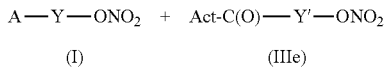

wherein Act, Y and Y' are as above defined and A is a radical of formula (IIa), (IIc), wherein $R_1$ is —H, $R_2$ is —COOH; $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)—
and $R_a$ and $R_c$ bind a group —Y—$ONO_2$
following the same procedures described in 1b').

83. The compounds of general formula (I) wherein:
s and s' are equal to 1;
s", m, m', m", are 0
Y and Y' can be equal or different and are as above defined;
A is selected among:
(IIa) wherein $R_1$ is —C(O)O—$R_{1x}$ and binds a group —Y'—$ONO_2$; $R_2$ is —COOH; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— and $R_a$ binds a group —Y—$ONO_2$;
(IIc) wherein $R_1$ is —C(O)O—$R_{1x}$ and binds a group —Y'—$ONO_2$; $R_2$ is —COOH; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— and $R_c$ binds a group —Y—$ONO_2$;
can be prepared as follows:
83a) by reacting a compound of formula (I) prepared as described in 72. with a compound of formula (IIIf):

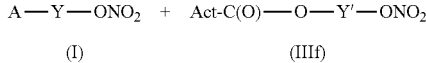

wherein Act, Y and Y' are as above defined and A is as defined in 82a), following the same procedures described in 3b).

84. The compounds of general formula (I) wherein:
s, s' and m are equal to 1;
s", m', m", are 0
Y and Y' can be equal or different and are as above defined;
B is:

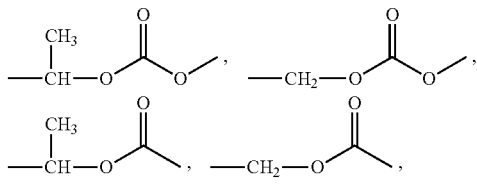

A is selected among:
(IIa) wherein $R_1$ is —C(O)O—$R_{1x}$ and binds a group —Y'—$ONO_2$; $R_2$ is —COOH; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_a$ binds a group —B—$ONO_2$;
(IIc) wherein $R_1$ is —C(O)—$R_{1x}$ and binds a group —Y'—$ONO_2$; $R_2$ is —COOH; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_c$ binds a group —B—Y—$ONO_2$;

can be prepared as follows:
84a) by reacting a compound of formula (I) prepared as described in 73. with a compound of formula (IIIe):

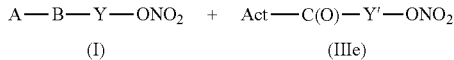

wherein Act, B, Y and Y' are as above defined and A is a radical of formula, (IIa), (IIc), wherein $R_1$ is —H, $R_2$ is —COOH; $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}O$— and $R_a$ and $R_c$ bind a group B—Y—$ONO_2$, following the same procedures described in 1b').

85. The compounds of general formula (I) wherein:
s, s' and m are equal to 1;
s", m', m", are 0
Y and Y' can be equal or different and are as above defined;
B is:

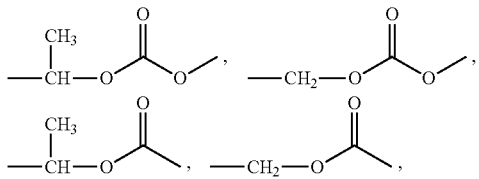

A is selected among:
(IIa) wherein $R_1$ is —C(O)O—$R_{1x}$ and binds a group —Y'—$ONO_2$; $R_2$ is —COOH; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_a$ binds a group —B—Y—$ONO_2$;
(IIc) wherein $R_1$ is —C(O)—$R_{1x}$ and it binds a group —Y'—$ONO_2$; $R_2$ is —COOH; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O— and $R_c$ binds a group —B—Y—$ONO_2$;
can be prepared as follows:
85a) by reacting a compound of formula (I) prepared as described in 73. with a compound of formula (IIIf):

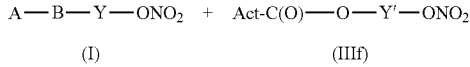

wherein Act, B, Y and Y' are as above defined and A is as defined in 84a), following the same procedures described in 3b).

86. The compound of general formula (I) wherein:
s and s' are equal to 1;
s", m, m', m" are equal to 0;
Y and Y' are equal and are as above defined;
A is selected from (IIa), (IIc) or (IIt) wherein $R_1$ is —C(O)—$R_{1x}$ and it binds a group —Y—$ONO_2$ or a group —Y'—$ONO_2$, $R_2$ is —COOH; $R_a$ of formula (IIa) and $R_c$ of formula (IIc) are $R_hNH(CH_2)_p$— wherein p is an integer from 0 to 4, or $R_iNH(=NH)NH$—$(CH_2)_3$—, and $R_h$ and $R_i$ are $R_{hh}$—C(O)— or $R_{ii}$—C(O)— and $R_a$ and $R_c$ bind a group —Y—$ONO_2$ or a group —Y'—$ONO_2$;
in formula (IIt) $R_1$ is —C(O)—$R_{1x}$ and it binds a group —Y—$ONO_2$ or a group —Y'—$ONO_2$, $R_2$ is —COOH; d is 2 d' is 1, $R_t$ is —C(O)—$R_{tt}$ and it binds a group —Y—$ONO_2$ or a group —Y'—$ONO_2$;
can be prepared as follows:
86a) by reacting a compound of formula A with a compound of formula (IIIe)

wherein Act and Y are as above defined and A is a compound of formula (IIa), (IIc) or (IIt) wherein $R_1$ is —H and $R_2$ is —COOH; $R_a$ of formula (IIa) and $R_c$ of formula (IIc) are $R_hNH(CH_2)_p$— wherein p is an integer from 0 to 4, $R_iNH(=NH)NH$—$(CH_2)_3$—, and $R_h$ and $R_i$ are —H;
in formula (IIt) $R_1$ is —H, $R_2$ is —COOH, d is 2 d' is 1, $R_t$ is —H; using a ratio A/(IIIe) 1:2 and applying the same procedure described in 1b'). Compounds A are commercially available.

87. The compounds of general formula (I) wherein:
s and s' are equal to 1;
s", m, m', m", are 0
Y and Y' are equal and are as above defined;
A is a radical selected from (IIa), (IIc) or (IIt) wherein $R_1$ is —C(O)—$R_{1x}$ and binds a group —Y—$ONO_2$ or a group —Y'—$ONO_2$, $R_2$ is —COOH;
$R_a$ of formula (IIa) and $R_c$ of formula (IIc) are $R_hNH(CH_2)_p$— wherein p is an integer from 0 to 4, or $R_iNH(=NH)NH$—$(CH_2)_3$—, and $R_h$ and $R_i$ are $R_{hh}$—C(O)— or $R_{ii}$—C(O)— and $R_a$ and $R_c$ bind a group —Y—$ONO_2$ or a group —Y'—$ONO_2$;
in formula (IIt) $R_1$ is —C(O)—$R_{1x}$ and binds a group —Y—$ONO_2$ or a group —Y'—$ONO_2$, $R_2$ is —COOH;
d is 2 d' is 1, $R_t$ is —C(O)—$R_{tt}$ and binds a group —Y—$ONO_2$ or a group —Y'—$ONO_2$;
can be prepared as follows.
87a) by reacting a compound of formula A with a compound of formula (IIIf)

wherein Act and Y are as above defined and A is as defined in 86a) using a ratio A/(IIIf) 1:2 and applying the same procedure described in 3b).

88. The compounds of general formula (I) wherein:
s is equal to 1;
s', s", m, m', m", are equal to 0;
Y is as above defined;
A is a radical of formula (IIa), (IIc) or (IIt) wherein $R_1$ is —H, $R_2$ is —C(O)O$R_{2x}$ and it binds a group —Y—$ONO_2$;
$R_a$ of formula (IIa) and $R_c$ of formula (IIc) are the groups $R_hNH(CH_2)_p$— wherein p is an integer from 0 to 4, $R_iNH(=NH)NH$—$(CH_2)_3$—, $R_h$ and $R_i$ are —H;
in formula (IIt) $R_1$ is —H, and $R_2$ is —C(O)O$R_{2x}$ and it binds a group —Y—$ONO_2$; d is 2 d' is 1, $R_t$ is —H;
can be obtained as follows:
88a) $R_a=R_c$ selected from $R_hNH(CH_2)_p$— wherein p is an integer from 0 to 4, $R_h$ is —H;
by reacting a compound of formula (I) wherein s, s', s", m, m', m", Y, Y', Y" are as above defined in 88. A is a radical of (IIa), (IIc) or (IIt) wherein $R_1$ is —C(O)OC(CH$_3$)$_3$; $R_2$ is —CO(O)$R_{2x}$ and bind; $R_a$ of formula (IIa) and $R_c$ of formula (IIc) are selected from $R_hNH(CH_2)_p$— wherein p is an integer from 0 to 4, or $R_h$ is —C(O)OC(CH$_3$)$_3$;
in formula (IIt) $R_1$ and $R_2$ are as above defined d is 2 d' is 1, $R_t$ is —C(O)OC(CH$_3$)$_3$;
with anhydrous or aqueous organic or inorganic acid to hydrolyze the —BOC protective groups following procedure well known in the literature.
88a') $R_a=R_c$ selected from $R_iNH(=NH)$—$(CH_2)_3$—, $R_t$ is —H:

by reacting a compound of formula (VIIa)

wherein Y, is as above defined; $A_{5a}$ is a radical of formula (IIa), (IIc) wherein $R_1$ is —C(O)OC(CH$_3$)$_3$; $R_2$ is —CO(O)$R_{2x}$; $R_a$ of formula (IIa) and $R_c$ of formula (IIc) are $R_{ia}$—NH(=NH)NH—(CH$_2$)$_3$— wherein $R_{ia}$ is the known protective group —Pbf (2,2,4,6,7-pentamethyl-dihydrobenzofuran-5-sulfonyl)-;

with anhydrous or aqueous organic or inorganic acid to hydrolyze the —HOC and the —Pbf protective groups following procedure well known in the literature.

88b) compounds described in 88a) and 88a') can be respectively obtained by reacting a compound of formula A or $A_5$ with a compound of formula (IIIi)

A+HO—Y—ONO$_2$→(I)  (IIIi)

$A_5$+HO—Y—ONO$_2$→(VIIIa)  (IIIi)

wherein Y is as above defined, and:

A is a radical of formula (IIa), (IIc) or (IIt) wherein $R_1$ is —C(O)OC(CH$_3$)$_3$; $R_2$ is —COOH; $R_a$ and $R_c$ are $R_h$NH(CH$_2$)$_p$— wherein p as above defined and $R_h$ is —C(O)OC(CH$_3$)$_3$; d and d' are as above defined, and $R_t$ is —C(O)OC(CH$_3$)$_3$;

$A_5$ is a radical of formula (IIa) or (IIc) wherein $R_1$ is —C(O)OC(CH$_3$)$_3$; $R_2$ is —COOH; $R_a$ and $R_c$ are $R_{ia}$NH(=NH)NH—(CH$_2$)$_3$— wherein $R_{ia}$ is as above defined using the same procedure described in 8b).

Compounds A and $A_5$ as above defined are commercially available or can be easily obtained from commercially available compounds by simple deprotection/protection steps as known in the literature.

89. The compounds of general formula (I) wherein:
s is equal to 1;
s', s", m, m', m" are equal to 0;
Y is as above defined;
A is a radical of formula (IIa), (IIc) or (IIt) wherein $R_1$ is —H, $R_2$ is —C(O)NHR$_{2xx}$ or —C(O)N(CH$_3$)R$_{2xx}$ and it binds a group —Y—ONO$_2$;
$R_a$ of formula (IIa) and $R_c$ of formula (IIc) are $R_h$NH(CH$_2$)$_p$— wherein p is an integer from 0 to 4, or $R_i$NH(=NH)NH—(CH$_2$)$_3$—, and $R_h$ and $R_i$ are —H;
in formula (IIt) $R_1$ is —H, $R_2$ is —C(O)NHR$_{2xx}$ or —C(O)N(CH$_3$)R$_{2xx}$ and it binds a group —Y—ONO$_2$; d is 2 d' is 1, $R_t$ is —H;
can be obtained as follows:

89a) $R_a$=$R_c$ are selected from $R_h$NH(CH$_2$)$_p$— wherein p is an integer from 0 to 4, $R_h$ is —H:
by reacting a compound of formula (I) wherein s, s', s", m, m', m", Y, Y', Y" are as above defined in 89. A is a radical of formula (IIa), (IIc) or (IIt) wherein $R_1$ is —C(O)OC(CH$_3$)$_3$; $R_2$ is —C(O)NHR$_{2xx}$ or —C(O)N(CH$_3$)R$_{2xx}$; $R_a$, $R_c$, p, d, d', $R_h$ and $R_t$ are as defined in 88a) with anhydrous or aqueous organic or inorganic acid to hydrolyze the —BOC protective groups.

89a') $R_a$=$R_c$ selected from $R_i$NH(=NH)NH—(CH$_2$)$_3$—, $R_i$ is —H:
by reacting a compound of formula (VIIIb):

whereinY, is as above defined; $A_6$ is a radical of formula (IIa), (IIc) wherein $R_1$ is —C(O)OC(CH$_3$)$_3$; $R_2$ is —C(O)NHR$_{2xx}$ or —C(O)N(CH$_3$)$_{2xx}$; $R_a$ of formula (IIa) and $R_c$ of formula (IIc) are $R_{ia}$—NH(=NH)NH—(CH$_2$)$_3$ wherein $R_{ia}$ is the —Pbf group as above defined;

with anhydrous or aqueous organic or inorganic acid to hydrolyze the —BOC and the —Pbf protective groups following procedure well known in the literature.

89b) compounds described in 89a) and 89a') can be respectively obtained by reacting a compound of formula A or a compound of formula $A_5$ already defined in 88b) with a compound of formula (IIIo)

A+W$_3$NH—Y—ONO$_2$→(I)  (IIIo)

$A_5$+W$_3$NH—Y—ONO$_2$→(VIIIb)  (IIIo)

using the same procedure described in 7b).

90. The compounds of general formula (I) wherein:
s and m are equal to 1;
s', s", m', m" are equal to 0;
Y is as above defined;
B is:

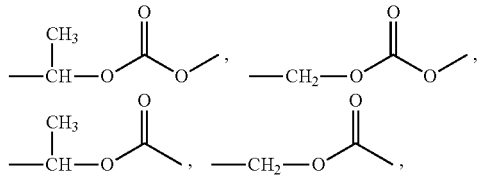

A is a radical of formula (IIa), (IIc) or (IIt) wherein $R_1$ is —H, $R_2$ is —C(O)OR$_{2x}$ and binds a group —B—Y—ONO$_2$;
$R_a$ of formula (IIa) and $R_c$ of formula (IIc) are $R_h$NH(CH$_2$)$_p$— wherein p is an integer from 0 to 4, or $R_i$NH(=NH)NH—(CH$_2$)$_3$—, and $R_h$ and $R_i$ are —H;
in formula (IIt) $R_1$ is —H, $R_2$ is —C(O)OR$_{2x}$ and it binds a group —B—Y—ONO$_2$; d is 2 d' is 1, $R_t$ is —H;
can be obtained as follows:

90a) $R_a$=$R_c$ selected from $R_h$NH(CH$_2$)$_p$— wherein p is an integer from 0 to 4, $R_h$ is —H:
by reacting a compound of formula (I) wherein B, s, s', s", m, m', m", Y, Y', Y" are as above defined in 90. A is a radical of formula (IIa), (IIc) or (IIt) wherein $R_1$ is —C(O)OC(CH$_3$)$_3$; $R_2$ is —C(O)OR$_{2x}$; B, $R_a$, $R_c$, p, d, d', $R_h$ and $R_t$ are as defined in 90. with anhydrous or aqueous organic or inorganic acid to hydrolyze the —BOC protective groups.

90a') $R_a$=$R_c$ selected from $R_i$NH(=NH)NH—(CH$_2$)$_3$—, $R_i$ is —H:
by reacting a compound of formula (VIIIc):

$A_{5a}$-B—Y—ONO$_2$  (VIIIc)

wherein B, and Y, are as above defined in 90. and $A_{5a}$ is as defined in 88a') with anhydrous or aqueous organic or inorganic acid to hydrolyze the —BOC and the —Pbf protective groups following procedure well known in the literature.

90b) compounds described in 90a) and 90a') can be respectively obtained by reacting a compound of formula A or a compound of formula $A_5$ already defined in 88b) with compounds (IIIg) or (IIIn) depending on the meaning of B, and applying the same procedure described in 4b) or 6b):

A or $A_5$+Hal-W$_1$—OC(O)—Y—ONO$_2$→(I) or (VIIIc)  (IIIg)

A or $A_5$+Hal-W$_1$—OC(O)—O—Y—ONO$_2$→(I) or (VIIIc)  (IIIn)

91. The compounds of general formula (I) wherein:
s and s' are equal to 1;
s", m, m', m" are equal to 0;
Y and Y' can be equal or different and are as above defined;

A is selected from (IIa), (IIc) and (IIt) wherein $R_1$ is —C(O)—$R_{1x}$ and binds a group —Y'—$ONO_2$, $R_2$ is —C(O)$OR_{2x}$ and binds a group —Y—$ONO_2$;

$R_a$ of formula (IIa) and $R_c$ of formula (IIc) are $R_h$NH($CH_2)_p$— wherein p is an integer from 0 to 4, or $R_i$NH(=NH)NH—($CH_2)_3$—, and $R_h$ and $R_i$ are —H;

in formula (IIt) $R_1$ is —C(O)—$R_{1x}$ and it binds a group —Y'—$ONO_2$, $R_2$ is —C(O)$OR_{2x}$ and $R_2$ binds a group —Y—$ONO_2$; d is 2 d' is 1, $R_t$ is —H:

can be obtained as follows:

91a) $R_a$=$R_c$ selected from $R_h$NH($CH_2)_p$— wherein p is an integer from 0 to 4, $R_h$ is —H:

by reacting a compound of formula (I) wherein s, s', s'', m, m', m'', Y, Y', Y'' are as above defined in 91. A is a radical of (IIa), (IIc) or (IIt) wherein $R_1$ is —C(O)—$R_{1x}$; $R_2$ is —C(O)$OR_{2x}$; $R_a$ of formula (IIa) and $R_c$ of formula (IIc) are selected from $R_h$NH($CH_2)_p$— wherein p is an integer from 0 to 4, $R_h$ is —C(O)OC($CH_3)_3$;

in formula (IIt) $R_1$ and $R_2$ are as above defined d is 2 d' is 1, $R_t$ is —C(O)OC($CH_3)_3$;

with anhydrous or aqueous organic or inorganic acid to hydrolyze the —BOC protective groups following procedure well known in the literature.

91a') $R_a$=$R_c$ selected from $R_i$NH(=NH)NH—($CH_2)_3$—, $R_i$ is —H:

by reacting a compound of formula (VIIId)

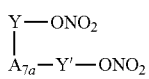

(VIIId)

wherein Y and Y' are as above defined; $A_{7a}$ is a radical of formula (IIa), (IIc) wherein $R_1$ is —C(O)—$R_{1x}$; $R_2$ is —CO(O); $R_a$ of formula (IIa) and $R_c$ of formula (IIc) are $R_{ia}$NH(=NH)NH—($CH_2)_3$— wherein $R_{ia}$ is group —Pbf as already defined;

with anhydrous or aqueous organic or inorganic acid to hydrolyze the —Pbf protective groups following procedure well known in the literature.

91b) $R_a$ and $R_c$ are selected from $R_h$NH($CH_2)_p$— wherein p is an integer from 0 to 4, $R_h$ is —H:

by reacting a compound of formula (I) with a compound of formula (IIIe)

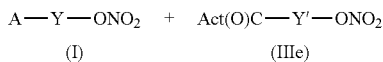

wherein Y and Y' are as above defined and A is a radical of formula (IIa), (IIc) or (IIt) wherein $R_1$ is —H, $R_2$ is —C(O)$OR_{2x}$ and binds the group —Y—$ONO_2$; $R_a$ and $R_c$ are $R_h$NH($CH_2)_p$— wherein p as above defined and $R_h$ is —C(O)OC($CH_3)_3$; d and d' are as above defined, and $R_t$ is —C(O)OC($CH_3)_3$; using the same procedure described in 1b').

91b') $R_a$=$R_c$ selected from $R_i$NH(=NH)NH—($CH_2)_3$—, $R_i$ is —H:

by reacting a compound of formula (VIIIe) with a compound of formula (IIIe):

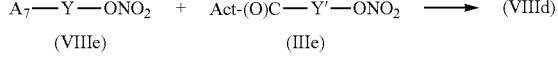

wherein Y and Y' are as above defined and $A_7$ is a radical of formula (IIa), (IIc) wherein $R_1$ is —H, $R_2$ is —C(O)$OR_{2x}$ and binds the group —Y—$ONO_2$; $R_a$ and $R_c$ are $R_{ia}$NH(=NH)NH—($CH_2)_3$— wherein $R_{ia}$ is group —Pbf as above defined; using the same procedure described in 1b').

91c) compounds described in 91b) and 91b') can be respectively prepared by deprotecting the Fmoc group of a compound of formula ($VIIIf_1$) or ($VIIIf_2$)

$A_{8a}$-Y—$ONO_2$→(I)     ($VIIIf_1$)

$A_{8b}$-Y—$ONO_2$→(VIIIe)     ($VIIIf_2$)

wherein Y is as above defined and:

$A_{8a}$ is a radical of formula (IIa), (IIc) or (IIt) wherein $R_1$ is the Fmoc protective group; $R_2$ is —C(O)$OR_{2x}$ and binds the group —Y—$ONO_2$; $R_a$ and $R_c$ are $R_h$NH($CH_2)_p$— wherein p is as above defined and $R_h$ is —C(O)OC($CH_3)_3$, $A_{8b}$ is a radical of formula (IIa) or (IIc) wherein $R_1$ is the Fmoc protective group; $R_2$ is —C(O)$OR_{2x}$ and binds the group —Y—$ONO_2$; $R_a$ and $R_c$ are $R_{ia}$NH(=NH)NH—($CH_2)_3$—, wherein $R_{ia}$ is the —Pbf group as above defined;

91d) compound of formula ($VIIIf_1$) or ($VIIIf_2$) are prepared by reacting a compound of formula $A_{9a}$ or $A_{9b}$ with composed (IIIi) using the same procedure described in 8b)

$A_{9a}$+HO—Y—$ONO_2$→($VIIIf_1$)     (IIIi)

$A_{9b}$+HO—Y—$ONO_2$→($VIIIf_2$)     (IIIi)

wherein Y is as above defined and:

$A_{9a}$ is a radical of formula (IIa), (IIc) or (IIt) wherein $R_1$ is the Fmoc protective group; $R_2$ is —COOH; $R_a$ and $R_c$ are $R_h$NH($CH_2)_p$— wherein p as above defined and $R_h$ is —C(O)OC($CH_3)_3$;

$A_{9b}$ is a radical of formula (IIa) or (IIc) wherein $R_1$ is the Fmoc protective group; $R_2$ is —COOH; $R_a$ and $R_c$ are $R_{ia}$NH(=NH)NH—($CH_2)_3$— wherein $R_{ia}$ is the —Pbf group as previously defined.

Compounds $A_{9a}$ and $A_{9b}$ are commercially available.

92. The compounds of general formula (I) wherein:

s and s' are equal to 1;

s'', m, m', m'' are equal to 0;

Y and Y' can be equal or different and are as above defined;

A is a radical of formula (IIa), (IIc) or (IIt) wherein $R_1$ is —C(O)—$R_{1x}$ and it binds a group —Y'—$ONO_2$, $R_2$ is —C(O)NH$R_{2xx}$ or —C(O)N($CH_3$)$R_{2xx}$ and it binds a group —Y—$ONO_2$;

$R_a$ of formula (IIa) and $R_c$ of formula (IIc) are —$R_h$NH($CH_2)_p$— wherein p is an integer from 0 to 4, or $R_i$NH(=NH)NH—($CH_2)_3$—, and $R_h$ and $R_i$ are —H;

in formula (IIt) $R_1$ is —C(O)—$R_{1x}$ and binds a group —Y'—$ONO_2$; $R_2$ is —C(O)NH$R_{2xx}$ or —C(O)N($CH_3$)$R_{2xx}$ and it binds a group —Y—$ONO_2$; d is 2 d' is 1, $R_t$ is —H;

can be obtained as follows:

92a) $R_a$=$R_c$ selected from $R_h$NH($CH_2)_p$— wherein p is an integer from 0 to 4, $R_h$ is —H:

by reacting a compound of formula (I) wherein s, s', s'', m, m', m'', Y, Y', Y'' are as above defined in 92. A is a radical of (IIa), (IIc) or (IIt) wherein $R_1$ is —C(O)—$R_{1x}$; $R_2$ is —C(O)NH$R_{2xx}$ or —C(O)N($CH_3$)$R_{2xx}$;

$R_a$ of formula (IIa) and $R_c$ of formula (IIc) are $R_h$NH($CH_2)_p$— wherein p is an integer from 0 to 4, $R_h$ is —C(O)OC($CH_3)_3$;

in formula (IIt) $R_1$ and $R_2$ are as above defined d is 2 d' is 1, $R_t$ is —C(O)OC($CH_3)_3$;

with anhydrous or aqueous organic or inorganic acid to hydrolyze the —BOC protective groups following procedure well known in the literature.

92a') $R_a=R_c$ selected from $R_iNH(=NH)NH—(CH_2)_3—$, $R_i$ is —H:

by reacting a compound of formula (VIIIg)

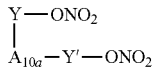
(VIIIg)

wherein Y and Y' are as above defined; $A_{10a}$ is a radical of formula (IIa), (IIc) wherein $R_1$ $R_1$ is —C(O)—$R_{1x}$; $R_2$ is —C(O)NHR$_{2xx}$ or —C(O)N(CH$_3$)R$_{2xx}$;

$R_a$ of formula (IIa) and $R_c$ of formula (IIc) are $R_{ia}$—NH(=NH)NH—(CH$_2$)$_3$— wherein $R_{ia}$ is the —Pbf group with anhydrous or aqueous organic or inorganic acid to hydrolyze the —Pbf protective groups following procedure well known in the literature.

92b) $R_a=R_c$ are selected from $R_hNH(CH_2)_p$— wherein p is an integer from 0 to 4, $R_h$ is —H:

by reacting a compound of formula (I) with a compound of formula (IIIe)

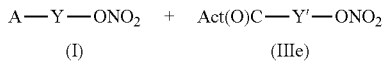

wherein Y and Y' are as above defined and A is a radical of formula (IIa), (IIc) or (IIt) wherein $R_1$ is $R_1$ is —H, $R_2$ is —C(O)NHR$_{2xx}$ or —C(O)N(CH$_3$)R$_{2xx}$ and binds the group —Y—ONO$_2$; $R_a$ and $R_c$ are $R_hNH(CH_2)_p$— wherein p as above defined and $R_h$ is —C(O)OC(CH$_3$)$_3$; d and d' are as above defined, and $R_t$ is —C(O)OC(CH$_3$)$_3$; using the same procedure described in 1b').

92b') $R_a=R_c$ selected from $R_iNH(=NH)NH—(CH_2)_3—$, $R_i$ is —H:

compound (VIIIg) is prepared by reacting a compound of formula (VIIIh) with a compound of formula (IIIe)

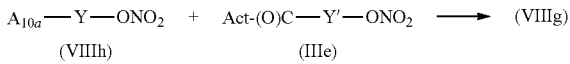

wherein Y and Y' are as above defined and $A_{10a}$ is a radical of formula (IIa), (IIc) wherein $R_1$ is —H, $R_2$ is —C(O)NHR$_{2xx}$ or —C(O)N(CH$_3$)R$_{2xx}$ and binds the group —Y—ONO$_2$; $R_a$ and $R_c$ are $R_{1a}$—NH(=NH)NH—(CH$_2$)$_3$— wherein $R_{ia}$ is as above defined using the same procedure described in 1b').

92c) compounds described in 92b) and 92b') can be prepared by deprotecting the Fmoc group of a compound, of formula (VIIIi$_1$) or (VIIIi$_2$)

$A_{11a}$-Y—ONO$_2$→(I)  (VIIIi$_1$)

$A_{11b}$-Y—ONO$_2$→(VIIIh)  (VIIIi$_2$)

wherein Y is as above defined and:

$A_{11a}$ is a radical of formula (IIa), (IIc) or (IIt) wherein $R_1$ is the Fmoc protective group; $R_2$ is —C(O)NHR$_{2xx}$ or —C(O)N(CH$_3$)R$_{2xx}$ and binds the group —Y—ONO$_2$; $R_a$ and $R_c$ are $R_hNH(CH_2)_p$— wherein p is as above defined and $R_h$ is —C(O)OC(CH$_3$)$_3$, $A_{11b}$ is a radical of formula (IIa) or (IIc) wherein $R_1$ is the Fmoc protective group; $R_2$ is —C(O)NHR$_{2xx}$ or —C(O)N(CH$_3$)R$_{2xx}$ and binds the group —Y—ONO$_2$; $R_a$ and $R_c$ are $R_{ia}$NH(=NH)NH—(CH$_2$)$_3$, wherein $R_{ia}$ is as above defined;

92d) compounds described on 92c) can be prepared by reacting a compound of formula $A_{9a}$ or a compound of formula $A_{9b}$ defined in 91d) with compound (IIIo) using the same procedure described in 7b)

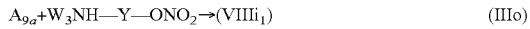
$A_{9a}+W_3NH$—Y—ONO$_2$→(VIIIi$_1$)  (IIIo)

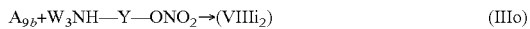
$A_{9b}+W_3NH$—Y—ONO$_2$→(VIIIi$_2$)  (IIIo)

wherein Y and W$_3$ are as above defined.

93. The compounds of general formula (I) wherein:

s and s' are equal to 1;

s", m, m' and m" are equal to 0;

Y and Y' can be equal or different and are as above defined;

A is a radical of formula (IIa), (IIc) and (IIt) wherein $R_1$ is —C(O)O—$R_{1x}$ and binds a group —Y'—ONO$_2$, $R_2$ is —C(O)OR$_{2x}$ and binds a group —Y—ONO$_2$;

$R_a$ of formula (IIa) and $R_c$ of formula (IIc) are $R_hNH(CH_2)_p$— wherein p is an integer from 0 to 4, or $R_iNH(=NH)NH—(CH_2)_3$, and $R_h$ and $R_i$ are —H;

in formula (IIt) $R_1$ is —C(O)O—$R_{1x}$ and binds a group —Y'—ONO$_2$, and $R_2$ is —C(O)OR$_{2x}$ and binds a group —Y—ONO$_2$; d is 2 d' is 1, $R_t$ is —H;

can be obtained as follows:

93a) $R_a=R_c$ selected from $R_hNH(CH_2)_p$— wherein p is an integer from 0 to 4, $R_h$ is —H:

by reacting a compound of formula (I) wherein s, s', s", m, m', m", Y, Y', Y" are as above defined in 93. A is a radical of formula (IIa), (IIc) or (IIt) wherein $R_1$ is —C(O)O—$R_{1x}$; $R_2$ is —C(O)OR$_{2x}$;

$R_a$ of formula (IIa) and $R_c$ of formula (IIc) are selected from $R_hNH(CH_2)_p$— wherein p is an integer from 0 to 4, $R_h$ is —C(O)OC(CH$_3$)$_3$;

in formula (IIt) $R_1$ and $R_2$ are as above defined d is 2 d' is 1, $R_t$ is —C(O)OC(CH$_3$)$_3$;

with anhydrous or aqueous organic or inorganic acid to hydrolyze the —BOC protective groups following procedure well known in the literature.

93a') $R_a=R_c$ selected from $R_iNH(=NH)NH—(CH_2)_3—$, $R_i$ is —H:

by reacting a compound of formula (VIIIj)

(VIIIj)

wherein Y and Y' are as above defined; $A_{11a}$ is a radical of formula (IIa), (IIc) wherein $R_1$ is —C(O)O—$R_{1x}$; $R_2$ is —C(O)OR$_{2x}$, $R_a$ of formula (IIa) and $R_c$ of formula (IIc) are $R_{ia}NH(=NH)NH—(CH_2)_3$— wherein $R_{ia}$ is as already defined;

with anhydrous or aqueous organic or inorganic acid to hydrolyze the —Pbf protective groups following procedure well known in the literature.

93b) $R_a=R_c$ are selected from $R_hNH(CH_2)_p$— wherein p is an integer from 0 to 4, $R_h$ is —H:

by reacting a compound of formula (I) with a compound of formula (IIIf)

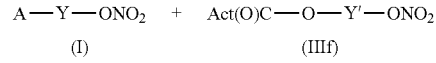

wherein Y and Y' are as above defined and A is a radical of formula (IIa), (IIc) or (IIt) already defined in 91b) and obtained as described in 91c), using the same procedure described in 3b).

93b') $R_a=R_c$ selected from $R_iNH(=NH)NH—(CH_2)_3—$, $R_i$—H:

Compound of formula (VIIIj) are prepared by reacting a compound of formula (VIIIe) already defined in 91b') and obtained as described in 91c) with a compound of formula (IIIf)

$$A_8—Y—ONO_2 \quad + \quad Act(O)C—O—Y'—ONO_2 \longrightarrow \text{(VIIIj)}$$
$$\text{(VIIIe)} \qquad\qquad \text{(IIIf)}$$

wherein $A_8$, Y and Y' are as above defined, using the same procedure described in 3b).

94. The compounds of general formula (I) wherein:
s and s' are equal to 1;
s", m, m' and m" are equal to 0;
Y and Y' can be equal or different and are as above defined;
A is selected from (IIa), (IIc) and (IIt) wherein $R_1$ is —C(O)O—$R_{1x}$ and binds a group —Y'—$ONO_2$, $R_2$ is —C(O)NHR$_{2xx}$ or —C(O)N(CH$_3$)R$_{2xx}$ and binds a group —Y—$ONO_2$;
$R_a$ of formula (IIa) and $R_c$ of formula (IIc) are $R_hNH(CH_2)_p$— wherein p is an integer from 0 to 4, or $R_iNH(=NH)NH—(CH_2)_3—$, and $R_h$ and $R_i$ are —H;
in formula (IIt) $R_1$ is —C(O)O—$R_{1x}$ and binds a group —Y'—$ONO_2$, and $R_2$ is —C(O)NHR$_{2xx}$ or —C(O)N(CH$_3$)R$_{2xx}$ and binds a group —Y—$ONO_2$; d is 2 d' is 1 $R_t$ is —H;
can be obtained as follows:
94a) $R_a=R_c$ selected from $R_hNH(CH_2)_p$— wherein p is an integer from 0 to 4, $R_h$ is —H;
by reacting a compound of formula (I) wherein s, s', s", m, m', m", Y, Y', Y" are as above defined in 94. A is a radical of (IIa), (IIc) or (IIt) wherein $R_1$ is —C(O)O—$R_{1x}$; $R_2$ is —C(O)NHR$_{2xx}$ or —C(O)N(CH$_3$)R$_{2xx}$;
$R_a$ of formula (IIa) and $R_c$ of formula (IIc) are selected from $R_hNH(CH_2)_p$— wherein p is an integer from 0 to 4, $R_h$ is —C(O)OC(CH$_3$)$_3$;
in formula (IIt) $R_1$ and $R_2$ are as above defined d is 2 d' is 1, $R_t$ as —C(O)OC(CH$_3$)$_3$;
with anhydrous or aqueous organic or inorganic acid to hydrolyze the —BOC protective groups following procedure well known in the literature.
94a') $R_a=R_c$ selected from $R_iNH(=NH)NH—(CH_2)_3—$, $R_i$ is —H:
by reacting a compound of formula (VIIIk)

$$\begin{array}{c} Y—ONO_2 \\ | \\ A_{12a}—Y'—ONO_2 \end{array} \qquad \text{(VIIIk)}$$

wherein Y and Y' are as above defined; $A_{12a}$ is a radical of formula (IIa), (IIc) wherein $R_1$ is —C(O)O—$R_{1x}$, $R_2$ is —C(O)NHR$_{2xx}$ or —C(O)N(CH$_3$)R$_{2xx}$;
$R_a$ of formula (IIa) and $R_c$ of formula (IIc) are $R_{ia}NH(=NH)NH—(CH_2)_3—$ wherein $R_{ia}$ is group —Pbf
with anhydrous or aqueous organic or inorganic acid to hydrolyze the —Pbf protective groups following procedure well known in the literature.

94b) $R_a=R_c$ are selected from $R_hNH(CH_2)_p$— wherein p is an integer from 0 to 4, $R_h$ is —H:
by reacting a compound of formula (I) with a compound of formula (IIIf)

$$A—Y—ONO_2 \quad + \quad Act(O)C—O—Y'—ONO_2$$
$$\text{(I)} \qquad\qquad \text{(IIIf)}$$

wherein Y and Y' are as above defined and A is a radical of formula (IIa), (IIc) or (IIt) already defined in 92b) and obtained as described in 92c), using the same procedure described in 3b).

94b') $R_a=R_c$ selected from $R_iNH(=NH)NH—(CH_2)_3—$, $R_i$ is —H:

Compound (VIIIk) are prepared by reacting a compound of formula (VIIIh) already defined in 92b') and obtained as described in 92c) with a compound of formula (IIIf)

$$A_{10}—Y—ONO_2 \quad + \quad Act(O)C—O—Y'—ONO_2 \longrightarrow \text{(VIIIk)}$$
$$\text{(VIIIh)} \qquad\qquad \text{(IIIf)}$$

wherein Y and Y' are as above defined using the same procedure described in 3b).

95. The compounds of general formula (I) wherein:
s, s' and s" are equal to 1;
m, m' and m" are equal to 0;
Y, Y' and Y" are as above defined, with the proviso that Y and Y' are equal;
A is selected from (IIa), (IIc) and (IIt) wherein $R_1$—C(O)—$R_{1x}$ and it binds a group —Y—$ONO_2$ or a group —Y'—$ONO_2$, $R_2$ is —C(O)OR$_{2x}$ and it binds a group —Y"—$ONO_2$;
$R_a$ of formula (IIa) and $R_c$ of formula (IIc) are $R_hNH(CH_2)_p$— wherein p is an integer from 0 to 4, or $R_iNH(=NH)NH—(CH_2)_3—$, wherein $R_h$ and $R_i$ are $R_{hh}$—C(O)— or $R_{ii}$—C(O)— and $R_a$ and $R_c$ bind a group —Y—$ONO_2$ or a group —Y'—$ONO_2$;
in formula (IIt) $R_1$ and $R_2$ are as above defined, d is 2 d' is 1, $R_t$ is —C(O)—$R_{tt}$ and it binds a group —Y—$ONO_2$ or a group —Y'—$ONO_2$;
can be prepared as follows:
95a) by reacting a compound of formula (I) with a compound of formula (IIIi)

$$\begin{array}{c} Y—ONO_2 \\ | \\ A—Y'—ONO_2 \\ \text{(I)} \end{array} \quad + \quad HO—Y"—ONO_2 \qquad \text{(IIIi)}$$

wherein in compounds (I), obtained as described in 86. Y and Y' are equal and are as above defined and A is selected from (IIa), (IIc) and (IIt) wherein $R_1$ is —C(O)—$R_{1x}$ and binds a group —Y—$ONO_2$ or a group —Y'—$ONO_2$ and $R_2$ is —COOH;
$R_a$ of formula (IIa) and $R_c$ of formula (IIc) are $R_hNH(CH_2)_p$— wherein p is an integer from 0 to 4, or $R_iNH(=NH)NH—(CH_2)_3—$, and $R_h$ and $R_i$ are $R_{hh}$—C(O)— or $R_{ii}$—C(O)— and bind a group —Y—$ONO_2$ or a group —Y'—$ONO_2$;
in formula (IIt) $R_1$ and $R_2$ are as above defined, d is 2 d' is 1, $R_t$ is —C(O)—$R_{tt}$ and it binds a group —Y—$ONO_2$ or a group —Y'—$ONO_2$;

96. The compounds of general formula (I) wherein:

s, s' and s" are equal to 1;

m, m' and m" are equal to 0;

Y, Y' and Y" are as above defined, with the proviso that Y and Y' are equal;

A is a radical of formula (IIa), (IIc) and (IIt) wherein $R_1$ is —C(O)O—$R_{1x}$ and it binds a group —Y—$ONO_2$ or a group —Y'—$ONO_2$, $R_2$ is —C(O)O$R_{2x}$ and it binds a group —Y"—$ONO_2$;

$R_a$ of formula (IIa) and $R_c$ of formula (IIc) are $R_h$NH$(CH_2)_p$— wherein p is an integer from 0 to 4, or $R_i$NH(=NH)NH—$(CH_2)_3$—, wherein $R_h$ and $R_i$ are $R_{hh}$—OC(O)— or $R_{ii}$—OC(O)— and $R_a$ and $R_c$ bind a group —Y—$ONO_2$ or a group —Y'—$ONO_2$;

in formula (IIt) $R_1$ and $R_2$ are as above defined, d is 2 d' is 1, $R_t$ is —C(O)O—$R_{tt}$ and binds a group —Y—$ONO_2$ or a group —Y'—$ONO_2$;

can be prepared as follows:

96a) by reacting a compound of formula (I) with a compound of formula (IIIi)

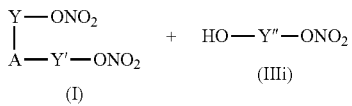

wherein in compounds (I), obtained as described in 87. Y and Y' are equal and are as above defined and A is selected from (IIa), (IIc) and (IIt) wherein $R_1$ is —C(O)O—$R_{1x}$ and binds a group —Y—$ONO_2$ or a group —Y'—$ONO_2$ and $R_2$ is —COOH;

$R_a$ of formula (IIa) and $R_c$ of formula (IIc) are $R_h$NH$(CH_2)_p$— wherein p is an integer from 0 to 4, or $R_i$NH(=NH)NH—$(CH_2)_3$—, and $R_h$ and $R_i$ are $R_{hh}$—OC(O)— or $R_{ii}$—OC(O)— and bind a group —Y—$ONO_2$ or a group —Y'—$ONO_2$;

in formula (IIt) $R_1$ and $R_2$ are as above defined, d is 2 d' is 1, $R_t$ is —C(O)O—$R_{tt}$; and binds a group —Y—$ONO_2$ or a group —Y'—$ONO_2$; using the same procedure described in 8b).

97. The compounds of general formula (I) wherein:

s, s' and s" are equal to 1;

m, m' and m" are equal to 0;

Y, Y' and Y" are as above defined, and Y and Y' are equal;

A is a radical of formula from (IIa), (IIc) or (IIt) wherein $R_1$ is —C(O)—$R_{1x}$ and it binds a group —Y—$ONO_2$ or a group —Y'—$ONO_2$, $R_2$ is —C(O)NH$R_{2xx}$ or —C(O)N$(CH_3)R_{2xx}$ and it binds a group —Y"—$ONO_2$;

$R_a$ of formula (IIa) and $R_c$ of formula (IIc) are $R_h$NH$(CH_2)_p$— wherein p is an integer from 0 to 4, or $R_i$NH(=NH)NH—$(CH_2)_3$—, wherein $R_h$ and $R_i$ are $R_{hh}$—C(O)— or $R_{ii}$—C(O)— and $R_a$ and $R_c$ bind a group —Y—$ONO_2$ or a group —Y'—$ONO_2$;

in formula (IIt) $R_1$ and $R_2$ are as above defined, d is 2 d' is 1, $R_t$ is —C(O)—$R_{tt}$ and binds a group —Y—$ONO_2$ or a group —Y'—$ONO_2$;

can be prepared as follows:

97a) by reacting a compound of formula (I) with a compound of formula (IIIo)

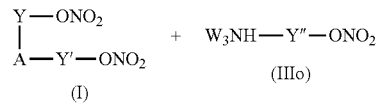

wherein in compounds (I), obtained as described in 86. Y and Y' are equal and are as above defined and A is selected from (IIa), (IIc) and (IIt) wherein $R_1$ is —C(O)—$R_{1x}$ and binds a group —Y—$ONO_2$ or a group —Y'—$ONO_2$ and $R_2$ is —COOH;

$R_a$ of formula (IIa) and $R_c$ of formula (IIc) are $R_h$NH$(CH_2)_p$— wherein p is an integer from 0 to 4, or $R_i$NH(=NH)NH—$(CH_2)_3$—, and $R_h$ and $R_i$ are $R_{hh}$—C(O)— or $R_{ii}$—C(O)— and bind a group —Y—$ONO_2$ or a group —Y'—$ONO_2$;

in formula (IIt) $R_1$ and $R_2$ are as above defined, d is 2 d' is 1, $R_t$ is —C(O)—$R_{tt}$ and binds a group —Y—$ONO_2$ or a group —Y'—$ONO_2$;

using the same procedure described in 7b).

98. The compounds of general formula (I) wherein:

s, s' and s" are equal to 1;

m, m' and m" are equal to 0;

Y, Y' and Y" are as above defined and Y and Y' are equal;

A is selected from (IIa), (IIc) and (IIt) wherein $R_1$ is —C(O)O—$R_{1x}$ and binds a group —Y—$ONO_2$ or a group —Y'—$ONO_2$, $R_2$ is —C(O)NH$R_{2xx}$ or —C(O)N$(CH_3)R_{2xx}$ and binds a group —Y"—$ONO_2$;

$R_a$ of formula (IIa) and $R_c$ of formula (IIc) are $R_h$NH$(CH_2)_p$— wherein p is an integer from 0 to 4, or $R_i$NH(=NH)NH—$(CH_2)_3$—, wherein $R_h$ and $R_i$ are $R_{hh}$—OC(O)— or $R_{ii}$—OC(O)— and $R_a$ and $R_c$ bind a group —Y—$ONO_2$ or a group —Y'—$ONO_2$;

in formula (IIt) $R_1$ and $R_2$ are as above defined, d is 2 d' is 1, $R_t$ is —C(O)O—$R_{tt}$ and binds a group —Y—$ONO_2$ or a group —Y'—$ONO_2$;

can be prepared as follows:

98a) by reacting a compound of formula (I) with a compound of formula (IIIo)

wherein in compounds (I), obtained as described in 87. Y and Y' are equal and are as above defined, $W_3$ is as above defined and A is selected from (IIa), (IIc) and (IIt) wherein $R_1$ is —C(O)O—$R_{1x}$ and binds a group —Y—$ONO_2$ or a group —Y'—$ONO_2$ and $R_2$ is —COOH;

$R_a$ of formula (IIa) and $R_c$ of formula (IIc) are $R_h$NH$(CH_2)_p$— wherein p is an integer from 0 to 4, or $R_i$NH(=NH)NH—$(CH_2)_3$—, and $R_h$ and $R_i$ are $R_{hh}$—OC(O)— or $R_{ii}$—OC(O)— and bind a group —Y—$ONO_2$ or a group —Y'—$ONO_2$;

in formula (IIt) $R_1$ and $R_2$ are as above defined, d is 2 d' is 1, $R_t$ is —C(O)O—$R_{tt}$ and binds a group —Y—$ONO_2$ or a group —Y'—$ONO_2$;

using the same procedure described in 7b).

99. The compounds of general formula (I) wherein:

s, s', s" and m" are equal to 1;

m, m' are equal to 0;

Y, Y' and Y" are as above defined, with the proviso that Y and Y' are equal;

B is:

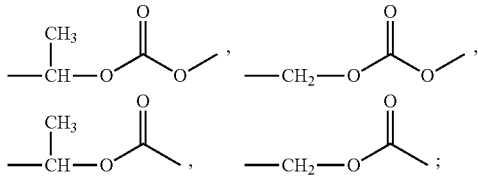

A is a radical of formula (IIa), (IIc) and (IIt) wherein $R_1$ is —C(O) and binds a group —Y—$ONO_2$ or a group —Y'—$ONO_2$, $R_2$ is —C(O)$OR_{2x}$ and binds a group —B—Y"—$ONO_2$;

$R_a$ of formula (IIa) and $R_c$ of formula (IIc) are $R_hNH(CH_2)_p$— wherein p is an integer from 0 to 4, or $R_iNH(=NH)NH—(CH_2)_3$—, wherein $R_h$ and $R_i$ are $R_{hh}$—C(O)— or $R_{ii}$—OC(O)— and $R_a$ and $R_c$ bind a group —Y—$ONO_2$ or a group —Y'—$ONO_2$;

in formula (IIt) $R_1$ and $R_2$ are as above defined d is 2 d' is 1, $R_t$ is —C(O)—$R_{tt}$ and binds a group —Y—$ONO_2$ or a group —Y'—$ONO_2$;

can be prepared as follows:

99a) by reacting a compound of formula (I) obtained as described in 86.

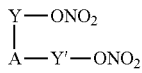

(I)

with compounds (IIIg) or (IIIn) depending on the meaning of B:

(I)+Hal-$W_1$—OC(O)O—Y'—$ONO_2$    (IIIg)

(I)+Hal-$W_1$—OC(O)—Y'—$ONO_2$    (IIIn)

wherein in compounds (I), obtained as described in 86. Y and Y' are equal and are as above defined and A is selected from (IIa), (IIc) and (IIt) wherein $R_1$ is —C(O)$R_{1x}$ and binds a group —Y—$ONO_2$ or a group —Y'—$ONO_2$ and $R_2$ is —COOH;

$R_a$ of formula (IIa) and $R_c$ of formula (IIc) are $R_hNH(CH_2)_p$— wherein p is an integer from 0 to 4, or $R_iNH(=NH)NH—(CH_2)_3$—, and $R_h$ and $R_i$ are $R_{hh}$—C(O)— and bind a group —Y—$ONO_2$ or a group —Y'—$ONO_2$;

in formula (IIt) $R_1$ and $R_2$ are as above defined, d is 2 d' is 1, $R_t$ is —C(O)—$R_{tt}$ and binds a group —Y—$ONO_2$ or a group —Y'—$ONO_2$;

and applying the same procedure described in 4b) or 6b).

100. The compounds of general formula (I) wherein:
s, s', s" and m" are equal to 1;
m, m' are equal to 0;
Y, Y' and Y" are as above defined, with the proviso that Y and Y' are equal;
B is:

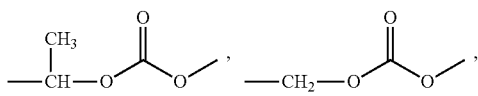

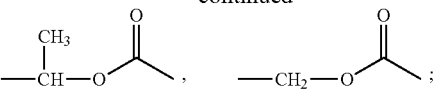

A is a radical of formula (IIa), (IIc) and (IIt) wherein $R_1$ is —C(O)O—$R_{1x}$ and it binds a group —Y—$ONO_2$ or a group —Y'—$ONO_2$, $R_2$ is —C(O)$OR_{2x}$ and it binds a group —B—Y"—$ONO_2$;

$R_a$ of formula (IIa) and $R_c$ of formula (IIc) are $R_hNH(CH_2)_p$— wherein p is an integer from 0 to 4, or $R_iNH(=NH)NH—(CH_2)_3$—, wherein $R_h$ and $R_i$ are $R_{hh}$—OC(O)— or $R_{ii}$—OC(O)— and $R_a$ and $R_c$ bind a group —Y—$ONO_2$ or a group —Y'—$ONO_2$;

in formula (IIt) $R_1$ and $R_2$ are as above defined, d is 2 d' is 1, $R_t$ is —C(O)O—$R_{tt}$ and it binds a group —Y—$ONO_2$ or a group —Y'—$ONO_2$;

can be prepared as follows:

100a) by reacting a compound of formula (I) obtained as described in 87.

(I)

with compounds (IIIg) or (IIIn) depending on the meaning of B:

(I)+Hal-$W_1$—OC(O)O—Y'—$ONO_2$    (IIIg)

(I)+Hal-$W_1$—OC(O)—Y'—$ONO_2$    (IIIn)

wherein is compounds (I) Y and Y' are equal and are as above defined and A is selected from (IIa), (IIc) and (IIt) wherein $R_1$ is —C(O)O—$R_{1x}$ and binds a group —Y—$ONO_2$ or a group —Y'—$ONO_2$ and $R_2$ is —COOH;

$R_a$ of formula (IIa) and $R_c$ of formula (IIc) are $R_hNH(CH_2)_p$— wherein p is an integer from 0 to 4, or $R_iNH(=NH)NH—(CH_2)_3$—, and $R_h$ and $R_i$ are $R_{hh}$—OC(O)— or $R_{ii}$—C(O)— and bind a group —Y—$ONO_2$ or a group —Y'—$ONO_2$;

in formula (IIt) $R_1$ and $R_2$ are as above defined, d is 2 d' is 1, $R_t$ is —C(O)O—$R_{tt}$ and binds a group —Y—$ONO_2$ or a group —Y'—$ONO_2$;

and applying the same procedure described in 4b) or 6b).

101. The compounds of general formula (I) wherein:
s and s' are equal to 1;
s", m, m' and m" are equal to 0;
Y and Y' can be equal or different and are as above defined;
A is a radical of formula (IIa), (IIc) or (IIt) wherein $R_1$ is —H, $R_2$ is —C(O)$OR_{2x}$ and it binds a group —Y—$ONO_2$;

$R_a$ of formula (IIa) and $R_c$ of formula (IIc) are $R_hNH(CH_2)_p$— wherein p is an integer from 0 to 4, or $R_iNH(=NH)NH—(CH_2)_3$—, wherein $R_h$ and $R_i$ are $R_{hh}$—C(O)— or $R_{ii}$—C(O)— and $R_a$ and $R_c$ bind a group —Y'—$ONO_2$ in formula (IIt) $R_1$ is —H, and $R_2$ is —C(O)$OR_{2x}$ and binds a group —Y—$ONO_2$; d is 2 d' is 1, $R_t$ is —C(O)—$R_{tt}$, and binds a group —Y'—$ONO_2$ can be obtained as follows:

101a) $R_a=R_c$ selected from $R_hNH(CH_2)_p$— wherein p is an integer from 0 to 4, $R_h$ is $R_{hh}$—C(O)—:

by reacting a compound of formula (I) wherein s, s', s", m, m', m", Y, Y', Y" are as above defined in 101., A is a radical of (IIa), (IIc) or (IIt) wherein $R_2$, d, d', $R_t$ are as defined in 101., $R_a$ and $R_c$ are selected from $R_hNH(CH_2)_p$— wherein p is an integer from 0 to 4, $R_h$ is $R_{hh}$—C(O)—; $R_i$ is —C(O)OC$(CH_3)_3$;

with anhydrous or aqueous organic or inorganic acid to hydrolyze the —BOC protective groups following procedure well known in the literature.

101a') $R_a=R_c$ selected from $R_iNH(=NH)NH$—$(CH_2)_3$—, $R_i$ is $R_{ii}$—OC(O)—;

by reacting a compound of formula (VIIIL)

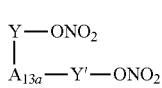

(VIIIL)

wherein Y and Y' are as above defined; $A_{13a}$ is a radical of formula (IIa), (IIc) wherein $R_1$ is the —Fmoc protective group;

$R_2$ is —C(O)O$R_{2x}$ and binds a group —Y—ONO$_2$; $R_a$ of formula (IIa) and $R_c$ of formula (IIc) are $R_iNH(=NH)NH$—$(CH_2)_3$— wherein $R_i$ is $R_{ii}$—C(O)— and binds a group —Y'—ONO$_2$ known procedure to remove the —Fmoc protective groups;

101b) $R_a=R_c$ are selected from $R_hNH(CH_2)_p$— wherein p is an integer from 0 to 4, $R_h$ is —H:

by reacting a compound of formula (I) with a compound of formula (IIIe)

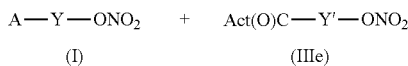

wherein Y and Y' are as above defined and A is a radical of formula (IIa), (IIc) or (IIt) wherein $R_1$ is —C(O)OC$(CH_3)_3$; —$R_2$ is —C(O)O$R_{2x}$ and binds the group —Y—ONO$_2$; $R_a$ and $R_c$ are selected from $R_hNH(CH_2)_p$— wherein p as above defined and $R_h$ is —H; in formula (IIt) d and d' are as above defined, and $R_t$ is —H;

using the same procedure described in 1b').

101b') $R_a=R_c$ selected from $R_iNH(=NH)NH$—$(CH_2)_3$—, $R_i$ is —H:

Compound (VIIIL) are prepared by reacting a compound of formula (VIIIm) with a compound of formula (IIIe)

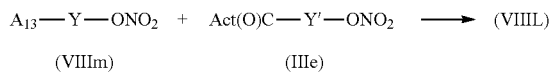

wherein Y and Y' are as above defined, and $A_{13}$ is a radical of formula (IIa), (IIc) wherein $R_1$ is the Fmoc protective group, $R_2$ is —C(O)O$R_{2x}$ and binds the group —Y—ONO$_2$; $R_a$ and $R_c$ are $R_iNH(=NH)NH$—$(CH_2)_3$— wherein $R_i$ is —H using the same procedure described in 1b').

101c) $R_a=R_c$ are selected from $R_{ha}NH(CH_2)_p$— wherein p an integer from 0 to 4, $R_{ha}$ is —Fmoc:

by deprotecting the Fmoc group of a compound of formula (VIIIn)

wherein Y is as above defined and $A_{14}$ as a radical of formula (IIa), (IIc) or (IIt) wherein $R_1$ is —C(O)OC$(CH_3)_3$; $R_2$ is —C(O)O$R_{2x}$ and binds the group —Y—ONO$_2$; $R_a$ and $R_c$ are $R_{ha}NH(CH_2)_p$— wherein p as above defined, and $R_{ha}$ is the Fmoc protective group; d and d' are as above defined, and $R_t$ is equal to $R_{ta}$ and is the Fmoc protective group 101'c) $R_a=R_c$ selected from $R_{ia}NH(=NH)NH$—$(CH_2)_3$—, $R_{ia}$=—Pbf Compound (VIIm) are prepared by deprotecting the —Pbf group of a compound of formula (VIIIo)

wherein Y is as above defined, and $A_{15a}$ is a radical of formula (IIa), (IIc) wherein $R_1$ is —Fmoc; $R_2$ is —C(O)O$R_{2x}$ and binds the group —Y—ONO$_2$; $R_a$ and $R_c$ are $R_{ia}NH(=NH)NH$—$(CH_2)_3$— $R_{ia}$ is —Pbf protective group;

101d) compound described in 101c) and 101c') can be prepared by reacting a compound of formula $A_{14}$ or $A_{15}$ with compound (IIIi) using the same procedure described in 8b)

wherein Y is as above defined and:

$A_{14}$ is a radical of formula (IIa), (IIc) or (IIt) wherein $R_1$ is —C(O)OC$(CH_3)_3$; $R_2$ is —COOH; $R_a$ and $R_c$ are $R_{ha}NH(CH_2)_p$— wherein p as above defined and by $R_{ha}$ is Fmoc protective group; d and d' are as above defined, and $R_t$ is $R_{ta}$ and is the Fmoc protective group.

$A_{15}$ is a radical of formula (IIa), (IIc) wherein $R_1$ is —Fmoc; $R_2$ is —COOH; $R_a$ and $R_c$ are selected from $R_{ia}NH(=NH)NH$—$(CH_2)_3$—, wherein $R_{ia}$ is —Pbf.

Compounds $A_{14}$ and $A_{15}$ are commercially available.

102. The compounds of general formula (I) wherein:

s and s' are equal to 1;

s'', m, m' and m'' are equal to 0;

Y and Y' can be equal or different and are as above defined;

A is selected from (IIa), (IIc) and (IIt) wherein $R_1$ is —H, $R_2$ is —C(O)O$R_{2x}$ and binds a group —Y—ONO$_2$;

$R_a$ of formula (IIa) and $R_c$ of formula (IIc) are $R_hNH(CH_2)_p$— wherein p is an integer from 0 to 4, or $R_iNH(=NH)NH$—$(CH_2)_3$—, wherein $R_h$ and $R_i$ are $R_{hh}$—OC(O)— or $R_{ii}$—OC(O)—, and binds a group —Y'—ONO$_2$ in formula (IIt) $R_1$ is —H, and $R_2$ is —C(O)O$R_{2x}$ and binds a group —Y—ONO$_2$; d is 2 d' is 1, $R_t$ is —C(O)O—$R_{tt}$, and binds a group —Y'—ONO$_2$ can be obtained as follows:

102a) $R_a=R_c$ selected from $R_hNH(CH_2)_p$— wherein p is an integer from 0 to 4, $R_h$ is $R_{hh}$—OC(O)—:

by reacting a compound of formula (I) wherein s, s', s'', m, m', m'', Y, Y', Y'' are as above defined in 102., A is a radical of (IIa), (IIc) or (IIt) wherein $R_2$, d, d', $R_t$ are as defined in 102., $R_a$ and $R_c$ are selected from $R_hNH(CH_2)_p$— wherein p is an integer from 0 to 4, $R_h$ is $R_{hh}$—OC(O)—; $R_1$ is —C(O)OC$(CH_3)_3$;

with anhydrous or aqueous organic or inorganic acid to hydrolyze the —BOC protective groups following procedure well known in the literature.

102a') $R_a=R_c$ selected from $R_iNH(=NH)NH$—$(CH_2)_3$—, $R_i$ is $R_{ii}$—OC(O)—;

by reacting a compound of formula (VIIIp)

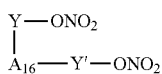
(VIIIp)

wherein Y and Y' are as above defined; $A_{16}$ is a radical of formula (IIa), (IIc) wherein $R_1$ is the —Fmoc protective group;
$R_2$ is —C(O)O$R_{2x}$ and binds a group —Y'—ONO$_2$; $R_a$ of formula (IIa) and $R_c$ of formula (IIc) are $R_iNH(=NH)NH—(CH_2)_3$— wherein $R_i$ is $R_{ii}$—OC(O)— and binds a group —Y'—ONO$_2$ by known procedure to remove the —Fmoc protective groups;
102b) $R_a=R_c$ are selected from $R_hNH(CH_2)_p$— wherein p is an integer from 0 to 4, $R_h$ is —H:
by reacting a compound of formula (I) with a compound of formula (IIIf)

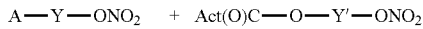

wherein Y and Y' are as above defined and A is as above defined in 101b), using the same procedure described in 3b).
102b') $R_a=R_c$ selected from $R_iNH(=NH)NH—(CH_2)_3$—, $R_i$ is —H:
by reacting a compound of formula (VIIIm) already described in 101b') and obtained as described in 101c') with a compound of formula (IIIf)

A$_{13}$—Y—ONO$_2$ + Act(O)C—O—Y'—ONO$_2$ ⟶ (VIIIp)

(VIIIm)         (IIIf)

wherein Y and Y' are as above defined and $A_{13'}$ is as defined in 101b') using the same procedure described in 3b).
103. The compounds of general formula (I) wherein:
s and s' are equal to 1;
s", m, m' and m" are equal to 0;
Y and Y' can be equal or different and are as above defined;
A is selected from (IIa), (IIc) and (IIt) wherein $R_1$ is —H, $R_2$ is —C(O)NHR$_{2xx}$ or —C(O)N(CH$_3$)R$_{2xx}$ and binds a group —Y—ONO$_2$;
$R_a$ of formula (IIa) and $R_c$ of formula (IIc) are $R_hNH(CH_2)_p$— wherein p is an integer from 0 to 4, or $R_iNH(=NH)NH—(CH_2)_3$—, wherein $R_h$ and $R_i$ are $R_{hh}$—OC(O)— or $R_{ii}$—OC(O)—, and binds a group —Y'—ONO$_2$
in formula (IIt) $R_1$ is —H, and $R_2$ is —C(O)NHR$_{2xx}$ or —C(O)N(CH$_3$)R$_{2xx}$ and binds a group —Y—ONO$_2$; d is 2 d' is 1, $R_t$ is —C(O)—R$_{tt}$, and binds a group —Y'—ONO$_2$
can be obtained as follows:
103a) $R_a=R_c$ selected from $R_hNH(CH_2)_p$— wherein p is an integer from 0 to 4, $R_h$ is $R_{hh}$—C(O):
by reacting a compound of formula (I) wherein s, s', a", m, m', m", Y, Y', Y" are as above defined in 103., A is a radical of (IIa), (IIc) or (IIt) wherein $R_2$, d, d', $R_t$ are as defined in 103., $R_a$ and $R_c$ are selected from $R_hNH(CH_2)_p$— wherein p is an integer from 0 to 4, $R_h$ is $R_{hh}$—C(O)—; $R_1$ is —C(O)OC(CH$_3$)$_3$;
with anhydrous or aqueous organic or inorganic acid to hydrolyze the —BOC protective groups following procedure well known in the literature.

103a') $R_a=R_c$ selected from $R_iNH(=NH)NH—(CH_2)_3$—, $R_i$ is $R_{ii}$—C(O)—;
by reacting a compound of formula (VIIIq)

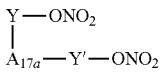
(VIIIq)

wherein Y and Y' are as above defined; $A_{17a}$ is a radical of formula (IIa), (IIc) wherein $R_1$ is the —Fmoc protective group; $R_2$ is —C(O)NHR$_{2xx}$ or —C(O)N(CH$_3$)R$_{2xx}$ and binds a group —Y'—ONO$_2$; $R_a$ of formula (IIa) and $R_c$ of formula (IIc) are $R_iNH(=NH)NH—(CH_2)_3$— wherein $R_i$ is $R_{ii}$—C(O)— and binds a group —Y'—ONO$_2$ by known procedure to remove the —Fmoc protective groups;
103b) $R_a=R_c$ are selected from $R_hNH(CH_2)_p$— wherein p is an integer from 0 to 4, $R_h$ is —H
by reacting a compound of formula (I) with a compound of formula (IIIe)

wherein Y and Y' are as above defined and A is a radical of formula (IIa), (IIc) or (IIt) wherein $R_1$ is —C(O)OC(CH$_3$)$_3$;
—$R_2$ is —C(O)NHR$_{2xx}$ or —C(O)N(CH$_3$)R$_{2xx}$ and binds the group —Y—ONO$_2$; $R_a$ and $R_c$ are $R_hNH(CH_2)_p$— wherein p as above defined and $R_h$ is —H; in formula (IIt) d and d' are as above defined, and $R_t$ is —H;
using the same procedure described in 1b').
103b') $R_a=R_c$ selected from $R_iNH(=NH)NH—(CH_2)_3$—, $R_i$ is —H:
by reacting a compound of formula (VIIIr) with a compound of formula (IIIe)

A$_{17}$—Y—ONO$_2$ + Act(O)C—O—Y'—ONO$_2$ ⟶ (VIIIq)

(VIIIr)         (IIIe)

wherein Y and Y' are as above defined and $A_{17}$ is a radical of formula (IIa), (IIc) wherein $R_1$ is the Fmoc protective group, $R_2$ is —C(O)NHR$_{2xx}$ or —C(O)N(CH$_3$)R$_{2xx}$ and binds the group —Y—ONO$_2$; $R_a$ and $R_c$ are $R_iNH(=NH)NH—(CH_2)_3$— wherein $R_i$ is —H using the same procedure described in 1b').
103c) $R_a=R_c$ are selected from $R_{ha}NH(CH_2)_p$— wherein p is an integer from 0 to 4, $R_{ha}$ is —Fmoc
Compound (I) described in 103b) can be prepared by deprotecting the Fmoc group of a compound of formula (VIIIs)

A$_{18}$—Y—ONO$_2$ ⟶ A—Y—ONO$_2$ (VIIIs)              (I)

wherein Y is as above defined and $A_{18}$ is a radical of formula (IIa), (IIc) or (IIt) wherein $R_1$ is —C(O)OC(CH$_3$)$_3$; —$R_2$ is —C(O)NHR$_{2xx}$ or —C(O)N(CH$_3$)R$_{2xx}$ and binds the group —Y—ONO$_2$; $R_a$ and $R_c$ are $R_{ha}NH(CH_2)_p$— wherein p as above defined and $R_{ha}$ is the Fmoc protective group; d and d' are as above defined, and $R_t$ is $R_{ta}$ and is the Fmoc group.

103c') $R_a=R_c$ selected from $R_{ia}NH(=NH)NH—(CH_2)_3—$, $R_{ia}=$—Pbf

Compound (VIIIr) described in 103b') by deprotecting the —Pbf group of a compound of formula (IIIt)

$$A_{19}—Y—ONO_2 \longrightarrow A_{17}—Y—ONO_2$$
$$\text{(VIIIt)} \qquad\qquad \text{(VIIIr)}$$

wherein Y is as above defined and $A_{19}$ is a radical of formula (IIa), (IIc) wherein $R_1$ is —Fmoc; —$R_2$ is —$C(O)NHR_{2xx}$ or —$C(O)N(CH_3)R_{2xx}$ and binds the group —Y—$ONO_2$; $R_a$ and $R_c$ are $R_{ia}NH(=NH)NH—(CH_2)_3— R_{ia}$ is the —Pbf protective group;

103d) compounds described in 103c) and 103c') can be prepared by reacting a compound of formula $A_{14}$ or $A_{15}$ described in 101d) with compound (IIIo) using the same procedure described in 7b)

$$A_{14}+W_3NH—Y—ONO_2 \to \text{(VIIIs)} \qquad \text{(IIIo)}$$

$$A_{15}+W_3NH—Y—ONO_2 \to \text{(VIIIt)} \qquad \text{(IIIo)}$$

wherein Y is as above defined and $W_3$ is H or —$CH_3$.

104. The compounds of general formula (I) wherein:
s and s' are equal to 1;
s", m, m' and m" are equal to 0;
Y and Y' can be equal or different and are as above defined;
A is selected from (IIa), (IIc) and (IIt) wherein $R_1$ is —H, $R_2$ is —$C(O)NHR_{2xx}$ or —$C(O)N(CH_3)R_{2xx}$ and binds the group —Y—$ONO_2$;
$R_a$ of formula (IIa) and $R_c$ of formula (IIc) are $R_hNH(CH_2)_p$— wherein p is as integer from 0 to 4, or $R_iNH(=NH)NH—(CH_2)_3$—, wherein $R_h$ and $R_i$ are $R_{hh}$—OC(O)— or $R_{ii}$—OC(O)—, and binds a group —Y'—$ONO_2$;
in formula (IIt) $R_1$ is —H; and $R_2$ is —$C(O)NHR_{2xx}$ or —$C(O)N(CH_3)R_{2xx}$ and binds the group —Y—$ONO_2$; d is 2 d' is 1, $R_t$ is —C(O)O—$R_{tt}$, and binds a group —Y'—$ONO_2$ can be obtained as follows:

104a) $R_a=R_c$ are selected from $R_hNH(CH_2)_p$— wherein p is an integer from 0 to 4, $R_h$ is $R_{hh}$—O—C(O)—:
by reacting a compound of formula (I) wherein s, s', s", m, m', m", Y, Y', Y" are as above defined in 104., A is a radical of (IIa), (IIc) or (IIt) wherein $R_2$, d, d', $R_t$ are as defined in 104., $R_a$ and $R_c$ are selected from $R_hNH(CH_2)_p$— wherein p is an integer from 0 to 4, $R_h$ is $R_{hh}$—O—C(O)—; $R_1$ is —C(O)OC(CH_3)_3$;
with anhydrous or aqueous organic or inorganic acid to hydrolyze the —BOC protective groups following procedure well known in the literature.

104a') $R_a=R_c$ are selected from $R_iNH(=NH)NH—(CH_2)_3$—, $R_t$ is $R_{ii}$—OC(O)—;
by reacting a compound of formula (VIIIu)

$$\begin{array}{c} Y—ONO_2 \\ | \\ A_{20}—Y'—ONO_2 \end{array} \qquad \text{(VIIIu)}$$

wherein Y and Y' are as above defined and $A_{20}$ is a radical of formula (IIa), (IIc) wherein $R_1$ is the —Fmoc protective group;
$R_2$ is —$C(O)NHR_{2xx}$ or —$C(O)N(CH_3)R_{2xx}$ and binds a group —Y—$ONO_2$; $R_a$ of formula (IIa) and $R_c$ of formula (IIc) are $R_iNH(=NH)NH—(CH_2)_3$— wherein $R_i$ is $R_{ii}$—

OC(O)— and binds a group —Y'—$ONO_2$ by known procedure to remove the —Fmoc protective groups;

104b) $R_a=R_c$ are selected from $R_hNH(CH_2)_p$— wherein p is an integer from 0 to 4, $R_h$ is —H
by reacting a compound of formula (I) with a compound of formula (IIIf)

$$A—Y—ONO_2 \quad + \quad Act(O)C—O—Y'—ONO_2$$
$$\text{(I)} \qquad\qquad\qquad \text{(IIIf)}$$

wherein Y and Y' are as above defined and A is as defined in 103b), using the same procedure described in 3b).

104b') $R_a=R_c$ selected from $R_iNH(=NH)NH—(CH_2)_3$—, $R_i$ is —H:
Compound (VIIIu) can be prepared by reacting a compound of formula (VIIIr) with a compound of formula (IIIf)

$$A_{17}—Y—ONO_2 \quad + \quad Act(O)C—O—Y'—ONO_2$$
$$\text{(VIIIr)} \qquad\qquad\qquad \text{(IIIf)}$$

wherein Y and Y' are as above defined and $A_{17}$ is as defined in 103b') using the same procedure described in 3b).

105. The compounds of general formula (I) wherein:
s, s' and m are equal to 1;
s", m' and m" are equal to 0;
Y and Y' are as above defined;
B is:

A is selected from (IIa), (IIc) and (IIt) wherein $R_1$ is —H, —$R_2$ is —$C(O)OR_{2x}$ and binds a group —B—Y—$ONO_2$;
$R_a$ of formula (IIa) and $R_c$ of formula (IIc) are $R_hNH(CH_2)_p$— wherein p is an integer from 0 to 4, or $R_iNH(=NH)NH—(CH_2)_3$—, wherein $R_h$ and $R_i$ are $R_{hh}$—C(O)— or $R_{ii}$—C(O)—, and bind a group —Y'—$ONO_2$
in formula (IIt) $R_1$ is —H, and $R_2$ is —$C(O)OR_{2x}$ and binds a group —B—Y—$ONO_2$, d is 2 d' is 1, $R_t$ is —C(O)—$R_{tt}$ and binds a group —Y'—$ONO_2$;

can be obtained as follows:

105a) $R_a=R_c$ are selected from $R_hNH(CH_2)_p$— wherein p is an integer from 0 to 4, $R_h$ is $R_{hh}$—C(O)—:
by reacting a compound of formula (I) wherein s, s', a", m, m', m", B, Y, Y', Y" are an above defined in 105., A is a radical of (IIa), (IIc) or (IIt) wherein $R_2$, d, d', $R_t$ are as defined in 105., $R_a$ and $R_c$ are selected from $R_hNH(CH_2)_p$— wherein p is an integer from 0 to 4, $R_h$ is —$R_{hh}$—C(O)—; $R_1$ is —C(O)OC(CH_3)_3$;
with anhydrous or aqueous organic or inorganic acid to hydrolyze the —BOC protective groups following procedure well known in the literature.

105a') $R_a=R_c$ are selected from $R_iNH(=NH)NH—(CH_2)_3$—, $R_i$ is $R_{ii}$—OC(O)—; by reacting a compound of formula (VIIIv)

$$\underset{\underset{A_{21_a}-Y'-ONO_2}{|}}{B-Y-ONO_2} \quad \text{(VIIIv)}$$

wherein B, Y and Y' are as above defined and $A_{21a}$ is a radical of formula (IIa), (IIc) wherein $R_1$ is the —Fmoc protective group;
$R_2$ is —C(O)OR$_{2x}$ and binds the group —B—Y—ONO$_2$; $R_a$ of formula (IIa) and $R_c$ of formula (IIc) are $R_i$NH(=NH)NH—(CH$_2$)$_3$ wherein $R_i$ is $R_{ii}$—C(O)— and binds a group —Y'—ONO$_2$ by known procedure to remove the —Fmoc protective groups;

105b) $R_a$=$R_c$ are selected from $R_h$NH(CH$_2$)$_p$— wherein p is an integer from 0 to 4, $R_h$ is —H
by reacting a compound of formula (I) with a compound of formula (IIIe)

$$A-B-Y-ONO_2 \quad + \quad Act(O)C-Y'-ONO_2$$
$$(I) \qquad\qquad\qquad (IIIe)$$

wherein Y and Y' are as above defined and A is a radical of formula (IIa), (IIc) or (IIt) wherein $R_1$ is —C(O)OC(CH$_3$)$_3$; —$R_2$ is —C(O)OR$_{2x}$ and binds the group —B—Y—ONO$_2$; $R_a$ and $R_c$ are $R_h$NH(CH$_2$)$_p$— wherein p as above defined and $R_h$ is —H; in formula (IIt) d and d' are as above defined, and $R_t$ is —H;
using the same procedure described in 1b');

105b') $R_a$=$R_c$ selected from $R_i$NH(=NH)NH—(CH$_2$)$_3$—, $R_i$ is —H:
Compound of formula (VIIIv) can be prepared by reacting a compound of formula (VIIIw) with a compound of formula (IIIe)

$$A_{21}-B-Y-ONO_2 \quad + \quad Act(O)C-Y'-ONO_2$$
$$(VIIIw) \qquad\qquad\qquad (IIIe)$$

wherein Y and Y' are as above defined and $A_{21}$ is a radical of formula (IIa), (IIc) wherein $R_1$ is the Fmoc protective group, $R_2$ is —C(O)OR$_{2x}$ and binds the group —B—Y—ONO$_2$; $R_a$ and $R_c$ are $R_i$NH(=NH)NH—(CH$_2$)$_3$— wherein $R_1$ is —H
using the same procedure described in 1b').

105c) $R_a$=$R_c$ are selected from $R_{ha}$NH(CH$_2$)$_p$— wherein p is an integer from 0 to 4, $R_{ha}$ is —Fmoc
Compound (I) described in 105b) by deprotecting the Fmoc group of a compound of formula (VIIIx)

$$A_{22}-B-Y-ONO_2 \longrightarrow A-B-Y-ONO_2$$
$$(VIIIx) \qquad\qquad\qquad (I)$$

wherein Y and B are as above defined and $A_{22}$ is a radical of formula (IIa), (IIc) or (IIt) wherein $R_1$ is —C(O)OC(CH$_3$)$_3$; $R_2$ is —C(O)OR$_{2x}$ and binds the group —B—Y—ONO$_2$; $R_a$ and $R_c$ are $R_{ha}$NH(CH$_2$)$_p$— wherein p as above defined and $R_{ha}$ is the Fmoc protective group; d and d' are as above defined, and $R_t$ is $R_{ta}$ and is the Fmoc protecting group.

105c') $R_a$=$R_c$ selected from $R_{ia}$NH(=NH)NH—(CH$_2$)$_3$—, $R_{ia}$=—Pbf
Compound described in 105b') are prepared by deprotecting the —Pbf group of a compound of formula (VIIIy)

$$A_{23}-B-Y-ONO_2 \longrightarrow A_{21}-B-Y-ONO_2$$
$$(VIIIy) \qquad\qquad\qquad (VIIIw)$$

wherein Y is as above defined and $A_{23}$ is a radical of formula (IIa), (IIc) wherein $R_1$ is —Fmoc; $R_2$ is —C(O)OR$_{2x}$ and binds the group —B—Y—ONO$_2$; $R_a$ and $R_c$ $R_{ia}$NH(=NH)NH—(CH$_2$)$_3$— $R_{ia}$ is the —Pbf protective group;

105d) compounds (VIIIx) and (VIIIy) are prepared by reacting respectively a compound of formula $A_{14}$ or $A_{15}$ described in 101d) with compound (IIIg) or (IIIn) depending on the meaning of B, and applying the same procedure described in 4b) or 6b):

$$A_{14} \text{ or } A_{15} + \text{Hal-W}_1-OC(O)O-Y-ONO_2 \qquad \text{(IIIg)}$$

$$A_{14} \text{ or } A_{15} + \text{Hal-W}_1-OC(O)-Y-ONO_2 \qquad \text{(IIIn)}$$

wherein Hal, $W_1$ and Y are as above.

106. The compounds of general formula (I) wherein:
s s' and m are equal to 1;
s", m' and m" are equal to 0;
Y and Y' can be equal or different and are as above defined;
B is:

$$\underset{\underset{CH_3}{|}}{-CH-O}\underset{\underset{O}{||}}{\overset{O}{\overset{||}{C}}}O\text{—} \text{,} \quad -CH_2-O\underset{\underset{O}{||}}{\overset{O}{\overset{||}{C}}}O\text{—} \text{,}$$

$$\underset{\underset{CH_3}{|}}{-CH-O}\underset{\underset{O}{||}}{\overset{O}{\overset{||}{C}}}\text{—} \text{,} \quad -CH_2-O\underset{\underset{O}{||}}{\overset{O}{\overset{||}{C}}}\text{—} \text{;}$$

A is a radical of formula (IIa), (IIc) or (IIt) wherein $R_1$ is —H, $R_2$ is —C(O)OR$_{2x}$ and binds a group —B—Y—ONO$_2$;
$R_a$ of formula (IIa) and $R_c$ of formula (IIc) are $R_h$NH(CH$_2$)$_p$— wherein p is an integer from 0 to 4, or $R_i$NH(=NH)NH—(CH$_2$)$_3$—, wherein $R_h$ and $R_i$ are $R_{hh}$—OC(O)— or $R_{ii}$—OC(O)—, and bind a group —Y'—ONO$_2$
in formula (IIt) $R_1$ is —H, and $R_2$ is —C(O)OR$_{2x}$ and binds a group —B—Y—ONO$_2$, d is 2 d' is 1, $R_t$ is —C(O)O—R$_{tt}$ and binds a group —Y'—ONO$_2$;
can be obtained as follows:

106a) $R_a$=$R_c$ selected from $R_h$NH(CH$_2$)$_p$— wherein p is an integer from 0 to 4, $R_h$ is $R_{hh}$—OC(O)—:
by reacting a compound of formula (I) wherein s, s', s", m, m', m", B, Y, Y', Y" are as above defined in 106., A is a radical of (IIa), (IIc) or (IIt) wherein $R_2$, d, d', $R_t$ are as defined in 106., $R_a$ and $R_c$ are selected from $R_h$NH(CH$_2$)$_p$— wherein p is an integer from 0 to 4, $R_h$ is —R$_{hh}$—OC(O)—; $R_1$ is —C(O)OC(CH$_3$)$_3$;
with anhydrous or aqueous organic or inorganic acid to hydrolyze the —BOC protective groups following procedure well known in the literature.

106a') $R_a$=$R_c$ selected from $R_i$NH(=NH)NH—(CH$_2$)$_3$—, $R_i$ is $R_{ii}$—OC(O)—;
by reacting a compound of formula (VIIIz)

$$\underset{\underset{A_{24}-Y'-ONO_2}{|}}{B-Y-ONO_2} \quad \text{(VIIIz)}$$

wherein B, Y and Y' are as above defined and $A_{24}$ is a radical of formula (IIa), (IIc) wherein $R_1$ is the —Fmoc protective group; $R_2$ is —C(O)O$R_{2x}$ and binds a group —B—Y—ONO$_2$; $R_a$ of formula (IIa) and $R_c$ of formula (IIc) are $R_i$NH(=NH)NH—(CH$_2$)$_3$— wherein $R_i$ is $R_{ii}$—OC(O)— and binds a group —Y'—ONO$_2$ by known procedure to remove the —Fmoc protective groups;

106b) $R_a$=$R_c$ are selected from $R_h$NH(CH$_2$)$_p$— wherein p is an integer from 0 to 4, $R_h$ is —H
by reacting a compound of formula (I) obtained as described in 105c) with a compound of formula (IIIf)

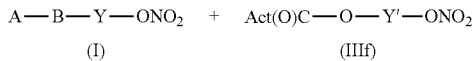

$$A—B—Y—ONO_2 \quad + \quad Act(O)C—O—Y'—ONO_2$$
$$(I) \qquad\qquad\qquad (IIIf)$$

wherein Act, B, Y and Y' are as above defined and A is as defined in 105b), using the same procedure described in 3b).

106b') $R_a$=$R_c$ selected from $R_i$NH(=NH)NH—(CH$_2$)$_3$—, $R_i$ is —H:
by reacting a compound of formula (VIIIw) obtained as described in 105c') with a compound of formula (IIIf)

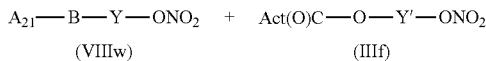

$$A_{21}—B—Y—ONO_2 \quad + \quad Act(O)C—O—Y'—ONO_2$$
$$(VIIIw) \qquad\qquad\qquad (IIIf)$$

wherein B, Y and Y' are as above defined and $A_{21}$ is as defined in 105b'), using the same procedure described in 3b).

107. The compounds of general formula (I) wherein:
s is equal to 1;
s', s", m, m' and m" are equal to 0;
Y is as above defined;
A is a radical of formula (IIa), (IIc) or (IIt) wherein $R_1$ is —C(O)—$R_{1x}$ and binds a group —Y'—ONO$_2$; $R_2$ is —COOH
$R_a$ of formula (IIa) and $R_c$ of formula (IIc) are $R_h$NH(CH$_2$)$_p$— wherein p is an integer from 0 to 4, or $R_i$NH(=NH)NH—(CH$_2$)$_3$—, wherein $R_h$ and $R_i$ are —H;
an formula (IIt) d is 2 d' is 1, $R_t$ is —H;
can be obtained as follows:
107a) $R_a$=$R_c$ selected from $R_h$NH(CH$_2$)$_p$— wherein p is an integer from 0 to 4, $R_h$ is —H
by reacting a compound of formula (I) wherein s, s', s", m, m', m", Y, Y', Y" are as above defined in 107., A is a radical of (IIa), (IIc) or (IIt) wherein $R_1$, $R_2$, d, d', are as defined in 107., $R_a$ of formula (IIa) and $R_c$ of formula (IIc) are selected from $R_h$NH(CH$_2$)$_p$— wherein p is an integer from 0 to 4, $R_h$ is —C(O)OC(CH$_3$)$_3$;
in formula (IIt) $R_1$ is —C(O)OC(CH$_3$)$_3$;
with anhydrous or aqueous organic or inorganic acid to hydrolyze the —BOC protective groups following procedure well known in the literature.

107a') $R_a$=$R_c$ selected from $R_i$NH(=NH)NH—(CH$_2$)$_3$—, $R_i$ is —H;
reacting a compound of formula (VIIIaa)

$$A_{25}\text{-}Y—ONO_2 \qquad\qquad (VIIIaa)$$

wherein Y is as above defined and $A_{25}$ is a radical of formula (IIa), (IIc) wherein $R_1$, $R_2$ are as defined in 107., $R_a$ of formula (IIa) and $R_c$ of formula (IIc) are selected from $R_{ia}$NH(=NH)NH—(CH$_2$)$_3$—, wherein $R_{ia}$ is the —Pbf protective group as already defined;
with anhydrous or aqueous organic or inorganic acid to hydrolyze the —Pbf protective groups following procedure well known in the literature.

107b) compounds described in 107a) and 107a') can be prepared by reacting a compound of formula A or a compound of formula $A_{26}$ with a compound of formula (IIIe)

$$A+Act(O)C—Y—ONO_2 \rightarrow (I) \qquad\qquad (IIIe)$$

$$A_{26}+Act(O)C—Y—ONO_2 \rightarrow (VIIIaa) \qquad\qquad (IIIe)$$

wherein Act and Y are as above defined and:
A is a compound of formula (IIa), (IIc) or (IIt) wherein $R_1$ is —H, $R_2$ is —COOH; $R_a$ of formula (IIa) and $R_c$ of formula (IIc) are $R_h$NH(CH$_2$)$_p$— wherein p is an integer from 0 to 4, $R_h$ is —C(O)OC(CH$_3$)$_3$; in formula (IIt) d and d' are as defined on 107., $R_t$ is —C(O)OC(CH$_3$)$_3$;
$A_{26}$ is a compound of formula (IIa) or (IIc) wherein $R_1$ is —H, $R_2$ is —COOH; $R_a$ of formula (IIa) and $R_c$ of formula (IIc) are $R_{ia}$NH(=NH)NH—(CH$_2$)$_3$—, wherein $R_{ia}$ is the —Pbf protective group as already defined;
using the same procedure described in 1b'),
Compounds A and $A_{26}$ are commercially available.

108. The compounds of general formula (I) wherein:
s is equal to 1;
s', s", m, m' and m" are equal to 0;
Y is as above defined;
A is selected from (IIa), (IIc) and (IIt) wherein $R_1$ is —C(O)O—$R_{1x}$ and binds a group —Y—ONO$_2$; $R_2$ is —COOH
$R_a$ of formula (IIa) and $R_c$ of formula (IIc) are $R_h$NH(CH$_2$)$_p$— wherein p is an integer front 0 to 4, or $R_i$NH(=NH)NH—(CH$_2$)$_3$—, wherein $R_h$ and $R_i$ are —H;
in formula (IIt) d is 2 d' is 1, $R_t$ is —H;
can be obtained as follows:
108a) $R_a$=$R_c$ selected from $R_h$NH(CH$_2$)$_p$— wherein p is an integer from 0 to 4, $R_h$ is —H
by reacting a compound of formula (I) wherein s, s', s", m, m', m", Y, Y', Y" are as above defined in 108., A is a radical of (IIa), (IIc) or (IIt) wherein $R_1$, $R_2$, d, d', are as defined in 108., $R_a$ of formula (IIa) and $R_c$ of formula (IIc) are selected from $R_h$NH(CH$_2$)$_p$— wherein p is an integer from 0 to 4, $R_h$ is —C(O)OC(CH$_3$)$_3$;
in formula (IIt) $R_t$ is —C(O)OC(CH$_3$)$_3$;
with anhydrous or aqueous organic or inorganic acid to hydrolyze the —BOC protective groups following procedure well known in the literature.

108a') $R_a$=$R_c$ selected from $R_i$NH(=NH)NH—(CH$_2$)$_3$—, $R_i$ is —H;
reacting a compound of formula (VIIIab)

$$A_{27}\text{-}Y—ONO_2 \qquad\qquad (VIIIab)$$

wherein Y is as above defined and $A_{27}$ is a radical of (IIa), (IIc) wherein $R_1$, $R_2$, are as defined in 108., $R_a$ of formula (IIa) and $R_c$ of formula (IIc) are selected from $R_{ia}$NH(=NH)NH—(CH$_2$)$_3$—, wherein $R_{ia}$ is the —Pbf protective group as already defined;
with anhydrous or aqueous organic or inorganic acid to hydrolyze the —Pbf protective groups following procedure well known in the literature.

108b) compounds described in 108a) and 108a') can be prepared by reacting a compound of formula A or a compound of formula $A_{26}$ both already defined in 107b) with a compound of formula (IIIf)

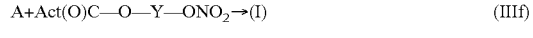
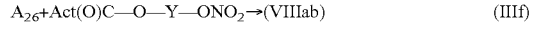

$$A+Act(O)C—O—Y—ONO_2 \rightarrow (I) \qquad\qquad (IIIf)$$

$$A_{26}+Act(O)C—O—Y—ONO_2 \rightarrow (VIIIab) \qquad\qquad (IIIf)$$

wherein Act and Y are as above defined, using the same procedure described, in 3b).

109. The compounds of general formula (I) wherein:
s is equal to 1;
s', s", m, m' and m" are equal to 0;

Y is as above defined;
A is selected from (IIa), (IIc) and (IIt) wherein $R_1$ is —H; $R_2$ is —COOH;
$R_a$ of formula (IIa) and $R_c$ of formula (IIc) are $R_hNH(CH_2)_p$— wherein p is an integer from 0 to 4, or $R_iNH(=NH)NH—(CH_2)_3$—, wherein $R_h$ and $R_i$ are $R_{hh}$—C(O)— or $R_{ii}$—C(O)—, and bind a group —Y—$ONO_2$;
in formula (IIt) d is 2 d' is 1, $R_t$ is —C(O)—$R_{tt}$, and binds a group —Y—$ONO_2$;
can be obtained as follows:
109a) by reacting a compound of formula (I) wherein s, s', s", m, m', m", Y, Y', Y" are as above defined in 109., A is a radical of (IIa), (IIc) or (IIt) wherein $R_2$, $R_a$, $R_c$, d, d' and $R_t$ are as defined in 109., $R_1$ is —C(O)OC($CH_3$)$_3$;
with anhydrous or aqueous organic or inorganic acid to hydrolyze the —BOC protective groups following procedure well known in the literature.
109b) by reacting a compound of formula A with a compound of formula (IIIe)

A+Act(O)C—Y—$ONO_2$ (IIIe)

wherein Act and Y are as above defined and A is a radical of (IIa), (IIc) or (IIt) wherein $R_1$ is —C(O)OC($CH_3$)$_3$; $R_2$ is —COOH;
$R_a$ of formula (IIa) and $R_c$ of formula (IIc) are $R_hNH(CH_2)_p$— wherein p is an integer from 0 to 4, or $R_iNH(=NH)NH—(CH_2)_3$—, wherein $R_h$ and $R_i$ are —H;
in formula (IIt) d and d' are as defined in 109., $R_t$ is —H;
using the same procedure described in 1b').
Compounds A are commercially available.
110. The compounds of general formula (I) wherein:
s is equal to 1;
s', s", m, m' and m" are equal to 0;
Y is as above defined;
A is selected from (IIa), (IIc) and (IIt) wherein $R_1$ is —H, $R_2$ is —COOH;
$R_a$ of formula (IIa) and $R_c$ of formula (IIc) are $R_hNH(CH_2)_p$— wherein p is an integer from 0 to 4, or $R_iNH(=NH)NH—(CH_2)_3$—, wherein $R_h$ and $R_i$ are $R_{hh}$—OC(O)— or $R_{ii}$—OC(O)—, and bind a group —Y—$ONO_2$;
in formula (IIt) d is 2 d' is 1, $R_t$ is —C(O)O—$R_{tt}$, and it binds a group —Y—$ONO_2$;
can be obtained as follows:
110a) by reacting a compound of formula (I) wherein s, s', s", m, m', m", Y, Y', Y" are as above defined in 110., A is a radical of (IIa), (IIc) or (IIt) wherein $R_2$, $R_a$, $R_c$, d, d' and $R_t$ are as defined in 110., $R_1$ is —C(O)OC($CH_3$)$_3$;
with anhydrous or aqueous organic or inorganic acid to hydrolyze the —BOC protective groups following procedure well known in the literature.
110b) by reacting a compound of formula A with a compound of formula (IIIf)

A+Act(O)C—O—Y—$ONO_2$ (IIIf)

wherein Act and Y are as above defined and A is as defined in 109b), using the same procedure described in 3b).
111. The compounds of general formula (I) wherein:
s, s' and m' are equal to 1;
s", m, m", are equal to 0;
Y and Y' are equal or different and are as above defined;
B is:

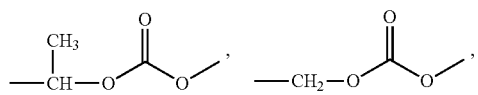

-continued

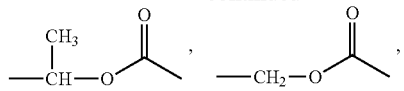

A is selected among:
i) (IIa) wherein $R_1$ is —H, $R_2$ is —C(O)$OR_{2x}$ and $R_2$ binds a group B—Y—$ONO_2$; $R_1$ is selected from $R_{bx}$—C(O)—S—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ is $R_{xx}$—C(O)— and $R_a$ binds a group —Y—$ONO_2$;
ii) (IIc) wherein $R_1$ is —H, $R_2$ is —C(O)$OR_{2x}$ and $R_2$ binds a group B—Y'—$ONO_2$; $R_c$ is selected from $R_{bx}$—C(O)—S—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ is $R_{xx}$—C(O)— and $R_c$ binds a group —Y—$ONO_2$;
iii) (IIs) wherein $R_1$ is —H, $R_3$ is —OC(O)$R_{3x}$ and $R_3$ binds a group —Y—$ONO_2$; $R_s$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_s$ binds a group B—Y'—$ONO_2$;
v) (IIn), wherein $R_1$ is —H, $R_2$ is —C(O)$OR_{2x}$, $R_2$ binds a group B—Y'—$ONO_2$; a is 1, b is 0 or 1; $R_x$ is $R_{xx}$—C(O)— and $R_x$ binds a group —Y—$ONO_2$;
can be prepared as follows:
111a) by reacting a compound of formula (I) wherein B, s, s', s", m, m', m", Y, Y', Y" are as above defined in 111., A is a radical, of formula (IIa), (IIc), (IIs) or (IIu) wherein; $R_2$, $R_3$, a, b, $R_a$, $R_c$, $R_g$ and $R_x$, are as defined in 111.; $R_1$ is —C(O)OC($CH_3$)$_3$, with anhydrous or aqueous organic or inorganic acid to hydrolyze the —BOC protective groups following procedure well known in the literature.
111b) by reacting a compound of formula (I) obtained in 36b) with a compound of formula (IIIg) or (IIIn) depending on the meaning of B

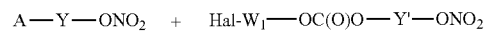
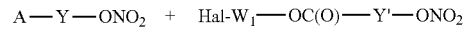

wherein Y and Y', Hal, $W_1$ are as above defined and in formula (I) A is selected among:
i) (IIa) wherein $R_1$ is —C(O)OC($CH_3$)$_3$, $R_2$ is —COOH, $R_a$ is selected from $R_{bx}$—C(O)—S—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ is $R_{xx}$—C(O)— and $R_a$ binds a group —Y—$ONO_2$;
ii) (IIc) wherein $R_1$ is —C(O)OC($CH_3$)$_3$, $R_2$ is —COOH, $R_c$ is selected from $R_{bx}$—C(O)—S—$CH_2$—, or $R_xO$—$CH_2$—, $R_xO$—CH($CH_3$)—, ($R_xO$)-p-$C_6H_4$—$CH_2$—, 4-($R_xO$)-3,5-diiodobenzyl-4-($R_xO$)-3-nitrobenzyl- wherein $R_x$ is $R_{xx}$—C(O)— and $R_c$ binds a group —Y—$ONO_2$;
iii) (IIs) wherein $R_1$ is —C(O)OC($CH_3$)$_3$, $R_3$ is —OC(O)$R_{3x}$ and $R_3$ binds a group —Y—$ONO_2$; $R_s$ is selected from $R_gC(O)CH_2$—NH—, $R_gC(O)CH_2$, $R_gC(O)(CH_2)_2$—, $R_gC(O)(CH_2)_4$—, wherein $R_g$ is —OH,
v) (IIu) wherein $R_1$ is —C(O)OC($CH_3$)$_3$, $R_2$ is —COOH, a is 1, b is 0 or 1; and $R_x$ is $R_{xx}$—C(O)— and $R_x$ binds a group —Y'—$ONO_2$;
following the same procedures described in 4b) or 6b).

112. The compounds of general formula (I) wherein:

s, s' and m' are equal to 1;

s", m, m", are 0

Y and Y' are equal or different and are as above defined;

B is

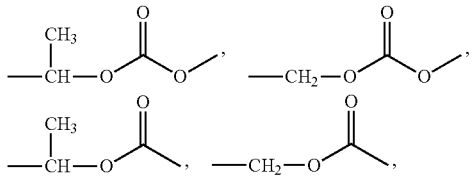

A is selected among:

i) (IIa) wherein $R_1$ is —H, $R_2$ is —C(O)O$R_{2x}$ and $R_2$ binds a group B—Y'—ONO$_2$; and $R_a$ is selected from $R_{bx}$—OC(O)—S—CH$_2$, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_x$ is $R_{xx}$—OC(O)— and $R_a$ binds a group —Y—ONO$_2$;

ii) (IIc) wherein $R_1$ is —H, $R_2$ is —C(O)O$R_{2x}$ and $R_2$ binds a group B—Y'—ONO$_2$; $R_c$ is selected from $R_{bx}$—OC(O)—S—CH$_2$, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_x$ is $R_{xx}$—OC(O)— and $R_c$ binds a group —Y—ONO$_2$;

iii) (IIs) wherein $R_1$ is —H, $R_3$ is —OC(O)O—$R_{3x}$ and $R_3$ binds a group —Y—ONO$_2$; $R_s$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_s$ binds a group B—Y'—ONO$_2$;

v) wherein $R_1$ is —H, $R_2$ is —C(O)O$R_{2x}$, $R_2$ binds a group —B—Y'—ONO$_2$; a is 1; b is 0 or 1; $R_x$ is $R_{xx}$—OC(O)— and $R_x$ binds a group —Y—ONO$_2$;

can be prepared as follows:

112a) by reacting a compound of formula (I) wherein B, s, s', s", m, m', m", Y, Y', Y" are as above defined in 112., A is a radical of formula (IIa), (IIc), (IIs) or (IIu) wherein; $R_2$, $R_3$, a, b, $R_a$, $R_c$, $R_g$ and $R_x$, are as defined in 112.; $R_1$ is —C(O)OC(CH$_3$)$_3$ with anhydrous or aqueous organic or inorganic acid to hydrolyze the —BOC protective groups following procedure well known in the literature.

112b) by reacting a compound of formula (I) obtained in 37b) with a compound of formula (IIIg) or (IIIn) depending on the meaning of B

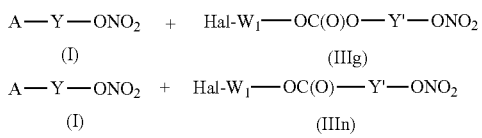

wherein Y and Y', Hal, $W_1$ are as above defined and in formula (I) A is as above defined in 111b);

following the same procedures described in 4b) or 6b).

113. The compounds of general formula (I) wherein:

s, s' and m' are equal to 1;

s", m, m", are 0

Y and Y' are equal or different and are as above defined;

B is:

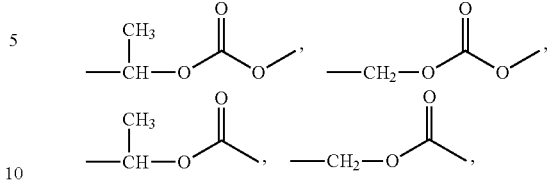

A is selected among:

i) (IIa) wherein $R_1$ is —H, $R_2$ is —C(O)O$R_{2x}$ and $R_2$ binds a group B—Y'—ONO$_2$; and $R_a$ is selected from $R_{bx}$—NH(O)C—S—CH$_2$, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_x$ is $R_{xx}$NH(O)C— and $R_c$ binds a group —Y—ONO$_2$;

ii) (IIc) wherein $R_1$ is —H, $R_2$ is —C(O)O$R_{2x}$ and $R_2$ binds a group B—Y'—ONO$_2$; $R_c$ is selected from $R_{bx}$—NH(O)C—S—CH$_2$, or $R_xO$—CH$_2$—, $R_xO$—CH(CH$_3$)—, ($R_xO$)-p-C$_6$H$_4$—CH$_2$—, 4-($R_xO$)-3,5-diiodobenzyl-4-($R_xO$)-3-nitrobenzyl- wherein $R_x$ is $R_{xx}$NH(O)C— and $R_c$ binds a group —Y—ONO$_2$;

iii) (IIs) wherein $R_1$ is —H, $R_3$ is —OC(O)—NH—$R_{3x}$ and $R_3$ binds a group —Y—ONO$_2$; $R_3$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_g$ binds a group B—Y'—ONO$_2$;

v) (IIu) wherein $R_1$ is —H, $R_2$ is —C(O)O$R_{2x}$, and $R_2$ binds a group B—Y'—ONO$_2$; a is 1; b is 0 or 1; $R_x$ is $R_{xx}$NHC(O)— and $R_x$ binds a group —Y—ONO$_2$;

can be prepared as follows:

113a) by reacting a compound of formula (I) wherein B, s, s', s", m, m', m", Y, Y', Y" are as above defined in 113., A is a radical of formula (IIa), (IIc), (IIs) or (IIu) wherein; $R_2$, $R_3$, a, b, $R_a$, $R_c$, $R_g$ and $R_x$, are as defined in 113.; $R_1$ is —C(O)OC(CH$_3$)$_3$ with anhydrous or aqueous organic or inorganic acid to hydrolyze the —BOC protective groups following procedure well known in the literature.

113b) by reacting a compound of formula (I) obtained in 38b) with a compound of formula (IIIg) or (IIIn) depending on the meaning of B

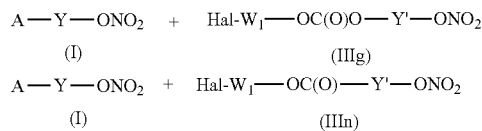

wherein Y and Y', Hal, $W_1$ are as above defined and in formula (I)

A is as above defined in 111b);

following the same procedures described in 4b) or 6b).

114. The compounds of general formula (I) wherein:

s is equal to 1;

m, m', m", s' and s" are 0

Y is as above defined;

A is a radical of formula (IIa)-(IIm), (IIo)-(IIr), (IIt)-(IIu) and (IIn) wherein $R_1$ is —C(O)—$R_{1x}$ and it binds the group —Y—ONO$_2$, $R_2$ is equal to the group $R_4$

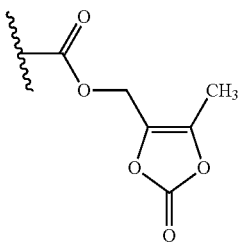

in formula (IIn) $R_n$ is —C(O)—$R_{nx}$, or is —$(CH_2)_2$—NH—$R_h$ wherein $R_h$ is —C(O)$R_{hh}$ and it binds the group —Y—$ONO_2$ $R_a$ of formula (IIa) is selected in group a)

$R_c$ of formula (IIc) is selected in group a')

in formula (IIt) d is an integer from 3 to 5, d' is 0;

can be prepared as follows 114a) by reacting a compound of formula A with a compound of formula (IIIa) or a compound of formula (IIIe)

wherein Y is as above defined and A is selected from (IIa)-(IIm), (IIo)-(IIr), (IIt)-(IIu) and (IIn) wherein $R_1$ is —H and $R_2$ is as above defined in 114.;

in formula (IIn) $R_n$ is H, or is —$(CH_2)_2$—NH—$R_h$ wherein $R_h$ is H;

$R_a$ of formula (IIa) is selected in group a);

$R_c$ of formula (IIc) is selected in group a');

in formula (IIt) d and d' are as above defined;

following the same procedure described in 1b) or 1b').

114b) compounds A as above defined can be prepared by reacting commercially available compounds of formula $A_2$ described in 1c) wherein $A_2$ is a radical of formula (IIa)-(IIm), (IIo)-(IIr), (IIt)-(IIu) and (IIn) wherein $R_2$—COOH or $R_{2a}$ wherein $R_{2a}$ is the group —COAct as already described in 8., $R_1$ is —C(O)OC$(CH_3)_3$, $R_n$ is —C(O)OC$(CH_3)_3$ or is —$(CH_2)_2$—NH—C(O)OC$(CH_3)_3$, $R_a$, $R_c$, d and d' are as defined in 114., with compounds (IIIx) or (IIIy):

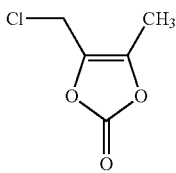

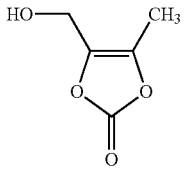

In case of (IIIx): in the presence of a inorganic or organic base in an aprotic polar or in an aprotic non-polar solvent such as DMF, THF or $CH_2Cl_2$ at temperatures range between 0° to 100° C.;

In case of (IIIy) following the same procedure described in 8b) for $R_2$ equal to —COOH or equal to $R_{2a}$ wherein $R_{2a}$ is the group —COAct. Compound (IIIx) is commercially available. Compound (IIIy) can be obtained from (IIIx) by first reacting with formic acid and TEA in acetonitrile and then hydrolyzing the formyl ester with hydrochloric acid in methanol/water at room temperature, as described for analogous compounds by Alexander in *J. Med. Chem.* 1996, 39, 480-486.

115. The compounds of general formula (I) wherein:

s is equal to 1;

m, m', m", s' and s" are 0

Y is as above defined,

A is a radical of formula (IIa)-(IIm), (IIo)-(IIr), (IIt)-(IIu) and (IIn) wherein $R_1$ is —C(O)O—$R_{1x}$ and it binds the group —Y—$ONO_2$, $R_2$ is equal to $R_4$, wherein $R_4$ is as defined in 114.;

in formula (IIn) $R_n$ is —C(O)O—$R_{nx}$ or —$(CH_2)_2$—NH—$R_h$ wherein $R_h$ is —C(O)O—$R_{hh}$, and it binds the group —Y—$ONO_2$ $R_a$ of formula (IIa) is selected in group a)

$R_c$ of formula (IIc) is selected in group a')

in formula (IIt) d is an integer from 3 to 5, d' is 0;

can be prepared as follows 115a) by reacting a compound of formula A with a compound of formula (IIIf)

wherein A is as above reported in 114a), Act and Y are as already defined, following the same procedure described in 3b).

116. The compounds of general formula (I) wherein:

s is equal to 1;

s', s", m, m', m", are 0

Y is as above defined;

A is selected among:

(IIa) wherein $R_1$ is —H, $R_2$ is —C(O)O$R_{2x}$ and $R_2$ binds a group —Y—$ONO_2$; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is equal to $R_{gg}$ and is equal to:

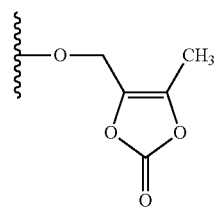

(IIc) wherein $R_1$ is —H, $R_2$ is equal to —C(O)O$R_{2x}$ and $R_2$ binds a group —Y—$ONO_2$; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is equal to $R_{gg}$ and is as above defined can be prepared as follows:

116a) by reacting a compound of formula (VIIIa)

wherein Y is as above defined and $A_{28a}$ is a radical of formula (IIa), (IIc), wherein $R_2$ is as above defined in 116.; $R_1$ is $R_{1a}$ and is the Fmoc group; $R_a$ and $R_c$ are $R_{gg}C(O)CH_2$—NH—, $R_{gg}C(O)CH_2$, $R_{gg}C(O)(CH_2)_2$—, $R_{gg}C(O)(CH_2)_4$—, wherein $R_{gg}$ is as above defined by known procedure to remove the —Fmoc protective groups;

116b) by reacting a compound of formula $A_{28}$ with a compound of formula (IIIi)

wherein Y is as above defined and $R_{28}$ is a compound of formula (IIa) or (IIc) wherein $R_1$ is $R_{1a}$ and is the Fmoc group;

$R_2$ is —COOH, $R_a$ and $R_c$ are selected from $R_{gg}C(O)CH_2$—NH—, $R_{gg}C(O)CH_2$, $R_{gg}C(O)(CH_2)_2$—, $R_{gg}C(O)(CH_2)_4$—, wherein $R_{gg}$ is as above defined in 116.;
following the same procedure described in 8b).
116c) by reacting a compound $A_{29}$

wherein $R_1$ is $R_{1a}$ is the Fmoc group; $R_2$ is —C(O)OC(CH$_3$)$_3$; $R_a$ and $R_c$ are selected from $R_{gg}C(O)CH_2$—NH—, $R_{gg}C(O)CH_2$, $R_{gg}C(O)(CH_2)_2$—, $R_{gg}C(O)(CH_2)_4$—, wherein $R_{gg}$ is as above defined in 116 with anhydrous or aqueous organic or inorganic acid, as well known in the literature to remove the t-butyl ester.
116d) by reacting a compound $A_{30}$

wherein $R_1$ is $R_{1a}$ and is the Fmoc group; $R_2$ is —C(O)OC(CH$_3$)$_3$; $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is —OH with compounds (IIIx) or (IIIy) as described in 114b). Compounds $A_{30}$ are commercially available.
117. The compounds of general formula (I) wherein:
s is equal to 1;
s', s", m, m', m", are 0
Y is as above defined;
R is a radical of formula
(IIa) wherein $R_1$ is —H, $R_2$ is —C(O)NHR$_{2xx}$ or —C(O)N(CH$_3$)R$_{2xx}$ and $R_2$ binds a group —Y—ONO$_2$; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gg}$ and is as defined in 116.; or
(IIc) wherein $R_1$ is —H, $R_2$ is —C(O)NHR$_{2xx}$ or —C(O)N(CH$_3$)R$_{2xx}$ and $R_2$ binds a group —Y—ONO$_2$; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gg}$ and is as defined in 116.; can be prepared as follows:
117a) by reacting a compound of formula (IXb)

(IXb)

wherein Y is as above defined and $A_{31}$ is a radical of formula (IIa), (IIc), wherein $R_2$ is as above defined in 117.; $R_1$ is $R_{1a}$ and is the Fmoc group; $R_a$ and $R_c$ are $R_{gg}C(O)CH_2$—NH—, $R_{gg}C(O)CH_2$, $R_{gg}C(O)(CH_2)_2$—, $R_{gg}C(O)(CH_2)_4$—, wherein $R_{gg}$ is as above defined by known procedure to remove the —Fmoc protective groups;
117b) by reacting a compound of formula $A_{28}$ with a compound of formula (IIIo)

(IIIo)

wherein Y is as above defined, $W_3$ is as above defined and $A_{28}$ is as defined in 116b),
following the same procedure described in 7b).
118. The compounds, of general formula (I) wherein:
s and m are equal to 1;
s', s", m', m", are 0
Y is as above defined;
B is:

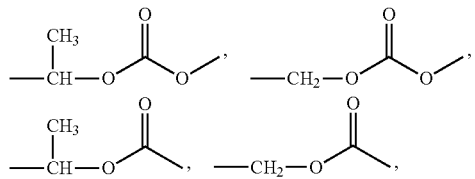

A is a radical selected among:
(IIa) wherein $R_1$ is —H, $R_2$ is —C(O)OR$_{2x}$ and $R_2$ binds a group —B—Y—ONO$_2$; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gg}$ and is as defined in 116.,
(IIc) wherein $R_1$ is —H, $R_2$ is —C(O)OR$_{2x}$ and $R_2$ binds a group —B—Y—ONO$_2$; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gg}$ and is as defined in 116.; can be prepared as follows:
118a) by reacting a compound of formula (VIIIc)

(IXc)

wherein B and Y are as above defined and $A_{28a}$ is as defined in 116a) a radical of formula (IIa), (IIc), wherein $R_2$ is as above defined in 118.; $R_1$ is $R_{1a}$ the Fmoc group; $R_a$ and $R_c$ are $R_{gg}C(O)CH_2$—NH—, $R_{gg}C(O)CH_2$, $R_{gg}C(O)(CH_2)_2$—, $R_{gg}C(O)(CH_2)_4$—, wherein $R_{gg}$ is as above defined by known procedure to remove the —Fmoc protective groups;
118b) compound (IXc) are prepared by reacting a compound of formula $A_{28}$ with a compound of formula (IIIg) or (IIIn) depending on the meaning of B

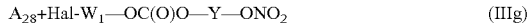

(IIIg)

$A_{28}$+Hal-W$_1$—OC(O)—Y—ONO$_2$ (IIIn)

wherein Y, Hal, W$_1$ are as above defined and $A_{28}$ is as defined in 116b),
following the same procedures described in 4b) or 6b).
119. The compounds of general formula (I) wherein:
s is equal to 1;
s', s", m, m', m", are 0
Y is as above defined;
A is selected among:
(IIa) wherein $R_1$ is —H, $R_2$ is equal to $R_4$ and is as defined in 114.; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_g$ binds a group —Y—ONO$_2$;
(IIc) wherein $R_1$ is —H, $R_2$ is equal to $R_4$ and is as defined in 114.; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_g$ binds a group —Y—ONO$_2$, can be prepared as follows:
119a) by reacting a compound of formula (Xa)

(Xa)

wherein Y is as above defined and $A_{32}$ is a radical of formula (IIa), (IIc), wherein $R_a$ and $R_c$ are as above defined in 119.; $R_1$ is —$R_{1a}$ and is the Fmoc group; $R_2$ is $R_4$ and is as defined in 114.;
following procedure well known in the literature to remove the Fmoc group.
119b) by reacting a compound of formula $A_{33}$ with a compound of formula (IIIi)

(IIIi)

wherein Y is as above defined and $A_{33}$ is a radical of formula (IIa), (IIc) wherein $R_1$ is —$R_{1a}$ and is the Fmoc group; $R_2$ is $R_4$ and is as defined in 114.; $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_c$ is —OH;
following the same procedure described in 8b).
119c) by reacting a compound $A_{34}$

wherein $R_1$ is $R_{1a}$ and is the Fmoc group; $R_2$ is $R_4$; $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is —C(O)OC ($CH_3$)$_3$ with anhydrous or aqueous organic or inorganic acid as well known in the literature to remove the t-butyl ester.

119d) by reacting a compound $A_{35}$ $$A_{35} \rightarrow A_{34}$$

wherein $R_1$ is $R_{1a}$ and is the Fmoc group; $R_2$ is —COOH; $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is —C(O)OC($CH_3$)$_3$ with compounds (IIIx) or (IIIy) as described in 114b). Compounds $A_{35}$ are commercially available.

120. The compounds of general formula (I) wherein:
s is equal to 1;
s', s", m, m', m", are 0
Y is as above defined;
A is selected among:
(IIa) wherein $R_1$ is —H, $R_2$ is $R_4$ and is as defined in 114.; $R_a$ is selected $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N($CH_3$)— and $R_g$ binds a group —Y—$ONO_2$;
(IIc) wherein $R_1$ is —H, $R_2$ is $R_4$ and is as defined in 114.; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N($CH_3$)— and $R_g$ binds a group —Y—$ONO_2$;
can be prepared as follows:
120a) by reacting a compound of formula (Xb)

$$A_{36}\text{-Y}\text{—}ONO_2 \quad (Xb)$$

wherein Y is as above defined and $A_{36}$ is a radical of formula (IIa), (IIc), wherein $R_a$ and $R_c$ are as above defined in 120.; $R_1$ is $R_{1a}$ and is the Fmoc group; $R_2$ is $R_4$ and is as defined in 114.; following procedure well known in the literature to remove the Fmoc group.
120b) by reacting a compound of formula $A_{33}$ with a compound of formula (IIIo):

$$A_{33}+W_3NH\text{—}Y\text{—}ONO_2 \rightarrow (Xb) \quad (IIIo)$$

wherein Y and $W_3$ are as above defined and $A_{33}$ is as defined in 119b) following the same procedure described in 7b).

121. The compounds of general formula (I) wherein:
s and m are equal to 1;
s', s", m', m", are 0
Y is as above defined;
B is:

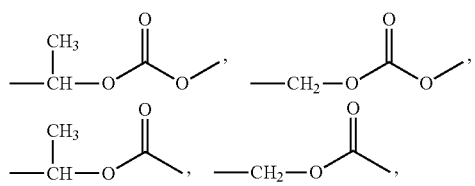

A is selected among:
(IIa) wherein $R_1$ is —H, $R_2$ is $R_4$ and is as defined in 114.; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O— and $R_g$ binds a group —B—Y—$ONO_2$;
(IIc) wherein $R_1$ is —H, and $R_2$ is $R_4$ as defined in 114.; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and $R_g$ binds a group —B—Y—$ONO_2$;
can be prepared as follows:
121a) by reacting a compound of formula (Xc)

$$A_{37}\text{-B}\text{—}Y\,ONO_2 \quad (Xc)$$

wherein B and Y are as above defined and $A_{37}$ is a radical of formula (IIa), (IIc), wherein $R_a$ and $R_c$ are as above defined in 121.; $R_1$ is $R_{1a}$ and is the Fmoc group; $R_2$ is $R_4$ and is as defined in 114.,
following procedure well known in the literature to remove the Fmoc group.
121b) compounds (Xc) are prepared by reacting a compound of formula $A_{33}$ with a compound of formula of formula (IIIg) or (IIIn) depending on the meaning of B $$A_{33}+Hal\text{-}W_1\text{—}OC(O)O\text{—}Y\text{—}ONO_2 \quad (IIIg)$$

$$A_{33}+Hal\text{-}W_1\text{—}OC(O)\text{—}Y\text{—}ONO_2 \quad (IIIn)$$

wherein Y, Hal, $W_1$ are as above defined and $A_3$ is as defined in 119b),
following the same procedures described in 4b) or 6b).

122. The compounds of general formula (I) wherein:
s and s' are equal to 1;
s", m, m', m", are 0
Y and Y' can be equal or different and are as above defined;
A is selected among:
(IIa) wherein $R_1$ is —C(O)—$R_{1x}$ and binds a group —Y'—$ONO_2$; $R_2$ is —C(O)$OR_{2x}$ and binds a group —Y—$ONO_2$; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is equal to $R_{gg}$ and is as defined in 116.,
(IIc) wherein $R_1$ is —C(O)—$R_{1x}$ and binds a group —Y'—$ONO_2$; $R_2$ is —C(O)$OR_{2x}$ and binds a group —Y—$ONO_2$; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is equal to $R_{gg}$ and is as defined in 116.; can be prepared as follows:
122a) by reacting a compound of formula (I) prepared as described in 116. with a compound of formula (IIIe):

$$\underset{(I)}{A\text{—}Y\text{—}ONO_2} \quad + \quad \underset{(IIIe)}{Act\text{-}C(O)\text{—}Y'\text{—}ONO_2}$$

wherein Act, Y and Y' are as above defined and A is a radical of formula (IIa), (IIc), wherein $R_1$ is —H, $R_2$ is —C(O)$OR_{2x}$ and binds a group —Y—$ONO_2$; $R_a$ and $R_c$ are selected from $R_{gg}C(O)CH_2$—NH—, $R_{gg}C(O)CH_2$, $R_{gg}C(O)(CH_2)_2$—, $R_{gg}C(O)(CH_2)_4$—, wherein $R_{gg}$ is as above defined;
following the same procedures described in 1b').

123. The compounds of general formula (I) wherein:
s and s' are equal to 1;
s", m, m', m", are 0
Y and Y' can be equal or different and are as above defined;
A is selected among:
(IIa) wherein $R_1$ is —C(O)O—$R_{1x}$ and binds a group —Y'—$ONO_2$; $R_2$ is —C(O)$OR_{2x}$ and binds a group —Y—$ONO_2$; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is equal to $R_{gg}$ and is as defined in 116.,
(IIc) wherein $R_1$ is —C(O)O—$R_{1x}$ and binds a group —Y'—$ONO_2$; $R_2$ is —C(O)$OR_{2x}$ and binds a group —Y—$ONO_2$; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is equal to $R_{gg}$ and is as defined in 116.; can be prepared as follows:

123a) by reacting a compound of formula (I) prepared as described in 116. with a compound of formula (IIIf):

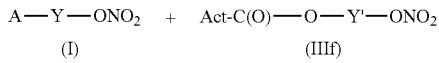

wherein Act, Y and Y' are as above defined and A is as defined in 122a);
following the same procedures described in 3b).
124. The compounds of general formula (I) wherein:
s and s' are equal to 1;
s", m, m', m", are 0
Y and Y' can be equal or different and are as above defined;
A is selected among:
(IIa) wherein $R_1$ is —C(O)—$R_{1x}$ and binds a group —Y'—$ONO_2$; $R_2$ is —C(O)$NHR_{2xx}$ or —C(O)N($CH_3$)$R_{2xx}$ and binds a group —Y—$ONO_2$; $R_a$ is selected $R_gC(O)CH_2$—NH—, $R_gC(O)CH_2$, $R_gC(O)(CH_2)_2$—, $R_gC(O)(CH_2)_4$—, wherein $R_g$ is equal to $R_{gg}$ and is as defined in 116.,
(IIc) wherein $R_1$ is —C(O)—$R_{1x}$ and binds a group —Y'—$ONO_2$; $R_2$ is —C(O)$NHR_{2xx}$ or —C(O)N($CH_3$)$R_{2xx}$ and binds a group —Y—$ONO_2$; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is equal to $R_{gg}$ and is as defined in 116.; can be prepared as follows:
124a) by reacting a compound of formula (I) prepared as described in 117. with a compound of formula (IIIe):

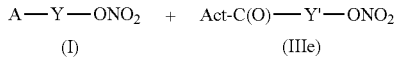

wherein Act, Y and Y' are as above defined and A is a radical of formula (IIa), (IIc), wherein $R_1$ is —H, $R_2$ is —C(O)$NHR_{2xx}$ or —C(O)$NCH_3R_{2xx}$ binds a group —Y—$ONO_2$; $R_a$ and $R_c$ are selected from $R_{gg}C(O)CH_2$—NH—, $R_{gg}C(O)CH_2$, $R_{gg}C(O)(CH_2)_2$—, $R_{gg}C(O)(CH_2)_4$—, wherein $R_{gg}$ is as above defined;
following the same procedures described in 1b').
125. The compounds of general formula (I) wherein:
s and s' are equal to 1;
s", m, m', m", are 0
Y and Y' can be equal or different and are as above defined;
A is selected among:
(IIa) wherein $R_a$ is —C(O)O—$R_{1x}$ and binds a group —Y'—$ONO_2$; $R_2$ is —C(O)$NHR_{2xx}$ or —C(O)N($CH_3$)$R_{2xx}$ and binds a group —Y—$ONO_2$; $R_a$ is selected $R_gC(O)CH_2$—NH—, $R_gC(O)CH_2$, $R_gC(O)(CH_2)_2$—, $R_gC(O)(CH_2)_4$—, wherein $R_g$ is equal to $R_{gg}$ and is as defined in 116.,
(IIc) wherein $R_1$ is —C(O)O—$R_{1x}$ and binds a group —Y'—$ONO_2$; $R_2$ is —C(O)$NHR_{2xx}$ or —C(O)N($CH_3$)$R_{2xx}$ and binds a group —Y—$ONO_2$; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is equal to $R_{gg}$ and is as defined in 116.; can be prepared as follows:
125a) by reacting a compound of formula (I) prepared as described in 117. with a compound of formula (IIIf):

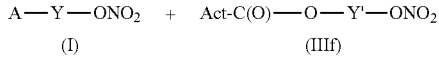

wherein Act, Y and Y' are as above defined and A is as above defined in 124a), following the same procedures described in 3b).
126. The compounds of general formula (I) wherein:
s, s' and m are equal to 1;
s", m', m", are 0
Y and Y' can be equal or different and are as above defined;
B is:

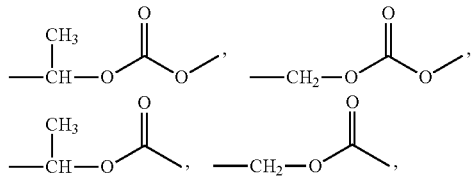

A is selected among:
(IIa) wherein $R_1$ is —C(O)—$R_{1x}$ and binds a group —Y'—$ONO_2$; $R_2$ is —C(O)$OR_{2x}$ and binds a group —B—Y—$ONO_2$; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is equal to $R_{gg}$ and is as defined in 116.;
(IIc) wherein $R_1$ is —C(O)—$R_{1x}$ and binds a group —Y'—$ONO_2$; $R_2$ is —C(O)$OR_{2x}$ and binds a group —B—Y—$ONO_2$; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is equal to $R_{gg}$ and is as defined in 116.;
can be prepared as follows.
126a) by reacting a compound of formula (I) prepared as described in 118. with a compound of formula (IIIe):

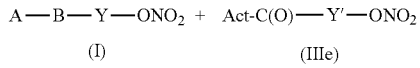

wherein Act, B, Y and Y' are as above defined and A is a radical of formula (IIa), (IIc), wherein $R_1$ is —H, $R_2$ is —C(O)$OR_{2x}$ and binds a group B—Y—$ONO_2$; $R_a$ and $R_c$ are selected from $R_{gg}C(O)CH_2$—NH—, $R_{gg}C(O)CH_2$, $R_{gg}C(O)(CH_2)_2$—, $R_{gg}C(O)(CH_2)_4$—, wherein $R_{gg}$ is as above defined;
following the same procedures described in 1b').
127. The compounds of general formula (I) wherein:
s, s' and m are equal to 1;
s", m', m", are 0
Y and Y' can be equal or different and are as above defined;
B is:

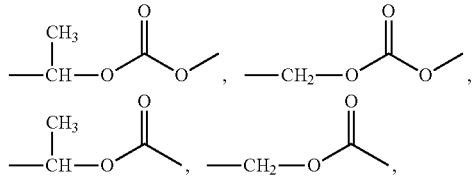

A is selected among:
(IIa) wherein $R_1$ is —C(O)O—$R_{1x}$ and binds a group —Y'—$ONO_2$; $R_2$ is —C(O)$OR_{2x}$ and binds a group —B—Y—$ONO_2$; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is equal to $R_{gg}$ and is as defined in 116.;

(IIc) wherein $R_1$ is —C(O)O—$R_{1x}$ and binds a group —Y'—ONO$_2$; $R_2$ is —C(O)O$R_{2x}$ and binds a group —B—Y—ONO$_2$; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is equal to $R_{gg}$ and is as defined in 116.; can be prepared as follows:

127a) by reacting a compound of formula (I) prepared as described in 118. with a compound of formula (IIIf):

$$A—B—Y—ONO_2 + Act-C(O)—O—Y'—ONO_2$$
$$(I) \qquad\qquad\qquad (IIIf)$$

wherein Act, B, Y and Y' are as above defined and A is as defined in 126a), following the same procedures described in 3b).

128. The compounds of general formula (I) wherein:
s and s' are equal to 1;
s", m, m', m", are 0
Y and Y' can be equal or different and are as above defined;
A is selected among:
(IIa) wherein $R_1$ is —C(O)—$R_{1x}$ and it binds a group —Y'—ONO$_2$; $R_2$ is equal to $R_4$ and is as defined in 114.; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and binds a group —Y—ONO$_2$
(IIc) wherein $R_1$ is —C(O)—$R_{1x}$ and binds a group —Y'—ONO$_2$; $R_2$ is equal to $R_4$ and is as defined in 114.; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O— and binds a group —Y'—ONO$_2$;
can be prepared as follows:
128a) by reacting a compound of formula (I) prepared as described in 119. with a compound of formula (IIIe):

$$A—Y—ONO_2 + Act-C(O)—Y'—ONO_2$$
$$(I) \qquad\qquad\qquad (IIIe)$$

wherein Act, Y and Y' are as above defined and A is a radical of formula (IIa), (IIc), wherein $R_1$ is —H, $R_2$ is equal to $R_4$; $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and binds a group —Y'—ONO$_2$ following the same procedures described in 1b').

129. The compounds of general formula (I) wherein:
s and s' are equal to 1;
s", m, m', m", are 0
Y and Y' can be equal or different and are as above defined;
A is selected among:
(IIa) wherein $R_1$ is —C(O)O—$R_{1x}$ and it binds a group —Y'—ONO$_2$; $R_2$ is equal to $R_4$ and is as defined in 114.; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and binds a group —Y—ONO$_2$;
(IIc) wherein $R_1$ is —C(O)O—$R_{1x}$ and binds a group —Y'—ONO$_2$; $R_2$ is equal to $R_4$ and is as defined in 114.; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$—O—, and binds a group —Y—ONO$_2$;
can be prepared as follows:
129a) by reacting a compound of formula (I) prepared as described in 119. with a compound of formula (IIIf):

$$A—Y—ONO_2 + Act-C(O)—O—Y'—ONO_2$$
$$(I) \qquad\qquad\qquad (IIIf)$$

wherein Act, Y and Y' are as above defined and A is a radical of formula (IIa), (IIc), wherein $R_1$ is —H, $R_2$ is equal to $R_4$; $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}$O— and binds a group —Y—ONO$_2$, following the same procedures described in 3b).

130. The compounds of general formula (I) wherein:
s and s' are equal to 1;
s", m, m', m", are 0
Y and Y' can be equal or different and are as above defined;
A is selected among:
(IIa) wherein $R_1$ is —C(O)—$R_{1x}$ and it binds a group —Y'—ONO$_2$; $R_2$ is equal to $R_4$ and is as defined in 114.; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— binds $R_a$ binds a group —Y—ONO$_2$
(IIc) wherein $R_1$ is —C(O)—$R_{1x}$ and it binds a group —Y'—ONO$_2$; $R_2$ is equal to $R_4$ and is as defined in 114.; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— and $R_c$ binds a group —Y—ONO$_2$;
can be prepared as follows:
130a) be reacting a compound of formula (I) prepared as described in 120. with a compound of formula (IIIe):

$$A—Y—ONO_2 + Act-C(O)—Y'—ONO_2$$
$$(I) \qquad\qquad\qquad (IIIe)$$

wherein Act, Y and Y' are as above defined and A is a radical of formula (IIa), (IIc), wherein $R_1$ is —H, $R_2$ is -equal to $R_4$; $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— and binds a group —Y—ONO$_2$
following the same procedures described in 1b').

131. The compounds of general formula (I) wherein:
s and s' are equal to 1;
s", m, m', m", are 0
Y and Y' can be equal or different and are as above defined;
A is selected among:
(IIa) wherein $R_1$ is —C(O)O—$R_{1x}$ and binds a group —Y'—ONO$_2$; $R_2$ is equal to $R_4$ and is as defined in 114.; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— and binds a group —Y—ONO$_2$
(IIc) wherein $R_1$ is —C(O)O—$R_{1x}$ binds a group —Y'—ONO$_2$; $R_2$ is is -equal to $R_4$ and is as defined in 114.; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gxx}$—NH— or $R_{gxx}$—N(CH$_3$)— and binds a group —Y—ONO$_2$;
can be prepared as follows:
131a) by reacting a compound of formula (I) prepared as described in 120. with a compound of formula (IIIf):

$$A—Y—ONO_2 + Act-C(O)—O—Y'—ONO_2$$
$$(I) \qquad\qquad\qquad (IIIf)$$

wherein Act, Y and Y' are as above defined and A is as defined in 130a), following the same procedures described in 3b).

132. The compounds of general formula (I) wherein:
s, s' and m are equal to 1;
s", m', m", are 0
Y and Y' can be equal or different and are as above defined;
B is:

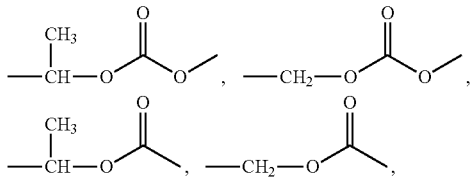

A is selected among:
(IIa) wherein $R_1$ is —C(O)—$R_{1x}$ and binds a group —Y'—ONO$_2$; $R_2$ is equal to $R_4$ and is as defined in 114.; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}O$—, and binds a group —B—Y—ONO$_2$;
(IIc) wherein $R_1$ is —C(O)—$R_{1x}$ and binds a group —Y'—ONO$_2$; $R_2$ is -equal to $R_4$ and is as defined in 114.; $R_c$ selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}O$—, and binds a group —B—Y—ONO$_2$;
can be prepared as follows:
132a) by reacting a compound of formula (I) prepared as described in 121. with a compound of formula (IIIe):

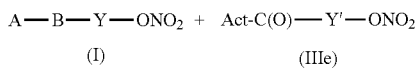

wherein Act, B, Y and Y' are as above defined and A is a radical of formula (IIa), (IIc), wherein $R_1$ is —H, $R_2$ is equal $R_4$; $R_a$ and $R_c$ are selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}O$— and binds a group B—Y—ONO$_2$;
following the same procedures described in 1b').

133. The compounds of general formula (I), wherein:
s, s' and m are equal to 1;
s", m', m", are 0
Y and Y' can be equal or different and are as above defined;
B is:

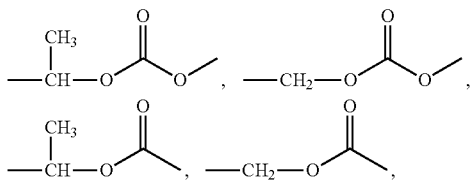

A is selected among:
(IIa) wherein $R_1$ is —C(O)O—$R_{1x}$ and binds a group —Y'—ONO$_2$; $R_2$ is equal to $R_4$ and is as defined in 114.; $R_a$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}O$—, and binds a group —B—Y—ONO$_2$;
(IIc) wherein $R_1$ is —C(O)O—$R_{1x}$ and it binds a group —Y'—ONO$_2$; $R_2$ is equal to $R_4$ and is as defined in 114.; $R_c$ is selected from $R_gC(O)CH_2$—NH—, $R_gC(O)CH_2$, $R_gC(O)(CH_2)_2$—, $R_gC(O)(CH_2)_4$—, wherein $R_g$ is $R_{gx}O$— and $R_g$ binds a group —B—Y—ONO$_2$;
can be prepared as follows:
133a) by reacting a compound of formula (I) prepared as described in 121. with a compound of formula (IIIf):

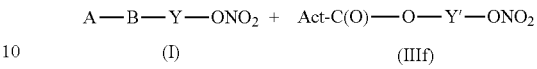

wherein Act, B, Y and Y' are as above defined and A is as defined in 132a), following the same procedures described in 3b).

134. The compounds of general formula (I) wherein:
s and s' are equal to 1;
s", m, m', m" are equal to 0;
Y and Y' are equal and are as above defined;
A is selected from (IIa), (IIc) or (IIt) wherein $R_1$ is —C(O)—$R_{1x}$ and it binds a group —Y—ONO$_2$ or a group —Y'—ONO$_2$, $R_2$ is equal to $R_4$ and is as defined in 114.; $R_a$ of formula (IIa) and $R_c$ of formula (IIc) are $R_hNH(CH_2)_p$— wherein p is an integer from 0 to 4, or $R_iNH(=NH)NH$—$(CH_2)_3$—, and $R_h$ and $R_i$ are $R_{hh}$—C(O)— or $R_{ii}$—C(O)— and $R_a$ and $R_c$ bind a group —Y—ONO$_2$ or a group —Y'—ONO$_2$;
in formula (IIt) $R_1$ is —C(O)—$R_{1x}$ and it binds a group —Y—ONO$_2$ or a group —Y'—ONO$_2$; $R_2$ is equal to $R_4$ and is as defined in 114.; d is 2 d' is 1, $R_t$ is —C(O)—$R_{tt}$ and it binds a group —Y—ONO$_2$ or a group —Y'—ONO$_2$;
can be prepared as follows:
134a) by reacting a compound of formula A with a compound of formula (IIIe)

$$A+Act-(O)C-Y-ONO_2 \quad (IIIe)$$

wherein Act and Y are as above defined and A is a compound of formula (IIa), (IIc) or (IIt) wherein $R_1$ is —H and $R_2$ is equal to $R_4$;
$R_a$ of formula (IIa) and $R_c$ of formula (IIc) are $R_hNH(CH_2)_p$— wherein p is an integer from 0 to 4, or $R_iNH(=NH)NH$—$(CH_2)_3$—, and $R_h$ and $R_i$ are —H;
in formula (IIt) $R_1$ is —H, $R_2$ is $R_4$; d is 2 d' is 1, $R_t$ is —H;
using a ratio A/(IIIe) 1:2 and applying the same procedure described in 1b').
134b) by reacting a compound of formula $A_{38}$ $$A_{38} \rightarrow A$$

wherein $A_{38}$ is a compound of formula (IIa), (IIc) or (IIt) wherein $R_1$ is —C(O)OC(CH$_3$)$_3$ and $R_2$ is equal to $R_4$;
$R_a$ of formula (IIa) and $R_c$ of formula (IIc) are $R_hNH(CH_2)_p$— wherein p is an integer from 0 to 4 and $R_h$ is —C(O)OC(CH$_3$)$_3$; or $R_{ia}NH(=NH)NH$—$(CH_2)_3$—, wherein $R_{ia}$ is the —Pbf group as already described;
in formula (IIt) $R_1$ is —C(O)OC(CH$_3$)$_3$, is $R_2$ is $R_4$; d is 2 d' is 1, $R_t$ is —C(O)OC(CH$_3$)$_3$;
with organic or inorganic acid as already described to hydrolize the —BOC protecting groups;
134c) by reacting commercially available compounds of formula $A_{39}$ with compounds (IIIx) or (IIIy) using the procedures described in 114b)

$$A_{39}+(IIIx) \rightarrow A_{38}$$

$$A_{39}+(IIIy) \rightarrow A_{38}$$

wherein $A_{39}$ is a radical of formula (IIa), (IIc) or (IIt) wherein $R_1$ is —C(O)OC(CH$_3$)$_3$ and $R_2$ is equal to —COOH or $R_{2a}$ wherein $R_{2a}$ is as described in 8b); d is 2 d' is 1, $R_t$ is —C(O)OC(CH$_3$)$_3$; $R_a$ of formula (IIa) and $R_c$ of formula (IIc) are: $R_h$NH(CH$_2$)$_p$— wherein p is an integer from 0 to 4, $R_h$ is —C(O)OC(CH$_3$)$_3$;

or $R_{ia}$NH(=NH)NH—(CH$_2$)$_3$— wherein $R_{ia}$ is as previously defined.

135. The compounds of general formula (I) wherein:
s and s' are equal to 1;
s", m, m', m", are equal to 0;
Y and Y' are equal and are as above defined;
A is a radical selected from (IIa), (IIc) and (IIt) wherein $R_1$ is —C(O)O—$R_{1x}$ and binds a group —Y—ONO$_2$ or a group —Y'—ONO$_2$; $R_2$ is equal to $R_4$ and is as defined in 114., $R_a$ of formula (IIa) and $R_c$ of formula (IIc) are $R_h$NH(CH$_2$)$_p$— wherein p is an integer from 0 to 4, or $R_i$NH(=NH)NH—(CH$_2$)$_3$—, and $R_h$ and $R_i$ are $R_{hh}$—OC(O)— or $R_{ii}$—OC(O)— and $R_a$ and $R_c$ bind a group —Y—ONO$_2$ or a group —Y'—ONO$_2$;
in formula (IIt) $R_1$ is —C(O)O—$R_{1x}$ and binds a group —Y—ONO$_2$ or a group —Y'—ONO$_2$, $R_2$ is equal to $R_4$ and is as defined in 114.; d is 2 d' is 1, $R_t$ is —C(O)O—$R_{tt}$ and binds a group —Y—ONO$_2$ or a group —Y'—ONO$_2$;
can be prepared as follows:
135a) by reacting a compound of formula A with a compound of formula (IIIf)

$$A+Act-(O)C—O—Y—ONO_2 \qquad (IIIf)$$

wherein Act and Y are as above defined and A is as defined in 134a) using a ratio A/(IIIf) 1:2 and applying the same procedure described in 3b).

136. The compounds of general formula (I) wherein:
s is equal to 1;
s', s", m, m' and m" are equal to 0;
Y is as above defined;
A is a radical of formula (IIa), (IIc) or (IIt) wherein $R_1$ is —C(O)—$R_{1x}$ and binds a group —Y—ONO$_2$; $R_2$ is equal to $R_4$ and is as defined in 114.; $R_a$ of formula (IIa) and $R_c$ of formula (IIc) are $R_h$NH(CH$_2$)$_p$— wherein p is on integer from 0 to 4, or $R_i$NH(=NH)NH—(CH$_2$)$_3$—, wherein $R_h$ and $R_i$ are —H;
in formula (IIt) d is 2 d' is 1, $R_t$ is —H;
can be obtained as follows:
136a) $R_a=R_c$ selected from $R_h$NH(CH$_2$)$_p$— wherein p is an integer from 0 to 4, $R_h$ is —H
by reacting a compound of formula (I) wherein s, s', s", m, m', m", Y, Y', Y" are as above defined in 136., A is a radical of (IIa), (IIc) or (IIt) wherein $R_1$, $R_2$, d, d', are as defined in 136., $R_a$ of formula (IIa) and $R_c$ of formula (IIc) are selected from $R_h$NH(CH$_2$)$_p$— wherein p is an integer from 0 to 4, $R_h$ is —C(O)OC(CH$_3$)$_3$;
in formula (IIt) $R_t$ is —C(O)OC(CH$_3$)$_3$;
with anhydrous or aqueous organic or inorganic acid to hydrolyze the —BOC protective groups following procedure well known in the literature.
136a') $R_a=R_c$ selected from $R_i$NH(=NH)NH—(CH$_2$)$_3$—, $R_i$ is —H;
reacting a compound of formula (Xd)

$$A_{40}\text{-Y—ONO}_2 \qquad (Xd)$$

wherein Y is as above defined and $A_{40}$ is a radical of formula (IIa), (IIc) wherein $R_1$ and $R_2$ are as defined in 136., $R_a$ of formula (IIa) and $R_c$ of formula (IIc) are selected from $R_{ia}$NH(=NH)NH—(CH$_2$)$_3$—, wherein $R_{ia}$ is the —Pbf protective group as already defined;
with anhydrous or aqueous organic or inorganic acid to hydrolyze the —Pbf protective groups following procedure well known in the literature.

136b) compounds described in 136a) and 136a') are respectively obtained by reacting a compound of formula $A_{41}$ or a compound of formula $A_{42}$ with a compound of formula (IIIe)

$$A_{41}+Act(O)C—Y'—ONO_2 \rightarrow (I) \qquad (IIIe)$$

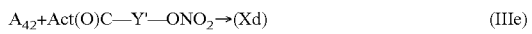

$$A_{42}+Act(O)C—Y'—ONO_2 \rightarrow (Xd) \qquad (IIIe)$$

wherein Act and Y are as above defined and:
$A_{41}$ is a compound of formula (IIa), (IIc) or (IIt) wherein $R_1$ is —H, $R_2$ is equal to $R_4$; $R_a$ of formula (IIa) and $R_c$ of formula (IIc) are $R_h$NH(CH$_2$)$_p$— wherein p is an integer from 0 to 4, $R_h$ is —C(O)OC(CH$_3$)$_3$; in formula (IIt) d and d' are as defined, in 136.,
$R_t$ is —C(O)OC(CH$_3$)$_3$;
$A_{42}$ is a compound of formula (IIa) or (IIc) wherein $R_1$ is —H, $R_2$ is equal to $R_4$; $R_a$ of formula (IIa) and $R_c$ of formula (IIc) are $R_{ia}$NH(=NH)NH—(CH$_2$)$_3$—, wherein $R_{ia}$ is the —Pbf protective group as already defined;
using the same procedure described 1b').

136c) compounds $A_{41}$ and $A_{42}$ are respectively obtained by reacting a compound of formula A or a compound of formula $A_{26}$, both described in 107b) with a compound of formula (IIIx) or (IIIy) as already described in 114b).

137. The compounds of general formula (I) wherein:
s is equal to 1;
s', s", m, m' and m" are equal to 0;
Y is as above defined;
A is selected from (IIa), (IIc) and (IIt) wherein $R_1$ is —C(O)O—$R_{1x}$ and binds a group —Y—ONO$_2$; $R_2$ is equal to $R_4$ and is as defined in 114.; $R_a$ of formula (IIa) and $R_c$ of formula (IIc) are $R_h$NH(CH$_2$)$_p$— wherein p is an integer from 0 to 4, or $R_i$NH(=NH)NH—(CH$_2$)$_3$, wherein $R_h$ and $R_i$ are —H;
in formula (IIt) d is 2 d' is 1, $R_t$ is —H;
can be obtained as follows:
137a) $R_a=R_c$ selected from $R_h$NH(CH$_2$)$_p$— wherein p is an integer from 0 to 4, $R_h$ is —H
by reacting a compound of formula (I) wherein s, s', s", m, m', m", Y, Y', Y" are as above defined in 137., A is a radical of (IIa), (IIc) or (IIt) wherein $R_1$, $R_2$, d, d', are as defined in 137., $R_a$ of formula (IIa) and $R_c$ of formula (IIc) are selected from $R_h$NH(CH$_2$)$_p$— wherein p is an integer from 0 to 4, $R_h$ is —C(O)OC(CH$_3$)$_3$;
in formula (IIt) $R_t$ is —C(O)OC(CH$_3$)$_3$;
with anhydrous or aqueous organic or inorganic acid to hydrolyze the —BOC protective groups following procedure well known in the literature.
137a') $R_a=R_c$ selected from $R_i$NH(=NH)NH—(CH$_2$)$_3$—, $R_i$ is —H;
reacting a compound of formula (Xe)

$$A_{43}\text{-Y—ONO}_2 \qquad (Xe)$$

wherein Y is as above defined and $A_{43}$ is a radical of (IIa), (IIc) wherein $R_1$ and $R_2$ are as defined in 137., $R_a$ of formula (IIa) and $R_c$ of formula (IIc) are selected from $R_{ia}$NH(=NH)NH—(CH$_2$)$_3$—, wherein $R_{ia}$ is the Pbf protective group as already defined;
with anhydrous or aqueous organic or inorganic acid to hydrolyze the —Pbf protective groups following procedure well known in the literature.

137b) compounds described in 137a) and 137a') are respectively obtained by reacting a compound of formula $A_{41}$ or a compound of formula $A_{42}$ both already defined in 136b) with a compound of formula (IIIf)

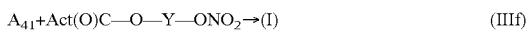

$A_{41}$+Act(O)C—O—Y—ONO$_2$→(I)　(IIIf)

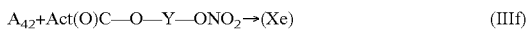

$A_{42}$+Act(O)C—O—Y—ONO$_2$→(Xe)　(IIIf)

wherein Act and Y are as above defined, using the same procedure described in 3b).
138. The compounds of general formula (I) wherein:
s is equal to 1;
s', s", m, m' and m" are equal to 0;
Y is as above defined;
A is selected from (IIa), (IIc) and (IIt) wherein $R_1$ is —H; $R_2$ is equal to $R_4$ and is as defined in 114.; $R_a$ of formula (IIa) and $R_c$ of formula (IIc) are $R_hNH(CH_2)_p$— wherein p is an integer from 0 to 4, or $R_iNH(=NH)NH$—$(CH_2)_3$—, wherein $R_h$ and $R_i$ are $R_{hh}$—C(O)— or $R_{ii}$—C(O)—, and bind a group —Y—ONO$_2$;
in formula (IIt) d is 2 d' is 1, $R_t$ is —C(O)—$R_{tt}$, and binds a group —Y—ONO$_2$;
can be obtained as follows:
138a) by reacting a compound of formula (I) wherein s, s', s", m, m', m", Y, Y', Y" are as above defined in 138., A is a radical of (IIa), (IIc) or (IIt) wherein $R_2$, $R_a$, $R_c$, d, d' and $R_t$ are as defined in 138., $R_1$ is —C(O)OC(CH$_3$)$_3$;
with anhydrous or aqueous organic or inorganic acid to hydrolyze the —BOC protective groups following procedure well known in the literature.
138b) by reacting a compound of formula A with a compound of formula (IIIe)

A+Act(O)C—Y—ONO$_2$　(IIIe)

wherein Act and Y are as above defined and A is a radical of (IIa), (IIc) or (IIt) wherein $R_1$ is —C(O)OC(CH$_3$)$_3$; $R_2$ is equal to $R_4$; $R_a$ of formula (IIa) and $R_c$ of formula (IIc) are $R_hNH(CH_2)_p$— wherein p is an integer from 0 to 4, or $R_iNH(=NH)NH$—$(CH_2)_3$—, wherein $R_h$ and $R_i$ are —H;
in formula (IIt) d and d' are as defined in 138., $R_t$ is —H; using the same procedure described in 1b').
138c) by reacting a compound of formula A with a compound of formula (IIIx) or (IIIy)

A+(IIIx)

A+(IIIy)

wherein A is a radical of formula (IIa), (IIc) or (IIt) wherein $R_1$ is —C(O)OC(CH$_3$)$_3$; $R_2$ is —COOH or $R_{2a}$ wherein $R_{2a}$ is the group —COAct as already described in 8; $R_a$ of formula (IIa) and $R_c$ of formula (IIc) are $R_hNH(CH_2)_p$— wherein p is an integer from 0 to 4, or $R_iNH(=NH)NH$—$(CH_2)_3$—, wherein $R_h$ and $R_i$ are —H;
in formula (IIt) d and d' are as defined in 138., $R_t$ is —H; using the same procedures described in 114b).
130. The compounds of general formula (I) wherein:
s is equal to 1;
s', s", m, m' and m" are equal to 0;
Y is as above defined;
A is selected from (IIa), (IIc) and (IIt) wherein $R_1$ is —H; $R_2$ is equal to $R_4$ and is as defined in 114.,
$R_a$ of formula (IIa) and $R_c$ of formula (IIc) are $R_hNH(CH_2)_p$— wherein p is an integer from 0 to 4, or $R_iNH(=NH)NH$—$(CH_2)_3$—,
wherein $R_h$ and $R_i$ are $R_{hh}$—OC(O)— or $R_{ii}$—OC(O)—; and bind a group —Y—ONO$_2$;
in formula (IIt) d is 2 d' is 1, $R_t$ is —C(O)O—$R_{tt}$, and it binds a group —Y—ONO$_2$;

can be obtained as follows:
139a) by reacting a compound of formula (I) wherein s, s', s", m, m', m", Y, Y', Y" are as above defined in 139., A is a radical of (IIa), (IIc) or (IIt) wherein $R_2$, $R_a$, $R_c$, d, d' and $R_t$ are as defined in 139., $R_1$ is —C(O)OC(CH$_3$)$_3$;
with anhydrous or aqueous organic or inorganic acid to hydrolyze the —BOC protective groups following procedure well known in the literature.
139b) by reacting a compound of formula A described in 138b) with a compound of formula (IIIf)

A+Act(O)C—O—Y—ONO$_2$　(IIIf)

wherein Act and Y are as above defined using the same procedure described in 3b).

EXAMPLE 1

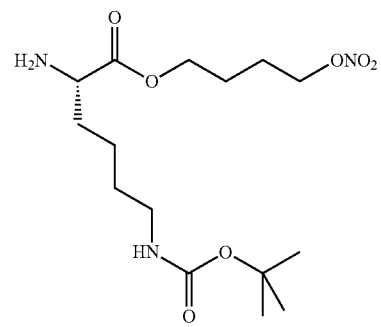

(S)-4-(nitrooxy)butyl 2-amino-6-(tert-butoxycarbonylamino)hexanoate (Corresponding to Compound 18)

Step A: (S)-4-(nitrooxy)butyl 1-(9H-fluoren-9-yl)-13,13-dimethyl-3,11-dioxo-2,12-dioxa-4,10-diazatetradecane-5-carboxylate Commercial N(α)-Fmoc-N(ε)-Boc-L-lysine pentafluorophenyl ester (6.51 mmol) and 4-(nitrooxy)-1-butanol (6.55 mmol) were dissolved in DMF (12 ml) and the mixture was cooled to 0° C. N,N-dimethylaminopyridine (DMAP) (6.55 mmol) were added and the reaction was slowly warmed to room temperature and stirred for 4 hours. Then the mixture was concentrate under reduced pressure and diluted with EtOAc, washed with 5% aqueous Na$_2$HPO$_4$ and brine.
The organic layer was dried over sodium sulphate and concentrated under reduced pressure.
The residue was purified by flash chromatography (n-hexan/EtOAc 70:30 as eluent) yielding the title compound (2.52 g, 66%).

Step B: (S)-4-(nitrooxy)butyl 2-amino-6-(tert-butoxycarbonylamino)hexanoate

To a solution of S)-4-(nitrooxy)butyl 1-(9H-fluoren-9-yl)-13,13-dimethyl-3,11-dioxo-2,12-dioxa-4,10-diazatetradecane-5-carboxylate (2.52 g, 4.30 mmol) in CH$_3$CN (30 ml), piperidine (2.12 ml, 21.5 mmol) was added in the dark, the reaction was stirred at rt for 25 min. Then the mixture was concentrated to a small volume and diluted with EtOAc (150 ml) and washed with 5% aqueous NaHPO$_4$ (2×70 ml). The organic layer was dried over sodium sulphate and concentrated under reduced pressure.

The residue was purified by flash chromatography (CH$_2$Cl$_2$/MeOH 98:2 as eluent), yielding the title compound (0.960 g, 61%).

$^1$H-NMR (DMSO-d$_6$): 6.78 (1H, t), 4.55 (2H, t), 4.07 (2H, m), 3.26 (2H, t), 2.87 (1H, m), 1.73-1.65 (4H, m), 1.64-1.40 (2H, m), 1.37 (9H, s), 1.36-1.22 (4H, s).

EXAMPLE 2

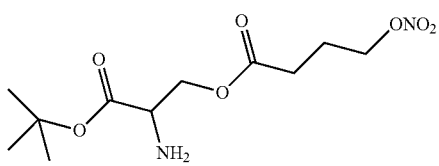

2-Amino-3-tert-butoxy-3-oxopropyl 4-(nitrooxy)butanoate (Corresponding to Compound 405)

Step A: tert-butyl 2-(((9H-fluoren-9-yl)methoxy)carbonylamino)-3-hydroxypropanoate To a solution of commercial N-Fmoc-L-serine (1.5 g, 4.58 mmol) in EtOAc (40 ml), a solution of t-butyl 2,2,2-trichloroacetimidate (4.00 g, 18.32 mmol) in cyclohexane (18 ml) was added dropwise. After stirring at room temperature for 24 hrs, the solution was evaporated and the residue was purified by flash chromatography (n-Hexane/EtOAc 70:3), yielding the title compound (1.20 g, 68%).

Step B: 2-(((9H-fluoren-9-yl)methoxy)carbonylamino)-3-tert-butoxy-3-oxopropyl 4-(nitrooxy)butanoate To a solution of 2-(((9H-fluoren-9-yl)methoxy)carbonylamino)-3-tert-butoxy-3-oxopropyl 4-(nitrooxy)butanoate (1.20 g, 3.13 mmol), 4-(nitrooxy)butyric acid pentafluorophenyl ester (1.18 g, 3.76 mmol) and scandium trifluoromethanesulfonate (0.308 g, 0.626 mmol) in CH$_2$Cl$_2$ (25 ml) cooled to 0° C., was added N,N-dimethylaminopyridine (DMAP) (0.459 g, 3.76 mmol). The resulting mixture was stirred at room temperature for 18 hours. Then it was diluted with CH$_2$Cl$_2$ and washed with 5% aqueous Na$_2$HPO$_4$ and brine. The organic layer was dried over sodium sulphate and concentrated under reduced pressure.

The residue was purified by flash chromatography (n-hexane/EtOAc 70:30 as eluent) affording the title compound (1.26 g, 78%).

Step C: 2-Amino-3-tert-butoxy-3-oxopropyl 4-(nitrooxy)butanoate

To a solution of 2-(((9H-fluoren-9-yl)methoxy)carbonylamino)-3-tert-butoxy-3-oxopropyl 4-(nitrooxy)butanoate 1.26 g, 2.45 mmol) in CH$_3$CN (15 ml), piperidine (1.21 ml, 12.2 mmol) was added in the dark, the reaction was stirred at room temperature for 25 min. Then the mixture was concentrated to a small volume and diluted with EtOAc (80 ml) and washed with 5% aqueous NaHPO$_4$. The organic layer was dried over sodium sulphate and concentrated under reduced pressure. The residue was purified by flash chromatography (CH$_2$Cl$_2$/MeOH 98:2 as eluent) yielding the title compound (0.500 g, 70%).

$^1$H-NMR (CDCl$_3$): 6.49, 4.61-4.50 (3H, m), 3.95 (2H, d), 2.43 (2H, t), 2.22-2.08 (2H, m), 1.05 (9H, s).

EXAMPLE 3

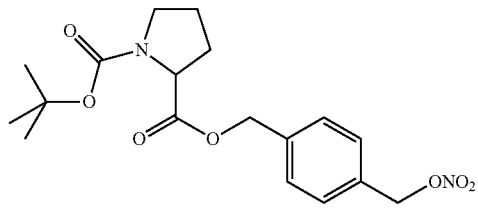

1-tert-Butyl 2-(4-(nitrooxymethyl)benzyl)pyrrolidine-1,2-dicarboxylate (Corresponding to Compound 7)

Step A: 1-tert-butyl 2-(4-(chloromethyl)benzyl)pyrrolidine-1,2-dicarboxylate

N-Boc-L-prolin (2.47 g, 11.5 mmol) and 4-(chloromethyl)benzyl alcohol (1.50 g, 9.58 mmol) were dissolved in CH$_2$Cl$_2$ (50 ml) and the mixture was cooled to 0° C. N-Ethyl-N'-(3-dimethylaminopropyl)carbodiimide (EDC) (2.75 g, 14.4 mmol) and N,N-dimethylaminopyridine (DMAP) (0.235 g, 1.92 mmol) were added and the reaction was slowly warmed to room temperature and stirred for 4 hours. Then the mixture was diluted with CH$_2$Cl$_2$ (200 ml) and washed with 5% aqueous NaHCO$_3$, 5% aqueous Na$_2$HPO$_4$ and brine. The organic layer was dried over sodium sulphate and concentrated under reduced pressure. The residue was purified by flash chromatography (n-hexane/EtOAc 80:20 as eluent) affording the title compound. (2.98 g, 88%).

Step B: 1-tert-Butyl 2-(4-(nitrooxymethyl)benzyl)pyrrolidine-1,2-dicarboxylate

To a solution of 1-tert-butyl 2-(4-(chloromethyl)benzyl)pyrrolidine-1,2-dicarboxylate (0.630 g, 1.78 mmol) in CH$_3$CN (13 ml), AgNO$_3$ (0.756 g, 4.45 mmol) was added and the reaction was heated in a microwave apparatus (150° C., 20 min). The formed salts were filtered off and the solvent was concentrated, then the residue was diluted with EtOAc (100 ml) and washed with brine. The organic layer was dried over sodium sulphate and concentrated under reduced pressure yielding the title compound (0.655 g, 96%).

$^1$H-NMR (CDCl$_3$): 7.41 (4H, d), 5.44 (2H, s), 5.30-5.10 (2H, m), 4.42-4.27 (2H, m), 3.57-3.42 (2H, m), 2.30-2.15 (1H, m), 2.00-1.85 (3H, m), 1.48-1.35 (9H, m).

EXAMPLE 4

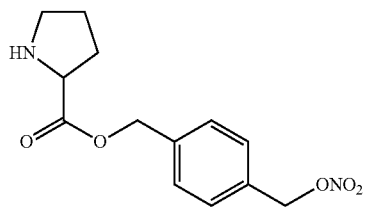

4-[(nitrooxy)methyl]benzylpyrrolidine-2-carboxylate hydrochloride (Corresponding to Compound 3)

To a solution of 1-tert-Butyl 2-(4-(nitrooxymethyl)benzyl) pyrrolidine-1,2-dicarboxylate, obtained in Example 3, (0.543 g, 1.43 mmol) in $CH_2Cl_2$ (14 ml) cooled to 0° C., $HCl_{gas}$ was bubbled for 2 hours. The solvent was concentrated and the residue was treated with diethyl ether, affording the title compound (0.446 g, 99%).
$^1$H-NMR (CDCl$_3$): 9.16 (bs), 7.40 (4H, d), 5.43 (2H, s) 5.31-5.17 (2H, m), 4.52 (1H, m), 3.52 (2H, m), 2.49-2.38 (1H, m), 2.20-2.00 (3H, m).

EXAMPLE 5

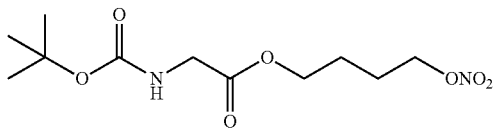

4-(nitrooxy)butyl 2-(tert-butoxycarbonylamino)acetate (Corresponding to Compound 16)

Applying the same procedure described in Example 1, starting from commercially available N-Boc-L-glycine, N-hydroxysuccinimido ester (2.33 g, 8.56 mmol), the title compound was obtained. (3.00 g, 80%).
$^1$H-NMR (CDCl$_3$) 5.04 (1H, bt), 4.49 (2H, t), 4.20 (2H, t), 3.91 (2H, d), 1.81 (4H, m), 1.46 (9H, s).

EXAMPLE 6

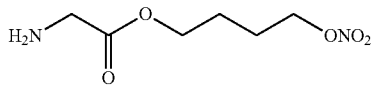

4-(nitrooxy)butyl 2-aminoacetate hydrochloride (Corresponding to Compound 21)

The title compound was obtained as a white solid starting from 4-(nitrooxy)butyl 2-(tert-butoxycarbonylamino)acetate, prepared as described in Example 5 following the procedure described in Example 4 (2.34 g, quantitative yield).
$^1$H-NMR (CDCl$_3$): 4.53 (2H, t), 4.29 (2H, t), 4.04 (2H, d), 3.74 (2H, d), 1.84 (4H, m).

EXAMPLE 7

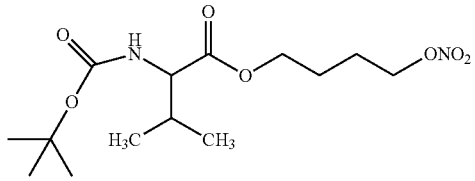

4-(Nitrooxy)butyl 2-(tert-butoxycarbonylamino)-3-methylbutanoate (Corresponding to Compound 149)

Step A: 4-chloro 2-(tert-butoxycarbonylamino)-3-methylbutanoate

N-Boc-L-valine (3.48 g, 16.0 mmol), 4-chloro-1-butanol (3.47 g, 32.0 mmol) and N-hydroxybenzotriazole (HOBT) (3.24 g, 24.0 mmol) were dissolved in $CH_2Cl_2$ (80 ml) and the mixture was cooled to 0° C. N-Methylmorpholine (NMM) (3.24 g, 32.0 mmol) and N,N,N',N'-tetramethyl-O-(1H-benzotriazol-1-yl)uronium hexafluorophosphate (HBTU) (6.67 g, 17.6 mmol) were added and the reaction was slowly warmed to room temperature and stirred for 24 hours. Then the mixture was diluted with $CH_2Cl_2$ (200 ml) and washed with 5% aqueous NaHCO$_3$, HCl 1N and brine. The organic layer was dried over sodium sulphate and concentrated under reduced pressure. The residue was purified by flash chromatography (n-hexane/EtOAc 90:10) affording the title compound (2.98 g, 64%).

Step B: 4-(Nitrooxy)butyl 2-(tert-butoxycarbonylamino)-3-methylbutanoate methylbutanoate To a solution of 4-chlorobutyl 2-tert-butoxycarbonylamino)-3-methylbutanoate (0.630 g, 1.78 mmol) in $CH_3CN$ (13 ml), AgNO$_3$ (0.756 g, 4.45 mmol) was added and the reaction was heated in a microwave apparatus (150° C., 20 min). The formed salts were filtered off and the solvent was concentrated. Then the residue was diluted with EtOAc (100 ml) and washed with brine, dried over sodium sulphate and concentrated under reduced pressure yielding the title compound (0.655 g).
$^1$H-NMR (CDCl$_3$): 5.00 (1H, d), 4.50 (2H, t), 4.24-4.16 (3H, m), 2.20-2.09 (1H, m), 1.90-1.74 (4H, m), 1.46 (9H, s), 0.99 (3H, d), 0.92 (3H, d).

EXAMPLE 8

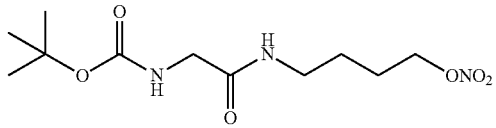

tert-butyl 2-(4-(nitrooxy)butylamino)-2-oxoethylcarbamate (Corresponding to Compound (12))

Step A: tert-butyl 2-(4-hydroxybutylamino)-2-oxoethylcarbamate

4-Amino-1-butanol (0.686 g, 7.70 mmol) and triethylamine (0.779 g, 7.70 mmol) were dissolved in $CH_2Cl_2$ (40 ml) and the mixture was cooled to 0° C. A suspension of commercial N-Boc-glycine N-hydroxysuccinimido ester (2.10 g; 7.70 mmol) in $CH_2Cl_2$ (40 ml) was added and the reaction was slowly warmed to room temperature and stirred for 24 hours. Then, the mixture was diluted with $CH_2Cl_2$ (150 ml) and washed with 5% aqueous Na$_2$HPO$_4$ and brine. The aqueous layer was extracted twice with $CH_2Cl_2$ and twice with a mixture of EtOAc/MeOH 98:2. The organic layers were dried over sodium sulphate and concentrated under reduced pressure. The residue was purified by flash chromatography (n-hexane/i-prOH 80:20 affording the title compound (2.16 g).

Step B:
2-(4-(nitrooxy)butylamino)-2-oxoethylcarbamate

To a solution of tert-butyl 2-(4-hydroxybutylamino)-2-oxoethylcarbamate (2.16 g, 8.77 mmol), tetraethylammonium nitrate (3.37 g, 17.54 mmol) and 2,6-di-tert-butyl-4-methylpyridine (2.71 g, 13.16 mmol) in $CH_2Cl_2$ (60 ml) cooled to −70° C. and under nitrogen, a solution of trifluoromethansulfonic anhydride (2.72 g, 9.65 mmol) in $CH_2Cl_2$ (40 ml) was added drop wise. The resulting mixture was stirred for 3 hours at −65° C. Then the mixture was slowly warmed to room temperature, diluted with $CH_2Cl_2$ and washed with 5% aqueous $Na_2HPO_4$. The organic layer was dried over sodium sulphate and concentrated under reduced pressure.

The residue was purified by flash chromatography $CH_2Cl_2$/$CH_3CN$ 70:30 as eluent) affording the title compound. (2.04 g, 80%).

$^1$H-NMR (CDCl$_3$) 6.30 (1H, s), 5.15 (1H, s), 4.48 (2H, t), 3.79 (2H, d), 3.37-3.31 (2H, m), 1.80-1.74 (2H, m), 1.67-1.62 (2H, m), 1.63 (9H, s).

EXAMPLE 9

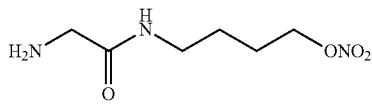

4-(2-Aminoacetamido)butyl nitrate hydrochloride
(Corresponding to Compound 23)

The title compound was obtained as a white solid from tert-butyl 2-(4-(nitrooxy)butylamino)-2-oxoethylcarbamate (Example 8) following the procedure described in Example 4. (1.58 g, quantitative yield).

$^1$H-NMR (CDCl$_3$) 8.55 (1H, s), 8.17 (2H, s), 4.54 (2H, t), 3.55-3.48 (2H, m), 3.18-3.12 (2H, m), 1.72-1.65 (2H, m), 1.53-1.48 (2H, m).

EXAMPLE 10

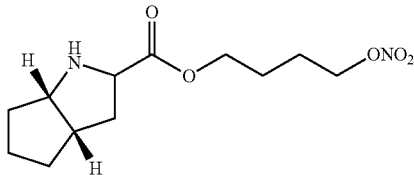

(2S,3aS,6aS)-4-(Nitrooxy)butyl
octahydrocyclopenta[b]pyrrole-2-carboxylate
(Corresponding to Compound 512

Step A: (2S,3aS,6aS)-1-(9H-fluoren-9-yl)methyl
2-benzylhexahydrocyclopenta[b]pyrrole-1,2(2H)-dicarboxylate To a solution of commercial (2S,3aS,6aS)-benzyl octahydrocyclopenta[b]pyrrole-2-carboxylatehydrochloride (1.00 g, 3.60 mmol) and TEA (1.15 ml, 7.92 mmol) in $CH_3CN$ (15 ml) cooled in an ice bath 9-fluorenylmethoxycarbonyl chloride (1.01 g, 4.25 mmol) was added. The resulting mixture was stirred at room temperature overnight. Then the mixture was concentrated and diluted with $CH_2Cl_2$ (50 ml), washed with a solution of $Na_2HPO_4$ 5% (2×30 ml) and brine (1×30 ml). The organic phase was dried over sodium sulphate and concentrated under reduced pressure to give an oil that slowly crystallized on storage affording the title compound (1.68 g, 100%).

Step B: (2S,3aS,6aS)-1-(((9H-fluoren-9-yl)methoxy)
carbonyl)octahydrocyclopenta[b]pyrrole-2-carboxylic acid To a solution of (2S,3aS,6aS)-1-(9H-fluoren-9-yl)methyl 2-benzylhexahydrocyclopenta[b]pyrrole-1,2(2H)-dicarboxylate (1.68 g, 3.6 mmol) in EtOH 95% (15 ml) was added Palladium on carbon 10% (0.2 g, 0.18 mmol) and cyclohexene (3.5 ml, 36 mmol). The resulting mixture was refluxed for 7 h. The solvent was evaporated and the crude was diluted with $CH_2Cl_2$ (20 ml). The suspension was filtered on celite the organic phase was evaporated under vacuum. The residue was purified by flash chromatography ($CH_2Cl_2$/$CH_3CN$ 50:50) to give the title compound as a white foam (0.5 g, 37%)

Step C: (2S,3aS,6aS)-(9H-fluoren-9-yl)methyl 2-(4-chlorobutyl) hexahydrocyclopenta[b]pyrrole-1,2
(2H)-dicarboxylate (2S,3aS,6aS)-1-(((9H-fluoren-9-yl)methoxy)carbonyl)octahydrocyclopenta[b]pyrrole-2-carboxylic acid (0.250 g, 0.66 mmol) and 4-chloro-1-butanol (0.1 ml, 0.99 mmol) were dissolved under nitrogen in $CH_2Cl_2$ (5 ml) and the mixture was cooled to 0° C. N-ethyl-N'-(3-dimethylaminopropyl)carbodiimide hydrochloride (EDC) (0.190 g, 0.99 mmol) and N,N-dimethylaminopyridine (DMAP) (0.016 g, 0.13 mmol) were added and the reaction was slowly warmed to room temperature and stirred for 4 h. Then the mixture was diluted with $CH_2Cl_2$ (10 ml) and washed with 5% aqueous $NaHCO_3$, 5% aqueous $Na_2HPO_4$ and brine. The organic layer was dried over sodium sulphate, concentrated under reduced pressure and purified by flash chromatography (n-hexane/EtOAc 80:20 as eluent) affording the title compound as an oil (0.14 g, 45%)

Step D: (2S,3aS,6aS)-1-(9H-fluoren-9-yl)methyl 2-(4-(nitrooxy)butyl)hexahydrocyclopenta[b]pyrrole-1,2(2H)-dicarboxylate To a solution of (2S,3aS,6aS)-1-(((9H-fluoren-9-yl)methoxy)carbonyl)octahydrocyclopenta[b]pyrrole-2-carboxylic acid (0.13 g, 0.27 mmol) in $CH_3CN$ (1.7 ml), $AgNO_3$ (0.118 g, 0.69 mmol) was added and the reaction was heated to 150° C. for 20 min in a microwave apparatus. The formed salts were filtered off and the solvent was concentrated affording the title compound as a yellow solid (0.133 g, 100%).

To a solution of (2S,3aS,6aS)-1-(9H-fluoren-9-yl)methyl 2-(4-(nitrooxy)butyl)hexahydrocyclopenta[b]pyrrole-1,2 (2H)-dicarboxylate (0.133 g, 0.27 mmol) in $CH_3CN$ (2 ml), piperidine (133 μl, 1.35 mmol) was added in the dark; the reaction was stirred at room temperature for 25 min. Then the solution was evaporated, diluted with pH 3 aqueous buffer and the aqueous phase was extracted with hexane. The solution was basified to pH 9 and finally extracted with diethyl ether. The organic layer was dried over sodium sulphate and concentrated under reduced pressure affording the title compound as an oil (0.04 g, 50%).

¹H-NMR (DMSO-d₆) 4.55 (2H, t); 4.13-3.96 (3H, m); 3.81 (1H, m); 3.68 (1H, bs); 2.66-2.51 (1H, m); 2.34-2.19 (1H, m); 1.81-1.31 (11H, m).

EXAMPLE 11

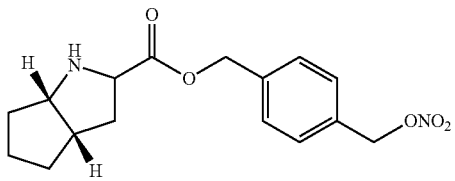

(2S,3aS,6aS)-4-(nitrooxymethyl)benzyl octahydrocyclopenta[b]pyrrole-2-carboxylate (Corresponding to Compound 520)

The title compound was prepared following the procedure described in Example 10 using 4-(chloromethyl)benzyl alcohol instead of 4-chloro-1-butanol in Step C.

¹H-NMR (DMSO-d₆): 7.51-7.21 (4H, m); 5.47 (2H, s); 5.09 (2H, s) 4.10 (1H, m); 3.82 (1H, m); 3.68 (1H, m); 2.62 (1H, m); 2.38 (1H, m); 1.92-1.05 (9H, m)

EXAMPLE 12

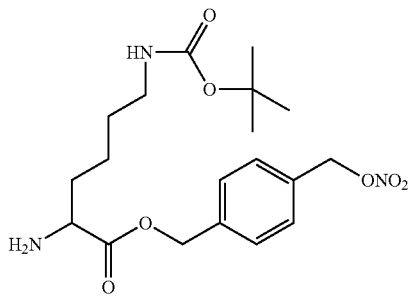

4-[(nitrooxy)methyl]benzyl 2-amino-6-(tert-butoxycarbonylamino)hexanoate (Corresponding to Compound 24)

The title compound was prepared following procedure already described in Examples 1 and 11 (0.010 g, 10%).

¹H-NMR (DMSO-d₆): 7.48-7.61 (8H, m); 6.78 (1H, t); 5.54 (2H, s); 5.15 (2H, s); 4.07 (1H, m); 2.87 (1H, m); 1.73-1.65 (2H, m); 1.36-1.22 (13H, m).

EXAMPLE 13

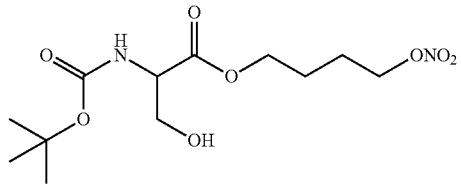

4-(nitrooxy)butyl 2-(tert-butoxycarbonylamino)-3-hydroxypropanoate (Corresponding to Compound (45))

Starting from Boc-L-serine and following the procedure described in Example 3 the title was obtained as an oil (0.350 g, 48%).

¹H-NMR (CDCl₃): 5.44 (1H, bs); 4.50 (2H, t); 4.38 (1H, m); 4.25 (2H, m); 3.97 (2H, m); 1.84 (4H, m); 1.47 (9H, s).

EXAMPLE 14

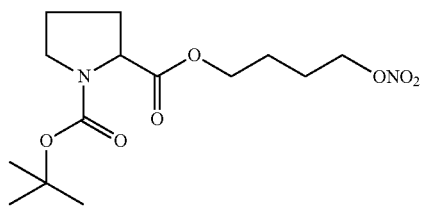

1-tert-butyl 2-(4-(nitrooxy)butyl)pyrrolidine-1,2-dicarboxylate

Starting from Boc-L-Proline and 4-chloro-1-butanol and following the procedure described in Example 3 the title compound was obtained as an oil.

¹H-NMR (CDCl₃): 4.50 (2H, t), 4.10-4.40 (3H, m), 3.65-3.33 (2H, m), 2.34-1.70 (8H, m), 1.45 (9H, d).

EXAMPLE 15

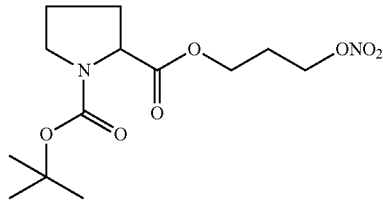

1-tert-butyl 2-(3-(nitrooxy)propyl)pyrrolidine-1,2-dicarboxylate

Starting from Boc-L-Proline and 3-bromo-1-propanol and following the procedure described in Example 3 the title compound was obtained as an oil.

$^1$H-NMR (CDCl$_3$): 4.56-4.52 (2H, m); 4.31-4.19 (3H, m); 3.57-3.35 (2H, m); 2.28-1.80 (6H, m); 1.43 (9H, d).

EXAMPLE 16

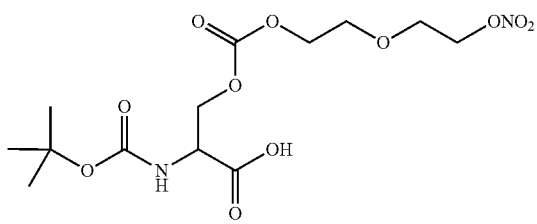

2,2-dimethyl-15-(nitrooxy)-4,9-dioxo-3,8,10,13-tetraoxa-5-azapentadecane-6-carboxylic acid (Corresponding to Compound 400)

Into a solution or N-Boc-L-Serine (1.66 g, 8.12 mmol), diisopropylethyl amine (DIPEA) (1.41 ml, 8.12 mmol), N,N-dimethylaminopyridine (DMAP) (1.19 g, 9.74 mmol) and scandium triflate (1.20 g, 2.43 mmol) in CH$_2$Cl$_2$ (40 ml), cooled to –10° C., a solution of 2-[2-(nitrooxy)ethoxy]ethyl 4-nitrophenyl carbonate in CH$_2$Cl$_2$ (40 ml) was added dropwise. The reaction was slowly warmed to room temperature and stirred for 24 h. Then the organic phase was washed with pH 3 aqueous buffer and concentrated under reduced pressure. The crude was partitioned between aqueous 5% aqueous Na$_2$HPO$_4$ and diethyl ether and extracted twice with diethyl ether. The aqueous phase was acidified to pH 3 and extracted with CH$_2$Cl$_2$. The organic phase was finally dried over sodium sulphate and concentrated under reduced pressure to give the title compound as an oil. (2.4 g, 80%)

$^1$H-NMR (CDCl$_3$): 5.54 (1H, bs); 4.63 (2H, m); 4.52 (3H, m); 4.29 (2H, m); 3.86-3.69 (4H, m); 1.46 (9H, s).

EXAMPLE 17

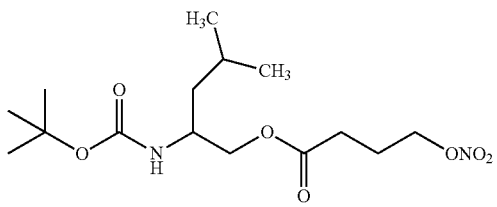

2-(tert-butoxycarbonylamino)-4-methylpentyl 4-hydroxybutanoate (Corresponding to Compound (510))

Step A:
2-(tert-butoxycarbonylamino)-4-methylpentyl 4-bromobutanoate tert-Butyl 1-hydroxy-4-methylpentan-2-ylcarbamate (2.00 g, 9.20 mmol) and 4-bromo-butyric acid (2.57 g, 15.38 mmol) were dissolved in CH$_2$Cl$_2$ (40 ml) and the mixture was cooled to 0° C. EDC (4.20 g, 21.90 mmol) and DMAP (0.27 g, 2.21 mmol) were added and the reaction was slowly warmed to room temperature and stirred overnight. Then the reaction was treated with a solution of 5% aqueous NaH$_2$PO$_4$ (100 ml). The organic layer was washed with a solution of 10% aqueous Na$_2$CO$_3$ (100 ml) and brine, dried over Na$_2$SO$_4$, filtered and concentrated. The obtained crude clear oil corresponding to the title compound (3.30 g) was used without any further purification.

Step B:
2-(tert-Butoxycarbonylamino)-4-methylpentyl 4-(nitrooxy)butanoate

To a solution of crude 2-(tert-butoxycarbonylamino)-4-methylpentyl 4-bromobutanoate (3.30 g) in CH$_3$CN (60 ml), AgNO$_3$ (4.20 g, 24.52 mmol) was added. The resulting solution (divided into 5 vials) was heated in a microwave apparatus (120° C., 3 minutes). Then the formed salts were filtered off, the solvent was concentrated and the residue purified by flash chromatography (n-hexane/EtOAc 80:20 as eluent) affording the title compound (1.05 g, yield: 33.5%) as a clear oil.

$^1$H-NMR (CDCl$_3$): 4.54 (2H, t); 4.48-4.34 (1H, m); 2.49 (2H, t); 2.18-1.99 (2H, m); 1.79-1.57 (1H, m); 1.39-1.22 (2H, m); 1.00-0.86 (6H, m).

EXAMPLE 18

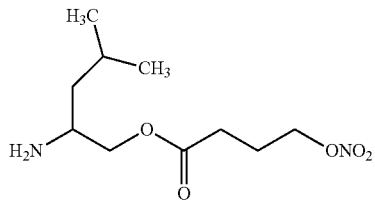

2-Amino-4-methylpentyl 4-(nitrooxy)butanoate hydrochloride (Corresponding to Compound 507)

The title compound was prepared from 2-(tert-butoxycarbonylamino)-4-methylpentyl 4-(nitrooxy)butanoate (described in Example 17) following the procedure described in Example 4 (0.71 g, 90%).

¹H-NMR (DMSO-d₆): 4.56 (2H, t); 4.27-4.22 (1H, m); 4.11-4.06 (1H, m); 3.39-3.32 (2H, m); 2.51 (2H, t); 2.01-1.92 (2H, m); 1.75-1.68 (1H, m); 1.51-1.38 (2H, m); 0.90 (6H, d).

EXAMPLE 19

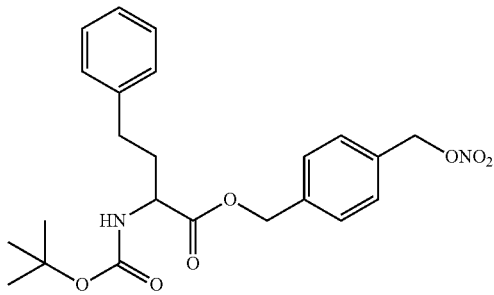

4-[(Nitrooxy)methyl]benzyl 2-(tert-butoxycarbonylamino)-4-phenylbutanoate (Corresponding to Compound 13)

The title compound was prepared as a clear oil from 2-(tert-butoxycarbonylamino)-4-phenylbutanoic acid following procedure described in Example 3.

¹H-NMR (CDCl₃): 7.34 (4H, m); 5.07-5.04 (1H, m); 4.49 (2H, t); 4.36-4.34 (1H, m); 4.23-4.11 (2H, m); 2.70 (2H, t); 2.19-2.11 (1H, m); 2.02-1.94 (1H, m); 1.92-1.76 (4H, m); 1.61 (9H, s).

EXAMPLE 20

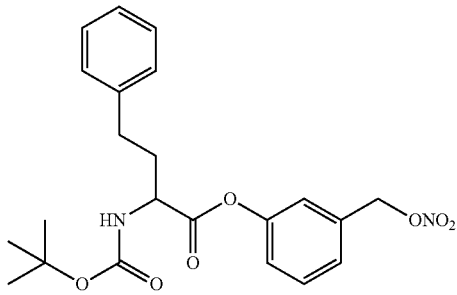

3-[(Nitrooxy)methyl]phenyl 2-(tert-butoxycarbonylamino)-4-phenylbutanoate (Corresponding to Compound 86)

Starting from 2-(tert-butoxycarbonylamino)-4-phenylbutanoic acid and 3-(bromomethyl)phenyl alcohol and following the procedure reported in Example 3 the title compound was obtained as an oil.

¹H-NMR (CDCl₃): 7.50-7.16 (7H, m); 7.15-7.05 (2H, m); 5.42 (2H, s); 5.07 (1H, d); 4.65-4.47 (1H, m); 2.80 (2H, t); 2.44-2.23 (1H, m); 2.23-1.99 (1H, m); 1.48 (9H, s).

EXAMPLE 21

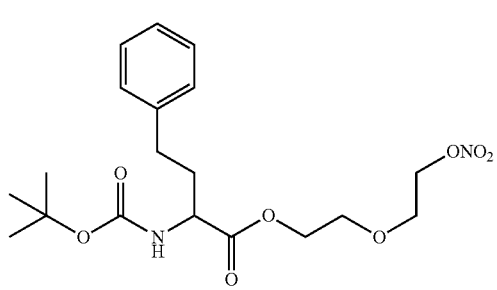

2-(2-(Nitrooxy)ethoxy)ethyl 2-(tert-butoxycarbonylamino)-4-phenylbutanoate

Starting from 2-(tert-butoxycarbonylamino)-4-phenylbutanoic acid and 2-chloroethoxyethyl alcohol and following the procedure reported in Example 3 the title compound was obtained as an oil.

¹H-NMR (CDCl₃): 7.19-7.03 (5H, m); 5.08 (1H, d); 4.50-4.45 (2H, m); 4.22-4.06 (3H, m); 3.65-3.55 (4H, m); 2.56 (2H, t); 2.08-1.80 (2H, m); 1.32 (9H, s).

EXAMPLE 22

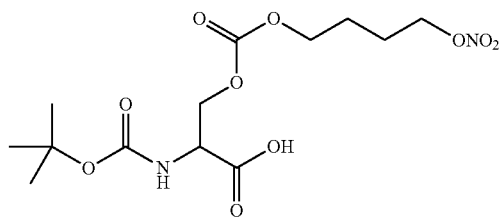

2,2-Dimethyl-14-(nitrooxy)-4,9-dioxo-3,8,10-trioxa-5-azatetradecane-6-carboxylic acid (Corresponding to Compound (401))

The title compound was prepared from N-Boc-L-serine and 4-chlorobutyl chloroformate following procedure described in Example 16.

¹H-NMR (CDCl₃): 5.50 (1H, d); 4.52-4.40 (5H, m); 4.19 (2H, t); 1.88-1.75 (4H, m); 1.46 (9H, s).

EXAMPLE 23

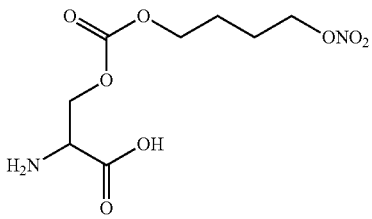

2-amino-3-((4-(nitrooxy)butoxy)carbonyloxy)propanoic acid hydrochloride (Corresponding to Compound (407))

The title compound was obtained as a white solid from 2,2-dimethyl-14-(nitrooxy)-4,9-dioxo-3,8,10-trioxa-5-azatetradecane-6-carboxylic acid (described in Example 22) following procedure described in Example 4.

¹H-NMR (DMSO-d₆): 4.60-4.41 (4H, m); 4.18-4.13 (3H, m); 1.78-1.65 (4H, m).

EXAMPLE 24

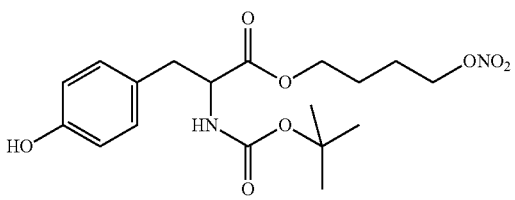

4-(nitrooxy)butyl 2-(tert-butoxycarbonylamino)-3-(4-hydroxyphenyl)propanoate (Corresponding to Compound 67)

To a solution of Boc-(L)-tyrosine 5.0 g, 17.77 mmol) in N,N-dimethylformamide (40 ml) cesium carbonate (5.79 g, 17.77 mmol) was added. The reaction was cooled at 0° C. and a solution or 4-bromobutyl nitrate (17.77 mmol) in dichloromethane (20% w/w, 17.06 g) was added drop wise. The reaction was stirred at 0° C. for 20 minutes and then at room temperature for 22 hours. The mixture was poured into a 5% aqueous NaH₂PO₄ solution and extracted with diethyl ether (40×4 ml), the organic layers were dried over sodium sulfate and concentrated under reduced pressure. The residue was purified by flash chromatography (n-hexane/EtOAc from 9:1 to 1:1 as eluent affording the title compound.

¹H-NMR (CDCl₃): 7.00 (2H, d, J=8 Hz); 6.76 (2H, d, J=8 Hz); 5.01 (1H, bd, J=8 Hz); 4.51 (1H, m); 4.42 (2H, t, J=6 Hz); 4.12 (2H, m); 3.00 (2H, d, J=6 Hz); 1.69 (4H, m); 1.44 (9H, s).

EXAMPLE 25

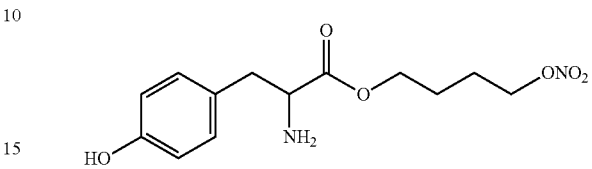

4-(nitrooxy)butyl 2-amino-3-(4-hydroxyphenyl)propanoate (Corresponding to Compound (58))

The title compound was obtained from 4-(nitrooxy)butyl 2-(tert-butoxycarbonylamino)-3-(4-hydroxyphenyl)propanoate (described in Example 24) following procedure described in Example 4.

¹H-NMR (CDCl₃): 7.05 (2H, dd, J=9 and 3 Hz); 6.74 (2H, dd, J=9 and 3 Hz); 4.45 (2H, t, J=6 Hz); 4.15 (2H, t, J=6 Hz); 3.73 (1H, m); 2.93 (2H, m); 1.73 (4H, m).

EXAMPLE 26

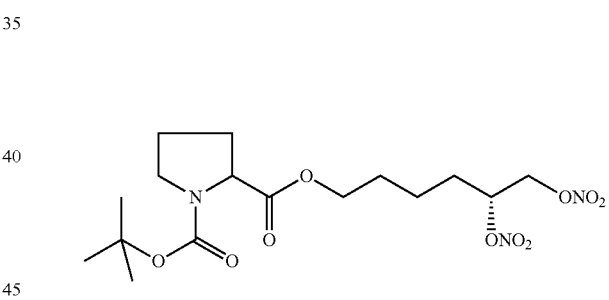

2-(R)-5,6-bis(nitrooxy)hexyl 1-tert-butyl pyrrolidine-1,2-dicarboxylate (Corresponding to Compound 4, 5-(R)-isomer)

To a solution of N-Boc-L-Proline (288 mg, 1.34 mmol) and (2R)-6-hydroxypentane-1,2-diyl dinitrate (obtained as described in WO2005070868(A1)) (300 mg, 1.34 mmol) in CH₂Cl₂ (6 ml) was added at 0° C. EDAC (257 mg, 1.34 mmol), and then DMAP (catalytic). The reaction was stirred overnight at rt. The organic layer was washed successively with H₂O, HCl 0.1M, H₂O and brine, dried over Na₂SO₄, filtered and evaporated. The residue was purified by column chromatography on silica (15% to 25% AcOEt in n-Hexane in 20 CV then 25% to 35% in 5 CV) to give the title compound (413 mg, 73%).

¹H-NMR (300 MHz, CDCl₃) δ 5.30 (m, 1H), 4.77 (m, 1H), 4.50 (m, 1H), 4.31 (d, J=11.5 Hz, 1H), 4.19 (m, 2H), 3.47 (m, 2H), 1.94 (m, 3H), 1.76 (m, 4H), 1.56 (m, 3H), 1.45 (d, J=12.67 Hz, 9H).

EXAMPLE 27

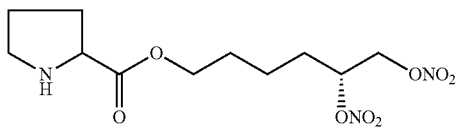

(R)-5,6-bis(nitrooxy)hexylpyrrolidine-2-carboxylate
(Corresponding to Compound 1; 5(R)-isomer)

To a solution of [(5R)-5,6-dinitroxyloxane-1-yl]N-tButoxy-L-proline ester (410 mg, 0.97 mmol) in CH₂Cl₂ (3 mL) was added TFA (223 µL, 2.91 mmol, 3 eq). The reaction was stirred at RT for 3 hrs. The organic layer was washed with H₂O, K₂CO₃ diluted, H₂O and brine, dried over Na₂SO₄, filtered and evaporated yielding the title compound (215 mg, 69%).

¹H-NMR (300 MHz, CDCl₃) δ 5.31 (ddd, J=13.23, 6.51, 3.09 Hz, 1H), 4.77 (dd, J=12.88, 3.07 Hz, 1H), 4.50 (dd, J=12.87, 6.46 Hz, 1H), 4.17 (t, J=6.30 Hz, 2H), 3.82 (dd, J=8.46, 5.25 Hz, 1H), 3.13 (dd, J=16.88, 6.54 Hz, 1H), 2.42 (s, 2H), 2.17 (m, 1H), 1.78 (m, 6H), 1.52 (m, 3H).

EXAMPLE 28

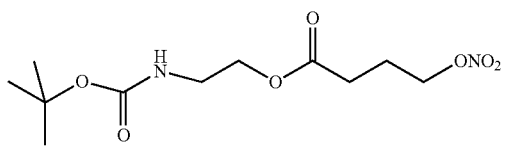

2-(tert-butoxycarbonylamino)ethyl 4-(nitrooxy)butanoate (Corresponding to Compound (508))

Step A: 2-(tert-butoxycarbonylamino)ethyl 4-bromobutanoate

N-Boc-ethanolamine (2.10 g; 13.0 mmol), 4-Bromobutyric acid (2.18 g; 13.0 mmol) and N,N-dimethylaminopyridine (0.318 g; 2.60 mmol) were dissolved in CH₂Cl₂ (35 mL) and the mixture was cooled to 0° C.; EDAC (3.75 g; 13.6 mmol) was added and the reaction was slowly warmed to room temperature and stirred for 18 hours. Then the mixture was diluted with CH₂Cl₂, washed with aqueous Na₂HPO₄ (5%, 2×50 ml) aqueous NaH₂PO₄, (5%, 2×50 ml) and brine (1×40 ml). The organic layer was dried over sodium sulfate and concentrated under reduced pressure.

The residue was purified by flash chromatography (hexane/EtOAc=75/25; R_f=40), yielding the title compound (3.03 g, 75%).

Step B: 2-(tert-butoxycarbonylamino)ethyl 4-(nitrooxy)butanoate

To a solution of 2-(tert-butoxycarbonylamino)ethyl 4-bromobutanoate (3.03 g; 9.77 mmol) in CH₃CN (80 mL), AgNO₃ (4.15 g; 24.4 mmol) was added and the reaction was performed at the microwave (120° C., 7 min). The formed salts were filtered off and the solvent was concentrated; then the residue was diluted with EtOAc and washed with water (40 ml); the organic layer was dried over sodium sulfate and concentrated under reduced pressure.

The residue was purified by flash chromatography (hexane/EtOAc=7/3; R_f=0.40), yielding the title compound (1.48 g, 52%).

¹H-NMR (300 MHz, CDCl₃): 4.77 (1H, s); 4.54 (2H, t); 4.17 (2H, t); 3.44-3.38 (2H, m); 2.49 (2H, t); 2.13-2.04 (2H, m); 1.46 (9H, s).

EXAMPLE 29

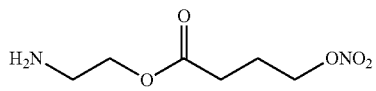

2-aminoethyl 4-(nitrooxy)butanoate hydrochloride
(Corresponding to Compound (509))

The title compound was obtained as a white solid starting from 2-(tert-butoxycarbonylamino)ethyl 4-(nitrooxy)butanoate, prepared, as described in Example 28 following the procedure described in Example 4 (1.16 g; quantitative yield).

¹H-NMR (DMSO-d₆): 8.25 (2H, s); 4.56 (2H, t); 4.23 (2H, t); 3.06 (2H, t); 2.51 (2H, t); 2.01-1.91 (2H, m).

EXAMPLE 30

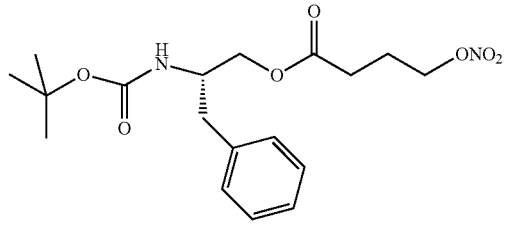

(S)-2-(tert-butoxycarbonylamino)-3-phenylpropyl 4-(nitrooxy)butanoate (Corresponding to Compound (511))

The title compound was prepared from (S)-tert-butyl 1-hydroxy-3-phenylpropan-2-ylcarbamate and 4-Bromobutyric acid following the procedure described in Example 29.

$^1$H-NMR (300 MHz, CDCl$_3$): 7.35-7.25 (5H, m); 4.56-4.54 (1H, m); 4.52 (2H, t); 4.15-4.04 (3H, m); 2.84-2.81 (2H, m); 2.50 (2H, t); 2.13-2.04 (2H, m); 1.32 (9H, s).

EXAMPLE 31

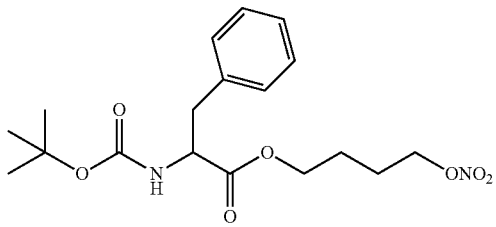

(S)-4-(nitrooxy)butyl 2-(tert-butoxycarbonylamino)-3-phenylpropanoate (Corresponding to Compound (15))

The title compound was prepared from (S)-2-(tert-butoxycarbonylamino)-5-phenylpropanoic acid and 4-chloro-1-butanol following the procedure described in Example 3.

$^1$H-NMR (300 MHz, CDCl$_3$): 7.31 (3H, m), 7.16 (2H, d), 4.98 (1H, bd), 4.56 (1H, bm), 4.41 (2H, t), 4.12 (2H, m), 3.08 (2H, d), 1.69 (4H, m), 1.93 (9H, s).

EXAMPLE 32

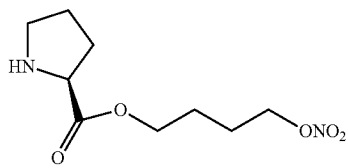

(S)-4-hydroxybutyl pyrrolidine-2-carboxylate

The title compound was prepared from Boc-Proline and 4-chloro-1-butanol following the procedure described in Example 3, eventually hydrolyzing the Boc protective group as described in Example 4.

$^1$H-NMR (CDCl$_3$): 4.5 (3H, m), 4.3 (2H, bt), 3.57 (2H, m), 2.45 (1H, m) 2.13 (3H, m), 1.87 (4H, m).

EXAMPLE 33

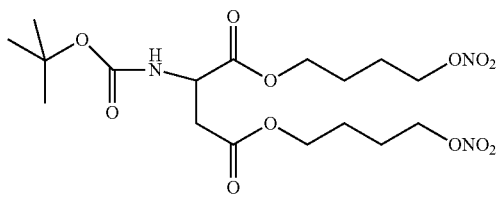

((S)-bis(4-nitrooxy)butyl) 2-(tert-butoxycarbonylamino)succinate (Corresponding to Compound (468))

The title compound was prepared from L-Boc-Aspartic acid and 4-chloro-1-butanol following the procedure described in Example 3.

$^1$H-NMR (CDCl$_3$): 5.48 (1H, bd), 4.58 (1H, bd), 4.51 (4H, t), 4.23 (2H, t), 2.93 (2H, m), 1.81 (8H, m), 1.47 (9H, s).

EXAMPLE 34

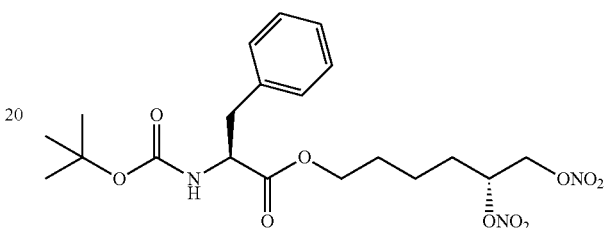

(S)—((R)-5,6-bis(nitrooxy)hexyl) 2-(tert)-butoxycarbonylamino)-3-phenylpropanoate (Corresponding to Compound (123), 5(R)-isomer))

The title compound was prepared from Boc-L-Phenylalanine and (2R)-6-hydroxypentane-1,2-diyl dinitrate (obtained as described in WO2005070868(A1)) following the procedure described in Example 26.

EXAMPLE 35

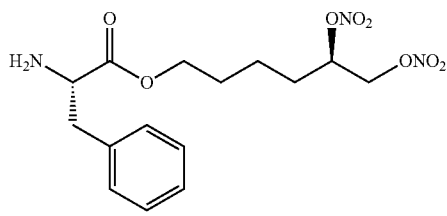

(S)—((R)-5,6-bis(nitrooxy)hexyl) 2-amino-3-phenylpropanoate (Corresponding to Compound 14 5(R)-isomer)

The title compound was prepared from (S)—((R)-5,6-bis)nitrooxy)hexyl) 2-(tert-butoxycarbonylamino)-3-phenylpropanoate (prepared as described in Example 34) following procedure described in Example 4.

$^1$H-NMR (CDCl$_3$): 9.04-8.65 (2H, m), 7.47-7.14 (5H, m), 5.31-5.15 (1H, m), 4.80-4.65 (1H, m), 4.55-4.31 (1H, m), 4.23-3.96 (2H, m); 3.60-3.42 (1H, m); 3.42-3.23 (1H, m); 1.74-1.46 (4H, m); 1.45-1.15 (2H, m).

EXAMPLE 35

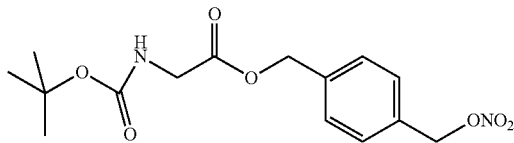

4-[(nitrooxy)methyl]benzyl 2-(tert-butoxycarbonylamino)acetate (Corresponding to Compound (87))

The title compound was prepared from N-Boc-Glycine N-hydroxysuccinimido ester and 4-(chloromethyl)benzyl alcohol following procedures reported in Example 3.
$^1$H-NMR (CDCl$_3$): 7.41 (4H, s), 5.44 (2H, s), 5.19 (2H, s), 5.02 (1H, bs), 3.97 (2H, d), 1.47 (9H, s).

EXAMPLE 36

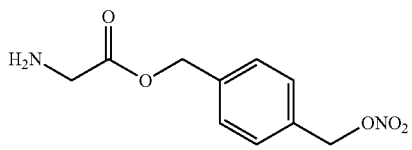

4-[(nitrooxy)methyl]benzyl 2-aminoacetate (Corresponding to Compound (33))

The title compound was prepared from 4-[(nitrooxy)methyl]benzyl 2-(tert-butoxycarbonylamino)acetate (prepared in Example 35) following procedures reported in Example 4.
$^1$H-NMR (CDCl$_3$): 8.66-8.34 (2H, m), 7.59-7.40 (4H, m), 5.59 (2H, s), 5.26 (2H, s), 3.87 (2H, s).

EXAMPLE 37

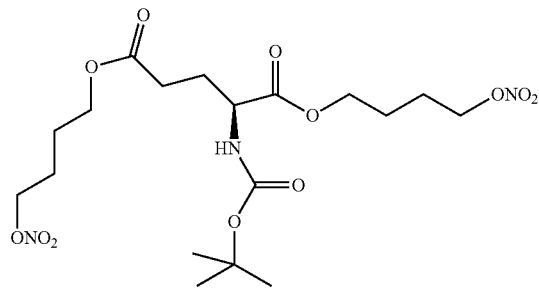

(S)-bis(4-nitrooxy)butyl) 2-(tert-butoxycarbonylamino)pentanedioate (Corresponding to Compound (87)) (472))

The title compound was prepared from L-Boc-Glutamic acid and 4-chloro-1-butanol following procedure described in Example 3, eventually hydrolyzing the Boc protective group as described in Example 4.
$^1$H-NMR (CDCl$_3$): 5.28 (1H, bd), 4.48 (1H, bd), 4.19 (2H, t), 4.07 (2H, t), 2.40 (3H, m), 2.03 (1H, m), 1.72 (8H, m), 1.45 (9H, s).

EXAMPLE 38

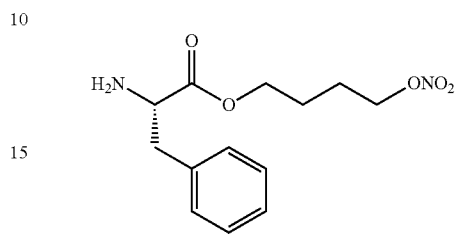

(S)-4-(nitrooxy)butyl 2-amino-3-phenylpropanoate (Corresponding to Compound (40))

The title compound was prepared from (S)-4-(nitrooxy)butyl 2-(tert-butoxycarbonylamino)-3-phenylpropanoate (prepared as described in Example 31) following procedure described in Example 4.
$^1$H-NMR (DMSO): 8.7 (3H, bs), 7.30 (5H, m), 4.47 (2H, d), 4.25 (1H, t), 4.08 (2H, t), 3.15 (2H, m), 1.54 (4H, m).

PHARMACOLOGICAL EXAMPLE

The ability of the compounds of the present invention to release nitric oxide was assessed testing their vasorelaxant activity in isolated rabbit thoracic aorta preparations (Wanstall J. C. et al., Br. J. Pharmacol., 134:463-472, 2001).

The compounds of the invention that were tested are the compounds of the following formulas: 7, 8, 9, 12, 13, 15, 86, 87, 123, 407, 508, 511;
and compounds reported in Examples 14, 15, and 21.

Method

Male New Zealand rabbits were anaesthetized with thiopental-Na (50 mg/kg, iv), sacrificed by exsanguinations and then the thorax was opened and the aorta dissected. Single ring preparations (4 mm in length) of thoracic aorta were set up in physiological salt solution (PSS) at 37° C. in small organ chambers (5 ml). The composition of PSS was (mM): NaCl 130, NaHCO$_3$ 14.9, KH$_2$PO$_4$ 1.2, MgSO$_4$ 1.2, HEPES 10, CaCl$_2$, ascorbic acid 170 and glucose 1.1 (95%)$_2$/5% CO$_2$; pH 7.4). Each ring was mounted under 2 g passive tension in 5 ml organ bath. Isometric tension was recorded with a Grass transducer (Grass FT03) attached to a BIOPAC MP150 System. Preparations were allowed to equilibrate for 1 h, then contracted submaximally with noradrenaline (NA, 1 µM) and, when the contraction was stable, acetylcholine (ACh, 10 µM) was added. A relaxant response to ACh indicated the presence of a functional endothelium. When a stable precontraction was reached, a cumulative concentration-response curve to either of the vasorelaxant agents was obtained in the presence of a functional endothelium. Time intervals between different concentrations were based on the time needed to reach a full response.

Moreover, the nitric oxide-dependent vascular relaxation elicited by the tested compounds was examined preincubating the aortic rings with the soluble guanylyl cyclase inhibitor ODQ (1H-(1,2,4)-oxadiazol(4,3-a)quinoxalin-1-one) at 10 µM for 20 min. Responses to vasorelaxing agents were measured from the plateau of NA contraction. The $IC_{50}$ (concentration giving 50% reversal of NA contraction) was interpolated from the plots of relaxant-response vs log molar concentration of tested compound.

During the experimental period, the plateau obtained with NA was stable without significant spontaneous loss of contraction in the aortic rings.

As shown in the following Table 1, the compounds of the invention were able to induce relaxation in a concentration-dependent manner. Furthermore, in experiments performed in the presence of ODQ (10 μM), the vascular relaxation of the tested compounds was inhibited.

TABLE 1

| Compound | $IC_{50}$ (μM) ± sem |
|---|---|
| Example 15 | 1.2 ± 0.33 |
| Example 14 | 1.9 ± 0.4 |
| Compound 8 | 2.6 ± 0.6 |
| Compound 7 | 2.4 ± 0.5 |
| Compound 9 | 4.5 ± 1.4 |
| Compound 86 | 5.2 ± 0.9 |
| Compound 13 | 10.2 ± 0.5 |
| Example 21 | 8.0 ± 1.8 |
| Compound 87 | 2.1 ± 0.4 |
| Compound 12 | 10.2 ± 4.2 |
| Compound 508 | 4.4 ± 0.7 |
| Compound 15 | 12.6 ± 6.4 |
| Compound 511 | 9.5 ± 3.6 |
| Compound 123 | 0.64 ± 0.14 |
| Compound 407 | 16 ± 6.4 |

$IC_{50}$ is the concentration which inhibits 50% of the response.

The invention claimed is:

1. A compound and pharmaceutically acceptable salts or stereoisomers thereof selected from the group consisting of:

(7)
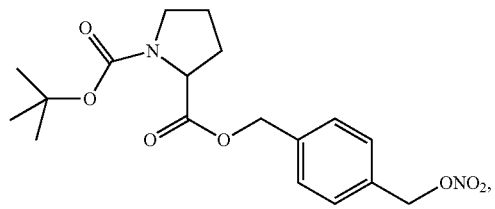

(8)
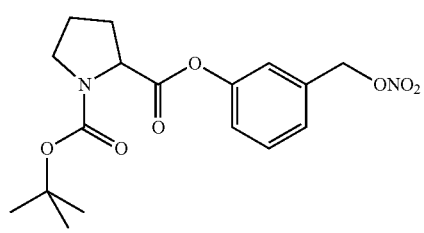

(9)
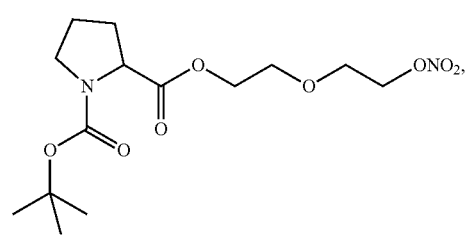

-continued

(12)
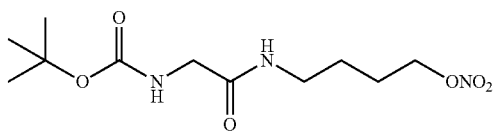

(13)
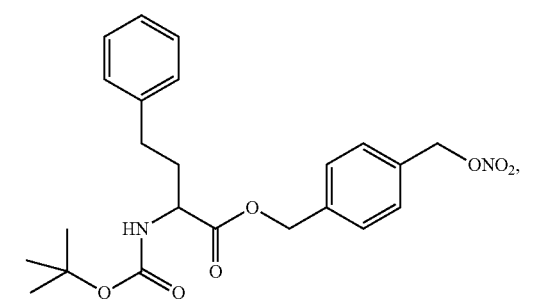

(15)
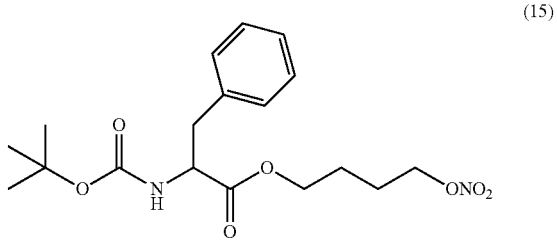

(86)
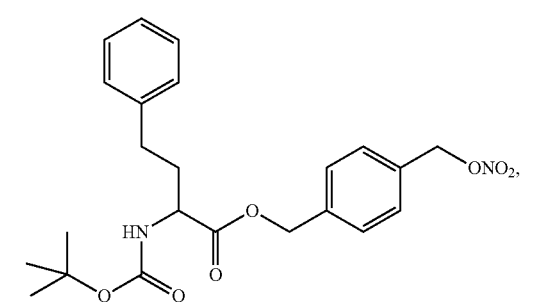

(87)
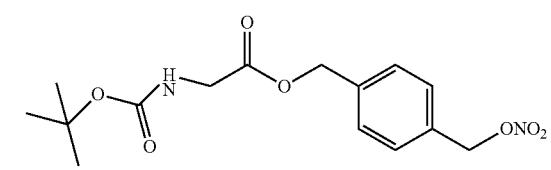

(123)
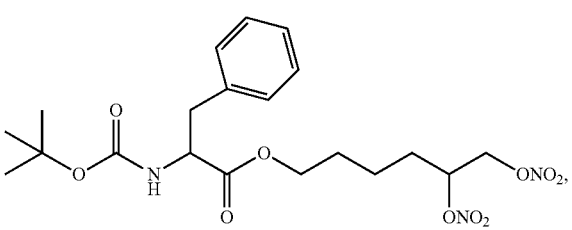

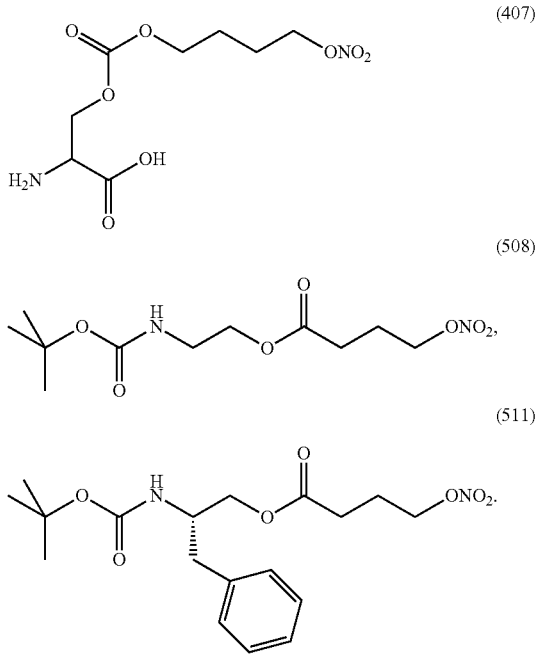

2. A medicament comprising a compound according to claim 1 and one or more pharmaceutically acceptable excipients.

3. A pharmaceutical composition comprising a compound according to claim 1 and one or more pharmaceutically acceptable excipients.

4. A composition comprising at least a compound of formula (I) according to claim 1 and at least one therapeutic agent selected from the group consisting of: anti-inflammatory drugs, drugs used to treat cardiovascular diseases, drugs for treating ocular diseases, and drugs for treating respiratory disorders.

5. A medicament comprising the composition according to claim 4 and one or more pharmaceutically acceptable excipients.

6. The composition according to claim 4 wherein the compound and the at least one therapeutic agent are administered simultaneously or sequentially.

7. A pharmaceutical composition comprising the composition according to claim 4 and one or more pharmaceutically acceptable excipients.

8. A method for treating a condition comprising administering a compound according to claim 1, wherein the condition is selected from the group consisting of cardiovascular diseases, inflammation, pain, fever, gastrointestinal disorders, ophthalmic diseases including glaucoma, hepatic disorders, renal diseases, respiratory disorders, immunological diseases, bone metabolism dysfunctions, central and peripheral nervous system diseases, sexual dysfunctions, infectious diseases, inhibition of platelet aggregation and platelet adhesion, pathological conditions resulting from abnormal cell proliferation and vascular diseases.

9. A method for treating a condition comprising administering the composition according to claim 4, wherein the condition is selected from the group consisting of cardiovascular diseases, inflammation, pain, fever, gastrointestinal disorders, ophthalmic diseases including glaucoma, hepatic disorders, renal diseases, respiratory disorders, immunological diseases, bone metabolism dysfunctions, central and peripheral nervous system diseases, sexual dysfunctions, infectious diseases, inhibition of platelet aggregation and platelet adhesion, pathological conditions resulting from abnormal cell proliferation and vascular diseases.

* * * * *